United States Patent [19]
Ligon et al.

[11] Patent Number: 6,117,670
[45] Date of Patent: *Sep. 12, 2000

[54] PYRROLNITRIN BIOSYNTHESIS GENES AND USES THEREOF

[75] Inventors: James Madison Ligon, Apex; Dwight Steven Hill, Cary; Stephen Ting Lam, Raleigh; Philip Eugene Hammer, Cary, all of N.C.; Karl-Heinz van Pee, Bannewitz; Sabine Kirner, Puchheim, both of Germany; Thomas R. Young, Vero Beach, Fla.

[73] Assignee: Novartis Finance Corporation, New York, N.Y.

[*] Notice: This patent is subject to a terminal disclaimer.

[21] Appl. No.: 09/028,934

[22] Filed: Feb. 24, 1998

Related U.S. Application Data

[63] Continuation-in-part of application No. 08/729,214, Oct. 9, 1996, Pat. No. 5,817,502, which is a continuation-in-part of application No. 08/258,261, Jun. 8, 1994, Pat. No. 5,639,949, said application No. 08/729,214, is a continuation-in-part of application No. PCT/IB95/00414, May 30, 1995, and application No. 08/258,261, Jun. 8, 1994, Pat. No. 5,639,949.

[51] Int. Cl.$^7$ .................................................. F04B 22/03
[52] U.S. Cl. ............................... 435/252.33; 435/252.3; 435/320.1; 435/189; 435/232; 536/23.1; 536/23.2; 536/23.7
[58] Field of Search .................................. 435/232, 189, 435/252.3, 252.33, 320.1; 536/23.1, 23.2, 23.7

[56] References Cited

U.S. PATENT DOCUMENTS

| | | | |
|---|---|---|---|
| 4,306,027 | 12/1981 | Alexander et al. | 435/253 |
| 4,456,684 | 6/1984 | Weller et al. | 435/34 |
| 4,695,455 | 9/1987 | Barnes et al. | 424/93 |
| 4,729,951 | 3/1988 | Ferenczy et al. | 435/80 |
| 4,798,723 | 1/1989 | Dart et al. | 424/93 |
| 4,812,512 | 3/1989 | Bernestein et al. | 424/417 |
| 4,880,745 | 11/1989 | Kijima et al. | 435/252.3 |
| 4,940,840 | 7/1990 | Suslow et al. | 800/205 |
| 4,948,413 | 8/1990 | Maekawa et al. | 71/65 |
| 4,952,496 | 8/1990 | Studier et al. | 435/91 |
| 4,970,147 | 11/1990 | Huala et al. | 435/69.1 |
| 4,975,277 | 12/1990 | Janisiewicz et al. | 424/93 |
| 4,994,495 | 2/1991 | Clough et al. | 514/574 |
| 4,999,381 | 3/1991 | Crowley et al. | 514/618 |
| 5,008,276 | 4/1991 | Clough et al. | 514/335 |
| 5,041,290 | 8/1991 | Gindrat et al. | 424/93 |
| 5,049,379 | 9/1991 | Handelsmon et al. | 424/115 |
| 5,059,605 | 10/1991 | Clough et al. | 514/269 |
| 5,068,105 | 11/1991 | Lewis et al. | 424/93 |
| 5,279,951 | 1/1994 | Terasawa et al. | 435/192.3 |

FOREIGN PATENT DOCUMENTS

| | | |
|---|---|---|
| 0357119A2 | 9/1989 | European Pat. Off. . |
| 0414404 | 2/1991 | European Pat. Off. . |
| 468220A2 | 6/1991 | European Pat. Off. . |
| 0471564 | 2/1992 | European Pat. Off. . |
| 543195A2 | 10/1992 | European Pat. Off. . |
| 89-09264 | 10/1989 | WIPO . |
| WO/9105475 | 5/1991 | WIPO . |
| 9208355 | 5/1992 | WIPO . |
| 95/33818 | 12/1995 | WIPO . |

OTHER PUBLICATIONS

Albright et al., *Annu. Rev. Genet.*, 23:311–336 (1989).
Baker et al., *Biological Control of Plant Pathogens*, 61–106 (American Phytopathological Society, St. Paul, Minn. 1982).
Bourret et al., *Annu. Rev. Biochem.*, 60:401–441 (1991).
Brisbane et al., *Antimicrobiol. Agents and Chemotherapy*, 31(12):1967–1971 (1987).
Brisbane et al., *Soil Biol. Biochem.*, 21(8):1019–1026 (1989).
Chen et al., "Cloning and Expression of a DNA Sequence Conferring Cephamycin C Production", *Biotechnology*, 6(10):1222–1224 (1988).
Clarke et al., *J. Bacteriol.* 154:508–512 (1983).
Cook et al., *Soil Biol. Biochem.*, 8:269–273 (1976).
Ding et al., *Gene*, 33(3):212–321 (1985).
Ditta et al., *PNAS:USA*, 77:7347–7351 (1980).
Gaffney et al., "Global Regulation of Expression of Antifungal Factors by *Pseudomonas fluorescens* biological Control Strain", *Molecular Plant–Microbe Interactions*, 7(4):455–463 (1994).
Gambello et al., *J. Bacteriology*, 173(9): 3000–3009 (1991).
Gurusiddaiah et al., *Antimicrobiol. Agents and Chemotherapy*, 79(3): 488–495 (1986).
Gutterson et al., *Journal of Bacteriology*, 165(3):696–703 (1986).
Hain et al., "Disease resistance results from foreign phytoalexin expression in a novel plant", *Nature*, 361:153–156 (1993).
Hamden et al., *Applied and Environ. Microbiol.* 57:3270–3277 (1991).
Horn et al., *J. Bacteriology*, 170(10):4699–4705(1988).
Howell et al., *Can. J. Microbiol.*, 29:321–324 (1983).
Howell et al., *Phytopathology*, 69(5):480–482 (1979).
Howell et al., *Phytopathology*, 69:480–482 (1979).
Howell et al., *Phytopathology*, 70:712–715 (1980).

(List continued on next page.)

*Primary Examiner*—Nashaat Nashed
*Attorney, Agent, or Firm*—J. Timothy Meigs

[57] ABSTRACT

The present invention is directed to the production of pyrrolnitrin in a host via recombinant expression of the polypeptides needed to biologically synthesize pyrrolnitrin. Genes isolated from *P. fluorescens, P. pyrrocinia, B. cepacia*, and *M. fulvus* that encode polypeptides necessary to produce pyrrolnitrin are provided, along with methods for identifying and isolating genes needed to recombinantly biosynthesize pyrrolnitrin from any organism capable of producing pyrrolnitrin. The isolated genes may be transformed and expressed in a desired host organisms to produce pyrrolnitrin according to the invention for a variety of purposes, including protecting the host from a pathogen, developing the host as a biocontrol agent, and producing large, uniform amounts of pyrrolnitrin.

38 Claims, No Drawings

OTHER PUBLICATIONS

Howie et al., *Phytopathology*, 79(10):1160 (1989).
Inouye et al., *J. Bacteriology*, 155(3):1192–1199 (1983).
James et al., *Applied and Environmental Microbiology*, 52(5):1183–1189 (1986).
Jayaswal et al., *Can. J. Microbiol.*, 38(4):309–312 (1992).
Jeenes et al., *Mol. Gen. Genet.*, 203:421–429 (1986).
Kaphammer et al., *J. Bacteriology*, 172(10):5856–5862 (1990).
Keel et al., *Symbiosis*, 9(1–3):327–341 (1990).
Kirner et al., *Microbiology*, 142:2129–2135 (1996).
Klee et al., *The Plant Cell*, 3:1187–1193 (1991).
Kloepper et al., *Phytopathology*, 71:1020–1024 (1981).
Kraus et al., *Phytopathology*, 79(8):910 (1989).
Kroos et al., *PNAS USA*, 81:5816–5820 (1984).
Lam et al., "Genetic regulation of biocontrol factors in *Pseudomonas fluorescens*", Third International Workshop on Plant–Promoting Rhizobacteria, Australia 97–99 (1994).
Laville et al., *PNAS USA*, 89:1562–1566 (1992).
Lievens et al., *Pesticide Science*, 27(2):141–154 (1989).
Loper, *Phytopathology*, 78:166–171 (1988).
Maruzen Oil Abstract, 27 (1979).
Mekalanos, J.J., *J. Bacteriology*, 174:1–7 (1992).
Mermod et al., *J. Bacteriology*, 167(2):447–454 (1986).
Mohr et al., *Molecular Microbiology*, 4(12):2103–2110 (1990).
Moolenaar et al., *Nucl. Acids Res.*, 15(10):4273–4289 (1989).
Orlik–Eisel et al., *Microbiology*, 153(6): 561–568 (1990).
Pfender et al., *Phytopathology*, 83:1223–1228 (1993).
Ramos et al., *Science*, 235(4788):593–596 (1987).
Rothmel et al., *J. Bacteriology*, 173(15):4717–4724(1991).
Schell, M.A., *Gene*, 36(3):301–309 (1985).
Scher et al., *Phytopathology*, 70:412–417 (1980).
Schroth et al., *Science*, 216:1376–1381 (1982).
Spena et al., *Mol. Gen. Genet.*, 227:205–212 (1991).
Starnbach et al., *Molecular Microbiology*, 6(4):459–469 (1992).
Stock et al., *Microbiological Reviews*, 53(4): 450–490 (1989).
Tanaka et al., *J. Bacteriology*, 170(8):3593–3600 (1988).
Thomashow et al., *J. Bacteriology*, 170:3499–3508 (1988).
Toder et al., *Molecular Microbiology*, 5(8):2003–2010 (1991).
Toohey et al., "Toxicity of Phenazine Carboxylic Acids to Some Bacteria, Algae, Higher Plants, and Animals", *Canadian Journal of Botany*, 43:1151–1155 (1965).
Weller et al., *Journal of Cellular Biochemistry*, Supplement 13A:134, Abstract CB 104 (1989).
Weller et al., *Phytopathology*, 73:463–469 (1983).
Wolfframm et al., *FEBS Letter*, 238:325–328 (1988).
"Nikkomycin–Antibiotic for Plants", *NTIS TECH NOTES*, 5:374 (1990) European Search Report dated Sep. 28, 1995.
Hoffmann–LaRoche & Co., "Phenazine Derivatives and a Process for the Manufacture Thereof", *GB–A–1 285 010* Patent Specification, 1–8 (1972).
Weisner et al., *J. Biol. Chem.* 263: 13725–13732 (1988).
VanPee, K–H., *Biotech. Adv.* 8:185–205 (1990).

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 7001 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 423..2036
      (D) OTHER INFORMATION: /product= "PrnA"

(ix) FEATURE:
    (A) NAME/KEY: CDS
    (B) LOCATION: 2039..3121
    (D) OTHER INFORMATION: /product= "PrnB"

(ix) FEATURE:
    (A) NAME/KEY: CDS
    (B) LOCATION: 3167..4867
    (D) OTHER INFORMATION: /product= "PrnC"

(ix) FEATURE:
    (A) NAME/KEY: CDS
    (B) LOCATION: 4895..5983
    (D) OTHER INFORMATION: /product= "PrnD"

(ix) FEATURE:
    (A) NAME/KEY: misc_feature
    (B) LOCATION: 1..7001
    (D) OTHER INFORMATION: /note= "Four open reading frames
    (ORFs) were identified within this DNA sequence and are
       transcribed as a single message, as described in
       Examples 10 and 12 of the specification."

(xi) SEQUENCE DESCRIPTION: SEQ ID NO:1:

```
GAATTCCGAC AACGCCGAAG AAGCGCGGAA CCGCTGAAAG AGGAGCAGGA ACTGGAGCAA      60

ACGCTGTCCC AGGTGATCGA CAGCCTGCCA CTGCGCATCG AGGGCCGATG AACAGCATTG     120

GCAAAAGCTG GCGGTGCGCA GTGCGCGAGT GATCCGATCA TTTTTGATCG GCTCGCCTCT     180

TCAAAATCGG CGGTGGATGA AGTCGACGGC GGACTGATCA GGCGCAAAAG AACATGCGCC     240

AAAACCTTCT TTTATAGCGA ATACCTTTGC ACTTCAGAAT GTTAATTCGG AAACGGAATT     300

TGCATCGCTT TTCCGGCAGT CTAGAGTCTC TAACAGCACA TTGATGTGCC TCTTGCATGG     360

ATGCACGAAG ACTGGCGGCC TCCCCTCGTC ACAGGCGGCC CGCCTTTGAA ACAAGGAGTG     420

TT ATG AAC AAG CCG ATC AAG AAT ATC GTC ATC GTG GGC GGC GGT ACT        467
   Met Asn Lys Pro Ile Lys Asn Ile Val Ile Val Gly Gly Gly Thr
   1               5                  10                  15

GCG GGC TGG ATG GCC GCC TCG TAC CTC GTC CGG GCC CTC CAA CAG CAG       515
Ala Gly Trp Met Ala Ala Ser Tyr Leu Val Arg Ala Leu Gln Gln Gln
                20                  25                  30

GCG AAC ATT ACG CTC ATC GAA TCT GCG GCG ATC CCT CGG ATC GGC GTG       563
Ala Asn Ile Thr Leu Ile Glu Ser Ala Ala Ile Pro Arg Ile Gly Val
            35                  40                  45

GGC GAA GCG ACC ATC CCA AGT TTG CAG AAG GTG TTC TTC GAT TTC CTC       611
Gly Glu Ala Thr Ile Pro Ser Leu Gln Lys Val Phe Phe Asp Phe Leu
        50                  55                  60

GGG ATA CCG GAG CGG GAA TGG ATG CCC CAA GTG AAC GGC GCG TTC AAG       659
Gly Ile Pro Glu Arg Glu Trp Met Pro Gln Val Asn Gly Ala Phe Lys
    65                  70                  75

GCC GCG ATC AAG TTC GTG AAT TGG AGA AAG TCT CCC GAC CCC TCG CGC       707
Ala Ala Ile Lys Phe Val Asn Trp Arg Lys Ser Pro Asp Pro Ser Arg
80                  85                  90                  95

GAC GAT CAC TTC TAC CAT TTG TTC GGC AAC GTG CCG AAC TGC GAC GGC       755
Asp Asp His Phe Tyr His Leu Phe Gly Asn Val Pro Asn Cys Asp Gly
                100                 105                 110

GTG CCG CTT ACC CAC TAC TGG CTG CGC AAG CGC GAA CAG GGC TTC CAG       803
Val Pro Leu Thr His Tyr Trp Leu Arg Lys Arg Glu Gln Gly Phe Gln
            115                 120                 125

CAG CCG ATG GAG TAC GCG TGC TAC CCG CAG CCC GGG GCA CTC GAC GGC       851
Gln Pro Met Glu Tyr Ala Cys Tyr Pro Gln Pro Gly Ala Leu Asp Gly
        130                 135                 140

AAG CTG GCA CCG TGC CTG TCC GAC GGC ACC CGC CAG ATG TCC CAC GCG       899
Lys Leu Ala Pro Cys Leu Ser Asp Gly Thr Arg Gln Met Ser His Ala
    145                 150                 155
```

```
TGG CAC TTC GAC GCG CAC CTG GTG GCC GAC TTC TTG AAG CGC TGG GCC      947
Trp His Phe Asp Ala His Leu Val Ala Asp Phe Leu Lys Arg Trp Ala
160             165                 170                 175

GTC GAG CGC GGG GTG AAC CGC GTG GTC GAT GAG GTG GTG GAC GTT CGC      995
Val Glu Arg Gly Val Asn Arg Val Val Asp Glu Val Val Asp Val Arg
                180                 185                 190

CTG AAC AAC CGC GGC TAC ATC TCC AAC CTG CTC ACC AAG GAG GGG CGG     1043
Leu Asn Asn Arg Gly Tyr Ile Ser Asn Leu Leu Thr Lys Glu Gly Arg
            195                 200                 205

ACG CTG GAG GCG GAC CTG TTC ATC GAC TGC TCC GGC ATG CGG GGG CTC     1091
Thr Leu Glu Ala Asp Leu Phe Ile Asp Cys Ser Gly Met Arg Gly Leu
        210                 215                 220

CTG ATC AAT CAG GCG CTG AAG GAA CCC TTC ATC GAC ATG TCC GAC TAC     1139
Leu Ile Asn Gln Ala Leu Lys Glu Pro Phe Ile Asp Met Ser Asp Tyr
225                 230                 235

CTG CTG TGC GAC AGC GCG GTC GCC AGC GCC GTG CCC AAC GAC GAC GCG     1187
Leu Leu Cys Asp Ser Ala Val Ala Ser Ala Val Pro Asn Asp Asp Ala
240                 245                 250                 255

CGC GAT GGG GTC GAG CCG TAC ACC TCC TCG ATC GCC ATG AAC TCG GGA     1235
Arg Asp Gly Val Glu Pro Tyr Thr Ser Ser Ile Ala Met Asn Ser Gly
                260                 265                 270

TGG ACC TGG AAG ATT CCG ATG CTG GGC CGG TTC GGC AGC GGC TAC GTC     1283
Trp Thr Trp Lys Ile Pro Met Leu Gly Arg Phe Gly Ser Gly Tyr Val
            275                 280                 285

TTC TCG AGC CAT TTC ACC TCG CGC GAC CAG GCC ACC GCC GAC TTC CTC     1331
Phe Ser Ser His Phe Thr Ser Arg Asp Gln Ala Thr Ala Asp Phe Leu
        290                 295                 300

AAA CTC TGG GGC CTC TCG GAC AAT CAG CCG CTC AAC CAG ATC AAG TTC     1379
Lys Leu Trp Gly Leu Ser Asp Asn Gln Pro Leu Asn Gln Ile Lys Phe
305                 310                 315

CGG GTC GGG CGC AAC AAG CGG GCG TGG GTC AAC AAC TGC GTC TCG ATC     1427
Arg Val Gly Arg Asn Lys Arg Ala Trp Val Asn Asn Cys Val Ser Ile
320                 325                 330                 335

GGG CTG TCG TCG TGC TTT CTG GAG CCC CTG GAA TCG ACG GGG ATC TAC     1475
Gly Leu Ser Ser Cys Phe Leu Glu Pro Leu Glu Ser Thr Gly Ile Tyr
                340                 345                 350

TTC ATC TAC GCG GCG CTT TAC CAG CTC GTG AAG CAC TTC CCC GAC ACC     1523
Phe Ile Tyr Ala Ala Leu Tyr Gln Leu Val Lys His Phe Pro Asp Thr
            355                 360                 365

TCG TTC GAC CCG CGG CTG AGC GAC GCT TTC AAC GCC GAG ATC GTC CAC     1571
Ser Phe Asp Pro Arg Leu Ser Asp Ala Phe Asn Ala Glu Ile Val His
        370                 375                 380

ATG TTC GAC GAC TGC CGG GAT TTC GTC CAA GCG CAC TAT TTC ACC ACG     1619
Met Phe Asp Asp Cys Arg Asp Phe Val Gln Ala His Tyr Phe Thr Thr
385                 390                 395

TCG CGC GAT GAC ACG CCG TTC TGG CTC GCG AAC CGG CAC GAC CTG CGG     1667
Ser Arg Asp Asp Thr Pro Phe Trp Leu Ala Asn Arg His Asp Leu Arg
400                 405                 410                 415

CTC TCG GAC GCC ATC AAA GAG AAG GTT CAG CGC TAC AAG GCG GGG CTG     1715
Leu Ser Asp Ala Ile Lys Glu Lys Val Gln Arg Tyr Lys Ala Gly Leu
                420                 425                 430

CCG CTG ACC ACC ACG TCG TTC GAC GAT TCC ACG TAC TAC GAG ACC TTC     1763
Pro Leu Thr Thr Thr Ser Phe Asp Asp Ser Thr Tyr Tyr Glu Thr Phe
            435                 440                 445

GAC TAC GAA TTC AAG AAT TTC TGG TTG AAC GGC AAC TAC TAC TGC ATC     1811
Asp Tyr Glu Phe Lys Asn Phe Trp Leu Asn Gly Asn Tyr Tyr Cys Ile
        450                 455                 460

TTT GCC GGC TTG GGC ATG CTG CCC GAC CGG TCG CTG CCG CTG TTG CAG     1859
Phe Ala Gly Leu Gly Met Leu Pro Asp Arg Ser Leu Pro Leu Leu Gln
465                 470                 475
```

```
CAC CGA CCG GAG TCG ATC GAG AAA GCC GAG GCG ATG TTC GCC AGC ATC      1907
His Arg Pro Glu Ser Ile Glu Lys Ala Glu Ala Met Phe Ala Ser Ile
480                 485                 490                 495

CGG CGC GAG GCC GAG CGT CTG CGC ACC AGC CTG CCG ACA AAC TAC GAC      1955
Arg Arg Glu Ala Glu Arg Leu Arg Thr Ser Leu Pro Thr Asn Tyr Asp
                500                 505                 510

TAC CTG CGG TCG CTG CGT GAC GGC GAC GCG GGG CTG TCG CGC GGC CAG      2003
Tyr Leu Arg Ser Leu Arg Asp Gly Asp Ala Gly Leu Ser Arg Gly Gln
            515                 520                 525

CGT GGG CCG AAG CTC GCA GCG CAG GAA AGC CTG TA GTG AAA CGC ACC       2050
Arg Gly Pro Lys Leu Ala Ala Gln Glu Ser Leu     Met Glu Arg Thr
        530                 535                   1

TTG GAC CGG GTA GGC GTA TTC GCG GCC ACC CAC GCT GCC GTG GCG GCC      2098
Leu Asp Arg Val Gly Val Phe Ala Ala Thr His Ala Ala Val Ala Ala
 5              10                  15                  20

TGC GAT CCG CTG CAG GCG CGC GCG CTC GTT CTG CAA CTG CCG GGC CTG      2146
Cys Asp Pro Leu Gln Ala Arg Ala Leu Val Leu Gln Leu Pro Gly Leu
                25                  30                  35

AAC CGT AAC AAG GAC GTG CCC GGT ATC GTC GGC CTG CTG CGC GAG TTC      2194
Asn Arg Asn Lys Asp Val Pro Gly Ile Val Gly Leu Leu Arg Glu Phe
            40                  45                  50

CTT CCG GTG CGC GGC CTG CCC TGC GGC TGG GGT TTC GTC GAA GCC GCC      2242
Leu Pro Val Arg Gly Leu Pro Cys Gly Trp Gly Phe Val Glu Ala Ala
        55                  60                  65

GCC GCG ATG CGG GAC ATC GGG TTC TTC CTG GGG TCG CTC AAG CGC CAC      2290
Ala Ala Met Arg Asp Ile Gly Phe Phe Leu Gly Ser Leu Lys Arg His
    70                  75                  80

GGA CAT GAG CCC GCG GAG GTG GTG CCC GGG CTT GAG CCG GTG CTG CTC      2338
Gly His Glu Pro Ala Glu Val Val Pro Gly Leu Glu Pro Val Leu Leu
85                  90                  95                  100

GAC CTG GCA CGC GCG ACC AAC CTG CCG CCG CGC GAG ACG CTC CTG CAT      2386
Asp Leu Ala Arg Ala Thr Asn Leu Pro Pro Arg Glu Thr Leu Leu His
                105                 110                 115

GTG ACG GTC TGG AAC CCC ACG GCG GCC GAC GCG CAG CGC AGC TAC ACC      2434
Val Thr Val Trp Asn Pro Thr Ala Ala Asp Ala Gln Arg Ser Tyr Thr
            120                 125                 130

GGG CTG CCC GAC GAA GCG CAC CTG CTC GAG AGC GTG CGC ATC TCG ATG      2482
Gly Leu Pro Asp Glu Ala His Leu Leu Glu Ser Val Arg Ile Ser Met
        135                 140                 145

GCG GCC CTC GAG GCG GCC ATC GCG TTG ACC GTC GAG CTG TTC GAT GTG      2530
Ala Ala Leu Glu Ala Ala Ile Ala Leu Thr Val Glu Leu Phe Asp Val
    150                 155                 160

TCC CTG CGG TCG CCC GAG TTC GCG CAA AGG TGC GAC GAG CTG GAA GCC      2578
Ser Leu Arg Ser Pro Glu Phe Ala Gln Arg Cys Asp Glu Leu Glu Ala
165                 170                 175                 180

TAT CTG CAG AAA ATG GTC GAA TCG ATC GTC TAC GCG TAC CGC TTC ATC      2626
Tyr Leu Gln Lys Met Val Glu Ser Ile Val Tyr Ala Tyr Arg Phe Ile
                185                 190                 195

TCG CCG CAG GTC TTC TAC GAT GAG CTG CGC CCC TTC TAC GAA CCG ATT      2674
Ser Pro Gln Val Phe Tyr Asp Glu Leu Arg Pro Phe Tyr Glu Pro Ile
            200                 205                 210

CGA GTC GGG GGC CAG AGC TAC CTC GGC CCC GGT GCC GTA GAG ATG CCC      2722
Arg Val Gly Gly Gln Ser Tyr Leu Gly Pro Gly Ala Val Glu Met Pro
        215                 220                 225

CTC TTC GTG CTG GAG CAC GTC CTC TGG GGC TCG CAA TCG GAC GAC CAA      2770
Leu Phe Val Leu Glu His Val Leu Trp Gly Ser Gln Ser Asp Asp Gln
    230                 235                 240

ACT TAT CGA GAA TTC AAA GAG ACG TAC CTG CCC TAT GTG CTT CCC GCG      2818
Thr Tyr Arg Glu Phe Lys Glu Thr Tyr Leu Pro Tyr Val Leu Pro Ala
245                 250                 255                 260
```

| | |
|---|---|
| TAC AGG GCG GTC TAC GCT CGG TTC TCC GGG GAG CCG GCG CTC ATC GAC<br>Tyr Arg Ala Val Tyr Ala Arg Phe Ser Gly Glu Pro Ala Leu Ile Asp<br>                    265                    270                    275 | 2866 |
| CGC GCG CTC GAC GAG GCG CGA GCG GTC GGT ACG CGG GAC GAG CAC GTC<br>Arg Ala Leu Asp Glu Ala Arg Ala Val Gly Thr Arg Asp Glu His Val<br>            280                    285                    290 | 2914 |
| CGG GCT GGG CTG ACA GCC CTC GAG CGG GTC TTC AAG GTC CTG CTG CGC<br>Arg Ala Gly Leu Thr Ala Leu Glu Arg Val Phe Lys Val Leu Leu Arg<br>       295                    300                    305 | 2962 |
| TTC CGG GCG CCT CAC CTC AAA TTG GCG GAG CGG GCG TAC GAA GTC GGG<br>Phe Arg Ala Pro His Leu Lys Leu Ala Glu Arg Ala Tyr Glu Val Gly<br>          310                    315                    320 | 3010 |
| CAA AGC GGC CCC GAA ATC GGC AGC GGG GGG TAC GCG CCC AGC ATG CTC<br>Gln Ser Gly Pro Glu Ile Gly Ser Gly Gly Tyr Ala Pro Ser Met Leu<br>325                    330                    335                    340 | 3058 |
| GGT GAG CTG CTC ACG CTG ACG TAT GCC GCG CGG TCC CGC GTC CGC GCC<br>Gly Glu Leu Leu Thr Leu Thr Tyr Ala Ala Arg Ser Arg Val Arg Ala<br>                    345                    350                    355 | 3106 |
| GCG CTC GAC GAA TCC TGATGCGCGC GACCCAGTGT TATCTCACAA GGAGAGTTTG<br>Ala Leu Asp Glu Ser<br>            360 | 3161 |
| CCCCC ATG ACT CAG AAG AGC CCC GCG AAC GAA CAC GAT AGC AAT CAC<br>      Met Thr Gln Lys Ser Pro Ala Asn Glu His Asp Ser Asn His<br>       1                 5                            10 | 3208 |
| TTC GAC GTA ATC ATC CTC GGC TCG GGC ATG TCC GGC ACC CAG ATG GGG<br>Phe Asp Val Ile Ile Leu Gly Ser Gly Met Ser Gly Thr Gln Met Gly<br>15                  20                   25                    30 | 3256 |
| GCC ATC TTG GCC AAA CAA CAG TTT CGC GTG CTG ATC ATC GAG GAG TCG<br>Ala Ile Leu Ala Lys Gln Gln Phe Arg Val Leu Ile Ile Glu Glu Ser<br>           35                    40                    45 | 3304 |
| TCG CAC CCG CGG TTC ACG ATC GGC GAA TCG TCG ATC CCC GAG ACG TCT<br>Ser His Pro Arg Phe Thr Ile Gly Glu Ser Ser Ile Pro Glu Thr Ser<br>            50                    55                    60 | 3352 |
| CTT ATG AAC CGC ATC ATC GCT GAT CGC TAC GGC ATT CCG GAG CTC GAC<br>Leu Met Asn Arg Ile Ile Ala Asp Arg Tyr Gly Ile Pro Glu Leu Asp<br>              65                    70                    75 | 3400 |
| CAC ATC ACG TCG TTT TAT TCG ACG CAA CGT TAC GTC GCG TCG AGC ACG<br>His Ile Thr Ser Phe Tyr Ser Thr Gln Arg Tyr Val Ala Ser Ser Thr<br>        80                    85                    90 | 3448 |
| GGC ATT AAG CGC AAC TTC GGC TTC GTG TTC CAC AAG CCC GGC CAG GAG<br>Gly Ile Lys Arg Asn Phe Gly Phe Val Phe His Lys Pro Gly Gln Glu<br>95                    100                    105                    110 | 3496 |
| CAC GAC CCG AAG GAG TTC ACC CAG TGC GTC ATT CCC GAG CTG CCG TGG<br>His Asp Pro Lys Glu Phe Thr Gln Cys Val Ile Pro Glu Leu Pro Trp<br>           115                    120                    125 | 3544 |
| GGG CCG GAG AGC CAT TAT TAC CGG CAA GAC GTC GAC GCC TAC TTG TTG<br>Gly Pro Glu Ser His Tyr Tyr Arg Gln Asp Val Asp Ala Tyr Leu Leu<br>           130                    135                    140 | 3592 |
| CAA GCC GCC ATT AAA TAC GGC TGC AAG GTC CAC CAG AAA ACT ACC GTG<br>Gln Ala Ala Ile Lys Tyr Gly Cys Lys Val His Gln Lys Thr Thr Val<br>           145                    150                    155 | 3640 |
| ACC GAA TAC CAC GCC GAT AAA GAC GGC GTC GCG GTG ACC ACC GCC CAG<br>Thr Glu Tyr His Ala Asp Lys Asp Gly Val Ala Val Thr Thr Ala Gln<br>160                    165                    170 | 3688 |
| GGC GAA CGG TTC ACC GGC CGG TAC ATG ATC GAC TGC GGA GGA CCT CGC<br>Gly Glu Arg Phe Thr Gly Arg Tyr Met Ile Asp Cys Gly Gly Pro Arg<br>175                    180                    185                    190 | 3736 |
| GCG CCG CTC GCG ACC AAG TTC AAG CTC CGC GAA GAA CCG TGT CGC TTC<br>Ala Pro Leu Ala Thr Lys Phe Lys Leu Arg Glu Glu Pro Cys Arg Phe<br>           195                    200                    205 | 3784 |

-continued

```
AAG ACG CAC TCG CGC AGC CTC TAC ACG CAC ATG CTC GGG GTC AAG CCG    3832
Lys Thr His Ser Arg Ser Leu Tyr Thr His Met Leu Gly Val Lys Pro
        210                 215                 220

TTC GAC GAC ATC TTC AAG GTC AAG GGG CAG CGC TGG CGC TGG CAC GAG    3880
Phe Asp Asp Ile Phe Lys Val Lys Gly Gln Arg Trp Arg Trp His Glu
            225                 230                 235

GGG ACC TTG CAC CAC ATG TTC GAG GGC GGC TGG CTC TGG GTG ATT CCG    3928
Gly Thr Leu His His Met Phe Glu Gly Gly Trp Leu Trp Val Ile Pro
    240                 245                 250

TTC AAC AAC CAC CCG CGG TCG ACC AAC AAC CTG GTG AGC GTC GGC CTG    3976
Phe Asn Asn His Pro Arg Ser Thr Asn Asn Leu Val Ser Val Gly Leu
255                 260                 265                 270

CAG CTC GAC CCG CGT GTC TAC CCG AAA ACC GAC ATC TCC GCA CAG CAG    4024
Gln Leu Asp Pro Arg Val Tyr Pro Lys Thr Asp Ile Ser Ala Gln Gln
                275                 280                 285

GAA TTC GAT GAG TTC CTC GCG CGG TTC CCG AGC ATC GGG GCT CAG TTC    4072
Glu Phe Asp Glu Phe Leu Ala Arg Phe Pro Ser Ile Gly Ala Gln Phe
            290                 295                 300

CGG GAC GCC GTG CCG GTG CGC GAC TGG GTC AAG ACC GAC CGC CTG CAA    4120
Arg Asp Ala Val Pro Val Arg Asp Trp Val Lys Thr Asp Arg Leu Gln
        305                 310                 315

TTC TCG TCG AAC GCC TGC GTC GGC GAC CGC TAC TGC CTG ATG CTG CAC    4168
Phe Ser Ser Asn Ala Cys Val Gly Asp Arg Tyr Cys Leu Met Leu His
    320                 325                 330

GCG AAC GGC TTC ATC GAC CCG CTC TTC TCC CGG GGG CTG GAA AAC ACC    4216
Ala Asn Gly Phe Ile Asp Pro Leu Phe Ser Arg Gly Leu Glu Asn Thr
335                 340                 345                 350

GCG GTG ACC ATC CAC GCG CTC GCG GCG CGC CTC ATC AAG GCG CTG CGC    4264
Ala Val Thr Ile His Ala Leu Ala Ala Arg Leu Ile Lys Ala Leu Arg
                355                 360                 365

GAC GAC GAC TTC TCC CCC GAG CGC TTC GAG TAC ATC GAG CGC CTG CAG    4312
Asp Asp Asp Phe Ser Pro Glu Arg Phe Glu Tyr Ile Glu Arg Leu Gln
            370                 375                 380

CAA AAG CTT TTG GAC CAC AAC GAC GAC TTC GTC AGC TGC TGC TAC ACG    4360
Gln Lys Leu Leu Asp His Asn Asp Asp Phe Val Ser Cys Cys Tyr Thr
        385                 390                 395

GCG TTC TCG GAC TTC CGC CTA TGG GAC GCG TTC CAC AGG CTG TGG GCG    4408
Ala Phe Ser Asp Phe Arg Leu Trp Asp Ala Phe His Arg Leu Trp Ala
    400                 405                 410

GTC GGC ACC ATC CTC GGG CAG TTC CGG CTC GTG CAG GCC CAC GCG AGG    4456
Val Gly Thr Ile Leu Gly Gln Phe Arg Leu Val Gln Ala His Ala Arg
415                 420                 425                 430

TTC CGC GCG TCG CGC AAC GAG GGC GAC CTC GAT CAC CTC GAC AAC GAC    4504
Phe Arg Ala Ser Arg Asn Glu Gly Asp Leu Asp His Leu Asp Asn Asp
                435                 440                 445

CCT CCG TAT CTC GGA TAC CTG TGC GCG GAC ATG GAG GAG TAC TAC CAG    4552
Pro Pro Tyr Leu Gly Tyr Leu Cys Ala Asp Met Glu Glu Tyr Tyr Gln
            450                 455                 460

TTG TTC AAC GAC GCC AAA GCC GAG GTC GAG GCC GTG AGT GCC GGG CGC    4600
Leu Phe Asn Asp Ala Lys Ala Glu Val Glu Ala Val Ser Ala Gly Arg
        465                 470                 475

AAG CCG GCC GAT GAG GCC GCG GCG CGG ATT CAC GCC CTC ATT GAC GAA    4648
Lys Pro Ala Asp Glu Ala Ala Ala Arg Ile His Ala Leu Ile Asp Glu
    480                 485                 490

CGA GAC TTC GCC AAG CCG ATG TTC GGC TTC GGG TAC TGC ATC ACC GGG    4696
Arg Asp Phe Ala Lys Pro Met Phe Gly Phe Gly Tyr Cys Ile Thr Gly
495                 500                 505                 510

GAC AAG CCG CAG CTC AAC AAC TCG AAG TAC AGC CTG CTG CCG GCG ATG    4744
Asp Lys Pro Gln Leu Asn Asn Ser Lys Tyr Ser Leu Leu Pro Ala Met
                515                 520                 525
```

| | | |
|---|---|---|
| CGG CTG ATG TAC TGG ACG CAA ACC CGC GCG CCG GCA GAG GTG AAA AAG<br>Arg Leu Met Tyr Trp Thr Gln Thr Arg Ala Pro Ala Glu Val Lys Lys<br>                  530                     535               540 | 4792 |
| TAC TTC GAC TAC AAC CCG ATG TTC GCG CTG CTC AAG GCG TAC ATC ACG<br>Tyr Phe Asp Tyr Asn Pro Met Phe Ala Leu Leu Lys Ala Tyr Ile Thr<br>                  545                     550               555 | 4840 |
| ACC CGC ATC GGC CTG GCG CTG AAG AAG TAGCCGCTCG ACGACGACAT<br>Thr Arg Ile Gly Leu Ala Leu Lys Lys<br>560                     565 | 4887 |
| AAAAACG ATG AAC GAC ATT CAA TTG GAT CAA GCG AGC GTC AAG AAG CGT<br>       Met Asn Asp Ile Gln Leu Asp Gln Ala Ser Val Lys Lys Arg<br>        1                    5                      10 | 4936 |
| CCC TCG GGC GCG TAC GAC GCA ACC ACG CGC CTG GCC GCG AGC TGG TAC<br>Pro Ser Gly Ala Tyr Asp Ala Thr Thr Arg Leu Ala Ala Ser Trp Tyr<br>15                 20                   25                     30 | 4984 |
| GTC GCG ATG CGC TCC AAC GAG CTC AAG GAC AAG CCG ACC GAG TTG ACG<br>Val Ala Met Arg Ser Asn Glu Leu Lys Asp Lys Pro Thr Glu Leu Thr<br>                35                    40                    45 | 5032 |
| CTC TTC GGC CGT CCG TGC GTG GCG TGG CGC GGA GCC ACG GGG CGG GCC<br>Leu Phe Gly Arg Pro Cys Val Ala Trp Arg Gly Ala Thr Gly Arg Ala<br>             50                    55                     60 | 5080 |
| GTG GTG ATG GAC CGC CAC TGC TCG CAC CTG GGC GCG AAC CTG GCT GAC<br>Val Val Met Asp Arg His Cys Ser His Leu Gly Ala Asn Leu Ala Asp<br>         65                    70                    75 | 5128 |
| GGG CGG ATC AAG GAC GGG TGC ATC CAG TGC CCG TTT CAC CAC TGG CGG<br>Gly Arg Ile Lys Asp Gly Cys Ile Gln Cys Pro Phe His His Trp Arg<br>80                 85                   90 | 5176 |
| TAC GAC GAA CAG GGC CAG TGC GTT CAC ATC CCC GGC CAT AAC CAG GCG<br>Tyr Asp Glu Gln Gly Gln Cys Val His Ile Pro Gly His Asn Gln Ala<br>95                 100               105             110 | 5224 |
| GTG CGC CAG CTG GAG CCG GTG CCG CGC GGG GCG CGT CAG CCG ACG TTG<br>Val Arg Gln Leu Glu Pro Val Pro Arg Gly Ala Arg Gln Pro Thr Leu<br>                 115               120             125 | 5272 |
| GTC ACC GCC GAG CGA TAC GGC TAC GTG TGG GTC TGG TAC GGC TCC CCG<br>Val Thr Ala Glu Arg Tyr Gly Tyr Val Trp Val Trp Tyr Gly Ser Pro<br>             130                   135             140 | 5320 |
| CTG CCG CTG CAC CCG CTG CCC GAA ATC TCC GCG GCC GAT GTC GAC AAC<br>Leu Pro Leu His Pro Leu Pro Glu Ile Ser Ala Ala Asp Val Asp Asn<br>             145               150               155 | 5368 |
| GGC GAC TTT ATG CAC CTG CAC TTC GCG TTC GAG ACG ACC ACG GCG GTC<br>Gly Asp Phe Met His Leu His Phe Ala Phe Glu Thr Thr Thr Ala Val<br>160                 165               170 | 5416 |
| TTG CGG ATC GTC GAG AAC TTC TAC GAC GCG CAG CAC GCA ACC CCG GTG<br>Leu Arg Ile Val Glu Asn Phe Tyr Asp Ala Gln His Ala Thr Pro Val<br>175                 180               185             190 | 5464 |
| CAC GCA CTC CCG ATC TCG GCC TTC GAA CTC AAG CTC TTC GAC GAT TGG<br>His Ala Leu Pro Ile Ser Ala Phe Glu Leu Lys Leu Phe Asp Asp Trp<br>             195               200             205 | 5512 |
| CGC CAG TGG CCG GAG GTT GAG TCG CTG GCC CTG GCG GGC GCG TGG TTC<br>Arg Gln Trp Pro Glu Val Glu Ser Leu Ala Leu Ala Gly Ala Trp Phe<br>             210               215             220 | 5560 |
| GGT GCC GGG ATC GAC TTC ACC GTG GAC CGG TAC TTC GGC CCC CTC GGC<br>Gly Ala Gly Ile Asp Phe Thr Val Asp Arg Tyr Phe Gly Pro Leu Gly<br>             225               230             235 | 5608 |
| ATG CTG TCA CGC GCG CTC GGC CTG AAC ATG TCG CAG ATG AAC CTG CAC<br>Met Leu Ser Arg Ala Leu Gly Leu Asn Met Ser Gln Met Asn Leu His<br>240                 245               250 | 5656 |
| TTC GAT GGC TAC CCC GGC GGG TGC GTC ATG ACC GTC GCC CTG GAC GGA<br>Phe Asp Gly Tyr Pro Gly Gly Cys Val Met Thr Val Ala Leu Asp Gly<br>255                 260               265             270 | 5704 |

-continued

| | | | | | | | | | | | | | | |
|---|---|---|---|---|---|---|---|---|---|---|---|---|---|---|
| GAC | GTC | AAA | TAC | AAG | CTG | CTC | CAG | TGT | GTG | ACG | CCG | GTG | AGC | GAA | GGC | 5752
| Asp | Val | Lys | Tyr | Lys | Leu | Leu | Gln | Cys | Val | Thr | Pro | Val | Ser | Glu | Gly |
| | | | 275 | | | | | 280 | | | | | 285 | | |

```
GAC GTC AAA TAC AAG CTG CTC CAG TGT GTG ACG CCG GTG AGC GAA GGC        5752
Asp Val Lys Tyr Lys Leu Leu Gln Cys Val Thr Pro Val Ser Glu Gly
            275                 280                 285

AAG AAC GTC ATG CAC ATG CTC ATC TCG ATC AAG AAG GTG GGC GGC ATC        5800
Lys Asn Val Met His Met Leu Ile Ser Ile Lys Lys Val Gly Gly Ile
            290                 295                 300

CTG CGC CGC GCG ACC GAC TTC GTG CTG TTC GGG CTG CAG ACC AGG CAG        5848
Leu Arg Arg Ala Thr Asp Phe Val Leu Phe Gly Leu Gln Thr Arg Gln
            305                 310                 315

GCC GCG GGG TAC GAC GTC AAA ATC TGG AAC GGA ATG AAG CCG GAC GGC        5896
Ala Ala Gly Tyr Asp Val Lys Ile Trp Asn Gly Met Lys Pro Asp Gly
        320                 325                 330

GGC GGC GCG TAC AGC AAG TAC GAC AAG CTC GTG CTC AAG TAC CGG GCG        5944
Gly Gly Ala Tyr Ser Lys Tyr Asp Lys Leu Val Leu Lys Tyr Arg Ala
335                 340                 345                 350

TTC TAT CGA GGC TGG GTC GAC CGC GTC GCA AGT GAG CGG TGATGCGTGA         5993
Phe Tyr Arg Gly Trp Val Asp Arg Val Ala Ser Glu Arg
                355                 360

AGCCGAGCCG CTCTCGACCG CGTCGCTGCG CCAGGCGCTC GCGAACCTGG CGAGCGGCGT       6053

GACGATCACG GCCTACGGCG CGCCGGGCCC GCTTGGGCTC GCGGCCACCA GCTTCGTGTC       6113

GGAGTCGCTC TTTGCGAGGT ATTCATGACT ATCTGGCTGT TGCAACTCGT GCTGGTGATC       6173

GCGCTCTGCA ACGTCTGCGG CCGCATTGCC GAACGGCTCG GCCAGTGCGC GGTCATCGGC       6233

GAGATCGCGG CCGGTTTGCT GTTGGGGCCG TCGCTGTTCG GCGTGATCGC ACCGAGTTTC       6293

TACGACCTGT TGTTCGGCCC CCAGGTGCTG TCAGCGATGG CGCAAGTCAG CGAAGTCGGC       6353

CTGGTACTGC TGATGTTCCA GGTCGGCCTG CATATGGAGT TGGGCGAGAC GCTGCGCGAC       6413

AAGCGCTGGC GCATGCCCGT CGCGATCGCA GCGGGCGGGC TCGTCGCACC GGCCGCGATC       6473

GGCATGATCG TCGCCATCGT TTCGAAAGGC ACGCTCGCCA GCGACGCGCC GGCGCTGCCC       6533

TATGTGCTCT TCTGCGGTGT CGCACTTGCG GTATCGGCGG TGCGGTGAT GGCGCGCATC        6593

ATCGACGACC TGGAGCTCAG CGCCATGGTG GGCGCGCGGC ACGCAATGTC TGCCGCGATG       6653

CTGACGGATG CGCTCGGATG GATGCTGCTT GCAACGATTG CCTCGCTATC GAGCGGGCCC       6713

GGCTGGGCAT TTGCGCGCAT GCTCGTCAGC CTGCTCGCGT ATCTGGTGCT GTGCGCGCTG       6773

CTGGTGCGCT TCGTGGTTCG ACCGACCCTT GCGCGGCTCG CGTCGACCGC GCATGCGACG       6833

CGCGACCGCT TGGCCGTGTT GTTCTGCTTC GTAATGTTGT CGGCACTCGC GACGTCGCTG       6893

ATCGGATTCC ATAGCGCTTT TGGCGCACTT GCCGCGGCGC TGTTCGTGCG CCGGGTGCCC       6953

GGCGTCGCGA AGGAGTGGCG CGACAACGTC GAAGGTTTCG TCAAGCTT                    7001
```

(2) INFORMATION FOR SEQ ID NO:2:

(i) SEQUENCE CHARACTERISTICS:
        (A) LENGTH: 538 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Lys Pro Ile Lys Asn Ile Val Ile Val Gly Gly Gly Thr Ala
 1               5                  10                  15

Gly Trp Met Ala Ala Ser Tyr Leu Val Arg Ala Leu Gln Gln Gln Ala
            20                  25                  30

Asn Ile Thr Leu Ile Glu Ser Ala Ala Ile Pro Arg Ile Gly Val Gly
        35                  40                  45
```

-continued

```
Glu Ala Thr Ile Pro Ser Leu Gln Lys Val Phe Phe Asp Phe Leu Gly
 50                  55                  60

Ile Pro Glu Arg Glu Trp Met Pro Gln Val Asn Gly Ala Phe Lys Ala
 65                  70                  75                  80

Ala Ile Lys Phe Val Asn Trp Arg Lys Ser Pro Asp Pro Ser Arg Asp
                 85                  90                  95

Asp His Phe Tyr His Leu Phe Gly Asn Val Pro Asn Cys Asp Gly Val
                100                 105                 110

Pro Leu Thr His Tyr Trp Leu Arg Lys Arg Glu Gln Gly Phe Gln Gln
                115                 120                 125

Pro Met Glu Tyr Ala Cys Tyr Pro Gln Pro Gly Ala Leu Asp Gly Lys
130                 135                 140

Leu Ala Pro Cys Leu Ser Asp Gly Thr Arg Gln Met Ser His Ala Trp
145                 150                 155                 160

His Phe Asp Ala His Leu Val Ala Asp Phe Leu Lys Arg Trp Ala Val
                165                 170                 175

Glu Arg Gly Val Asn Arg Val Val Asp Glu Val Val Asp Val Arg Leu
                180                 185                 190

Asn Asn Arg Gly Tyr Ile Ser Asn Leu Leu Thr Lys Glu Gly Arg Thr
                195                 200                 205

Leu Glu Ala Asp Leu Phe Ile Asp Cys Ser Gly Met Arg Gly Leu Leu
210                 215                 220

Ile Asn Gln Ala Leu Lys Glu Pro Phe Ile Asp Met Ser Asp Tyr Leu
225                 230                 235                 240

Leu Cys Asp Ser Ala Val Ala Ser Ala Val Pro Asn Asp Asp Ala Arg
                245                 250                 255

Asp Gly Val Glu Pro Tyr Thr Ser Ser Ile Ala Met Asn Ser Gly Trp
                260                 265                 270

Thr Trp Lys Ile Pro Met Leu Gly Arg Phe Gly Ser Gly Tyr Val Phe
                275                 280                 285

Ser Ser His Phe Thr Ser Arg Asp Gln Ala Thr Ala Asp Phe Leu Lys
290                 295                 300

Leu Trp Gly Leu Ser Asp Asn Gln Pro Leu Asn Gln Ile Lys Phe Arg
305                 310                 315                 320

Val Gly Arg Asn Lys Arg Ala Trp Val Asn Asn Cys Val Ser Ile Gly
                325                 330                 335

Leu Ser Ser Cys Phe Leu Glu Pro Leu Glu Ser Thr Gly Ile Tyr Phe
                340                 345                 350

Ile Tyr Ala Ala Leu Tyr Gln Leu Val Lys His Phe Pro Asp Thr Ser
                355                 360                 365

Phe Asp Pro Arg Leu Ser Asp Ala Phe Asn Ala Glu Ile Val His Met
370                 375                 380

Phe Asp Asp Cys Arg Asp Phe Val Gln Ala His Tyr Phe Thr Thr Ser
385                 390                 395                 400

Arg Asp Asp Thr Pro Phe Trp Leu Ala Asn Arg His Asp Leu Arg Leu
                405                 410                 415

Ser Asp Ala Ile Lys Glu Lys Val Gln Arg Tyr Lys Ala Gly Leu Pro
                420                 425                 430

Leu Thr Thr Thr Ser Phe Asp Asp Ser Thr Tyr Glu Thr Phe Asp
                435                 440                 445

Tyr Glu Phe Lys Asn Phe Trp Leu Asn Gly Asn Tyr Tyr Cys Ile Phe
450                 455                 460
```

```
Ala Gly Leu Gly Met Leu Pro Asp Arg Ser Leu Pro Leu Leu Gln His
465                 470                 475                 480

Arg Pro Glu Ser Ile Glu Lys Ala Glu Ala Met Phe Ala Ser Ile Arg
            485                 490                 495

Arg Glu Ala Glu Arg Leu Arg Thr Ser Leu Pro Thr Asn Tyr Asp Tyr
        500                 505                 510

Leu Arg Ser Leu Arg Asp Gly Asp Ala Gly Leu Ser Arg Gly Gln Arg
            515                 520                 525

Gly Pro Lys Leu Ala Ala Gln Glu Ser Leu
        530                 535

(2) INFORMATION FOR SEQ ID NO:3:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:3:

Val Glu Arg Thr Leu Asp Arg Val Gly Val Phe Ala Ala Thr His Ala
1               5                   10                  15

Ala Val Ala Ala Cys Asp Pro Leu Gln Ala Arg Ala Leu Val Leu Gln
                20                  25                  30

Leu Pro Gly Leu Asn Arg Asn Lys Asp Val Pro Gly Ile Val Gly Leu
            35                  40                  45

Leu Arg Glu Phe Leu Pro Val Arg Gly Leu Pro Cys Gly Trp Gly Phe
        50                  55                  60

Val Glu Ala Ala Ala Ala Met Arg Asp Ile Gly Phe Phe Leu Gly Ser
65                  70                  75                  80

Leu Lys Arg His Gly His Glu Pro Ala Glu Val Val Pro Gly Leu Glu
                85                  90                  95

Pro Val Leu Leu Asp Leu Ala Arg Ala Thr Asn Leu Pro Pro Arg Glu
            100                 105                 110

Thr Leu Leu His Val Thr Val Trp Asn Pro Thr Ala Ala Asp Ala Gln
        115                 120                 125

Arg Ser Tyr Thr Gly Leu Pro Asp Glu Ala His Leu Leu Glu Ser Val
130                 135                 140

Arg Ile Ser Met Ala Ala Leu Glu Ala Ala Ile Ala Leu Thr Val Glu
145                 150                 155                 160

Leu Phe Asp Val Ser Leu Arg Ser Pro Glu Phe Ala Gln Arg Cys Asp
                165                 170                 175

Glu Leu Glu Ala Tyr Leu Gln Lys Met Val Glu Ser Ile Val Tyr Ala
            180                 185                 190

Tyr Arg Phe Ile Ser Pro Gln Val Phe Tyr Asp Glu Leu Arg Pro Phe
        195                 200                 205

Tyr Glu Pro Ile Arg Val Gly Gly Gln Ser Tyr Leu Gly Pro Gly Ala
    210                 215                 220

Val Glu Met Pro Leu Phe Val Leu Glu His Val Leu Trp Gly Ser Gln
225                 230                 235                 240

Ser Asp Asp Gln Thr Tyr Arg Glu Phe Lys Glu Thr Tyr Leu Pro Tyr
                245                 250                 255

Val Leu Pro Ala Tyr Arg Ala Val Tyr Ala Arg Phe Ser Gly Glu Pro
            260                 265                 270
```

-continued

```
Ala Leu Ile Asp Arg Ala Leu Asp Glu Ala Arg Ala Val Gly Thr Arg
            275                 280                 285

Asp Glu His Val Arg Ala Gly Leu Thr Ala Leu Glu Arg Val Phe Lys
            290                 295                 300

Val Leu Leu Arg Phe Arg Ala Pro His Leu Lys Leu Ala Glu Arg Ala
305                 310                 315                 320

Tyr Glu Val Gly Gln Ser Gly Pro Glu Ile Gly Ser Gly Gly Tyr Ala
            325                 330                 335

Pro Ser Met Leu Gly Glu Leu Leu Thr Leu Thr Tyr Ala Ala Arg Ser
            340                 345                 350

Arg Val Arg Ala Ala Leu Asp Glu Ser
            355                 360
```

(2) INFORMATION FOR SEQ ID NO:4:

(i) SEQUENCE CHARACTERISTICS:
        (A) LENGTH: 567 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Gln Lys Ser Pro Ala Asn Glu His Asp Ser Asn His Phe Asp
1               5                   10                  15

Val Ile Ile Leu Gly Ser Gly Met Ser Gly Thr Gln Met Gly Ala Ile
            20                  25                  30

Leu Ala Lys Gln Gln Phe Arg Val Leu Ile Glu Glu Ser Ser His
            35                  40                  45

Pro Arg Phe Thr Ile Gly Glu Ser Ser Ile Pro Glu Thr Ser Leu Met
50                  55                  60

Asn Arg Ile Ile Ala Asp Arg Tyr Gly Ile Pro Glu Leu Asp His Ile
65                  70                  75                  80

Thr Ser Phe Tyr Ser Thr Gln Arg Tyr Val Ala Ser Ser Thr Gly Ile
            85                  90                  95

Lys Arg Asn Phe Gly Phe Val Phe His Lys Pro Gly Gln Glu His Asp
            100                 105                 110

Pro Lys Glu Phe Thr Gln Cys Val Ile Pro Glu Leu Pro Trp Gly Pro
            115                 120                 125

Glu Ser His Tyr Tyr Arg Gln Asp Val Asp Ala Tyr Leu Leu Gln Ala
            130                 135                 140

Ala Ile Lys Tyr Gly Cys Lys Val His Gln Lys Thr Thr Val Thr Glu
145                 150                 155                 160

Tyr His Ala Asp Lys Asp Gly Val Ala Val Thr Thr Ala Gln Gly Glu
            165                 170                 175

Arg Phe Thr Gly Arg Tyr Met Ile Asp Cys Gly Gly Pro Arg Ala Pro
            180                 185                 190

Leu Ala Thr Lys Phe Lys Leu Arg Glu Glu Pro Cys Arg Phe Lys Thr
            195                 200                 205

His Ser Arg Ser Leu Tyr Thr His Met Leu Gly Val Lys Pro Phe Asp
            210                 215                 220

Asp Ile Phe Lys Val Lys Gly Gln Arg Trp Arg Trp His Glu Gly Thr
225                 230                 235                 240

Leu His His Met Phe Glu Gly Gly Trp Leu Trp Val Ile Pro Phe Asn
            245                 250                 255
```

```
Asn His Pro Arg Ser Thr Asn Asn Leu Val Ser Val Gly Leu Gln Leu
            260                 265                 270

Asp Pro Arg Val Tyr Pro Lys Thr Asp Ile Ser Ala Gln Gln Glu Phe
            275                 280                 285

Asp Glu Phe Leu Ala Arg Phe Pro Ser Ile Gly Ala Gln Phe Arg Asp
            290                 295                 300

Ala Val Pro Val Arg Asp Trp Val Lys Thr Asp Arg Leu Gln Phe Ser
305                 310                 315                 320

Ser Asn Ala Cys Val Gly Asp Arg Tyr Cys Leu Met Leu His Ala Asn
            325                 330                 335

Gly Phe Ile Asp Pro Leu Phe Ser Arg Gly Leu Glu Asn Thr Ala Val
            340                 345                 350

Thr Ile His Ala Leu Ala Ala Arg Leu Ile Lys Ala Leu Arg Asp Asp
            355                 360                 365

Asp Phe Ser Pro Glu Arg Phe Glu Tyr Ile Glu Arg Leu Gln Gln Lys
            370                 375                 380

Leu Leu Asp His Asn Asp Asp Phe Val Ser Cys Cys Tyr Thr Ala Phe
385                 390                 395                 400

Ser Asp Phe Arg Leu Trp Asp Ala Phe His Arg Leu Trp Ala Val Gly
            405                 410                 415

Thr Ile Leu Gly Gln Phe Arg Leu Val Gln Ala His Ala Arg Phe Arg
            420                 425                 430

Ala Ser Arg Asn Glu Gly Asp Leu Asp His Leu Asp Asn Asp Pro Pro
            435                 440                 445

Tyr Leu Gly Tyr Leu Cys Ala Asp Met Glu Glu Tyr Tyr Gln Leu Phe
            450                 455                 460

Asn Asp Ala Lys Ala Glu Val Glu Ala Val Ser Ala Gly Arg Lys Pro
465                 470                 475                 480

Ala Asp Glu Ala Ala Arg Ile His Ala Leu Ile Asp Glu Arg Asp
            485                 490                 495

Phe Ala Lys Pro Met Phe Gly Phe Gly Tyr Cys Ile Thr Gly Asp Lys
            500                 505                 510

Pro Gln Leu Asn Asn Ser Lys Tyr Ser Leu Leu Pro Ala Met Arg Leu
            515                 520                 525

Met Tyr Trp Thr Gln Thr Arg Ala Pro Ala Glu Val Lys Lys Tyr Phe
            530                 535                 540

Asp Tyr Asn Pro Met Phe Ala Leu Leu Lys Ala Tyr Ile Thr Thr Arg
545                 550                 555                 560

Ile Gly Leu Ala Leu Lys Lys
            565

(2) INFORMATION FOR SEQ ID NO:5:

(i) SEQUENCE CHARACTERISTICS:
        (A) LENGTH: 363 amino acids
        (B) TYPE: amino acid
        (D) TOPOLOGY: linear (ii) MOLECULE TYPE: protein (xi) SEQUENCE DESCRIPTION: SEQ ID NO:5:

Met Asn Asp Ile Gln Leu Asp Gln Ala Ser Val Lys Lys Arg Pro Ser
1               5                   10                  15

Gly Ala Tyr Asp Ala Thr Thr Arg Leu Ala Ala Ser Trp Tyr Val Ala
                20                  25                  30
```

```
Met Arg Ser Asn Glu Leu Lys Asp Lys Pro Thr Glu Leu Thr Leu Phe
        35                  40                  45

Gly Arg Pro Cys Val Ala Trp Arg Gly Ala Thr Gly Arg Ala Val Val
        50                  55                  60

Met Asp Arg His Cys Ser His Leu Gly Ala Asn Leu Ala Asp Gly Arg
65                      70                  75                  80

Ile Lys Asp Gly Cys Ile Gln Cys Pro Phe His His Trp Arg Tyr Asp
                    85                  90                  95

Glu Gln Gly Gln Cys Val His Ile Pro Gly His Asn Gln Ala Val Arg
                100                 105                 110

Gln Leu Glu Pro Val Pro Arg Gly Ala Arg Gln Pro Thr Leu Val Thr
        115                 120                 125

Ala Glu Arg Tyr Gly Tyr Val Trp Val Trp Tyr Gly Ser Pro Leu Pro
        130                 135                 140

Leu His Pro Leu Pro Glu Ile Ser Ala Ala Asp Val Asp Asn Gly Asp
145                 150                 155                 160

Phe Met His Leu His Phe Ala Phe Glu Thr Thr Thr Ala Val Leu Arg
                    165                 170                 175

Ile Val Glu Asn Phe Tyr Asp Ala Gln His Ala Thr Pro Val His Ala
                    180                 185                 190

Leu Pro Ile Ser Ala Phe Glu Leu Lys Leu Phe Asp Asp Trp Arg Gln
        195                 200                 205

Trp Pro Glu Val Glu Ser Leu Ala Leu Ala Gly Ala Trp Phe Gly Ala
        210                 215                 220

Gly Ile Asp Phe Thr Val Asp Arg Tyr Phe Gly Pro Leu Gly Met Leu
225                 230                 235                 240

Ser Arg Ala Leu Gly Leu Asn Met Ser Gln Met Asn Leu His Phe Asp
                    245                 250                 255

Gly Tyr Pro Gly Gly Cys Val Met Thr Val Ala Leu Asp Gly Asp Val
                    260                 265                 270

Lys Tyr Lys Leu Leu Gln Cys Val Thr Pro Val Ser Glu Gly Lys Asn
        275                 280                 285

Val Met His Met Leu Ile Ser Ile Lys Lys Val Gly Gly Ile Leu Arg
290                 295                 300

Arg Ala Thr Asp Phe Val Leu Phe Gly Leu Gln Thr Arg Gln Ala Ala
305                 310                 315                 320

Gly Tyr Asp Val Lys Ile Trp Asn Gly Met Lys Pro Asp Gly Gly Gly
                    325                 330                 335

Ala Tyr Ser Lys Tyr Asp Lys Leu Val Leu Lys Tyr Arg Ala Phe Tyr
                340                 345                 350

Arg Gly Trp Val Asp Arg Val Ala Ser Glu Arg
        355                 360

(2) INFORMATION FOR SEQ ID NO:6:

(i) SEQUENCE CHARACTERISTICS:
        (A) LENGTH: 28958 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

(xi) SEQUENCE DESCRIPTION: SEQ ID NO:6:

```
CGATCGCGTC GGCCTCGACA CCGTCGAAGA GGTCACGCTC GAAGCTCCCC TCGCTCTCCC      60
CTCTCAAGGC ACCATTCTCA TCCAGATCTC CGTCGGACCC ATGGACGAGG CGGGACGAAG     120
GTCGCTCTCC CTCCATGGCC GGACCGAGGA CGCTCCTCAG GACGCCCCTT GGACGCGCCA     180
CGCGAGCGGG TCGCTCGCTA AAGCTGCCCC CTCCCTCTCC TTCGATCTTC ACGAATGGGC     240
TCCTCCGGGG GGCACGCCGG TGGACACCCA AGGCTCTTAC GCAGGCCTCG AAAGCGGGGG     300
GCTCGCCTAT GGGCCTCAGT TCCAGGGACT TCGCTCCGTC TGGAAGCGCG GCGACGAGCT     360
CTTCGCCGAG GCCAAGCTCC CGGACGCAGG CGCCAAGGAT GCCGCTCGGT TCGCCCTCCA     420
CCCCGCCCTG TTCGACAGCG CCCTGCACGC GCTTGTCCTT GAAGACGAGC GGACGCCGGG     480
CGTCGCTCTG CCCTTCTCGT GGAGAGGAGT CTCGCTGCGC TCCGTCGGCG CCACCACCCT     540
GCGCGTGCGC TTCCATCGTC CGAATGGCAA GTCCTCCGTG TCGCTCCTCC TCGGCGACGC     600
CGCAGGCGAG CCCCTCGCCT CGGTCCAAGC GCTCGCCACG CGCATCACGT CCCAGGAGCA     660
GCTCCGCACC CAGGGAGCTT CCCTCCACGA TGCTCTCTTC CGGGTTGTCT GGAGAGATCT     720
GCCCAGCCCT ACGTCGCTCT CTGAGGCCCC GAAGGGTGTC CTCCTAGAGA CAGGGGGTCT     780
CGACCTCGCG CTGCAGGCGT CTCTCGCCCG CTACGACGGT CTCGCTGCCC TCCGGAGCGC     840
GCTCGACCAA GGCGCTTCGC CTCCGGGCCT CGTCGTCGTC CCCTTCATCG ATTCGCCCTC     900
TGGCGACCTC ATAGAGAGCG CTCACAACTC CACCGCGCGC GCCCTCGCCT TGCTGCAAGC     960
GTGGCTTGAC GACGAACGCC TCGCCTCCTC GCGCCTCGTC CTGCTCACCC GACAGGCCAT    1020
CGCAACCCAC CCCGACGAGG ACGTCCTCGA CCTCCCTCAC GCTCCTCTCT GGGGCCTTGT    1080
GCGCACCGCG CAAAGCGAAC ACCCGGAGCT CCCTCTCTTC CTCGTCGACC TGGACCTCGG    1140
TCAGGCCTCG GAGCGCGCCC TGCTCGGCGC GCTCGACACA GGAGAGCGTC AGCTCGCTCT    1200
CCGCCATGGA AAATGCCTCG TCCCGAGGTT GGTGAATGCA CGCTCGACAG AGGCGCTCAT    1260
CGCGCCGAAC GTATCCACGT GGAGCCTTCA TATCCCGACC AAAGGCACCT TCGACTCGCT    1320
CGCCCTCGTC GACGCTCCTC TAGCCCGTGC GCCCCTCGCA CAAGGCCAAG TCCGCGTCGC    1380
CGTGCACGCG GCAGGTCTCA ACTTCCGCGA TGTCCTCAAC ACCCTTGGCA TGCTTCCGGA    1440
CAACGCGGGG CCGCTCGGCG GCGAAGGCGC GGGCATTGTC ACCGAAGTCG GCCCAGGTGT    1500
TTCCCGATAC ACTGTAGGCG ACCGGGTGAT GGGCATCTTC CGCGGAGGCT TTGGCCCCAC    1560
GGTCGTCGCC GACGCCCGCA TGATCTGCCC CATCCCCGAT GCCTGGTCCT TCGTCCAAGC    1620
CGCCAGCGTC CCCGTCGTCT TTCTCACCGC CTACTATGGA CTCGTCGATG TCGGGCATCT    1680
CAAGCCCAAT CAACGTGTCC TCATCCATGC GGCCGCAGGC GGCGTCGGTA CTGCCGCCGT    1740
CCAGCTCGCG CGCCACCTCG GCGCCGAAGT CTTCGCCACC GCCAGTCCAG GGAAGTGGGA    1800
CGCTCTGCGC GCGCTCGGCT CGACGATGC GCACCTCGCG TCCTCACGTG ACCTGGAATT    1860
CGAGCAGCAT TTCCTGCGCT CCACACGAGG GCGCGGCATG GATGTCGTCC TCAACGCCTT    1920
GGCGCGCGAG TTCGTCGACG CTTCGCTGCG TCTCCTGCCG AGCGGTGGAA GCTTTGTCGA    1980
GATGGGCAAG ACGGATATCC GCGAGCCCGA CGCCGTAGGC CTCGCCTACC CCGGCGTCGT    2040
TTACGCGCC TTCGATCTCT TGGAGGCTGG ACCGGATCGA ATTCAAGAGA TGCTCGCAGA    2100
GCTGCTCGAC CTGTTCGAGC GCGGCGTGCT TCGTCCGCCG CCCATCACGT CCTGGGACAT    2160
CCGGCATGCC CCCCAGGCGT TCCGCGCGCT CGCTCAGGCG CGGCATATTG GAAAGTTCGT    2220
CCTCACCGTT CCCGTCCCAT CGATCCCCGA AGGCACCATC CTCGTCACGG GAGGCACCGG    2280
CACGCTCGGC GCGCTCATCG CGCGCCACCT CGTCGCCAAT CGCGGCGACA AGCACCTGCT    2340
```

```
CCTCACCTCG CGAAAGGGTG CGAGCGCTCC GGGGGCCGAG GCATTGCGGA GCGAGCTCGA    2400

AGCTCTGGGG GCTGCGGTCA CGCTCGCCCG GTGCGACGCG GCCGATCCAC GCGCGCTCCA    2460

AGCCCTCTTG GACAGCATCC CGAGCGCTCA CCCGCTCACG GCCGTCGTGC ACGCCGCCGG    2520

CGCCCTTGAC GATGGGCTGA TCAGCGACAT GAGCCCCGAG CGCATCGACC GCGTCTTTGC    2580

TCCCAAGCTC GACGCCGCTT GGCACTTGCA TCAGCTCACC CAGGACAAGG CCGCTCGGGG    2640

CTTCGTCCTC TTCTCGTCCG CCTCCGGCGT CCTCGGCGGT ATGGGTCAAT CCAACTACGC    2700

GGGGGGCAAT GCGTTCCTTG ACGCGCTCGC GCATCACCGA CGCGTCCATG GGCTCCCAGG    2760

CTCCTCGCTC GCATGGGGCC ATTGGGCCGA GCGCAGCGGA ATGACCCGAC AACCTCAGCG    2820

GCGTCGATAC CGCTCGCATG AGGCGCGCGG TCTCCGATCC ATCGCCTCGG ACGAGGGTCT    2880

CGCCCTCTTC GATATGGCGC TCGGGCGCCC GGAGCCCGCG CTGGTCCCCG CCCGCTTCGA    2940

CATGAACGCG CTCGGCGCGA AGGCCGACGG GCTACCCTCG ATGTTCCAGG GTCTCGTCCG    3000

CGCTCGCGTC GCGCGCAAGG TCGCCAGCAA TAATGCCCTG GCCGCGTCGC TCACCCAGCG    3060

CCTCGCCTCC CTCCCGCCCA CCGACCGCGA GCGCATGCTG CTCGATCTCG TCCGCGCCGA    3120

AGCCGCCATC GTCCTCGGCC TCGCCTCGTT CGAATCGCTC GATCCCCGTC GCCCTCTTCA    3180

AGAGCTCGGT CTCGATTCCC TCATGGCCAT CGAGCTCCGA AATCGACTCG CCGCCGCCAC    3240

AGGCTTGCGA CTCCAAGCCA CCCTCCTCTT CGACCACCCG ACGCCCGCCG CGCTCGCGAC    3300

CCTGCTGCTC GGGAAGCTCC TCCAGCATGA AGCTGCCGAT CCTCGCCCCT TGGCCGCAGA    3360

GCTCGACAGG CTAGAGGCCA CTCTCTCCGC GATAGCCGTG GACGCTCAAG CACGCCCGAA    3420

GATCATATTA CGCCTGCAAT CCTGGTTGTC GAAGTGGAGC GACGCTCAGG CTGCCGACGC    3480

TGGACCGATT CTCGGCAAGG ATTTCAAGTC TGCTACGAAG GAAGAGCTCT TCGCTGCTTG    3540

TGACGAAGCG TTCGGAGGCC TGGGTAAATG AATAACGACG AGAAGCTTGT CTCCTACCTA    3600

CAGCAGGCGA TGAATGAGCT TCAGCGTGCT CATCAGCCCC TCCGCGCGGT CGAAGAGAAG    3660

GAGCACGAGC CCATCGCCAT CGTGGCGATG AGCTGCCGCT TCCCGGGCGA CGTGCGCACG    3720

CCCGAGGATC TCTGGAAGCT CTTGCTCGAT GGGAAAGATG CTATCTCCGA CCTTCCCCCA    3780

AACCGTGGTT GGAAGCTCGA CGCGCTCGAC GTCCACGGTC GCTCCCCAGT CCGAGAGGGA    3840

GGCTTCTTCT ACGACGCAGA CGCCTTCGAT CCGGCCTTCT TCGGGATCAG CCCACGCGAG    3900

GCGCTCGCCA TCGATCCCCA GCAGCGGCTC CTCCTCGAGA TCTCATGGGA AGCCTTCGAG    3960

CGTGCGGGCA TCGACCCTGC CTCGCTCCAA GGGAGCCAAA GCGGCGTCTT CGTCGGCGTG    4020

ATACACAACG ACTACGACGC ATTGCTGGAG AACGCAGCTG GCGAACACAA AGGATTCGTT    4080

TCCACCGGCA GCACAGCGAG CGTCGCCTCC GGCCGGATCG CGTATACATT CGGCTTTCAA    4140

GGGCCCGCCA TCAGCGTGGA CACGGCGTGC AGCTCCTCGC TCGTCGCGGT TCACCTCGCC    4200

TGCCAGGCCC TGCGCCGTGG CGAATGCTCC CTGGCGCTCG CCGGCGGCGT GACCGTCATG    4260

GCCACGCCAG CAGTCTTCGT CGCGTTCGAT TCCGAGAGCG CGGGCGCCCC CGATGGTCGC    4320

TGCAAGTCGT TCTCGGTGGA GGCCAACGGT TCGGGCTGGG CCGAGGGCGC CGGGATGCTC    4380

CTGCTCGAGC GCCTCTCCGA TGCCGTCCAA AACGGTCATC CCGTCCTCGC CGTCCTTCGA    4440

GGCTCCGCCG TCAACCAGGA CGGCCGGAGC CAAGGCCTCA CCGCGCCCAA TGGCCCTGCC    4500

CAAGAGCGCG TCATCCGGCA AGCGCTCGAC AGCGCGCGGC TCACTCCAAA GGACGTCGAC    4560

GTCGTCGAGG CTCACGGCAC GGGAACCACC CTCGGAGACC CCATCGAGGC ACAGGCCATT    4620

CTTGCCACCT ATGGCGAGGC CCATTCCCAA GACAGACCCC TCTGGCTTGG AAGTCTCAAG    4680

TCCAACCTGG GACATGCTCA GGCCGCGGCC GGCGTGGGAA GCGTCATCAA GATGGTGCTC    4740
```

```
GCGTTGCAGC AAGGCCTCTT GCCCAAGACC CTCCATGCCC AGAATCCCTC CCCCCACATC   4800

GACTGGTCTC CGGGCACGGT AAAGCTCCTG AACGAGCCCG TCGTCTGGAC GACCAACGGG   4860

CATCCTCGCC ACGCCGGCGT CTCCGCCTTC GGCATCTCCG GCACCAACGC CCACGTCATC   4920

CTCGAAGAGG CCCCCGCCAT CGCCCGGGTC GAGCCCGCAG CGTCACAGCC CGCGTCCGAG   4980

CCGCTTCCCG CAGCGTGGCC CGTGCTCCTG TCGGCCAAGA GCGAGGCGGC CGTGCGCGCC   5040

CAGGCAAAGC GGCTCCGCGA CCACCTCCTC GCCAAAAGCG AGCTCGCCCT CGCCGATGTG   5100

GCCTATTCGC TCGCGACCAC GCGCGCCCAC TTCGAGCAGC GCGCCGCTCT CCTCGTCAAA   5160

GGCCGCGACG AGCTCCTCTC CGCCCTCGAT GCGCTGGCCC AAGGACATTC CGCCGCCGTG   5220

CTCGGACGAA GCGGGGCCCC AGGAAAGCTC GCCGTCCTCT TCACGGGCA AGGAAGCCAG   5280

CGGCCCACCA TGGGCCGCGG CCTCTACGAC GTTTTCCCCG TCTTCCGGGA CGCCCTCGAC   5340

ACCGTCGGCG CCCACCTCGA CCGCGAGCTC GACCGCCCCC TGCGCGACGT CCTCTTCGCT   5400

CCCGACGGCT CCGAGCAGGC CGCGCGCCTC GAGCAAACCG CCTTCACCCA GCCGGCCCTG   5460

TTTGCCCTCG AAGTCGCCCT CTTTCAGCTT CTACAATCCT TCGGTCTGAA GCCCGCTCTC   5520

CTCCTCGGAC ACTCCATTGG CGAGCTCGTC GCCGCCCACG TCGCCGGCGT CCTTTCTCTC   5580

CAGGACGGCT GCACCCTCGT CGCCGCCCGC GCAAAGCTCA TGCAAGCGCT CCCACAAGGC   5640

GGCGCCATGG TCACCCTCCG AGCCTCCGAG GAGGAAGTCC GCGACCTTCT CCAGCCCTAC   5700

GAAGGCCGAG CTAGCCTCGC CGCCCTCAAT GGGCCTCTCT CCACCGTCGT CGCTGGCGAT   5760

GAAGACGCGG TGGTGGAGAT CGCCCGCCAG GCCGAAGCCC TCGGACGAAA GACCACACGC   5820

CTGCGCGTCA GCCACGCCTT CCATTCCCCG CACATGGACG GAATGCTCGA CGACTTCCGC   5880

CGCGTCGCCC AGAGCCTCAC CTACCATCCC GCACGCATCC CCATCATCTC CAACGTCACC   5940

GGCGCGCGCG CCACGGACCA CGAGCTCGCC TCGCCCGACT ACTGGGTCCG CCACGTTCGC   6000

CACACCGTCC GCTTCCTCGA CGGCGTACGT GCCCTTCACG CCGAAGGGGC ACGTGTCTTT   6060

CTCGAGCTCG GCCTCACGC TGTCCTCTCC GCCCTTGCGC AAGACGCCCT CGGACAGGAC   6120

GAAGGCACGT CGCCATGCGC CTTCCTTCCC ACCCTCCGCA AGGGACGCGA CGACGCCGAG   6180

GCGTTCACCG CCGCGCTCGG CGCTCTCCAC TCCGCAGGCA TCACACCCGA CTGGAGCGCT   6240

TTCTTCGCCC CCTTCGCTCC ACGCAAGGTC TCCCTCCCCA CCTATGCCTT CCAGCGCGAG   6300

CGCTTCTGGC CCGACGCCTC CAAGGCACCC GGCGCCGACG TCAGCCACCT TGCTCCGCTC   6360

GAGGGGGGGC TCTGGCAAGC CATCGAGCGC GGGGACCTCG ATGCGCTCAG CGGTCAGCTC   6420

CACGTGGACG GCGACGAGCG GCGCGCCGCG CTCGCCCTGC TCCTTCCCAC CCTCTCGAGC   6480

TTTCGCCACG AGCGGCAAGA GCAGAGCACG GTCGACGCCT GGCGCTACCG TATCACCTGG   6540

AAGCCTCTGA CCACCGCCGA AACACCCGCC GACCTCGCCG GCACCTGGCT CGTCGTCGTG   6600

CCGGCCGCTC TGGACGACGA CGCGCTCCCC TCCGCGCTCA CCGAGGCGCT CACCCGGCGC   6660

GGCGCGCGCG TCCTCGCCTT GCGCCTGAGC CAGGCCCACC TGGACCGCGA GGCTCTCGCC   6720

GAGCATCTGC GCCAGGCTTG CGCCGAGACC GCCCCGATTC GCGGCGTGCT CTCGCTCCTC   6780

GCCCTCGACG AGCGCCCCCT CGCAGACCGT CCTGCCCTGC CCGCCGGACT CGCCCTCTCG   6840

CTTTCTCTCG CTCAAGCCCT CGGCGACCTC GACCTCGAGG CGCCCTTGTG GTTCTTCACG   6900

CGCGGCGCCG TCTCCATTGG ACACTCTGAC CCCCTCGCCC ATCCCGCCCA GGCCATGACC   6960

TGGGGCTTGG GCCGCGTCAT CGGCCTCGAG CACCCCGACC GGTGGGGAGG TCTCGTCGAC   7020

GTCTGCGCTG GGGTCGACGA GAGCGCCGTG GGCCGCTTGC TGCCGGCCCT CGCCGAGCGC   7080

CACGACGAAG ACCAGCTCGC TCTCCGCCCG GCCGGACTCT ACGCTCGCCG CATCGTCCGC   7140
```

```
GCCCCGCTCG GCGATGCGCC TCCCGCGCGC GACTTCACGC CCGGAGGCAC CATTCTCATC    7200

ACCGGCGGCA CCGGCGCCAT TGGCGCTCAC GTCGCCCGAT GGCTCGCTCG AAGAGGCGCT    7260

CAGCACCTCG TCCCTCATCAG CCGCCGAGGC GCCGAGGCCC CTGGCGCCTC GGAGCTCCAC    7320

GACGAGCTCT CGGCCCTCGG CGCGCGCACC ACCCTCGCCG CGTGCGATGT CGCCGACCGG    7380

AATGCTGTCG CCACGCTTCT TGAGCAGCTC GACGCCGAAG GTCGCAGGT CCGCGCCGTG    7440

TTCCACGCGA GCGGCATCGA ACACCACGCT CCGCTCGACG CCACCTCTTT CAGGGATCTC    7500

GCCGAGGTTG TCTCCGGCAA GGTCGAAGGT GCAAAGCACC TCCACGACCT GCTCGGCTCT    7560

CGACCCCTCG ACGCCTTTGT TCTCTTTTCG TCCGGCGCGG CCGTCTGGGG CGGCGGACAG    7620

CAAGGCGGCT ACGCGGCCGC AAACGCCTTC CTCGACGCCC TTGCCGAGCA TCGGCGCAGC    7680

GCTGGATTGA CAGCGACGTC GGTGGCCTGG GGCGCGTGGG GCGGCGGCGG CATGGCCACC    7740

GATCAGGCGG CAGCCCACCT CCAACAGCGC GGTCTGTCGC GGATGGCCCC CTCGCTTGCC    7800

CTGGCGGCGC TCGCGCTGGC TCTGGAGCAC GACGAGACCA CCGTCACCGT CGCCGACATC    7860

GACTGGGCGC GCTTTGCGCC TTCGTTCAGC GCCGCTCGCC CCCGCCCGCT CCTGCGCGAT    7920

TTGCCCGAGG CGCAGCGCGC TCTCGAGACC AGCGAAGGCG CGTCCTCCGA GCATGGCCCG    7980

GCCCCCGACC TCCTCGACAA GCTCCGGAGC CGCTCGGAGA GCGAGCAGCT TCGTCTGCTC    8040

GTCTCGCTGG TGCGCCACGA GACGGCCCTC GTCCTCGGCC ACGAAGGCGC CTCCCATGTC    8100

GACCCCGACA AGGGCTTCCT CGATCTCGGT CTCGATTCGC TCATGGCCGT CGAGCTTCGC    8160

CGGCGCTTGC AACAGGCCAC CGGCATCAAG CTCCCGGCCA CCCTCGCCTT CGACCATCCC    8220

TCTCCTCATC GAGTCGCGCT CTTCTTGCGC GACTCGCTCG CCCACGCCCT CGGCACGAGG    8280

CTCTCCGTCG AGCCCGACGC CGCCGCGCTC CCGGCGCTTC GCGCCGCGAG CGACGAGCCC    8340

ATCGCCATCG TCGGCATGGC CCTCCGCCTG CCGGGCGGCG TCGGCGATGT CGACGCTCTT    8400

TGGGAGTTCC TGGCCCAGGG ACGCGACGGC GTCGAGCCCA TTCCAAAGGC CCGATGGGAT    8460

GCCGCTGCGC TCTACGACCC CGACCCCGAC GCCAAGACCA AGAGCTACGT CCGGCATGCC    8520

GCCATGCTCC ACCAGGTCGA CCTCTTCGAC CCTGCCTTCT TTGGCATCAG CCCCCGGGAG    8580

GCCAAACACC TCGACCCCCA GCACCGCCTG CTCCTCGAAT CTGCCTGGCA GGCCCTCGAA    8640

GACGCCGGCA TCGTCCCCCC CACCCTCAAG GATTCCCCCA CCGGCGTCTT CGTCGGCATC    8700

GGCGCCAGCG AATACGCATT GCGAGAGGCG AGCACCGAAG ATTCCGACGC TTATGCCCTC    8760

CAAGGCACCG CCGGGTCCTT TGCCGCGGGG CGCTTGGCCT ACACGCTCGG CCTGCAAGGG    8820

CCCGCGCTCT CGGTCGACAC CGCCTGCTCC TCCTCGCTCG TCGCCCTCCA CCTCGCCTGC    8880

CAAGCCCTCC GACAGGGCGA GTGCAACCTC GCCCTCGCCG CGGGCGTCTC CGTCATGGCC    8940

TCCCCCGAGG GCTTCGTCCT CCTTTCCCGC CTGCGCGCCT TGGCGCCCGA CGGCCGCTCC    9000

AAGACCTTCT CGGCCAACGC CGACGGCTAC GGACGCGGAG AAGGCGTCAT CGTCCTTGCC    9060

CTCGAGCGGC TCGGTGACGC CCTCGCCCGA GGACACCGCG TCCTCGCCCT CGTCCGCGGC    9120

ACCGCCATCA ACCACGACGG CGCGTCGAGC GGTATCACCG CCCCCAACGG CACCTCCCAG    9180

CAGAAGGTCC TCCGCGCCGC GCTCCACGAC GCCCGCATCA CCCCGCCGA CGTCGACGTC    9240

GTCGAGTGCC ATGGCACCGG CACCTCCTTG GGAGACCCCA TCGAGGTGCA AGCCCTGGCC    9300

GCCGTCTACG CCGACGGCAG ACCCGCTGAA AAGCCTCTCC TTCTCGGCGC GCTCAAGACC    9360

AACATCGGCC ATCTCGAGGC CGCCTCCGGC CTCGCGGGCG TCGCCAAGAT CGTCGCCTCC    9420

CTCCGCCATG ACGCCCTGCC CCCCACCCTC CACACGGGCC CGCGCAATCC CTTGATTGAT    9480

TGGGATACAC TCGCCATCGA CGTCGTTGAT ACCCCGAGGT CTTGGGCCCG CCACGAAGAT    9540
```

```
AGCAGTCCCC GCCGCGCCGG CGTCTCCGCC TTCGGACTCT CCGGCACCAA CGCCCACGTC    9600

ATCCTCGAGG AGGCTCCCGC CGCCCTGTCG GGCGAGCCCG CCACCTCACA GACGGCGTCG    9660

CGACCGCTCC CCGCGGCGTG TGCCGTGCTC CTGTCGGCCA GGAGCGAGGC CGCCGTCCGC    9720

GCCCAGGCGA AGCGGCTCCG CGACCACCTC CTCGCCCACG ACGACCTCGC CCTTATCGAT    9780

GTGGCCTATT CGCAGGCCAC CACCCGCGCC CACTTCGAGC ACCGCGCCGC TCTCCTGGCC    9840

CGCGACCGCG ACGAGCTCCT CTCCGCGCTC GACTCGCTCG CCCAGGACAA GCCCGCCCCG    9900

AGCACCGTTC TCGGCCGGAG CGGAAGCCAC GGCAAGGTCG TCTTCGTCTT TCCTGGGCAA    9960

GGCTCGCAGT GGGAAGGGAT GGCCCTCTCC CTGCTCGACT CCTCGCCGGT CTTCCGCGCT   10020

CAGCTCGAAG CATGCGAGCG CGCGCTCGCT CCTCACGTCG AGTGGAGCCT GCTCGCCGTC   10080

CTGCGCCGCG ACGAGGGCGC CCCCTCCCTC GACCGCGTCG ACGTCGTACA GCCCGCCCTC   10140

TTTGCCGTCA TGGTCTCCCT GGCCGCCCTC TGGCGCTCGC TCGGCGTCGA GCCCGCCGCC   10200

GTCGTCGGCC ACAGCCAGGG CGAGATCGCC GCCGCCTTCG TCGCAGGCGC TCTCTCCCTC   10260

GAGGACGCGG CGCGCATCGC CGCCCTGCGC AGGAAAGCGC TCACCACCGT CGGCGGCAAC   10320

GGCGGCATGG CCGCCGTCGA GCTCGGCGCC TCCGACCTCC AGACCTACCT CGCTCCCTGG   10380

GGCGACAGGC TCTCCACCGC CGCCGTCAAC AGCCCCAGGG CTACCCTCGT ATCCGGCGAG   10440

CCCGCCGCCG TCGACGCGCT GCTCGACGTC CTCACCGCCA CCAAGGTGTT CGCCCGCAAG   10500

ATCCGCGTCG ACTACGCCTC CCACTCCGCC CAGATGGACG CCGTCCAAGA CGAGCTCGCC   10560

GCAGGTCTAG CCAACATCGC TCCTCGGACG TGCGAGCTCC CTCTTTATTC GACCGTCACC   10620

GGCACCAGGC TCGACGGCTC CGAGCTCGAC GGCGCGTACT GGTATCGAAA CCTCCGGCAA   10680

ACCGTCCTGT TCTCGAGCGC GACCGAGCGG CTCCTCGACG ATGGGCATCG CTTCTCCGTC   10740

GAGGTCAGCC CCCATCCCGT GCTCACGCTC GCCCTCCGCG AGACCTGCGA GCGCTCACCG   10800

CTCGATCCCG TCGTCGTCGG CTCCATTCGA CGAGAAGAAG GCCACCTCGC CCGCCTGCTC   10860

CTCTCCTGGG CGGAGCTCTC TACCCGAGGC CTCGCGCTCG ACTGGAAGGA CTTCTTCGCG   10920

CCCTACGCTC CCCGCAAGGT CTCCCTCCCC ACCTACCCCT TCCAGCGAGA GCGGTTCTGG   10980

CTCGACGTCT CCACGGACGA ACGCTTCCGA CGTCGCCTCC GCAGGCCTGA CCTCGGCCGA   11040

CCAATCCCGC TGCTCGGCGC CGCCGTCGCC TTCGCCGACC GCGGTGGCTT TCTCTTTACA   11100

GGGCGGCTCT CCCTCGCAGA GCACCCGTGG CTCGAAGGCC ATGCCGTCTT CGGCACACCC   11160

ATCCTACCGG GCACCGGCTT TCTCGAGCTC GCCCTGCACG TCGCCCACCG CGTCGGCCTC   11220

GACACCGTCG AAGAGCTCAC GCTCGAGGCC CCTCTCGCTC TCCCATCGCA GGACACCGTC   11280

CTCCTCCAGA TCTCCGTCGG GCCCGTGGAC GACGCAGGAC GAAGGGCGCT CTCTTTCCAT   11340

AGCCGACAAG AGGACGCGCT TCAGGATGGC CCCTGGACTC GCCACGCCAG CGGCTCTCTC   11400

TCGCCGGCGA CCCCATCCCT CTCCGCCGAT CTCCACGAGT GGCCTCCCTC GAGTGCCATC   11460

CCGGTGGACC TCGAAGGCCT CTACGCAACC CTCGCCAACC TCGGGCTTGC CTACGGCCCC   11520

GAGTTCCAGG GCCTCCGCTC CGTCTACAAG CGCGGCGACG AGCTCTTTGC CGAAGCCAAG   11580

CTCCCGGAAG CGGCCGAAAA GGATGCCGCC CGGTTTGCCC TCCACCCTGC GCTGCTCGAC   11640

AGCGCCCTGC ATGCACTGGC CTTTGAGGAC GAGCAGAGAG GGACGGTCGC TCTGCCCTTC   11700

TCGTGGAGCG GAGTCTCGCT GCGCTCCGTC GGTGCCACCA CCTTGCGCGT GCGCTTCCAC   11760

CGTCCCAAGG GTGAATCCTC CGTCTCGATC GTCCTGGCCG ACGCCGCAGG TGACCCTCTT   11820

GCCTCGGTGC AAGCGCTCGC CATGCGGACG ACGTCCGCCG CGCAGCTCCG CACCCCGGCA   11880

GCTTCCCACC ATGATGCGCT CTTCCGCGTC GACTGGAGCG AGCTCCAAAG CCCCACTTCA   11940
```

```
CCGCCTGCCG CCCCGAGCGG CGTCCTTCTC GGCACAGGCG GCCACGATCT CGCGCTCGAC    12000

GCCCCGCTCG CCCGCTACGC CGACCTCGCT GCCCTCCGAA GCGCCCTCGA CCAGGGCGCT    12060

TCGCCTCCCG GCCTCGTCGT CGCCCCCTTC ATCGATCGAC CGGCAGGCGA CCTCGTCCCG    12120

AGCGCCCACG AGGCCACCGC GCTCGCACTC GCCCTCTTGC AAGCCTGGCT CGCCGACGAA    12180

CGCCTCGCCT CGTCGCGCCT CGTCCTCGTC ACCCGACGCG CCGTCGCCAC CCACACCGAA    12240

GACGACGTCA AGGACCTCGC TCACGCGCCG CTCTGGGGGC TCGCGCGCTC CGCGCAAAGT    12300

GAGCACCCAG ACCTCCCGCT CTTCCTCGTC GACATCGACC TCAGCGAGGC CTCCCAGCAG    12360

GCCCTGCTAG GCGCGCTCGA CACAGGAGAA CGCCAGCTCG CCCTCCGCAA CGGGAAACCC    12420

CTCATCCCGA GGTTGGCGCA ACCACGCTCG ACGGACGCGC TCATCCCGCC GCAAGCACCC    12480

ACGTGGCGCC TCCATATTCC GACCAAAGGC ACCTTCGACG CGCTCGCCCT CGTCGACGCC    12540

CCCGAGGCCC AGGCGCCCCT CGCACACGGC CAAGTCCGCA TCGCCGTGCA CGCGGCAGGG    12600

CTCAACTTCC GCGATGTCGT CGACACCCTT GGCATGTATC CGGGCGACGC GCCGCCGCTC    12660

GGAGGCGAAG GCGCGGGCAT CGTTACTGAA GTCGGTCCAG GTGTCTCCCG ATACACCGTA    12720

GGCGACCGGG TGATGGGGGT CTTCGGCGCA GCCTTTGGTC CCACGGCCAT CGCCGACGCC    12780

CGCATGATCT GCCCCATCCC CCACGCCTGG TCCTTCGCCC AAGCCGCCAG CGTCCCCATC    12840

ATCTATCTCA CCGCCTACTA TGGACTCGTC GATCTCGGGC ATCTGAAACC CAATCAACGT    12900

GTCCTCATCC ATGCGGCCGC CGGCGGCGTC GGGACGGCCG CCGTTCAGCT CGCACGCCAC    12960

CTCGGCGCCG AGGTCTTTGC CACCGCCAGT CCAGGGAAGT GGAGCGCTCT CCGCGCGCTC    13020

GGCTTCGACG ATGCGCACCT CGCGTCCTCA CGTGACCTGG GCTTCGAGCA GCACTTCCTG    13080

CGCTCCACGC ATGGGCGCGG CATGGATGTC GTCCTCGACT GTCTGGCACG CGAGTTCGTC    13140

GACGCCTCGC TGCGCCTCAT GCCGAGCGGT GGACGCTTCA TCGAGATGGG AAAGACGGAC    13200

ATCCGTGAGC CCGACGCGAT CGGCCTCGCC TACCCTGGCG TCGTTTACCG CGCCTTCGAC    13260

GTCACAGAGG CCGGACCGGA TCGAATTGGG CAGATGCTCG CAGAGCTGCT CAGCCTCTTC    13320

GAGCGCGGTG TGCTTCGTCT GCCACCCATC ACATCCTGGG ACATCCGTCA TGCCCCCCAG    13380

GCCTTCCGCG CGCTCGCCCA GGCGCGGCAT GTTGGGAAGT TCGTCCTCAC CATTCCCCGT    13440

CCGATCGATC CCGAGGGGAC CGTCCTCATC ACGGGAGGCA CCGGGACGCT AGGAGTCCTG    13500

GTCGCACGCC ACCTCGTCGC GAAACACAGC GCCAAACACC TGCTCCTCAC CTCGAGGAAG    13560

GGCGCGCGTG CTCCGGGCGC GGAGGCTCTG CGAAGCGAGC TCGAAGCGCT GGGGGCCTCG    13620

GTCACCCTCG TCGCGTGCGA CGTGGCCGAC CCACGCGCCC TCCGGACCCT CCTGGACAGC    13680

ATCCCGAGGG ATCATCCGAT CACGGCCGTC GTGCACGCCG CCGGCGCCCT CGACGACGGG    13740

CCGCTCGGTA GCATGAGCGC CGAGCGCATC GCTCGCGTCT TTGACCCCAA GCTCGATGCC    13800

GCTTGGTACT TGCATGAGCT CACCCAGGAC GAGCCGGTCG CGGCCTTCGT CCTCTTCTCG    13860

GCCGCCTCCG GCGTCCTTGG TGGTCCAGGT CAGTCGAACT ACGCCGCTGC CAATGCCTTC    13920

CTCGATGCGC TCGCACATCA CCGGCGCGCC CAAGGACTCC CAGCCGCTTC GCTCGCCTGG    13980

GGCTACTGGG CCGAGCGCAG TGGGATGACC CGGCACCTCA GCGCCGCCGA CGCCGCTCGC    14040

ATGAGGCGCG CCGGCGTCCG GCCCCTCGAC ACTGACGAGG CGCTCTCCCT CTTCGATGTG    14100

GCTCTCTTGC GACCCGAGCC CGCTCTGGTC CCCGCCCCCT TCGACTACAA CGTGCTCAGC    14160

ACGAGTGCCG ACGGCGTGCC CCCGCTGTTC CAGCGTCTCG TCCGCGCTCG CATCGCGCGC    14220

AAGGCCGCCA GCAATACTGC CCTCGCCTCG TCGCTTGCAG AGCACCTCTC CTCCCTCCCG    14280

CCCGCCGAAC GCGAGCGCGT CCTCCTCGAT CTCGTCCGCA CCGAAGCCGC CTCCGTCCTC    14340
```

```
GGCCTCGCCT CGTTCGAATC GCTCGATCCC CATCGCCCTC TACAAGAGCT CGGCCTCGAT    14400

TCCCTCATGG CCCTCGAGCT CCGAAATCGA CTCGCCGCCG CCGCCGGGCT GCGGCTCCAG    14460

GCTACTCTCC TCTTCGACTA TCCAACCCCG ACTGCGCTCT CACGCTTTTT CACGACGCAT    14520

CTCTTCGGGG GAACCACCCA CCGCCCCGGC GTACCGCTCA CCCCGGGGGG GAGCGAAGAC    14580

CCTATCGCCA TCGTGGCGAT GAGCTGCCGC TTCCCGGGCG ACGTGCGCAC GCCCGAGGAT    14640

CTCTGGAAGC TCTTGCTCGA CGGACAAGAT GCCATCTCCG GCTTTCCCCA AAATCGCGGC    14700

TGGAGTCTCG ATGCGCTCGA CGCCCCCGGT CGCTTCCCAG TCCGGGAGGG GGGCTTCGTC    14760

TACGACGCAG ACGCCTTCGA TCCGGCCTTC TTCGGGATCA GTCCACGTGA AGCGCTCGCC    14820

GTTGATCCCC AACAGCGCAT TTTGCTCGAG ATCACATGGG AAGCCTTCGA GCGTGCAGGC    14880

ATCGACCCGG CCTCCCTCCA AGGAAGCCAA AGCGGGGTCT TCGTTGGCGT ATGGCAGAGC    14940

GACTACCAAT GCATCGCTGG TGAACGCGAC TGGCGAATAC AAGGACTCGT TGCCACCGGT    15000

AGCGCAGCGC GTCCGTCCGG CCGAATCGCA TACACGTTCG GACTTCAAGG GCCCGCCATC    15060

AGCGTGGAGA CGGCGTGCAG CTTCCTCGTC GCGGTTCACC TCGCCTGCCA GGCCCCCCCC    15120

CACGGCGAAT ACTCCCTGGC GCTCGCTGGC GGCGTGACCA TCATGGCCAC GCCAGCCATA    15180

TTCATCGCGT TCGACTCCGA GAGCGCGGGT GCCCCCGACG TCGCTGCAA GGCCTTCTCG    15240

CCGGAAGCCG ACGGTTCGGG CTGGGCCGAA GGCGCCGGGA TGCTCCTGCT CGAGCGCCTC    15300

TCCGATGCCG TCCAAAACGG TCATCCCGTC CTCGCCGTCC TTCGAGGCTC CGCCGTCAAC    15360

CAGGACGGCC GGAGCCAAGG CCTCACCGCG CCCAATGGCC CTGCCCAGGA GCGCGTCATC    15420

CGGCAAGCGC TCGACAGCGC GCGGCTCACT CCAAAGGACG TCGACGTCGT CGAGGCTCAC    15480

GGCACGGGAA CCACCCTCGG AGACCCCATC GAGGCACAGG CCGTTTTTGC CACCTATGGC    15540

GAGGCCCATT CCCAAGACAG ACCCCTCTGG CTTGGAAGCC TCAAGTCCAA CCTGGGACAT    15600

ACTCAGGCCG CGGCCGGCGT CGGCGGCATC ATCAAGATGG TGCTCGCGTT GCAGCACGGT    15660

CTCTTGCCCA AGACCCTCCA TGCCCAGAAT CCCTCCCCCC ACATCGACTG GTCTCCAGGC    15720

ATCGTAAAGC TCCTGAACGA GGCCGTCGCC TGGACGACCA GCGGACATCC TCGCCGCGCC    15780

GGTGTTTCCT CGTTCGGCGT CTCCGGCACC AACGCCCATG TCATCCTCGA AGAGGCTCCC    15840

GCCGCCACGC GGGCCGAGTC AGGCGCTTCA CAGCCTGCAT CGCAGCCGCT CCCCGCGGCG    15900

TGGCCCGTCG TCCTGTCGGC CAGGAGCGAG GCCGCCGTCC GCGCCCAGGC TCAAAGGCTC    15960

CGCGAGCACC TGCTCGCCCA AGGCGACCTC ACCCTCGCCG ATGTGGCCTA TTCGCTGGCC    16020

ACCACCCGCG CCCACTTCGA GCACCGCGCC GCTCTCGTAG CCCACGACCG CGACGAGCTC    16080

CTCTCCGCGC TCGACTCGCT CGCCCAGGAC AAGCCCGCAC CGAGCACCGT CCTCGGACGG    16140

AGCGGAAGCC ACGGCAAGGT CGTCTTCGTC TTTCCTGGGC AAGGCTCGCA GTGGGAAGGG    16200

ATGGCCCTCT CCCTGCTCGA CTCCTCGCCC GTCTTCCGCA CACAGCTCGA AGCATGCGAG    16260

CGCGCGCTCC GTCCTCACGT CGAGTGGAGC CTGCTCGCCG TCCTGCGCCG CGACGAGGGC    16320

GCCCCTCCC TCGACCGCGT CGACGTCGTG CAGCCCGCCC TCTTTGCCGT CATGGTCTCC    16380

CTGGCCGCCC TCTGGCGCTC GCTCGGCGTC GAGCCCGCCG CCGTCGTCGG CCACAGCCAG    16440

GGCGAGATAG CCGCCGCCTT CGTCGCAGGC GCTCTCTCCC TCGAGGACGC GGCCCGCATC    16500

GCCGCCCTGC GCAGCAAAGC GTCACCACCG TCGCCGGCAA CGGGCATGGC CGCCGTCGAG    16560

CTCGGCGCCT CCGACCTCCA GACCTACCTC GCTCCCTGGG GCGACAGGCT CTCCATCGCC    16620

GCCGTCAACA GCCCCAGGGC CACGCTCGTA TCCGGCGAGC CCGCCGCCGT CGACGCGCTG    16680

ATCGACTCGC TCACCGCAGC GCAGGTCTTC GCCCGAAGAG TCCGCGTCGA CTACGCCTCC    16740
```

-continued

```
CACTCAGCCC AGATGGACGC CGTCCAAGAC GAGCTCGCCG CAGGTCTAGC CAACATCGCT    16800

CCTCGGACGT GCGAGCTCCC TCTTTATTCG ACCGTCACCG GCACCAGGCT CGACGGCTCC    16860

GAGCTCGACG GCGCGTACTG GTATCGAAAC CTCCGGCAAA CCGTCCTGTT CTCGAGCGCG    16920

ACCGAGCGGC TCCTCGACGA TGGGCATCGC TTCTTCGTCG AGGTCAGCCC TCATCCCGTG    16980

CTCACGCTCG CCCTCCGCGA GACCTGCGAG CGCTCACCGC TCGATCCCGT CGTCGTCGGC    17040

TCCATTCGAC GCGACGAAGG CCACCTCCCC CGTCTCCTTG CTCTCTTGGG CCGAGCTCTA    17100

TGGCCGGGCC TCACGCCCGA GTGGAAGGCC TTCTTCGCGC CCTTCGCTCC CCGCAAGGTC    17160

TCACTCCCCA CCTACGCCTT CCAGCGCGAG CGTTTCTGGC TCGACGCCCC CAACGCACAC    17220

CCCGAAGGCG TCGCTCCCGC TGCGCCGATC GATGGGCGGT TTTGGCAAGC CATCGAACGC    17280

GGGGACCTCG ACGCGCTCAG CGGCCAGCTC CACGCGGACG GCGACGAGCA GCGCGCCGCC    17340

CTCGCCCTGC TCCTTCCCAC CCTCTCGAGC TTTCACCACC AGCGCCAAGA GCAGAGCACG    17400

GTCGACACCT GGCGCTACCG CATCACGTGG AGGCCTCTGA CCACCGCCGC CACGCCCGCC    17460

GACCTCGCCG GCACCTGGCT CCTCGTCGTG CCGTCCGCGC TCGGCGACGA CGCGCTCCCT    17520

GCCACGCTCA CCGATGCGCT TACCCGGCGC GGCGCGCGTG TCCTCGCGCT GCGCCTGAGC    17580

CAGGTTCACA TAGGCCGCGC GGCTCTCACC GAGCACCTGC GCGAGGCTGT TGCCGAGACT    17640

GCCCCGATTC GCGGCGTGCT CTCCCTCCTC GCCCTCGACG AGCGCCCCCT CGCGGACCAT    17700

GCCGCCCTGC CCGCGGGCCT TGCCCTCTCG CTCGCCCTCG TCCAAGCCCT CGGCGACCTC    17760

GCCCTCGAGG CTCCCTTGTG GCTCTTCACG CGCGGCGCCG TCTCGATTGG ACACTCCGAC    17820

CCACTCGCCC ATCCCACCCA GGCCATGATC TGGGGCTTGG GCCGCGTCGT CGGCCTCGAG    17880

CACCCCGAGC GGTGGGGCGG GCTCGTCGAC CTCGGCGCAG CGCTCGACGC GAGCGCCGCA    17940

GGCCGCTTGC TCCCGGCCCT CGCCCAGCGC CACGACGAAG ACCAGCTCGC GCTGCGCCCG    18000

GCCGGCCTCT ACGCACGCCG CTTCGTCCGC GCCCCGCTCG GCGATGCGCC TGCCGCTCGC    18060

GGCTTCATGC CCCGAGGCAC CATCCTCATC ACCGGTGGTA CCGGCGCCAT TGGCGCTCAC    18120

GTCGCCCGAT GGCTCGCTCG AAAAGGCGCT GAGCACCTCG TCCTCATCAG CCGACGAGGG    18180

GCCCAGGCCG AAGGCGCCGT GGAGCTCCAC GCCGAGCTCA CCGCCCTCGG CGCGCGCGTC    18240

ACCTTCGCCG CGTGCGATGT CGCCGACAGG AGCGCTGTCG CCACGCTTCT CGAGCAGCTC    18300

GACGCCGGAG GGCCACAGGT GAGCGCCGTG TTCCACGCGG GCGGCATCGA GCCCCACGCT    18360

CCGCTCGCCC CCACCTCCAT GGAGGATCTC GCCGAGGTTG TCTCCGGCAA GGTACAAGGT    18420

GCAAGACACC TCCACGACCT GCTCGGCTCT CGACCCCTCG ACGCCTTTGT TCTCTTCTCG    18480

TCCGGCGCGG TCGTCTGGGG CGGCGGACAA CAAGGCGGCT ATGCCGCTGC GAACGCCTTC    18540

CTCGATGCCC TGGCCGAGCA GCGGCGCAGC CTTGGGCTGA CGGCGACATC GGTGGCCTGG    18600

GGCGTGTGGG GCGGCGGCGG CATGGCTACC GGGCTCCTGG CAGCCCAGCT AGAGCAACGC    18660

GGTCTGTCGC CGATGGCCCC CTCGCTGGCC GTGGCGACGC TCGCGCTGGC GCTGGAGCAC    18720

GACGAGACCA CCCTCACCGT CGCCGACATC GACTGGGCGC GCTTTGCGCC TTCGTTCAGC    18780

GCCGCTCGCT CCCGCCCGCT CCTGCGCGAT TTGCCCGAGG CGCAGCGCGC TCTCGAAGCC    18840

AGCGCCGATG CGTCCTCCGA GCAAGACGGG GCCACAGGCC TCCTCGACAA GCTCCGAAAC    18900

CGCTCGGAGA GCGAGCAGAT CCACCTGCTC TCCTCGCTGG TGCGCCACGA AGCGGCCCTC    18960

GTCCTGGGCC ATACCGACGC CTCCCAGGTC GACCCCACA AGGGCTTCAT GGACCTCGGC    19020

CTCGATTCGC TCATGACCGT CGAGCTTCGT CGGCGCTTGC AGCAGGCCAC CGGCATCAAG    19080

CTCCCGGCCA CCCTCGCCTT CGACCATCCC TCTCCTCATC GCGTCGCGCT CTTCTTGCGC    19140
```

```
GACTCGCTCG CCCACGCCCT CGGCGCGAGG CTCTCCGTCG AGCGCGACGC CGCCGCGCTC   19200

CCGGCGCTTC GCTCGGCGAG CGACGAGCCC ATCGCCATCG TCGGCATGGC CCTCCGCTTG   19260

CCGGGCGGCA TCGGCGATGT CGACGCTCTT TGGGAGTTCC TCGCCCAAGG ACGCGACGCC   19320

GTCGAGCCCA TTCCCCATGC CCGATGGGAT GCCGGTGCCC TCTACGACCC CGACCCCGAC   19380

GCCAAGGCCA AGAGCTACGT CCGGCATGCC GCCATGCTCG ACCAGGTCGA CCTCTTCGAT   19440

CCTGCCTTCT TTGGCATCAG CCCTCGCGAG GCCAAATACC TCGACCCCCA GCACCGCCTG   19500

CTCCTCGAAT CTGCCTGGCT GGCCCTCGAG GACGCCGGCA TCGTCCCCTC CACCCTCAAG   19560

GATTCTCCCA CCGGCGTCTT CGTCGGCATC GGCGCCAGCG AATACGCACT GCGAAACACG   19620

AGCTCCGAAG AGGTCGAAGC GTATGCCCTC CAAGGCACCG CCGGGTCCTT TGCCGCGGGG   19680

CGCTTGGCCT ACACGCTCGG CCTGCAAGGG CCCGCGCTCT CGGTCGACAC CGCCTGCTCC   19740

TCCTCGCTCG TCGCCCTCCA CCTCGCCTGC CAAGCCCTCC GACAGGGCGA GTGCAACCTC   19800

GCCCTCGCCG CGGGCGTCTC CGTCATGGCC TCCCCCGGGC TCTTCGTCGT CCTTTCCCGC   19860

ATGCGTGCTT TGGCGCCCGA TGGCCGCTCC AAGACCTTCT CGACCAACGC CGACGGCTAC   19920

GGACGCGGAG AGGGCGTCGT CGTCCTTGCC CTCGAGCGGC TCGGCGACGC CCTCGCCCGA   19980

GGACACCGCG TCCTCGCCCT CGTCCGCGGC ACCGCCATGA ACCATGACGG CGCGTCGAGC   20040

GGCATCACCG CCCCCAATGG CACCTCCCAC CAGAAGGTCC TCCGCGCCGC GCTCCACGAC   20100

GCCCATATCG GCCCTGCCGA CGTCGACGTC GTCGAATGCC ATGGCACCGG CACCTCCTTG   20160

GGAGACCCCA TCGAGGTGCA AGCCCTGGCC GCCGTCTACG CCGATGGCAG ACCCGCTGAA   20220

AAGCCTCTCC TTCTCGGCGC ACTCAAGACC AACATTGGCC ATCTCGAGGC CGCCTCCGGC   20280

CTCGCGGGCG TCGCCAAGAT CGTCGCCTCC CTCCGCCATG ACGCCCTGCC CCCCACCCTC   20340

CACACGACCC CGCGCAATCC CCTGATCGAG TGGGATGCGC TCGCCATCGA CGTCGTCGAT   20400

GCCACGAGGG CGTGGGCCCG CCACGAAGAT GGCAGTCCCC GCCGCGCCGG CGTCTCCGCC   20460

TTCGGACTCT CCGGCACCAA CGCCCACGTT ATCCTCGAAG AGGCTCCCGC GATCCCGCAG   20520

GCCGAGCCCA CCGCGGCACA GCTCGCGTCG CAGCCGCTTC CCGCAGCCTG GCCCGTGCTC   20580

CTGTCGGCCA GGAGCGAGCC GGCCGTGCGC GCCCAGGCCC AGAGGCTCCG CGACCACCTC   20640

CTCGCCCACG ACGACCTCGC CCTGGCCGAT GTAGCCTACT CGCTCGCCAC CACCCGGGCT   20700

ACCTTCGAGC ACCGTGCCGC TCTCGTGGTC CACGACCGCG AAGAGCTCCT CTCCGCGCTC   20760

GATTCGCTCG CCCAGGGAAG GCCCGCCCCG AGCACCGTCG TCGAACGAAG CGGAAGCCAC   20820

GGCAAGGTCG TCTTCGTCTT TCCTGGGCAA GGCTCGCAGT GGGAAGGGAT GGCCCTCTCC   20880

CTGCTCGATA CCTCGCCGGT CTTCCGGGCA CAGCTCGAAG CGTGCGAGCG CGCCCTCGCG   20940

CCCCACGTGG ACTGGTCGCT GCTCGCGGTG CTCCGCGGCG AGGAGGGCGC GCCCCCGCTC   21000

GACCGGGTCG ACGTGGTCCA GCCCGCGCTG TTCTCGATGA TGGTCTCGCT GGCCGCCCTG   21060

TGGCGCTCCA TGGGCGTCGA GCCCGACGCG GTGGTCGGCC ATAGCCAGGG CGAGATCGCC   21120

GCGGCCTGTG TGGCGGGCGC GCTGTCGCTC GAGGACGCTG CCAAGCTGGT GGCGCTGCGC   21180

AGCCGTGCGC TCGTGGAGCT CGCCGGCCAG GGGGCCATGG CCGCGGTGGA GCTGCCGGAG   21240

GCCGAGGTCG CACGGCGCCT CCAGCGCTAT GGCGATCGGC TCTCCATCGG GGCGATCAAC   21300

AGCCCTCGTT TCACGACGAT CTCCGGCGAG CCCCCTGCCG TCGCCGCCCT GCTCCGCGAT   21360

CTGGAGTCCG AGGGCGTCTT CGCCCTCAAG CTGAGTTACG ACTTCGCCTC CCACTCCGCG   21420

CAGGTCGAGT CGATTCGCGA CGAGCTCCTC GATCTCCTGT CGTGGCTCGA GCCGCGCTCG   21480

ACGGCGGTCC CGTTCTACTC CACGGTGAGC GGCGCCGCGA TCGACGGGAG CGAGCTCGAC   21540
```

```
GCCGCCTACT GGTACCGGAA CCTCCGGCAG CCGGTCCGCT TCGCAGACGC TGTGCAAGGC    21600

CTCCTTGCCG GAGAACATCG CTTCTTCGTG GAGGTGAGCC CCAGTCCTGT GCTGACCTTG    21660

GCCTTGCACG AGCTCCTCGA AGCGTCGGAG CGCTCGGCGG CGGTGGTCGG CTCTCTGTGG    21720

AGCGACGAAG GGGATCTACG GCGCTTCCTC GTCTCGCTCT CCGAGCTCTA CGTCAACGGC    21780

TTCGCCCTGG ATTGGACGAC GATCCTGCCC CCCGGGAAGC GGGTGCCGCT GCCCACCTAC    21840

CCCTTCCAGC GCGAGCGCTT CTGGCTCGAC GCCTCCACGG CACCCGCCGC CGGCGTCAAC    21900

CACCTTGCTC CGCTCGAGGG GCGGTTCTGG CAGGCCATCG AGAGCGGGAA TATCGACGCG    21960

CTCAGCGGCC AGCTCCACGT GGACGGCGAC GAGCAGCGCG CCGCCCTTGC CCTGCTCCTT    22020

CCCACCCTCG CGAGCTTTCG CCACGAGCGG CAAGAGCAGG GCACGGTCGA CGCCTGGCGC    22080

TACCGCATCA CGTGGAAGCC TCTGACCACC GCCACCACGC CCGCCGACCT GGCCGGCACC    22140

TGGCTCCTCG TCGTGCCGGC CGCTCTGGAC GACGACGCGC TCCCCTCCGC GCTCACCGAG    22200

GCGCTCGCCC GGCGCGGCGC GCGCGTCCTC GCCGTGCGCC TGAGCCAGGC CCACCTGGAC    22260

CGCGAGGCTC TCGCCGAGCA CCTGCGCCAG GCTTGCGCCG AGACCGCGCC GCCTCGCGGC    22320

GTGCTCTCGC TCCTCGCCCT CGACGAAAGT CCCCTCGCCG ACCATGCCGC CGTGCCCGCG    22380

GGACTCGCCT TCTCGCTCAC CCTCGTCCAA GCCCTCGGCG ACATCGCCCT CGACGCGCCC    22440

TTGTGGCTCT TCACCCGCGG CGCCGTCTCC GTCGGACACT CCGACCCCAT CGCCCATCCG    22500

ACGCAGGCGA TGACCTGGGG CCTGGGCCGC GTCGTCGGCC TCGAGCACCC CGAGCGCTGG    22560

GGAGGGCTCG TCGACGTCGG CGCAGCGATC GACGCGAGCG CCGTGGGCCG CTTGCTCCCG    22620

GTCCTCGCCC TGCGCAACGA TGAGGACCAG CTCGCTCTCC GCCCGGCCGG GTTCTACGCT    22680

CGCCGCCTCG TCCGCGCTCC GCTCGGCGAC GCGCCGCCCG CACGTACCTT CAAGCCCCGA    22740

GGCACCCTCC TCATCACCGG AGGCACCGGC GCCGCTGGCG CTCACGTCGC CCGATGGCTC    22800

GCTCGAGAAG GCGCAGAGCA CCTCGTCCTC ATCAGCCGCC GAGGGGCCCA GGCCGAGGGC    22860

GCCTCGGAGC TCCACGCCGA GCTCACGGCC CTGGGCGCGC GCGTCACCTT CGCCGCGTGT    22920

GATGTCGCCG ACAGGAGCGC TGTCGCCACG CTTCTCGAGC AGCTCGACGC CGAAGGGTCG    22980

CAGGTCCGCG CCGTGTTCCA CGCGGGCGGC ATCGGGCGCC ACGCTCCGCT CGCCGCCACC    23040

TCTCTCATGG AGCTCGCCGA CGTTGTCTCT GCCAAGGTCC TAGGCGCAGG GAACCTCCAC    23100

GACCTGCTCG GTCCTCGACC CCTCGACGCC TTCGTCCTTT TCTCGTCCAT CGCAGGCGTC    23160

TGGGCGGCG GACAACAAGC CGGATACGCC GCCGGAAACG CCTTCCTCGA CGCCCTGGCC    23220

GACCAGCGGC GCAGTCTTGG ACAGCCGGAC ACGTCCGTGG TGTGGGCGC GTGGGCGGC    23280

GGCGGTGGTA TATTCACGGG GCCCCTGGCA GCCCAGCTGG AGCAACGTCG TCTGTCGCCG    23340

ATGGCCCCTT CGCTGGCCGT GGCGGCGCTC GCGCAAGCCC TGGAGCACGA CGAGACCACC    23400

GTCACCGTCG CCGACATCGA CTGGGCGCGC TTTGCGCCTT CGATCAGCGT CGCTCGCTCC    23460

CGCCGCTCCT GCGCGACTTG CCCGAGCAGC GCGCCCTCGA AGACAGAGAA GGCGCGTCCT    23520

CCTCCGAGCA CGGCCCGGCC CCCCGACCTC CTCGACAAGC TCCGGAGCCG CTCGGAGAGC    23580

GAGCAGCTCC GTCTGCTCGC CGCGCTGGTG TGCGACGAGA CGGCCCTCGT CCTCGGCCAC    23640

GAAGGCCGCT TCCCAGCTCG ACCCCGACAA GGCTTCTTCG ACCTCGGTCT CGATTCGATC    23700

ATGACCGTCG AGCTTCGTCG GCGCTTGCAA CAGGCCACCG GCATCAAGCT CCCGGCCACC    23760

CTCGCCTTCG ACCATCCCTC TCCTCATCGC GTCGCGCTCT TCATGCGCGA CTCGCTCGCC    23820

CACGCCCTCG GCACGAGGCT CTCCGCCGAG GCGACGCCGC CGCGCTCCGG CCGCGCCCTCG   23880

AGCGACGAGC CCATCGCCAT CGTCGGCATG GCCCTGCGCC TGCCGGGCGG CGTCGGCGAT    23940
```

```
GTCGACGCTC TTTGGGAGTT CCTCCACCAA GGGCGCGACG CGGTCGAGCC CATTCCACAG    24000

AGCCGCTGGG ACGCCGGTGC CCTCTACGAC CCCGACCCCG ACGCCGACGC CAAGAGCTAC    24060

GTCCGGCATG CCGCGATGCT CGACCAGATC GACCTCTTCG ACCCTGCCTT CTTCGGCATC    24120

AGCCCCCGGG AGGCCAAACA CCTCGACCCC CAGCACCGCC TGCTCCTCGA ATCTGCCTGG    24180

CTGGCCCTCG AGGACGCCGG CATCGTCCCC ACCTCCCTCA AGGACTCCCT CACCGGCGTC    24240

TTCGTCGGCA TCTGCGCCGG CGAATACGCG ATGCAAGAGG CGAGCTCGGA AGGTTCCGAG    24300

GTTTACTTCA TCCAAGGCAC TTCCGCGTCC TTTGGCGCGG GGGCTTGGC CTATACGCTC    24360

GGGCTCCAGG GGCCGCGATC TTCGGTCGAC ACCGCCTGCT CCTCCTCGCT CGTCTCCCTC    24420

CACCTCGCCT GCCAAGCCCT CCGACAGGGC GAGTGCAACC TCGCCCTCGC CGCGGGCGTG    24480

TCGCTCATGG TCTCCCCCCA GACCTTCGTC ATCCTTTCCC GTCTGCGCGC CTTGGCGCCC    24540

GACGGCCGCT CCAAGACCTT CTCGGACAAC GCCGACGGCT ACGGACGCGG AGAAGGCGTC    24600

GTCGTCCTTG CCCTCGAGCG GATCGGCGAC GCCCTCGCCC GGAGACACCG CGTCCTCGTC    24660

CTCGTCCGCG GCACCGCCAT CAACCACGAC GGCGCGTCGA GCGGTATCAC CGCCCCCAAC    24720

GGCACCTCCC AGCAGAAGGT CCTCCGGGCC GCGCTCCACG ACGCCCGCAT CACCCCCGCC    24780

GACGTCGACG TCGTCGAGTG CCATGGCACC GGCACCTCGC TGGGAGACCC CATCGAGGTG    24840

CAAGCCCTGG CCGCCGTCTA CGCCGACGGC AGACCCGCTG AAAAGCCTCT CCTTCTCGGC    24900

GCGCTCAAGA CCAACATCGG CCATCTCGAG GCCGCCTCCG GCCTCGCGGG CGTCGCCAAG    24960

ATGGTCGCCT CGCTCCGCCA CGACGCCCTG CCCCCCACCC TCCACGCGAC CCCACGCAAT    25020

CCCCTCATCG AGTGGGAGGC GCTCGCCATC GACGTCGTCG ATACCCCGAG GCCTTGGCCC    25080

CGCCACGAAG ATGGCAGTCC CCGCCGCGCC GGCATCTCCG CCTTCGGATT CTCGGGCACC    25140

AACGCCCACG TCATCCTCGA AGAGGCTCCC GCCGCCCTGC CGGCCGAGCC CGCCACCTCA    25200

CAGCCGGCGT CGCAAGCCGC TCCCGCGGCG TGGCCCGTGC TCCTGTCGGC CAGGAGCGAG    25260

GCCGCCGTCC GCGCCCAGGC GAAGCGGCTC CGCGACCACC TCGTCGCCCA CGACGACCTC    25320

ACCCTCGCGG ATGTGGCCTA TTCGCTGGCC ACCACCCGCG CCCACTTCGA GCACCGCGCC    25380

GCTCTCGTAG CCCACAACCG CGACGAGCTC CTCTCCGCGC TCGACTCGCT CGCCCAGGAC    25440

AAGCCCGCCC CGAGCACCGT CCTCGGACGG AGCGGAAGCC ACGGCAAGCT CGTCTTCGTC    25500

TTTCCTGGGC AAGGCTCGCA GTGGGAAGGG ATGGCCCTCT CGCTGCTCGA CTCCTCGCCC    25560

GTCTTCCGCG CTCAGCTCGA AGCATGCGAG CGCGCGCTCG CTCCTCACGT CGAGTGGAGC    25620

CTGCTCGCCG TCCTGCGCCG CGACGAGGGC GCCCCCTCCC TCGACCGCGT CGACGTCGTA    25680

CAGCCCGCCC TCTTTGCCGT CATGGTCTCC CTGGCGGCCC TCTGGCGCTC GCTCGGCGTA    25740

GAGCCCGCCG CCGTCGTCGG CCACAGTCAG GGCGAGATCG CCGCCGCCTT CGTCGCAGGC    25800

GCTCTCTCCC TCGAGGACGC GGCCCGCATC GCCGCCCTGC GCAGCAAAGC GCTCACCACC    25860

GTCGCCGGCA ACGGGGCCAT GGCCGCCGTC GAGCTCGGCG CCTCCGACCT CCAGACCTAC    25920

CTCGCTCCCT GGGGCGACAG GCTCTCCATC GCCGCCGTCA ACAGCCCCAG GGCCACGCTC    25980

GTGTCCGGCG AGCCCGCCGC CATCGACGCG CTGATCGACT CGCTCACCGC AGCGCAGGTC    26040

TTCGCCCGAA AAGTCCGCGT CGACTACGCC TCCCACTCCG CCCAGATGGA CGCCGTCCAA    26100

GACGAGCTCG CCGCAGGTCT AGCCAACATC GCTCCTCGGA CGTGCGAGCT CCCTCTTTAT    26160

TCGACCGTCA CCGGCACCAG GCTCGACGGC TCCGAGCTCG ACGGCGCGTA CTGGTATCGA    26220

AACCTCCGGC AAACCGTCCT GTTCTCGAGC GCGACCGAGC GGCTCCTCGA CGATGGGCAT    26280

CGCTTCTTCG TCGAGGTCAG CCCCCATCCC GTGCTCACGC TCGCCCTCCG CGAGACCTGC    26340
```

```
                                                        -continued

GAGCGCTCAC CGCTCGATCC CGTCGTCGTC GGCTCCATTC GACGCGACGA AGGCCACCTC   26400

GCCCGCCTGC TCCTCTCCTG GGCGGAGCTC TCTACCCGAG GCCTCGCGCT CGACTGGAAC   26460

GCCTTCTTCG CGCCCTTCGC TCCCCGCAAG GTCTCCCTCC CCACCTACCC CTTCCAACGC   26520

GAGCGCTTCT GGCTCGACGC CTCCACGGCG CACGCTGCCG ACGTCGCCTC CGCAGGCCTG   26580

ACCTCGGCCG ACCACCCGCT GCTCGGCGCC GCCGTCGCCC TCGCCGACCG CGATGGCTTT   26640

GTCTTCACAG GACGGCTCTC CCTCGCAGAG CACCCGTGGC TCGAAGACCA CGTCGTCTTC   26700

GGCATACCCT GTCCTGCCAG GCGCCGCCTC CTCGAGCTCG CCCTGCATGT CGCCCATCTC   26760

GTCGGCCTCG ACACCGTCGA AGACGTCACG CTCGACCCCC CCCTCGCTCT CCCATCGCAG   26820

GGCGCCGTCC TCCTCCAGAT CTCCGTCGGG CCCGCGGACG GTGCTGGACG AAGGGCGCTC   26880

TCCGTTCATA GCCGGCGCCA CGACGCGCTT CAGGATGGCC CCTGGACTCG CCACGCCAGC   26940

GGCTCTCTCG CGCAAGCTAG CCCGTCCCAT TGCCTTCGAT GCTCCGCGAA TGGCCCCCCC   27000

TCGGGCGCCA CCCAGGTGGA CACCCAAGGT TTCTACGCAG CCCTCGAGAG CGCTGGGCTT   27060

GCTTATGGCC CCGAGTTCCA GGGCCTCCGC CGCCGTCTAC AAGCGCGGCG ACGAGCTCTT   27120

CGCCGAAGCC AAGCTCCCGG ACGCCGCCGA AGAGGACGCC GCTCGTTTTG CCCTCCACCC   27180

CGCCCTGCTC GACAGCGCCT TGCAGGCGCT CGCCTTTGTA GACGACCAGG CAAAGGCCTT   27240

CAGGATGCCC TTCTCGTGGA GCGGAGTATC GCTGCGCTCC GGTCGGAGCC ACCACCCTGC   27300

GCGTGCGTTT CCACCGTCCT GAGGGCGAAT CCTCGCGCTC GCTCCTCCTC GCCGACGCCA   27360

GAGGCGAACC CATCGCCTCG GTGCAAGCGC TCGCCATGCG CGCCGCGTCC GCCGAGCAGC   27420

TCCGCAGACC CGGGAGCGTC CCACCTCGAT GCCCTCTTCC GCATCGACTG GAGCGAGCTG   27480

CAAAGCCCCA CCTCACCGCC CATCGCCCCG AGCGGTGCCC TCCTCGGCAC AGAAGGTCTC   27540

GACCTCGGGA CCAGGGTGCC TCTCGACCGC TATACCGACC TTGCTGCTCT ACGCAGCGCC   27600

CTCGACCAGG GCGCTTCGCC TCCAAGCCTC GTCATCGCCC CCTTCATCGC TCTGCCCGAA   27660

GGCGACCTCA TCGCGAGCGC CCGCGAGACC ACCGCGCACG CGCTCGCCCT CTTGCAAGCC   27720

TGGCTCGCCG ACGAGCGCCT CGCCTCCTCG CGCCTCGCCC TCGTCACCCG ACGCGCCGTC   27780

GCCACCCACG CTGAAGAAGA CGTCAAGGGC CTCGCTCACG CGCCTCTCTG GGGTCTCGCT   27840

CGCTCCGCGC AGAGCGAGCA CCCAGAGCGC CCTCTCGTCC TCGTCGACCT CGACGACAGC   27900

GAGGCCTCCC AGCACGCCCT GCTCGGCGCG CTCGACGCAA GAGAGCCAGA GATCGCCCTC   27960

CGCAACGGCA AACCCCTCGT TCCAAGGCTC TCACGCCTGC CCCAGGCGCC CACGGACACA   28020

GCGTCCCCCG CAGGCCTCGG AGGCACCGTC CTCATCACGG GAGGCACCGG CACGCTCGGC   28080

GCCCTGGTCG CGCGCCGCCT CGTCGTAAAC CACGACGCCA AGCACCTGCT CCTCACCTCG   28140

CGCCAGGGCG CGAGCGCTCC GGGTGCTGAT GTCTTGCGAA GCGAGCTCGA AGCTCTGGGG   28200

GCTTCGGTCA CCCTCGCCGC GTGCGACGTG GCCGATCCAC GCGCTCTAAA GGACCTTCTG   28260

GATAACATTC CGAGCGCTCA CCCGGTCGCC GCCGTCGTGC ATGCCGCCAG CGTCCTCGAC   28320

GGCGATCTGC TCGGCGCCAT GAGCCTCGAG CGGATCGACC GCGTCTTCGC CCCCAAGATC   28380

GATGCCGCCT GGCACTTGCA TCAGCTCACC CAAGATAAGC CCCTTGCCGC CTTCATCCTC   28440

TTCTCGTCCG TCGCCGGCGT CCTCGGCAGC TCAGGTCACT CCAACTACGC CGCTGCGAGC   28500

GCCTTCCTCG ATGCGCTTGC GCACCACCGG CGCGCGCAAG GGCTCCCTGC CTCATCGCTC   28560

GCGTGGAGCC ACTGGGCCGA GCGCAGCGCA ATGACAGAGC ACGTCAGCGC CGCCGGCGCC   28620

CCTCGCATGG AGCGCGCCGG CCTTCCCTCG ACCTCTGAGG AGAGGCTCGC CCTCTTCGAT   28680

GCGGCGCTCT TCCGAACCGA GACCGCCCTG GTCCCCGCGC GCTTCGACTT GAGCGCGCTC   28740
```

| | |
|---|---|
| AGGGCGAACG CCGGCAGCGT CCCCCCGTTG TTCCAACGTC TCGTCCGCGC TCGCACCGTA | 28800 |
| CGCAAGGCCG CCAGCAACAC CGCCCAGGCC TCGTCGCTTA CAGAGCGCCT CTCAGCCCTC | 28860 |
| CCGCCCGCCG AACGCGAGCG TGCCCTGCTC GATCTCATCC GCACCGAAGC CGCCGCCGTC | 28920 |
| CTCGGCCTCG CCTCCTTCGA ATCGCTCGAT CCCGATCG | 28958 |

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..13
        (D) OTHER INFORMATION: /note= "sequence of a plant
            consensus translation initiator (Clontech)"

(xi) SEQUENCE DESCRIPTION: SEQ ID NO:7:

| | |
|---|---|
| GTCGACCATG GTC | 13 |

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..12
        (D) OTHER INFORMATION: /note= "sequence of a plant
            consensus translation initiator (Joshi)"

(xi) SEQUENCE DESCRIPTION: SEQ ID NO:8:

| | |
|---|---|
| TAAACAATGG CT | 12 |

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..22
        (D) OTHER INFORMATION: /note= "sequence of an
            oligonucleotide for use in a molecular adaptor"

(xi) SEQUENCE DESCRIPTION: SEQ ID NO:9:

AATTCTAAAG CATGCCGATC GG                                          22

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..21
        (D) OTHER INFORMATION: /note= "sequence of an
            oligonucleotide for use in a molecular adaptor"

(xi) SEQUENCE DESCRIPTION: SEQ ID NO:10:

AATTCCGATC GGCATGCTTT A                                           21

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..22
        (D) OTHER INFORMATION: /note= "sequence of an
            oligonucleotide for use in a molecular adaptor"

(xi) SEQUENCE DESCRIPTION: SEQ ID NO:11:

AATTCTAAAC CATGGCGATC GG                                          22

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..21
        (D) OTHER INFORMATION: /note= "sequence of an
            oligonucleotide for use in a molecular adaptor"

(xi) SEQUENCE DESCRIPTION: SEQ ID NO:12:

AATTCCGATC GCCATGGTTT A                                           21

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..15
        (D) OTHER INFORMATION: /note= "sequence of an
            oligonucleotide for use in a molecular adaptor"

(xi) SEQUENCE DESCRIPTION: SEQ ID NO:13:

CCAGCTGGAA TTCCG                                        15

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..19
        (D) OTHER INFORMATION: /note= "sequence of an
            oligonucleotide for use in a molecular adaptor"

(xi) SEQUENCE DESCRIPTION: SEQ ID NO:14:

CGGAATTCCA GCTGGCATG                                  19

(2) INFORMATION FOR SEQ ID NO:15:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..11
        (D) OTHER INFORMATION: /note= "oligonucleotide used to
            introduce base change into SphI site of ORF1 of
            pyrrolnitrin gene cluster"

(xi) SEQUENCE DESCRIPTION: SEQ ID NO:15:

CCCCCTCATG C                                            11

(2) INFORMATION FOR SEQ ID NO:16:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..11
        (D) OTHER INFORMATION: /note= "oligonucleotide used to
            introduce base change into SphI site of ORF1 of
            pyrrolnitrin gene cluster"

(xi) SEQUENCE DESCRIPTION: SEQ ID NO:16:

GCATGAGGGG G                                                                                11

(2) INFORMATION FOR SEQ ID NO:17:

(i) SEQUENCE CHARACTERISTICS:
        (A) LENGTH: 4603 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 230..1594
        (D) OTHER INFORMATION: /gene= "phz1"
            /label= ORF1
            /note= "Open Reading Frame #1 for DNA sequence"

(ix) FEATURE:
        (A) NAME/KEY: CDS
        (B) LOCATION: 1598..2758
        (D) OTHER INFORMATION: /gene= "phz2"
            /label= ORF2
            /note= "Open Reading Frame #2 for DNA sequence"

(ix) FEATURE:
        (A) NAME/KEY: CDS
        (B) LOCATION: 2764..3597
        (D) OTHER INFORMATION: /gene= "phz3"
            /label= ORF3
            /note= "Open Reading Frame #3 for DNA sequence"

(ix) FEATURE:
        (A) NAME/KEY: misc_feature
        (B) LOCATION: 3597..4262
        (D) OTHER INFORMATION: /label= ORF4
            /note= "Open Reading Frame #4 of DNA sequence. This
            information is repeated in SEQ ID NO:21 due to
            overlapping ORFs."

(ix) FEATURE:
        (A) NAME/KEY: misc_feature
        (B) LOCATION: 1..4603
        (D) OTHER INFORMATION: /note= "Four open reading frames
        (ORFs) were identified within this DNA sequence as described
            in Example 18 of the specification."

(xi) SEQUENCE DESCRIPTION: SEQ ID NO:17:

GCATGCCGTG ACCTCCGCCG GTGGCGTGGC CGCCGGCCTG CACCTGGAAA CCACCCCTGA     60

CGACGTCAGC GAGTGCGCTT CCGATGCCGC CGGCCTGCAT CAGGTCGCCA GCCGCTACAA    120

AAGCCTGTGC GACCCGCGCC TGAACCCCTG GCAAGCCATT ACTGCGGTGA TGGCCTGGAA    180

-continued

```
AAACCAGCCC TCTTCAACCC TTGCCTCCTT TTGACTGGAG TTTGTCGTC ATG ACC             235
                                                      Met Thr
                                                        1

GGC ATT CCA TCG ATC GTC CCT TAC GCC TTG CCT ACC AAC CGC GAC CTG           283
Gly Ile Pro Ser Ile Val Pro Tyr Ala Leu Pro Thr Asn Arg Asp Leu
            5               10                  15

CCC GTC AAC CTC GCG CAA TGG AGC ATC GAC CCC GAG CGT GCC GTG CTG           331
Pro Val Asn Leu Ala Gln Trp Ser Ile Asp Pro Glu Arg Ala Val Leu
    20              25                  30

CTG GTG CAT GAC ATG CAG CGC TAC TTC CTG CGG CCC TTG CCC GAC GCC           379
Leu Val His Asp Met Gln Arg Tyr Phe Leu Arg Pro Leu Pro Asp Ala
35              40                  45                  50

CTG CGT GAC GAA GTC GTG AGC AAT GCC GCG CGC ATT CGC CAG TGG GCT           427
Leu Arg Asp Glu Val Val Ser Asn Ala Ala Arg Ile Arg Gln Trp Ala
                    55                  60                  65

GCC GAC AAC GGC GTT CCG GTG GCC TAC ACC GCC CAG CCC GGC AGC ATG           475
Ala Asp Asn Gly Val Pro Val Ala Tyr Thr Ala Gln Pro Gly Ser Met
                70                  75                  80

AGC GAG GAG CAA CGC GGG CTG CTC AAG GAC TTC TGG GGC CCG GGC ATG           523
Ser Glu Glu Gln Arg Gly Leu Leu Lys Asp Phe Trp Gly Pro Gly Met
            85                  90                  95

AAG GCC AGC CCC GCC GAC CGC GAG GTG GTC GGC GCC CTG ACG CCC AAG           571
Lys Ala Ser Pro Ala Asp Arg Glu Val Val Gly Ala Leu Thr Pro Lys
100                 105                 110

CCC GGC GAC TGG CTG CTG ACC AAG TGG CGC TAC AGC GCG TTC TTC AAC           619
Pro Gly Asp Trp Leu Leu Thr Lys Trp Arg Tyr Ser Ala Phe Phe Asn
115                 120                 125                 130

TCC GAC CTG CTG GAA CGC ATG CGC GCC AAC GGG CGC GAT CAG TTG ATC           667
Ser Asp Leu Leu Glu Arg Met Arg Ala Asn Gly Arg Asp Gln Leu Ile
                135                 140                 145

CTG TGC GGG GTG TAC GCC CAT GTC GGG GTA CTG ATT TCC ACC GTG GAT           715
Leu Cys Gly Val Tyr Ala His Val Gly Val Leu Ile Ser Thr Val Asp
                150                 155                 160

GCC TAC TCC AAC GAT ATC CAG CCG TTC CTC GTT GCC GAC GCG ATC GCC           763
Ala Tyr Ser Asn Asp Ile Gln Pro Phe Leu Val Ala Asp Ala Ile Ala
                165                 170                 175

GAC TTC AGC AAA GAG CAC CAC TGG ATG CCA TCG AAT ACG CCG CCA GCC           811
Asp Phe Ser Lys Glu His His Trp Met Pro Ser Asn Thr Pro Pro Ala
180                 185                 190

GTT GCG CCA TGT CAT CAC CAC CGA CGA GGT GGT GCT ATG AGC CAG ACC           859
Val Ala Pro Cys His His His Arg Arg Gly Gly Ala Met Ser Gln Thr
195                 200                 205                 210

GCA GCC CAC CTC ATG GAA CGC ATC CTG CAA CCG GCT CCC GAG CCG TTT           907
Ala Ala His Leu Met Glu Arg Ile Leu Gln Pro Ala Pro Glu Pro Phe
                215                 220                 225

GCC CTG TTG TAC CGC CCG GAA TCC AGT GGC CCC GGC CTG CTG GAC GTG           955
Ala Leu Leu Tyr Arg Pro Glu Ser Ser Gly Pro Gly Leu Leu Asp Val
                230                 235                 240

CTG ATC GGC GAA ATG TCG GAA CCG CAG GTC CTG GCC GAT ATC GAC TTG           1003
Leu Ile Gly Glu Met Ser Glu Pro Gln Val Leu Ala Asp Ile Asp Leu
                245                 250                 255

CCT GCC ACC TCG ATC GGC GCG CCT CGC CTG GAT GTA CTG GCG CTG ATC           1051
Pro Ala Thr Ser Ile Gly Ala Pro Arg Leu Asp Val Leu Ala Leu Ile
260                 265                 270

CCC TAC CGC CAG ATC GCC GAA CGC GGT TTC GAG GCG GTG GAC GAT GAG           1099
Pro Tyr Arg Gln Ile Ala Glu Arg Gly Phe Glu Ala Val Asp Asp Glu
275                 280                 285                 290

TCG CCG CTG CTG GCG ATG AAC ATC ACC GAG CAG CAA TCC ATC AGC ATC           1147
Ser Pro Leu Leu Ala Met Asn Ile Thr Glu Gln Gln Ser Ile Ser Ile
                295                 300                 305
```

| | | |
|---|---|---|
| GAG CGC TTG CTG GGA ATG CTG CCC AAC GTG CCG ATC CAG TTG AAC AGC | | 1195 |
| Glu Arg Leu Leu Gly Met Leu Pro Asn Val Pro Ile Gln Leu Asn Ser | | |
| 310 315 320 | | |
| GAA CGC TTC GAC CTC AGC GAC GCG AGC TAC GCC GAG ATC GTC AGC CAG | | 1243 |
| Glu Arg Phe Asp Leu Ser Asp Ala Ser Tyr Ala Glu Ile Val Ser Gln | | |
| 325 330 335 | | |
| GTG ATC GCC AAT GAA ATC GGC TCC GGG GAA GGC GCC AAC TTC GTC ATC | | 1291 |
| Val Ile Ala Asn Glu Ile Gly Ser Gly Glu Gly Ala Asn Phe Val Ile | | |
| 340 345 350 | | |
| AAA CGC ACC TTC CTG GCC GAG ATC AGC GAA TAC GGC CCG GCC AGT GCG | | 1339 |
| Lys Arg Thr Phe Leu Ala Glu Ile Ser Glu Tyr Gly Pro Ala Ser Ala | | |
| 355 360 365 370 | | |
| CTG TCG TTC TTT CGC CAT CTG CTG GAA CGG GAG AAA GGC GCC TAC TGG | | 1387 |
| Leu Ser Phe Phe Arg His Leu Leu Glu Arg Glu Lys Gly Ala Tyr Trp | | |
| 375 380 385 | | |
| ACG TTC ATC ATC CAC ACC GGC AGC CGT ACC TTC GTG GGT GCG TCC CCC | | 1435 |
| Thr Phe Ile Ile His Thr Gly Ser Arg Thr Phe Val Gly Ala Ser Pro | | |
| 390 395 400 | | |
| GAG CGC CAC ATC AGC ATC AAG GAT GGG CTC TCG GTG ATG AAC CCC ATC | | 1483 |
| Glu Arg His Ile Ser Ile Lys Asp Gly Leu Ser Val Met Asn Pro Ile | | |
| 405 410 415 | | |
| AGC GGC ACT TAC CGC TAT CCG CCC GCC GGC CCC AAC CTG TCG GAA GTC | | 1531 |
| Ser Gly Thr Tyr Arg Tyr Pro Pro Ala Gly Pro Asn Leu Ser Glu Val | | |
| 420 425 430 | | |
| ATG GAC TTC CTG GCG GAT CGC AAG GAA GCC GAC GAG CTC TAC ATG GTG | | 1579 |
| Met Asp Phe Leu Ala Asp Arg Lys Glu Ala Asp Glu Leu Tyr Met Val | | |
| 435 440 445 450 | | |
| GTG GAT GAA GAG CTG TAA ATG ATG GCG CGC ATT TGT GAG GAC GGC GGC | | 1627 |
| Val Asp Glu Glu Leu     Met Met Ala Arg Ile Cys Glu Asp Gly Gly | | |
| 455 1 5 10 | | |
| CAC GTC CTC GGC CCT TAC CTC AAG GAA ATG GCG CAC CTG GCC CAC ACC | | 1675 |
| His Val Leu Gly Pro Tyr Leu Lys Glu Met Ala His Leu Ala His Thr | | |
| 15 20 25 | | |
| GAG TAC TTC ATC GAA GGC AAG ACC CAT CGC GAT GTA CGG GAA ATC CTG | | 1723 |
| Glu Tyr Phe Ile Glu Gly Lys Thr His Arg Asp Val Arg Glu Ile Leu | | |
| 30 35 40 | | |
| CGC GAA ACC CTG TTT GCG CCC ACC GTC ACC GGC AGC CCA CTG GAA AGC | | 1771 |
| Arg Glu Thr Leu Phe Ala Pro Thr Val Thr Gly Ser Pro Leu Glu Ser | | |
| 45 50 55 | | |
| GCC TGC CGG GTC ATC CAG CGC TAT GAN CCG CAA GGC CGC GCG TAC TAC | | 1819 |
| Ala Cys Arg Val Ile Gln Arg Tyr Xaa Pro Gln Gly Arg Ala Tyr Tyr | | |
| 60 65 70 | | |
| AGC GGC ATG GCT GCG CTG ATC GGC AGC GAT GGC AAG GGC GGG CGT TCC | | 1867 |
| Ser Gly Met Ala Ala Leu Ile Gly Ser Asp Gly Lys Gly Gly Arg Ser | | |
| 75 80 85 90 | | |
| CTG GAC TCC GCG ATC CTG ATT CGT ACC GCC GAC ATC GAT AAC AGC GGC | | 1915 |
| Leu Asp Ser Ala Ile Leu Ile Arg Thr Ala Asp Ile Asp Asn Ser Gly | | |
| 95 100 105 | | |
| GAG GTG CGG ATC AGC GTG GGC TCG ACC ATC GTG CGC CAT TCC GAC CCG | | 1963 |
| Glu Val Arg Ile Ser Val Gly Ser Thr Ile Val Arg His Ser Asp Pro | | |
| 110 115 120 | | |
| ATG ACC GAG GCT GCC GAA AGC CGG GCC AAG GCC ACT GGC CTG ATC AGC | | 2011 |
| Met Thr Glu Ala Ala Glu Ser Arg Ala Lys Ala Thr Gly Leu Ile Ser | | |
| 125 130 135 | | |
| GCA CTG AAA AAC CAG GCG CCC TCG CGC TTC GGC AAT CAC CTG CAA GTG | | 2059 |
| Ala Leu Lys Asn Gln Ala Pro Ser Arg Phe Gly Asn His Leu Gln Val | | |
| 140 145 150 | | |
| CGC GCC GCA TTG GCC AGC CGC AAT GCC TAC GTC TCG GAC TTC TGG CTG | | 2107 |
| Arg Ala Ala Leu Ala Ser Arg Asn Ala Tyr Val Ser Asp Phe Trp Leu | | |
| 155 160 165 170 | | |

-continued

| | |
|---|---|
| ATG GAC AGC CAG CAG CGG GAG CAG ATC CAG GCC GAC TTC AGT GGG CGC<br>Met Asp Ser Gln Gln Arg Glu Gln Ile Gln Ala Asp Phe Ser Gly Arg<br>                      175                      180                      185 | 2155 |
| CAG GTG CTG ATC GTC GAC GCC GAA GAC ACC TTC ACC TCG ATG ATC GCC<br>Gln Val Leu Ile Val Asp Ala Glu Asp Thr Phe Thr Ser Met Ile Ala<br>                      190                      195                      200 | 2203 |
| AAG CAA CTG CGG GCC CTG GGC CTG GTA GTG ACG GTG TGC AGC TTC AGC<br>Lys Gln Leu Arg Ala Leu Gly Leu Val Val Thr Val Cys Ser Phe Ser<br>                      205                      210                      215 | 2251 |
| GAC GAA TAC AGC TTT GAA GGC TAC GAC CTG GTC ATC ATG GGC CCC GGC<br>Asp Glu Tyr Ser Phe Glu Gly Tyr Asp Leu Val Ile Met Gly Pro Gly<br>        220                      225                      230 | 2299 |
| CCC GGC AAC CCG AGC GAA GTC CAA CAG CCG AAA ATC AAC CAC CTG CAC<br>Pro Gly Asn Pro Ser Glu Val Gln Gln Pro Lys Ile Asn His Leu His<br>235                      240                      245                      250 | 2347 |
| GTG GCC ATC CGC TCC TTG CTC AGC CAG CAG CGG CCA TTC CTC GCG GTG<br>Val Ala Ile Arg Ser Leu Leu Ser Gln Gln Arg Pro Phe Leu Ala Val<br>                      255                      260                      265 | 2395 |
| TGC CTG AGC CAT CAG GTG CTG AGC CTG TGC CTG GGC CTG GAA CTG CAG<br>Cys Leu Ser His Gln Val Leu Ser Leu Cys Leu Gly Leu Glu Leu Gln<br>                270                      275                      280 | 2443 |
| CGC AAA GCC ATT CCC AAC CAG GGC GTG CAA AAA CAG ATC GAC CTG TTT<br>Arg Lys Ala Ile Pro Asn Gln Gly Val Gln Lys Gln Ile Asp Leu Phe<br>                      285                      290                      295 | 2491 |
| GGC AAT GTC GAA CGG GTG GGT TTC TAC AAC ACC TTC GCC GCC CAG AGC<br>Gly Asn Val Glu Arg Val Gly Phe Tyr Asn Thr Phe Ala Ala Gln Ser<br>300                      305                      310 | 2539 |
| TCG AGT GAC CGC CTG GAC ATC GAC GGC ATC GGC ACC GTC GAA ATC AGC<br>Ser Ser Asp Arg Leu Asp Ile Asp Gly Ile Gly Thr Val Glu Ile Ser<br>315                      320                      325                      330 | 2587 |
| CGC GAC AGC GAG ACC GGC GAG GTG CAT GCC CTG CGT GGC CCC TCG TTC<br>Arg Asp Ser Glu Thr Gly Glu Val His Ala Leu Arg Gly Pro Ser Phe<br>                335                      340                      345 | 2635 |
| GCC TCC ATG CAG TTT CAT GCC GAG TCG CTG CTG ACC CAG GAA GGT CCG<br>Ala Ser Met Gln Phe His Ala Glu Ser Leu Leu Thr Gln Glu Gly Pro<br>                350                      355                      360 | 2683 |
| CGC ATC ATC GCC GAC CTG CTG CGG CAC GCC CTG ATC CAC ACA CCT GTC<br>Arg Ile Ile Ala Asp Leu Leu Arg His Ala Leu Ile His Thr Pro Val<br>                365                      370                      375 | 2731 |
| GAG AAC AAC GCT TCG GCC GCC GGG AGA TAACC ATG CAC CAT TAC GTC<br>Glu Asn Asn Ala Ser Ala Ala Gly Arg      Met His His Tyr Val<br>380                      385                                1                      5 | 2778 |
| ATC ATC GAC GCC TTT GCC AGC GTC CCG CTG GAA GGC AAT CCG GTC GCG<br>Ile Ile Asp Ala Phe Ala Ser Val Pro Leu Glu Gly Asn Pro Val Ala<br>                      10                        15                        20 | 2826 |
| GTG TTC TTT GAC GCC GAT GAC TTG TCG GCC GAG CAA ATG CAA CGC ATT<br>Val Phe Phe Asp Ala Asp Asp Leu Ser Ala Glu Gln Met Gln Arg Ile<br>                25                        30                        35 | 2874 |
| GCC CGG GAG ATG AAC CTG TCG GAA ACC ACT TTC GTG CTC AAG CCA CGT<br>Ala Arg Glu Met Asn Leu Ser Glu Thr Thr Phe Val Leu Lys Pro Arg<br>        40                      45                      50 | 2922 |
| AAC TGC GGC GAT GCG CTG ATC CGG ATC TTC ACC CCG GTC AAC GAA CTG<br>Asn Cys Gly Asp Ala Leu Ile Arg Ile Phe Thr Pro Val Asn Glu Leu<br>        55                      60                      65 | 2970 |
| CCC TTC GCC GGG CAC CCG TTG CTG GGC ACG GAC ATT GCC CTG GGT GCG<br>Pro Phe Ala Gly His Pro Leu Leu Gly Thr Asp Ile Ala Leu Gly Ala<br>70                      75                      80                      85 | 3018 |
| CGC ACC GAC AAT CAC CGG CTG TTC CTG GAA ACC CAG ATG GGC ACC ATC<br>Arg Thr Asp Asn His Arg Leu Phe Leu Glu Thr Gln Met Gly Thr Ile<br>                90                      95                      100 | 3066 |

-continued

| | |
|---|---|
| GCC TTT GAG CTG GAG CGC CAG AAC GGC AGC GTC ATC GCC GCC AGC ATG<br>Ala Phe Glu Leu Glu Arg Gln Asn Gly Ser Val Ile Ala Ala Ser Met<br>105                                    110                          115 | 3114 |
| GAC CAG CCG ATA CCG ACC TGG ACG GCC CTG GGG CGC GAC GCC GAG TTG<br>Asp Gln Pro Ile Pro Thr Trp Thr Ala Leu Gly Arg Asp Ala Glu Leu<br>            120                            125                            130 | 3162 |
| CTC AAG GCC CTG GGC ATC AGC GAC TCG ACC TTT CCC ATC GAG ATC TAT<br>Leu Lys Ala Leu Gly Ile Ser Asp Ser Thr Phe Pro Ile Glu Ile Tyr<br>135                                    140                          145 | 3210 |
| CAC AAC GGC CCG CGT CAT GTG TTT GTC GGC CTG CCA AGC ATC GCC GCG<br>His Asn Gly Pro Arg His Val Phe Val Gly Leu Pro Ser Ile Ala Ala<br>150                           155                            160                   165 | 3258 |
| CTG TCG GCC CTG CAC CCC GAC CAC CGT GCC CTG TAC AGC TTC CAC GAC<br>Leu Ser Ala Leu His Pro Asp His Arg Ala Leu Tyr Ser Phe His Asp<br>            170                            175                            180 | 3306 |
| ATG GCC ATC AAC TGT TTT GCC GGT GCG GGA CGG CGC TGG CGC AGC CGG<br>Met Ala Ile Asn Cys Phe Ala Gly Ala Gly Arg Arg Trp Arg Ser Arg<br>                  185                            190                            195 | 3354 |
| ATG TTC TCG CCG GCC TAT GGG GTG GTC GAG GAT GCG NCC ACG GGC TCC<br>Met Phe Ser Pro Ala Tyr Gly Val Val Glu Asp Ala Xaa Thr Gly Ser<br>200                                    205                          210 | 3402 |
| GCT GCC GGG CCC TTG GCG ATC CAT CTG GCG CGG CAT GGC CAG ATC GAG<br>Ala Ala Gly Pro Leu Ala Ile His Leu Ala Arg His Gly Gln Ile Glu<br>            215                            220                            225 | 3450 |
| TTC GGC CAG CAG ATC GAA ATT CTT CAG GGC GTG GAA ATC GGC CGC CCC<br>Phe Gly Gln Gln Ile Glu Ile Leu Gln Gly Val Glu Ile Gly Arg Pro<br>230                                    235                          240                   245 | 3498 |
| TCA CTC ATG TTC GCC CGG GCC GAG GGC CGC GCC GAT CAA CTG ACG CGG<br>Ser Leu Met Phe Ala Arg Ala Glu Gly Arg Ala Asp Gln Leu Thr Arg<br>                  250                            255                            260 | 3546 |
| GTC GAA GTA TCA GGC AAT GGC ATC ACC TTC GGA CGG GGG ACC ATC GTT<br>Val Glu Val Ser Gly Asn Gly Ile Thr Phe Gly Arg Gly Thr Ile Val<br>            265                            270                            275 | 3594 |
| CTA TGAACAGTTC AGTACTAGGC AAGCCGCTGT TGGGTAAAGG CATGTCGGAA<br>Leu | 3647 |
| TCGCTGACCG GCACACTGGA TGCGCCGTTC CCCGAGTACC AGAAGCCGCC TGCCGATCCC | 3707 |
| ATGAGCGTGC TGCACAACTG GCTCGAACGC GCACGCCGCG TGGGCATCCG CGAACCCCGT | 3767 |
| GCGCTGGCGC TGGCCACGGC TGACAGCCAG GGCCGGCCTT CGACACGCAT CGTGGTGATC | 3827 |
| AGTGAGATCA GTGACACCGG GGTGCTGTTC AGCACCCATG CCGGAAGCCA GAAAGGCCGC | 3887 |
| GAACTGACAG AGAACCCCTG GCCTCGGGG ACGCTGTATT GGCGCGAAAC CAGCCAGCAG | 3947 |
| ATCATCCTCA ATGGCCAGGC CGTGCGCATG CCGGATGCCA AGGCTGACGA GGCCTGGTTG | 4007 |
| AAGCGCCCTT ATGCCACGCA TCCGATGTCA TCGGTGTCTC GCCAGAGTGA AGAACTCAAG | 4067 |
| GATGTTCAAG CCATGCGCAA CGCCGCCAGG GAACTGGCCG AGGTTCAAGG TCCGCTGCCG | 4127 |
| CGTCCCGAGG GTTATTGCGT GTTTGAGTTA CGGCTTGAAT CGCTGGAGTT CTGGGGTAAC | 4187 |
| GGCGAGGAGC GCCTGCATGA ACGCTTGCGC TATGACCGCA GCGCTGAAGG CTGGAAACAT | 4247 |
| CGCCGGTTAC AGCCATAGGG TCCCGCGATA AACATGCTTT GAAGTGCCTG GCTGCTCCAG | 4307 |
| CTTCGAACTC ATTGCGCAAA CTTCAACACT TATGACACCC GGTCAACATG AGAAAAGTCC | 4367 |
| AGATGCGAAA GAACGCGTAT TCGAAATACC AAACAGAGAG TCCGGATCAC CAAAGTGTGT | 4427 |
| AACGACATTA ACTCCTATCT GAATTTTATA GTTGCTCTAG AACGTTGTCC TTGACCCAGC | 4487 |
| GATAGACATC GGGCCAGAAC CTACATAAAC AAAGTCAGAC ATTACTGAGG CTGCTACCAT | 4547 |
| GCTAGATTTT CAAAACAAGC GTAAATATCT GAAAAGTGCA GAATCCTTCA AAGCTT | 4603 |

(2) INFORMATION FOR SEQ ID NO:18:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:18:

```
Met Thr Gly Ile Pro Ser Ile Val Pro Tyr Ala Leu Pro Thr Asn Arg
 1               5                  10                  15

Asp Leu Pro Val Asn Leu Ala Gln Trp Ser Ile Asp Pro Glu Arg Ala
            20                  25                  30

Val Leu Leu Val His Asp Met Gln Arg Tyr Phe Leu Arg Pro Leu Pro
        35                  40                  45

Asp Ala Leu Arg Asp Glu Val Val Ser Asn Ala Ala Arg Ile Arg Gln
    50                  55                  60

Trp Ala Ala Asp Asn Gly Val Pro Val Ala Tyr Thr Ala Gln Pro Gly
65                  70                  75                  80

Ser Met Ser Glu Glu Gln Arg Gly Leu Leu Lys Asp Phe Trp Gly Pro
                85                  90                  95

Gly Met Lys Ala Ser Pro Ala Asp Arg Glu Val Val Gly Ala Leu Thr
            100                 105                 110

Pro Lys Pro Gly Asp Trp Leu Leu Thr Lys Trp Arg Tyr Ser Ala Phe
        115                 120                 125

Phe Asn Ser Asp Leu Leu Glu Arg Met Arg Ala Asn Gly Arg Asp Gln
    130                 135                 140

Leu Ile Leu Cys Gly Val Tyr Ala His Val Gly Val Leu Ile Ser Thr
145                 150                 155                 160

Val Asp Ala Tyr Ser Asn Asp Ile Gln Pro Phe Leu Val Ala Asp Ala
                165                 170                 175

Ile Ala Asp Phe Ser Lys Glu His His Trp Met Pro Ser Asn Thr Pro
            180                 185                 190

Pro Ala Val Ala Pro Cys His His Arg Arg Gly Gly Ala Met Ser
        195                 200                 205

Gln Thr Ala Ala His Leu Met Glu Arg Ile Leu Gln Pro Ala Pro Glu
    210                 215                 220

Pro Phe Ala Leu Leu Tyr Arg Pro Glu Ser Ser Gly Pro Gly Leu Leu
225                 230                 235                 240

Asp Val Leu Ile Gly Glu Met Ser Glu Pro Gln Val Leu Ala Asp Ile
                245                 250                 255

Asp Leu Pro Ala Thr Ser Ile Gly Ala Pro Arg Leu Asp Val Leu Ala
            260                 265                 270

Leu Ile Pro Tyr Arg Gln Ile Ala Glu Arg Gly Phe Glu Ala Val Asp
        275                 280                 285

Asp Glu Ser Pro Leu Leu Ala Met Asn Ile Thr Glu Gln Gln Ser Ile
    290                 295                 300

Ser Ile Glu Arg Leu Leu Gly Met Leu Pro Asn Val Pro Ile Gln Leu
305                 310                 315                 320

Asn Ser Glu Arg Phe Asp Leu Ser Asp Ala Ser Tyr Ala Glu Ile Val
                325                 330                 335

Ser Gln Val Ile Ala Asn Glu Ile Gly Ser Glu Gly Ala Asn Phe
            340                 345                 350

Val Ile Lys Arg Thr Phe Leu Ala Glu Ile Ser Glu Tyr Gly Pro Ala
        355                 360                 365
```

```
Ser Ala Leu Ser Phe Phe Arg His Leu Leu Glu Arg Glu Lys Gly Ala
    370             375                 380
Tyr Trp Thr Phe Ile Ile His Thr Gly Ser Arg Thr Phe Val Gly Ala
385                 390                 395                 400
Ser Pro Glu Arg His Ile Ser Ile Lys Asp Gly Leu Ser Val Met Asn
                405                 410                 415
Pro Ile Ser Gly Thr Tyr Arg Tyr Pro Pro Ala Gly Pro Asn Leu Ser
                420                 425                 430
Glu Val Met Asp Phe Leu Ala Asp Arg Lys Glu Ala Asp Glu Leu Tyr
                435                 440                 445
Met Val Val Asp Glu Glu Leu
    450             455
```

(2) INFORMATION FOR SEQ ID NO:19:

(i) SEQUENCE CHARACTERISTICS:
        (A) LENGTH: 387 amino acids
        (B) TYPE: amino acid
        (D) TOPOLOGY: linear (ii) MOLECULE TYPE: protein (xi) SEQUENCE DESCRIPTION: SEQ ID NO:19:

```
Met Met Ala Arg Ile Cys Glu Asp Gly Gly His Val Leu Gly Pro Tyr
1               5                   10                  15
Leu Lys Glu Met Ala His Leu Ala His Thr Glu Tyr Phe Ile Glu Gly
                20                  25                  30
Lys Thr His Arg Asp Val Arg Glu Ile Leu Arg Glu Thr Leu Phe Ala
                35                  40                  45
Pro Thr Val Thr Gly Ser Pro Leu Glu Ser Ala Cys Arg Val Ile Gln
    50                  55                  60
Arg Tyr Xaa Pro Gln Gly Arg Ala Tyr Tyr Ser Gly Met Ala Ala Leu
65                  70                  75                  80
Ile Gly Ser Asp Gly Lys Gly Gly Arg Ser Leu Asp Ser Ala Ile Leu
                85                  90                  95
Ile Arg Thr Ala Asp Ile Asp Asn Ser Gly Glu Val Arg Ile Ser Val
                100                 105                 110
Gly Ser Thr Ile Val Arg His Ser Asp Pro Met Thr Glu Ala Ala Glu
                115                 120                 125
Ser Arg Ala Lys Ala Thr Gly Leu Ile Ser Ala Leu Lys Asn Gln Ala
                130                 135                 140
Pro Ser Arg Phe Gly Asn His Leu Gln Val Arg Ala Ala Leu Ala Ser
145                 150                 155                 160
Arg Asn Ala Tyr Val Ser Asp Phe Trp Leu Met Asp Ser Gln Gln Arg
                165                 170                 175
Glu Gln Ile Gln Ala Asp Phe Ser Gly Arg Gln Val Leu Ile Val Asp
                180                 185                 190
Ala Glu Asp Thr Phe Thr Ser Met Ile Ala Lys Gln Leu Arg Ala Leu
                195                 200                 205
Gly Leu Val Val Thr Val Cys Ser Phe Ser Asp Glu Tyr Ser Phe Glu
                210                 215                 220
Gly Tyr Asp Leu Val Ile Met Gly Pro Gly Pro Gly Asn Pro Ser Glu
225                 230                 235                 240
Val Gln Gln Pro Lys Ile Asn His Leu His Val Ala Ile Arg Ser Leu
                245                 250                 255
```

```
Leu Ser Gln Gln Arg Pro Phe Leu Ala Val Cys Leu Ser His Gln Val
            260                 265                 270

Leu Ser Leu Cys Leu Gly Leu Glu Leu Gln Arg Lys Ala Ile Pro Asn
            275                 280                 285

Gln Gly Val Gln Lys Gln Ile Asp Leu Phe Gly Asn Val Glu Arg Val
            290                 295                 300

Gly Phe Tyr Asn Thr Phe Ala Ala Gln Ser Ser Asp Arg Leu Asp
305                 310                 315                 320

Ile Asp Gly Ile Gly Thr Val Glu Ile Ser Arg Asp Ser Glu Thr Gly
                    325                 330                 335

Glu Val His Ala Leu Arg Gly Pro Ser Phe Ala Ser Met Gln Phe His
            340                 345                 350

Ala Glu Ser Leu Leu Thr Gln Glu Gly Pro Arg Ile Ile Ala Asp Leu
            355                 360                 365

Leu Arg His Ala Leu Ile His Thr Pro Val Glu Asn Asn Ala Ser Ala
            370                 375                 380

Ala Gly Arg
385

(2) INFORMATION FOR SEQ ID NO:20:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO:20:

Met His His Tyr Val Ile Ile Asp Ala Phe Ala Ser Val Pro Leu Glu
  1                 5                  10                  15

Gly Asn Pro Val Ala Val Phe Asp Ala Asp Asp Leu Ser Ala Glu
            20                  25                  30

Gln Met Gln Arg Ile Ala Arg Glu Met Asn Leu Ser Glu Thr Thr Phe
            35                  40                  45

Val Leu Lys Pro Arg Asn Cys Gly Asp Ala Leu Ile Arg Ile Phe Thr
 50                  55                  60

Pro Val Asn Glu Leu Pro Phe Ala Gly His Pro Leu Leu Gly Thr Asp
 65                  70                  75                  80

Ile Ala Leu Gly Ala Arg Thr Asp Asn His Arg Leu Phe Leu Glu Thr
                    85                  90                  95

Gln Met Gly Thr Ile Ala Phe Gly Leu Glu Arg Gln Asn Gly Ser Val
            100                 105                 110

Ile Ala Ala Ser Met Asp Gln Pro Ile Pro Thr Trp Thr Ala Leu Gly
            115                 120                 125

Arg Asp Ala Glu Leu Leu Lys Ala Leu Gly Ile Ser Asp Ser Thr Phe
            130                 135                 140

Pro Ile Glu Ile Tyr His Asn Gly Pro Arg His Val Phe Val Gly Leu
145                 150                 155                 160

Pro Ser Ile Ala Ala Leu Ser Ala Leu His Pro Asp His Arg Ala Leu
                    165                 170                 175

Tyr Ser Phe His Asp Met Ala Ile Asn Cys Phe Ala Gly Ala Gly Arg
            180                 185                 190

Arg Trp Arg Ser Arg Met Phe Ser Pro Ala Tyr Gly Val Val Glu Asp
            195                 200                 205
```

```
Ala Xaa Thr Gly Ser Ala Ala Gly Pro Leu Ala Ile His Leu Ala Arg
    210                 215                 220

His Gly Gln Ile Glu Phe Gly Gln Gln Ile Glu Ile Leu Gln Gly Val
225                 230                 235                 240

Glu Ile Gly Arg Pro Ser Leu Met Phe Ala Arg Ala Glu Gly Arg Ala
            245                 250                 255

Asp Gln Leu Thr Arg Val Glu Val Ser Gly Asn Gly Ile Thr Phe Gly
            260                 265                 270

Arg Gly Thr Ile Val Leu
        275
```

(2) INFORMATION FOR SEQ ID NO:21:

(i) SEQUENCE CHARACTERISTICS:
        (A) LENGTH: 1007 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..669
        (D) OTHER INFORMATION: /gene= "phz4"
            /label= ORF4
            /note= "This DNA sequence is repeated from SEQ ID
            NO:17 so that the overlapping ORF4 may be
            separately translated"

(xi) SEQUENCE DESCRIPTION: SEQ ID NO:21:

```
ATG AAC AGT TCA GTA CTA GGC AAG CCG CTG TTG GGT AAA GGC ATG TCG        48
Met Asn Ser Ser Val Leu Gly Lys Pro Leu Leu Gly Lys Gly Met Ser
 1               5                  10                  15

GAA TCG CTG ACC GGC ACA CTG GAT GCG CCG TTC CCC GAG TAC CAG AAG        96
Glu Ser Leu Thr Gly Thr Leu Asp Ala Pro Phe Pro Glu Tyr Gln Lys
                 20                  25                  30

CCG CCT GCC GAT CCC ATG AGC GTG CTG CAC AAC TGG CTC GAA CGC GCA       144
Pro Pro Ala Asp Pro Met Ser Val Leu His Asn Trp Leu Glu Arg Ala
             35                  40                  45

CGC CGC GTG GGC ATC CGC GAA CCC CGT GCG CTG GCG CTG GCC ACG GCT       192
Arg Arg Val Gly Ile Arg Glu Pro Arg Ala Leu Ala Leu Ala Thr Ala
         50                  55                  60

GAC AGC CAG GGC CGG CCT TCG ACA CGC ATC GTG GTG ATC AGT GAG ATC       240
Asp Ser Gln Gly Arg Pro Ser Thr Arg Ile Val Val Ile Ser Glu Ile
 65                  70                  75                  80

AGT GAC ACC GGG GTG CTG TTC AGC ACC CAT GCC GGA AGC CAG AAA GGC       288
Ser Asp Thr Gly Val Leu Phe Ser Thr His Ala Gly Ser Gln Lys Gly
                 85                  90                  95

CGC GAA CTG ACA GAG AAC CCC TGG GCC TCG GGG ACG CTG TAT TGG CGC       336
Arg Glu Leu Thr Glu Asn Pro Trp Ala Ser Gly Thr Leu Tyr Trp Arg
            100                 105                 110

GAA ACC AGC CAG CAG ATC ATC CTC AAT GGC CAG GCC GTG CGC ATG CCG       384
Glu Thr Ser Gln Gln Ile Ile Leu Asn Gly Gln Ala Val Arg Met Pro
        115                 120                 125

GAT GCC AAG GCT GAC GAG GCC TGG TTG AAG CGC CCT TAT GCC ACG CAT       432
Asp Ala Lys Ala Asp Glu Ala Trp Leu Lys Arg Pro Tyr Ala Thr His
    130                 135                 140
```

```
CCG ATG TCA TCG GTG TCT CGC CAG AGT GAA GAA CTC AAG GAT GTT CAA        480
Pro Met Ser Ser Val Ser Arg Gln Ser Glu Glu Leu Lys Asp Val Gln
145                 150                 155                 160

GCC ATG CGC AAC GCC GCC AGG GAA CTG GCC GAG GTT CAA GGT CCG CTG        528
Ala Met Arg Asn Ala Ala Arg Glu Leu Ala Glu Val Gln Gly Pro Leu
                165                 170                 175

CCG CGT CCC GAG GGT TAT TGC GTG TTT GAG TTA CGG CTT GAA TCG CTG        576
Pro Arg Pro Glu Gly Tyr Cys Val Phe Glu Leu Arg Leu Glu Ser Leu
            180                 185                 190

GAG TTC TGG GGT AAC GGC GAG GAG CGC CTG CAT GAA CGC TTG CGC TAT        624
Glu Phe Trp Gly Asn Gly Glu Glu Arg Leu His Glu Arg Leu Arg Tyr
                195                 200                 205

GAC CGC AGC GCT GAA GGC TGG AAA CAT CGC CGG TTA CAG CCA TAGGGTCCCG    676
Asp Arg Ser Ala Glu Gly Trp Lys His Arg Arg Leu Gln Pro
210                 215                 220

CGATAAACAT GCTTTGAAGT GCCTGGCTGC TCCAGCTTCG AACTCATTGC GCAAACTTCA     736

ACACTTATGA CACCCGGTCA ACATGAGAAA AGTCCAGATG CGAAAGAACG CGTATTCGAA    796

ATACCAAACA GAGAGTCCGG ATACCCAAAG TGTGTAACGA CATTAACTCC TATCTGAATT    856

TTATAGTTGC TCTAGAACGT TGTCCTTGAC CCAGCGATAG ACATCGGGCC AGAACCTACA    916

TAAACAAAGT CAGACATTAC TGAGGCTGCT ACCATGCTAG ATTTTCAAAA CAAGCGTAAA    976

TATCTGAAAA GTGCAGAATC CTTCAAAGCT T                                   1007

(2) INFORMATION FOR SEQ ID NO:22:

(i) SEQUENCE CHARACTERISTICS:
        (A) LENGTH: 222 amino acids
        (B) TYPE: amino acid
        (D) TOPOLOGY: linear (ii) MOLECULE TYPE: protein (xi) SEQUENCE DESCRIPTION: SEQ ID NO:22:

Met Asn Ser Ser Val Leu Gly Lys Pro Leu Leu Gly Lys Gly Met Ser
1               5                   10                  15

Glu Ser Leu Thr Gly Thr Leu Asp Ala Pro Phe Pro Glu Tyr Gln Lys
            20                  25                  30

Pro Pro Ala Asp Pro Met Ser Val Leu His Asn Trp Leu Glu Arg Ala
        35                  40                  45

Arg Arg Val Gly Ile Arg Glu Pro Arg Ala Leu Ala Leu Ala Thr Ala
    50                  55                  60

Asp Ser Gln Gly Arg Pro Ser Thr Arg Ile Val Val Ile Ser Glu Ile
65                  70                  75                  80

Ser Asp Thr Gly Val Leu Phe Ser Thr His Ala Gly Ser Gln Lys Gly
                85                  90                  95

Arg Glu Leu Thr Glu Asn Pro Trp Ala Ser Gly Thr Leu Tyr Trp Arg
            100                 105                 110

Glu Thr Ser Gln Gln Ile Ile Leu Asn Gly Gln Ala Val Arg Met Pro
        115                 120                 125

Asp Ala Lys Ala Asp Glu Ala Trp Leu Lys Arg Pro Tyr Ala Thr His
    130                 135                 140

Pro Met Ser Ser Val Ser Arg Gln Ser Glu Glu Leu Lys Asp Val Gln
145                 150                 155                 160

Ala Met Arg Asn Ala Ala Arg Glu Leu Ala Glu Val Gln Gly Pro Leu
                165                 170                 175

Pro Arg Pro Glu Gly Tyr Cys Val Phe Glu Leu Arg Leu Glu Ser Leu
            180                 185                 190
```

-continued

```
Glu Phe Trp Gly Asn Gly Glu Glu Arg Leu His Glu Arg Leu Arg Tyr
        195                 200                 205

Asp Arg Ser Ala Glu Gly Trp Lys His Arg Arg Leu Gln Pro
    210                 215                 220
```

(2) INFORMATION FOR SEQ ID NO:23:

(i) SEQUENCE CHARACTERISTICS:
        (A) LENGTH: 6250 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 615..2228
        (D) OTHER INFORMATION: /product= "PrnA"

(ix) FEATURE:
        (A) NAME/KEY: CDS
        (B) LOCATION: 2231..3313
        (D) OTHER INFORMATION: /product= "PrnB"

(ix) FEATURE:
        (A) NAME/KEY: CDS
        (B) LOCATION: 3368..5065
        (D) OTHER INFORMATION: /product= "PrnC"

(ix) FEATURE:
        (A) NAME/KEY: CDS
        (B) LOCATION: 5093..6202
        (D) OTHER INFORMATION: /product= "PrnD"

(xi) SEQUENCE DESCRIPTION: SEQ ID NO:23:

```
GAATTCATTC GTTCATTTCG CATTTATATA CAATAAATCC ATCGGTGCAC ACACCCCCAA      60

TTAAAGAGAG AATTTGTTTT TAAAAAAGTA AATAGTTTGC CGAAAAATAT TCACCGATAT     120

TTTCCGGGAT TGAGTATCTC TCTGGATCAA TTGAGATTGA TATGAAATTT TGCGAGGTGT     180

GCCATCGTGA ACACTGCTAT GGTGTATCGG AGTTACGTGC ATGGCACGGC AAGCCTCGGG     240

ATGCTGACGT TGCCTGAGCA TCTCGATGCG CTAATGGCGA TTGCCGCATC GGCAAGTCAT     300

TCTGTTGATT CGGCATCCCT TACGCGGTGT GCCGCCGATG CGATGGGCGC CTCGCATGGT     360

TCGATTGTGC TTCCATTTGA ACTGAGAGGG TAACAGCCTC AGATCAAACT CCGGGGCTGT     420

CGGTAAGGAT GTCCGGATAT TGCGTGAAGG GCGTCCTCCA TTTTGCCGAA CTTCGCTACG     480

ATTCGCTCTG CCTTCCCGGT GTCATTTGTC GTGAAGAGCC CGACACGTCA TGACGCGTTA     540

CCGGACGAGT TGCGAGTTCA GCTCGACAAG GCGGCACTAT CCATTCAGGT TTTAAATCCT     600

ATGAGAAACG TGTC ATG AGC AAC CCG ATC AAG AAT ATC GTC ATC GTG GGC      650
              Met Ser Asn Pro Ile Lys Asn Ile Val Ile Val Gly
                1               5                  10

GGC GGC ACC GCG GGC TGG ATG GCC GCC TCG TAC CTC GTC CGG GCG CTC      698
Gly Gly Thr Ala Gly Trp Met Ala Ala Ser Tyr Leu Val Arg Ala Leu
         15                  20                  25

CAG CAG CAG ACG AAC ATT ACG CTC ATC GAG TCT GCG GCG ATC CCC CGG      746
Gln Gln Gln Thr Asn Ile Thr Leu Ile Glu Ser Ala Ala Ile Pro Arg
     30                  35                  40

ATC GGC GTG GGC GAG GCG ACC ATC CCG AGT TTG CAG AAG GTG TTC TTC      794
Ile Gly Val Gly Glu Ala Thr Ile Pro Ser Leu Gln Lys Val Phe Phe
 45                  50                  55                  60
```

```
GAC TTC CTC GGG ATA CCG GAG CGG GAG TGG ATG CCC CAG GTG AAC GGC         842
Asp Phe Leu Gly Ile Pro Glu Arg Glu Trp Met Pro Gln Val Asn Gly
                65                  70                  75

GCG TTC AAG GCC GCC ATC AAG TTC GTG AAC TGG AGG AAG TCG CCC GAC         890
Ala Phe Lys Ala Ala Ile Lys Phe Val Asn Trp Arg Lys Ser Pro Asp
            80                  85                  90

CGC TCG CGC GAC GAT CAC TTC TAC CAT TTG TTC GGC AGC GTG CCG AAC         938
Arg Ser Arg Asp Asp His Phe Tyr His Leu Phe Gly Ser Val Pro Asn
                95                 100                 105

TGC GAC GGC GTG CCG CTT ACC CAC TAC TGG CTG CGC AAG CGC GAA CAG         986
Cys Asp Gly Val Pro Leu Thr His Tyr Trp Leu Arg Lys Arg Glu Gln
        110                 115                 120

GGC TTC CAG CAG CCG ATG GAG TAC GCG TGC TAC CCG CAG CCC GGG GCG        1034
Gly Phe Gln Gln Pro Met Glu Tyr Ala Cys Tyr Pro Gln Pro Gly Ala
125                 130                 135                 140

CTC GAC GGC AAG CTC GCA CCG TGC CTG TCC GAC GGC ACC CGC CAG ATG        1082
Leu Asp Gly Lys Leu Ala Pro Cys Leu Ser Asp Gly Thr Arg Gln Met
                145                 150                 155

TCC CAC GCG TGG CAC TTC GAC GCC CAC CTC GTG GCC GAC TTC CTG AAG        1130
Ser His Ala Trp His Phe Asp Ala His Leu Val Ala Asp Phe Leu Lys
            160                 165                 170

CGC TGG GCC GTC GAA CGC GGG GTG AAA CGC GTG GTC GAC GAG GTC GTG        1178
Arg Trp Ala Val Glu Arg Gly Val Lys Arg Val Val Asp Glu Val Val
        175                 180                 185

GAG GTT CGC CTG AAC GAC CGC GGC TAC ATC TCC AGC CTG TCC ACC AAG        1226
Glu Val Arg Leu Asn Asp Arg Gly Tyr Ile Ser Ser Leu Ser Thr Lys
190                 195                 200

GAG GGG CGC ACG CTG GAG GCG GAC CTG TTC ATC GAC TGC TCC GGC ATG        1274
Glu Gly Arg Thr Leu Glu Ala Asp Leu Phe Ile Asp Cys Ser Gly Met
205                 210                 215                 220

CGG GGG CTT CTG ATC AAC CAG GCC CTG AAG GAG CCC TTC ATC GAC ATG        1322
Arg Gly Leu Leu Ile Asn Gln Ala Leu Lys Glu Pro Phe Ile Asp Met
                225                 230                 235

TCC GAC TAC CTG CTG TGC GAC AGC GCG GTC GCC AGC GCC GTG CCC AAC        1370
Ser Asp Tyr Leu Leu Cys Asp Ser Ala Val Ala Ser Ala Val Pro Asn
            240                 245                 250

GCC GAC GCG CGT GTG GGG GTC GAG CCG TAC ACC TCC GCG ATC GCC ATG        1418
Ala Asp Ala Arg Val Gly Val Glu Pro Tyr Thr Ser Ala Ile Ala Met
        255                 260                 265

AAC TCG GGG TGG ACC TGG AAG ATT CCG ATG CTG GGC CGG TTC GGC AGC        1466
Asn Ser Gly Trp Thr Trp Lys Ile Pro Met Leu Gly Arg Phe Gly Ser
270                 275                 280

GGC TAC GTC TTC TCG AGC AAG TTC ACG TCG CGC GAC CAG GCC ACC GCC        1514
Gly Tyr Val Phe Ser Ser Lys Phe Thr Ser Arg Asp Gln Ala Thr Ala
285                 290                 295                 300

GAC TTC CTC AAC CTC TGG GGC CTC TCG GAC AAC CAG CCG CTC AAC CAG        1562
Asp Phe Leu Asn Leu Trp Gly Leu Ser Asp Asn Gln Pro Leu Asn Gln
                305                 310                 315

ATC AAG TTC CGG GTC GGG CGC AAC GGG CGG GCG TGG GTC AAC AAC TGC        1610
Ile Lys Phe Arg Val Gly Arg Asn Gly Arg Ala Trp Val Asn Asn Cys
            320                 325                 330

GTC GCC ATC GGG CTG TCG TCG TGC TTT CTG GAG CCC CTG GAA TCG ACG        1658
Val Ala Ile Gly Leu Ser Ser Cys Phe Leu Glu Pro Leu Glu Ser Thr
        335                 340                 345

GGA ATC TAC TTC ATC TAC GCG GCG CTT TAC CAG CTC GTG AAG CAC TTC        1706
Gly Ile Tyr Phe Ile Tyr Ala Ala Leu Tyr Gln Leu Val Lys His Phe
350                 355                 360

CCC GAT ACG TCG TTC GAT CCG CGC TTG ACC GAC GCG TTC AAC GCC GAG        1754
Pro Asp Thr Ser Phe Asp Pro Arg Leu Thr Asp Ala Phe Asn Ala Glu
365                 370                 375                 380
```

```
ATC GTC TAC ATG TTC GAC GAC TGC CGG GAT TTC GTC CAG GCG CAC TAT         1802
Ile Val Tyr Met Phe Asp Asp Cys Arg Asp Phe Val Gln Ala His Tyr
                385                 390                 395

TTC GCC ACG TCG CGC GAC GAC ACG CCG TTC TGG CTC GCG AAC CGG CAC         1850
Phe Ala Thr Ser Arg Asp Asp Thr Pro Phe Trp Leu Ala Asn Arg His
            400                 405                 410

GAC CTG CGG CTC TCG GAC GCC ATC AAG GAG AAG GTT CAG CGC TAC AAG         1898
Asp Leu Arg Leu Ser Asp Ala Ile Lys Glu Lys Val Gln Arg Tyr Lys
        415                 420                 425

GCG GGG CTG CCG CTG ACC ACC ACG TCG TTC GAC GAT TCC ACG TAC TAC         1946
Ala Gly Leu Pro Leu Thr Thr Thr Ser Phe Asp Asp Ser Thr Tyr Tyr
    430                 435                 440

GAA ACG TTC GAC TAC GAA TTC AAG AAC TTC TGG TTG AAC GGA AAC TAC         1994
Glu Thr Phe Asp Tyr Glu Phe Lys Asn Phe Trp Leu Asn Gly Asn Tyr
445                 450                 455                 460

TAC TGC ATC TTT GCC GGC TTG GGC ATG TTG CCC GAC CGG TCG CTG CCG         2042
Tyr Cys Ile Phe Ala Gly Leu Gly Met Leu Pro Asp Arg Ser Leu Pro
                465                 470                 475

CTC TTG CGG CAC CGA CCG GAG TCG ATC GAC AAG GCC GAG GCG ATG TTC         2090
Leu Leu Arg His Arg Pro Glu Ser Ile Asp Lys Ala Glu Ala Met Phe
            480                 485                 490

GCC CGC ATC CGG CGC GAG GCC GAG CGT CTG CGG ACC AGC CTG CCG ACG         2138
Ala Arg Ile Arg Arg Glu Ala Glu Arg Leu Arg Thr Ser Leu Pro Thr
        495                 500                 505

AAC TAC GAC TAC CTG CGA TCG CTG CGT GAC GGC GAC GCG GGG CTG TCT         2186
Asn Tyr Asp Tyr Leu Arg Ser Leu Arg Asp Gly Asp Ala Gly Leu Ser
    510                 515                 520

CGC AGC CAG CCC GGA TCG ACG CTC GCG GCG CCG GAA ATC CTG                 2228
Arg Ser Gln Pro Gly Ser Thr Leu Ala Ala Pro Glu Ile Leu
525                 530                 535

TA GTG GAG CGC ACC CTG GAC CGG GTA TGC GCA TTC GAG GCC ACG CAC          2275
   Val Glu Arg Thr Leu Asp Arg Val Cys Ala Phe Glu Ala Thr His
    1               5                   10                  15

GCC GCG GTG GCG GCC TGC GAT CCG CTG CGG GCG CGG GCG CTC GTT CTG         2323
Ala Ala Val Ala Ala Cys Asp Pro Leu Arg Ala Arg Ala Leu Val Leu
                20                  25                  30

CAA CTG CCT GGC CTG AAC CGT AAC AAG GAC GTG CCC GGC ATC GTC GGC         2371
Gln Leu Pro Gly Leu Asn Arg Asn Lys Asp Val Pro Gly Ile Val Gly
            35                  40                  45

CTG TTG CGC GAG TTC CTC CCG GCG CGC GGC GTG CCC TCC GGC TGG GGC         2419
Leu Leu Arg Glu Phe Leu Pro Ala Arg Gly Val Pro Ser Gly Trp Gly
        50                  55                  60

TTC GTC GAA GCC GCC GCC GCG ATG CGG GAC ATC GGG TTC TTC CTG GGG         2467
Phe Val Glu Ala Ala Ala Ala Met Arg Asp Ile Gly Phe Phe Leu Gly
    65                  70                  75

TCG CTC AAG CGG CAC GGA CAC GAG CCC GTG GAC GTG GTG CCC GGG CTC         2515
Ser Leu Lys Arg His Gly His Glu Pro Val Asp Val Val Pro Gly Leu
80                  85                  90                  95

GAG CCG GTG CTG CTC GAC CTG GCG CGC ACG ACC GAC CTG CCG CCG CGC         2563
Glu Pro Val Leu Leu Asp Leu Ala Arg Thr Thr Asp Leu Pro Pro Arg
                100                 105                 110

GAG ACG CTC CTG CAT GTG ACG GTC TGG AAC CCC GCG GCG GCC GAC GCG         2611
Glu Thr Leu Leu His Val Thr Val Trp Asn Pro Ala Ala Ala Asp Ala
            115                 120                 125

CAG CGG AGC TAC ACC GGG CTC CGC GAC GAA GCG CAC CTG CTC GAG AGC         2659
Gln Arg Ser Tyr Thr Gly Leu Arg Asp Glu Ala His Leu Leu Glu Ser
        130                 135                 140

GTG CGC ATC TCG ATG GCG GCC CTC GAG GCG GCC ATC GCG GTG ACC GTC         2707
Val Arg Ile Ser Met Ala Ala Leu Glu Ala Ala Ile Ala Val Thr Val
    145                 150                 155
```

-continued

| | |
|---|---|
| GAG CTG TCC GAC GTG CCC CTG CGG TCG CCC GCG TTC GCG CAA GGG TGC<br>Glu Leu Ser Asp Val Pro Leu Arg Ser Pro Ala Phe Ala Gln Gly Cys<br>160                            165                    170                  175 | 2755 |
| GAC GAG CTG GCG GCC TAT CTT CAG AAA ATG GTC GAA TCG GTC GTT TAC<br>Asp Glu Leu Ala Ala Tyr Leu Gln Lys Met Val Glu Ser Val Val Tyr<br>180                    185                    190 | 2803 |
| GCT TAC CGC TTC ATC TCG CTG CAG GTC TTC TAC AAC GAG CTC CGC CCC<br>Ala Tyr Arg Phe Ile Ser Leu Gln Val Phe Tyr Asn Glu Leu Arg Pro<br>195                    200                    205 | 2851 |
| TTC TAC GAA CCG ATT CGA GTC GGG GGC CAG AGC TAC CTC GGC CCC GGT<br>Phe Tyr Glu Pro Ile Arg Val Gly Gly Gln Ser Tyr Leu Gly Pro Gly<br>210                    215                    220 | 2899 |
| GCC GTG GAA ATG CCC CTC TTC GTG CTG GAG CAC GTC CTG TGG GGC TCA<br>Ala Val Glu Met Pro Leu Phe Val Leu Glu His Val Leu Trp Gly Ser<br>225                    230                    235 | 2947 |
| CAA TCG GAC CAC CCG GCT TAT CGA GAA TTC AAG GAG ACG TAC CTG CCC<br>Gln Ser Asp His Pro Ala Tyr Arg Glu Phe Lys Glu Thr Tyr Leu Pro<br>240                    245                    250                    255 | 2995 |
| TAC GTG CTT CCC GCG TAC AGG GCG GTC TAC GCC CGG TTC GCC GGG GAG<br>Tyr Val Leu Pro Ala Tyr Arg Ala Val Tyr Ala Arg Phe Ala Gly Glu<br>260                    265                    270 | 3043 |
| CCG GCG CTC GTC GAC CGC GTG CTC GAC GAA GTG CAA GCG GCC GGC GCG<br>Pro Ala Leu Val Asp Arg Val Leu Asp Glu Val Gln Ala Ala Gly Ala<br>275                    280                    285 | 3091 |
| CGG GGC GAG CCC GTC GGG GCC GGG CTG GCG GCC CTC GAC CCG GTC TTC<br>Arg Gly Glu Pro Val Gly Ala Gly Leu Ala Ala Leu Asp Pro Val Phe<br>290                    295                    300 | 3139 |
| GAG GTC CTG CTG CGC TTC CGG GCG CCT CAC CTC AAA TTG GCG GAG CGG<br>Glu Val Leu Leu Arg Phe Arg Ala Pro His Leu Lys Leu Ala Glu Arg<br>305                    310                    315 | 3187 |
| GCG TAC GAA GCC GGG CAA AGC GGC CCC GCC ATC GGC AGC GGG GGG TAC<br>Ala Tyr Glu Ala Gly Gln Ser Gly Pro Ala Ile Gly Ser Gly Gly Tyr<br>320                    325                    330                    335 | 3235 |
| GCG CCC AGC GCG CTC GTC GAT CTA CTC GCG CTC ACG CGT GCC GCG CGG<br>Ala Pro Ser Ala Leu Val Asp Leu Leu Ala Leu Thr Arg Ala Ala Arg<br>340                    345                    350 | 3283 |
| TTC CGC CTC CGC GCC GCG CTC GAC GAG CCC TGACACCTGA CACGTGCGTC<br>Phe Arg Leu Arg Ala Ala Leu Asp Glu Pro<br>355                    360 | 3333 |
| CATGTGTTCC ATCTCACAAG GAGAGTGTGC CCCC ATG ACT CAG AAC AGC CCC<br>                                                      Met Thr Gln Asn Ser Pro<br>                                                       1                    5 | 3385 |
| GCG AAC GGG CGC GAT AGC AAC CAC TTC GAC GTG ATC ATC CTC GGC TCG<br>Ala Asn Gly Arg Asp Ser Asn His Phe Asp Val Ile Ile Leu Gly Ser<br>          10                    15                    20 | 3433 |
| GGC ATG TCC GGC ACC CAG ATG GGA GCC ATC CTG GCC AGA CAA CGG TTT<br>Gly Met Ser Gly Thr Gln Met Gly Ala Ile Leu Ala Arg Gln Arg Phe<br>          25                    30                    35 | 3481 |
| AGC GTG CTG ATC ATC GAG GAG TCG TCG CAC CCG CGG TTC ACG ATC GGC<br>Ser Val Leu Ile Ile Glu Glu Ser Ser His Pro Arg Phe Thr Ile Gly<br>          40                    45                    50 | 3529 |
| GAA TCG TCG ATC CCC GAG ACG TCG CTT ATG AAT CGC ATC ATC GCC GAT<br>Glu Ser Ser Ile Pro Glu Thr Ser Leu Met Asn Arg Ile Ile Ala Asp<br>55                            60                    65                    70 | 3577 |
| CGC TAC GGC ATT CCG GAG CTC GAC CGC ATC ACG TCG TTC TAC TCG ACG<br>Arg Tyr Gly Ile Pro Glu Leu Asp Arg Ile Thr Ser Phe Tyr Ser Thr<br>          75                    80                    85 | 3625 |
| CAG CGT TAC GTC GCG TCG AGC ACG GGC ATC AAG CGC AAC TTC GGC TTC<br>Gln Arg Tyr Val Ala Ser Ser Thr Gly Ile Lys Arg Asn Phe Gly Phe<br>          90                    95                    100 | 3673 |

-continued

| | | |
|---|---|---|
| GTG TTC CAC AAG CCC GGC CAG GAG CAC GAC CCG AAG GAA TTC ACG CAG<br>Val Phe His Lys Pro Gly Gln Glu His Asp Pro Lys Glu Phe Thr Gln<br>          105                        110                        115 | 3721 |
| TGC GTC ATT CCC GAG CTG CCG TGG GGT CCG GAG AGC CAT TAT TAC CGG<br>Cys Val Ile Pro Glu Leu Pro Trp Gly Pro Glu Ser His Tyr Tyr Arg<br>120                       125                    130 | 3769 |
| CAA GAC GTC GAC GCC TAC CTG TTG CAA GCC GCC ATC AAA TAC GGC TGC<br>Gln Asp Val Asp Ala Tyr Leu Leu Gln Ala Ala Ile Lys Tyr Gly Cys<br>135                      140                    145                    150 | 3817 |
| ACG GTC CGC CAG AAG ACG AAC GTG ACC GAA TAC CAC GCC GAC AAA GAC<br>Thr Val Arg Gln Lys Thr Asn Val Thr Glu Tyr His Ala Asp Lys Asp<br>                155                    160                    165 | 3865 |
| GGC GTC GCA GTG ACC ACC GCC CAG GGC GAT CGG TTC ACC GGC CGG TAC<br>Gly Val Ala Val Thr Thr Ala Gln Gly Asp Arg Phe Thr Gly Arg Tyr<br>        170                        175                    180 | 3913 |
| ATG ATC GAC TGC GGA GGA CCC CGC GCG CCG CTC GCG ACC AAG TTC AAG<br>Met Ile Asp Cys Gly Gly Pro Arg Ala Pro Leu Ala Thr Lys Phe Lys<br>                185                    190                    195 | 3961 |
| CTC CGC GAA GAG CCG TGT CGC TTC AAG ACG CAC TCG CGC AGC CTC TAC<br>Leu Arg Glu Glu Pro Cys Arg Phe Lys Thr His Ser Arg Ser Leu Tyr<br>200                       205                    210 | 4009 |
| ACG CAC ATG CTC GGG GTC AAG CCG TTC GAC GAC ATC TTC AAG GTC AAG<br>Thr His Met Leu Gly Val Lys Pro Phe Asp Asp Ile Phe Lys Val Lys<br>215                       220                    225                    230 | 4057 |
| GGG CAA CGC TGG CGC TGG CAC GAG GGG ACC TTG CAC CAC ATG TTC GCG<br>Gly Gln Arg Trp Arg Trp His Glu Gly Thr Leu His His Met Phe Ala<br>                235                    240                    245 | 4105 |
| GGC GGC TGG CTC TGG GTG ATT CCG TTC AAC AAC CAC CCG CGG TCG ACC<br>Gly Gly Trp Leu Trp Val Ile Pro Phe Asn Asn His Pro Arg Ser Thr<br>        250                        255                    260 | 4153 |
| AAC AAC CTG GTG AGC GTC GGC CTG CAG CTC GAC CCG CGT GTC TAC CCG<br>Asn Asn Leu Val Ser Val Gly Leu Gln Leu Asp Pro Arg Val Tyr Pro<br>                265                    270                    275 | 4201 |
| AAA ACG GAC ATC TCC GCG CAG CAG GAA TTC GAC GAG TTC CTC GCG CGG<br>Lys Thr Asp Ile Ser Ala Gln Gln Glu Phe Asp Glu Phe Leu Ala Arg<br>280                       285                    290 | 4249 |
| TTC CCG AGC ATC GGG GCG CAG TTC CGG GAC GCC GTG CCG GTG CGC GAC<br>Phe Pro Ser Ile Gly Ala Gln Phe Arg Asp Ala Val Pro Val Arg Asp<br>295                       300                    305                    310 | 4297 |
| TGG GTC AAG ACC GAC CGC CTG CAA TTC TCG TCG AAC GCC TGC GTC GGC<br>Trp Val Lys Thr Asp Arg Leu Gln Phe Ser Ser Asn Ala Cys Val Gly<br>                315                    320                    325 | 4345 |
| GAC CGC TAC TGC CTG ATG CTG CAC GCG AAC GGG TTC ATC GAC CCG CTC<br>Asp Arg Tyr Cys Leu Met Leu His Ala Asn Gly Phe Ile Asp Pro Leu<br>        330                        335                    340 | 4393 |
| TTC TCC CGG GGG CTC GAG AAC ACC GCG GTG ACC ATC CAC GCG CTC GCG<br>Phe Ser Arg Gly Leu Glu Asn Thr Ala Val Thr Ile His Ala Leu Ala<br>                345                    350                    355 | 4441 |
| GCG CGC CTC ATC AAG GCG CTG CGC GAC GAC GAC TTC TCC CCC GAG CGC<br>Ala Arg Leu Ile Lys Ala Leu Arg Asp Asp Asp Phe Ser Pro Glu Arg<br>360                       365                    370 | 4489 |
| TTC GAG TAC ATC GAG CGC CTG CAG CAG AAG CTC TTG GAC CAC AAC GAC<br>Phe Glu Tyr Ile Glu Arg Leu Gln Gln Lys Leu Leu Asp His Asn Asp<br>375                       380                    385                    390 | 4537 |
| GAC TTC GTC AGC TGC TGC TAC ACG GCG TTC TCG GAC TTC CGC CTG TGG<br>Asp Phe Val Ser Cys Cys Tyr Thr Ala Phe Ser Asp Phe Arg Leu Trp<br>                395                    400                    405 | 4585 |
| GAC GCG TTC CAC CGG CTG TGG GCG GTC GGC ACG ATC CTC GGG CAG TTC<br>Asp Ala Phe His Arg Leu Trp Ala Val Gly Thr Ile Leu Gly Gln Phe<br>        410                        415                    420 | 4633 |

-continued

| | |
|---|---|
| CGG CTC GTG CAA GCC CAC GCG AGG TTC CGC GCG TCG CGT GAC GAG GGC<br>Arg Leu Val Gln Ala His Ala Arg Phe Arg Ala Ser Arg Asp Glu Gly<br>    425                              430                        435 | 4681 |
| GAC CTC GAT CAC CTC GAC GAC AAC CCC CCG TAC CTC GGG TAC CTG TGC<br>Asp Leu Asp His Leu Asp Asp Asn Pro Pro Tyr Leu Gly Tyr Leu Cys<br>440                              445                              450 | 4729 |
| GCG GAC ATG GAG GGG TAC TAC CAG TTG TTC AAC GAC GCC AAA GCC GAG<br>Ala Asp Met Glu Gly Tyr Tyr Gln Leu Phe Asn Asp Ala Lys Ala Glu<br>455                              460                        465                  470 | 4777 |
| GTC GAG GCC GTG AGC GCC GGG CGC AAG CCG GCC GAG GAG GCC GCG GCG<br>Val Glu Ala Val Ser Ala Gly Arg Lys Pro Ala Glu Glu Ala Ala Ala<br>                        475                        480                        485 | 4825 |
| CGG ATT CAC GCC CTC ATC GAC GAA CGA GAC TTC GCC AGG CCG ATG TTC<br>Arg Ile His Ala Leu Ile Asp Glu Arg Asp Phe Ala Arg Pro Met Phe<br>                490                        495                        500 | 4873 |
| GGC TTC GGG TAC TGC ATC ACC GGA GCC AAG CCG CAG CTC AAC AAC TCG<br>Gly Phe Gly Tyr Cys Ile Thr Gly Ala Lys Pro Gln Leu Asn Asn Ser<br>                505                        510                        515 | 4921 |
| AAG TAC AGC CTG CTG CCG GCG ATG AAG CTG TTG CAC TGG ACG CAA ACC<br>Lys Tyr Ser Leu Leu Pro Ala Met Lys Leu Leu His Trp Thr Gln Thr<br>520                              525                        530 | 4969 |
| AGC GCG CCG GCA GAG GTG AAA AGG TAC TTC GAC TAC AAC CCG ATG TTC<br>Ser Ala Pro Ala Glu Val Lys Arg Tyr Phe Asp Tyr Asn Pro Met Phe<br>535                              540                        545                  550 | 5017 |
| GCG CTG CTC AGG GCG TAC GTC ACG ACC CGC ATC GGC CTG GCG CTG AAG<br>Ala Leu Leu Arg Ala Tyr Val Thr Thr Arg Ile Gly Leu Ala Leu Lys<br>                        555                        560                        565 | 5065 |
| TAGTCGGCCG ACTCCGGAAC GAAAACG ATG AAC GAC GTT CAA TTG GAT CAA<br>                                               Met Asn Asp Val Gln Leu Asp Gln<br>                                                1                  5 | 5116 |
| GCG CGC ACC GAG GAG CAT CCC CCG GGG GTG TAC GAC GCG ACC ACG CGC<br>Ala Arg Thr Glu Glu His Pro Pro Gly Val Tyr Asp Ala Thr Thr Arg<br>       10                        15                              20 | 5164 |
| CTG GCC GCG AGC TGG TAC GTC GCG ATG CGC TCG GAC GAC CTC AAG GAC<br>Leu Ala Ala Ser Trp Tyr Val Ala Met Arg Ser Asp Asp Leu Lys Asp<br>25                              30                        35                        40 | 5212 |
| AAG CCG ACG GAG TTG ATG CTC TTC GGC CGT CCG TGC GTG GCG TGG CGC<br>Lys Pro Thr Glu Leu Met Leu Phe Gly Arg Pro Cys Val Ala Trp Arg<br>                         45                        50                        55 | 5260 |
| GGC GCG ACG GGG CGG GCC GTG GTG ATG GAC CGC CAC TGC TCG CAC CTC<br>Gly Ala Thr Gly Arg Ala Val Val Met Asp Arg His Cys Ser His Leu<br>                60                        65                        70 | 5308 |
| GGC GCG AAC CTG GCC GAC GGG CGG GTC GAG GAC GGG TGC ATC CAG TGC<br>Gly Ala Asn Leu Ala Asp Gly Arg Val Glu Asp Gly Cys Ile Gln Cys<br>75                              80                        85 | 5356 |
| CCG TTT CAC CAC TGG CGG TAC GAC GAG CAG GGC CAG TGC GTT CAC ATC<br>Pro Phe His His Trp Arg Tyr Asp Glu Gln Gly Gln Cys Val His Ile<br>                90                        95                        100 | 5404 |
| CCC GGC CAC AGC TCG GCG GTG AGC CGG CTG GAG CCC GTC CCG CGC GGG<br>Pro Gly His Ser Ser Ala Val Ser Arg Leu Glu Pro Val Pro Arg Gly<br>105                              110                        115                  120 | 5452 |
| GCG CGC CAG CCG ACG CTG GTC ACC GCC GAG CGA TAC GGC TAC GTG TGG<br>Ala Arg Gln Pro Thr Leu Val Thr Ala Glu Arg Tyr Gly Tyr Val Trp<br>                        125                        130                        135 | 5500 |
| GTC TGG TAC GGC TCC CCG CAG CCG CTG CAC CCG CTG CCC GAA ATC GCC<br>Val Trp Tyr Gly Ser Pro Gln Pro Leu His Pro Leu Pro Glu Ile Ala<br>                      140                        145                        150 | 5548 |
| GCC GCC GAC GTC GAC AAC GGC GAC TTC ATG CAC CTG CAC TTC GCG TTC<br>Ala Ala Asp Val Asp Asn Gly Asp Phe Met His Leu His Phe Ala Phe<br>155                              160                        165 | 5596 |

```
GAG ACG ACG ACG GCC GTC TTG CGG ATC GTC GAG AAC TTC TAC GAC GCG      5644
Glu Thr Thr Thr Ala Val Leu Arg Ile Val Glu Asn Phe Tyr Asp Ala
    170                 175                 180

CAG CAC GCG AAC CCC GTT CAC GCG CTC CCG ATC TCG GCC TTC GAG CTC      5692
Gln His Ala Asn Pro Val His Ala Leu Pro Ile Ser Ala Phe Glu Leu
185                 190                 195                 200

AAG CTC TTC GAC GAT TGG CGC CAG TGG CCG GAG GTC GAG TCG CTG GCC      5740
Lys Leu Phe Asp Asp Trp Arg Gln Trp Pro Glu Val Glu Ser Leu Ala
                205                 210                 215

CGG GCG GGC GCG TGG TTC GGT GCC GGG ATC GAC TTC ACC GTG GAC CGG      5788
Arg Ala Gly Ala Trp Phe Gly Ala Gly Ile Asp Phe Thr Val Asp Arg
            220                 225                 230

TAC TTC GGG CCC CTC GGC ATG CTG TCG CGC GCG CTC GGC CTG AGC ATG      5836
Tyr Phe Gly Pro Leu Gly Met Leu Ser Arg Ala Leu Gly Leu Ser Met
        235                 240                 245

TCG CAG ATG AAC CTG CAC TTC GAC GGC TAC CCC GGC GGG TGC GTC ATG      5884
Ser Gln Met Asn Leu His Phe Asp Gly Tyr Pro Gly Gly Cys Val Met
    250                 255                 260

ACC GTC GCC CTG GAC GGA GAC TTC AAA TAC AAG CTG CTC CAG TGC GTG      5932
Thr Val Ala Leu Asp Gly Asp Phe Lys Tyr Lys Leu Leu Gln Cys Val
265                 270                 275                 280

ACG CCG GTG AGC GAC GGC AAA AAC GTC ATG CAC ATG CTC ATC TCG ATC      5980
Thr Pro Val Ser Asp Gly Lys Asn Val Met His Met Leu Ile Ser Ile
                285                 290                 295

AAG AAG GTG GGC GGC GCC CTG CGC CGC GCG ACC GAC TAC GTG CTG TTC      6028
Lys Lys Val Gly Gly Ala Leu Arg Arg Ala Thr Asp Tyr Val Leu Phe
            300                 305                 310

GGG TTG CAG ACC AGA CAG GCC GCG GGG TAC GAC GTC AAG ATC TGG AAC      6076
Gly Leu Gln Thr Arg Gln Ala Ala Gly Tyr Asp Val Lys Ile Trp Asn
        315                 320                 325

GGG ATG AAG CCG GAC GGC GGC GGC GCG TAC AGC AAG TAC GAC AAG CTC      6124
Gly Met Lys Pro Asp Gly Gly Gly Ala Tyr Ser Lys Tyr Asp Lys Leu
    330                 335                 340

GTG CTC AAG TAC CGC GCG TTC TAC CGG GAC TGG GTC GAC CGC GTC GCC      6172
Val Leu Lys Tyr Arg Ala Phe Tyr Arg Asp Trp Val Asp Arg Val Ala
345                 350                 355                 360

GAG GCG ACC GCT CGA CCG CGC CGC CGC GAG TGAGCGGCGA TGCGTGAGTC        6222
Glu Ala Thr Ala Arg Pro Arg Arg Arg Glu
                365                 370

GGCGGCCCTG GCCGAGCCGG TCTCGGCC                                        6250

(2) INFORMATION FOR SEQ ID NO:24:

(i) SEQUENCE CHARACTERISTICS:
        (A) LENGTH: 538 amino acids
        (B) TYPE: amino acid
        (D) TOPOLOGY: linear (ii) MOLECULE TYPE: protein (xi) SEQUENCE DESCRIPTION: SEQ ID NO:24:

Met Ser Asn Pro Ile Lys Asn Ile Val Ile Gly Gly Gly Thr Ala
 1               5                  10                 15

Gly Trp Met Ala Ala Ser Tyr Leu Val Arg Ala Leu Gln Gln Thr
            20                  25                 30

Asn Ile Thr Leu Ile Glu Ser Ala Ala Ile Pro Arg Ile Gly Val Gly
        35                  40                 45

Glu Ala Thr Ile Pro Ser Leu Gln Lys Val Phe Phe Asp Phe Leu Gly
    50                  55                 60
```

-continued

```
Ile Pro Glu Arg Glu Trp Met Pro Gln Val Asn Gly Ala Phe Lys Ala
 65                  70                  75                  80

Ala Ile Lys Phe Val Asn Trp Arg Lys Ser Pro Asp Arg Ser Arg Asp
                 85                  90                  95

Asp His Phe Tyr His Leu Phe Gly Ser Val Pro Asn Cys Asp Gly Val
            100                 105                 110

Pro Leu Thr His Tyr Trp Leu Arg Lys Arg Glu Gln Gly Phe Gln Gln
        115                 120                 125

Pro Met Glu Tyr Ala Cys Tyr Pro Gln Pro Gly Ala Leu Asp Gly Lys
    130                 135                 140

Leu Ala Pro Cys Leu Ser Asp Gly Thr Arg Gln Met Ser His Ala Trp
145                 150                 155                 160

His Phe Asp Ala His Leu Val Ala Asp Phe Leu Lys Arg Trp Ala Val
                165                 170                 175

Glu Arg Gly Val Lys Arg Val Val Asp Glu Val Val Glu Val Arg Leu
            180                 185                 190

Asn Asp Arg Gly Tyr Ile Ser Ser Leu Ser Thr Lys Glu Gly Arg Thr
        195                 200                 205

Leu Glu Ala Asp Leu Phe Ile Asp Cys Ser Gly Met Arg Gly Leu Leu
    210                 215                 220

Ile Asn Gln Ala Leu Lys Glu Pro Phe Ile Asp Met Ser Asp Tyr Leu
225                 230                 235                 240

Leu Cys Asp Ser Ala Val Ala Ser Ala Val Pro Asn Ala Asp Ala Arg
                245                 250                 255

Val Gly Val Glu Pro Tyr Thr Ser Ala Ile Ala Met Asn Ser Gly Trp
            260                 265                 270

Thr Trp Lys Ile Pro Met Leu Gly Arg Phe Gly Ser Gly Tyr Val Phe
        275                 280                 285

Ser Ser Lys Phe Thr Ser Arg Asp Gln Ala Thr Ala Asp Phe Leu Asn
    290                 295                 300

Leu Trp Gly Leu Ser Asp Asn Gln Pro Leu Asn Gln Ile Lys Phe Arg
305                 310                 315                 320

Val Gly Arg Asn Gly Arg Ala Trp Val Asn Asn Cys Val Ala Ile Gly
                325                 330                 335

Leu Ser Ser Cys Phe Leu Glu Pro Leu Glu Ser Thr Gly Ile Tyr Phe
            340                 345                 350

Ile Tyr Ala Ala Leu Tyr Gln Leu Val Lys His Phe Pro Asp Thr Ser
        355                 360                 365

Phe Asp Pro Arg Leu Thr Asp Ala Phe Asn Ala Glu Ile Val Tyr Met
    370                 375                 380

Phe Asp Asp Cys Arg Asp Phe Val Gln Ala His Tyr Phe Ala Thr Ser
385                 390                 395                 400

Arg Asp Asp Thr Pro Phe Trp Leu Ala Asn Arg His Asp Leu Arg Leu
                405                 410                 415

Ser Asp Ala Ile Lys Glu Lys Val Gln Arg Tyr Lys Ala Gly Leu Pro
            420                 425                 430

Leu Thr Thr Thr Ser Phe Asp Ser Thr Tyr Tyr Glu Thr Phe Asp
        435                 440                 445

Tyr Glu Phe Lys Asn Phe Trp Leu Asn Gly Asn Tyr Tyr Cys Ile Phe
    450                 455                 460

Ala Gly Leu Gly Met Leu Pro Asp Arg Ser Leu Pro Leu Leu Arg His
465                 470                 475                 480
```

-continued

```
Arg Pro Glu Ser Ile Asp Lys Ala Glu Ala Met Phe Ala Arg Ile Arg
                485                 490                 495

Arg Glu Ala Glu Arg Leu Arg Thr Ser Leu Pro Thr Asn Tyr Asp Tyr
            500                 505                 510

Leu Arg Ser Leu Arg Asp Gly Asp Ala Gly Leu Ser Arg Ser Gln Pro
        515                 520                 525

Gly Ser Thr Leu Ala Ala Pro Glu Ile Leu
    530                 535
```

(2) INFORMATION FOR SEQ ID NO:25:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:25:

```
Val Glu Arg Thr Leu Asp Arg Val Cys Ala Phe Glu Ala Thr His Ala
  1               5                  10                  15

Ala Val Ala Ala Cys Asp Pro Leu Arg Ala Arg Ala Leu Val Leu Gln
             20                  25                  30

Leu Pro Gly Leu Asn Arg Asn Lys Asp Val Pro Gly Ile Val Gly Leu
         35                  40                  45

Leu Arg Glu Phe Leu Pro Ala Arg Gly Val Pro Ser Gly Trp Gly Phe
     50                  55                  60

Val Glu Ala Ala Ala Met Arg Asp Ile Gly Phe Phe Leu Gly Ser
 65                  70                  75                  80

Leu Lys Arg His Gly His Glu Pro Val Asp Val Pro Gly Leu Glu
                 85                  90                  95

Pro Val Leu Leu Asp Leu Ala Arg Thr Thr Asp Leu Pro Pro Arg Glu
            100                 105                 110

Thr Leu Leu His Val Thr Val Trp Asn Pro Ala Ala Ala Asp Ala Gln
        115                 120                 125

Arg Ser Tyr Thr Gly Leu Arg Asp Glu Ala His Leu Leu Glu Ser Val
    130                 135                 140

Arg Ile Ser Met Ala Ala Leu Glu Ala Ala Ile Ala Val Thr Val Glu
145                 150                 155                 160

Leu Ser Asp Val Pro Leu Arg Ser Pro Ala Phe Ala Gln Gly Cys Asp
                165                 170                 175

Glu Leu Ala Ala Tyr Leu Gln Lys Met Val Glu Ser Val Val Tyr Ala
            180                 185                 190

Tyr Arg Phe Ile Ser Leu Gln Val Phe Tyr Asn Glu Leu Arg Pro Phe
        195                 200                 205

Tyr Glu Pro Ile Arg Val Gly Gly Gln Ser Tyr Leu Gly Pro Gly Ala
    210                 215                 220

Val Glu Met Pro Leu Phe Val Leu Glu His Val Leu Trp Gly Ser Gln
225                 230                 235                 240

Ser Asp His Pro Ala Tyr Arg Glu Phe Lys Glu Thr Tyr Leu Pro Tyr
                245                 250                 255

Val Leu Pro Ala Tyr Arg Ala Val Tyr Ala Arg Phe Ala Gly Glu Pro
            260                 265                 270

Ala Leu Val Asp Arg Val Leu Asp Glu Val Gln Ala Ala Gly Ala Arg
        275                 280                 285
```

```
Gly Glu Pro Val Gly Ala Gly Leu Ala Ala Leu Asp Pro Val Phe Glu
    290                 295                 300

Val Leu Leu Arg Phe Arg Ala Pro His Leu Lys Leu Ala Glu Arg Ala
305                 310                 315                 320

Tyr Glu Ala Gly Gln Ser Gly Pro Ala Ile Gly Ser Gly Tyr Ala
                325                 330                 335

Pro Ser Ala Leu Val Asp Leu Leu Ala Leu Thr Arg Ala Ala Arg Phe
                340                 345                 350

Arg Leu Arg Ala Ala Leu Asp Glu Pro
                355                 360

(2) INFORMATION FOR SEQ ID NO:26:

(i) SEQUENCE CHARACTERISTICS:
        (A) LENGTH: 566 amino acids
        (B) TYPE: amino acid
        (D) TOPOLOGY: linear (ii) MOLECULE TYPE: protein (xi) SEQUENCE DESCRIPTION: SEQ ID NO:26:

Met Thr Gln Asn Ser Pro Ala Asn Gly Arg Asp Ser Asn His Phe Asp
  1               5                  10                  15

Val Ile Ile Leu Gly Ser Gly Met Ser Gly Thr Gln Met Gly Ala Ile
                 20                  25                  30

Leu Ala Arg Gln Arg Phe Ser Val Leu Ile Ile Glu Glu Ser Ser His
                35                  40                  45

Pro Arg Phe Thr Ile Gly Glu Ser Ser Ile Pro Glu Thr Ser Leu Met
    50                  55                  60

Asn Arg Ile Ile Ala Asp Arg Tyr Gly Ile Pro Glu Leu Asp Arg Ile
 65                  70                  75                  80

Thr Ser Phe Tyr Ser Thr Gln Arg Tyr Val Ala Ser Ser Thr Gly Ile
                 85                  90                  95

Lys Arg Asn Phe Gly Phe Val Phe His Lys Pro Gly Gln Glu His Asp
                100                 105                 110

Pro Lys Glu Phe Thr Gln Cys Val Ile Pro Glu Leu Pro Trp Gly Pro
    115                 120                 125

Glu Ser His Tyr Tyr Arg Gln Asp Val Asp Ala Tyr Leu Leu Gln Ala
    130                 135                 140

Ala Ile Lys Tyr Gly Cys Thr Val Arg Gln Lys Thr Asn Val Thr Glu
145                 150                 155                 160

Tyr His Ala Asp Lys Asp Gly Val Ala Val Thr Thr Ala Gln Gly Asp
                165                 170                 175

Arg Phe Thr Gly Arg Tyr Met Ile Asp Cys Gly Gly Pro Arg Ala Pro
                180                 185                 190

Leu Ala Thr Lys Phe Lys Leu Arg Glu Glu Pro Cys Arg Phe Lys Thr
                195                 200                 205

His Ser Arg Ser Leu Tyr Thr His Met Leu Gly Val Lys Pro Phe Asp
    210                 215                 220

Asp Ile Phe Lys Val Lys Gly Gln Arg Trp Arg Trp His Glu Gly Thr
225                 230                 235                 240

Leu His His Met Phe Ala Gly Gly Trp Leu Trp Val Ile Pro Phe Asn
                245                 250                 255

Asn His Pro Arg Ser Thr Asn Asn Leu Val Ser Val Gly Leu Gln Leu
                260                 265                 270
```

```
Asp Pro Arg Val Tyr Pro Lys Thr Asp Ile Ser Ala Gln Gln Glu Phe
            275                 280                 285

Asp Glu Phe Leu Ala Arg Phe Pro Ser Ile Gly Ala Gln Phe Arg Asp
            290                 295                 300

Ala Val Pro Val Arg Asp Trp Val Lys Thr Asp Arg Leu Gln Phe Ser
305                 310                 315                 320

Ser Asn Ala Cys Val Gly Asp Arg Tyr Cys Leu Met Leu His Ala Asn
                325                 330                 335

Gly Phe Ile Asp Pro Leu Phe Ser Arg Gly Leu Glu Asn Thr Ala Val
            340                 345                 350

Thr Ile His Ala Leu Ala Ala Arg Leu Ile Lys Ala Leu Arg Asp Asp
            355                 360                 365

Asp Phe Ser Pro Glu Arg Phe Glu Tyr Ile Glu Arg Leu Gln Gln Lys
            370                 375                 380

Leu Leu Asp His Asn Asp Asp Phe Val Ser Cys Cys Tyr Thr Ala Phe
385                 390                 395                 400

Ser Asp Phe Arg Leu Trp Asp Ala Phe His Arg Leu Trp Ala Val Gly
                405                 410                 415

Thr Ile Leu Gly Gln Phe Arg Leu Val Gln Ala His Ala Arg Phe Arg
            420                 425                 430

Ala Ser Arg Asp Glu Gly Asp Leu Asp His Leu Asp Asp Asn Pro Pro
            435                 440                 445

Tyr Leu Gly Tyr Leu Cys Ala Asp Met Glu Gly Tyr Tyr Gln Leu Phe
            450                 455                 460

Asn Asp Ala Lys Ala Glu Val Glu Ala Val Ser Ala Gly Arg Lys Pro
465                 470                 475                 480

Ala Glu Glu Ala Ala Arg Ile His Ala Leu Ile Asp Glu Arg Asp
                485                 490                 495

Phe Ala Arg Pro Met Phe Gly Phe Gly Tyr Cys Ile Thr Gly Ala Lys
            500                 505                 510

Pro Gln Leu Asn Asn Ser Lys Tyr Ser Leu Leu Pro Ala Met Lys Leu
            515                 520                 525

Leu His Trp Thr Gln Thr Ser Ala Pro Ala Glu Val Lys Arg Tyr Phe
            530                 535                 540

Asp Tyr Asn Pro Met Phe Ala Leu Leu Arg Ala Tyr Val Thr Thr Arg
545                 550                 555                 560

Ile Gly Leu Ala Leu Lys
            565

(2) INFORMATION FOR SEQ ID NO:27:

(i) SEQUENCE CHARACTERISTICS:
        (A) LENGTH: 370 amino acids
        (B) TYPE: amino acid
        (D) TOPOLOGY: linear (ii) MOLECULE TYPE: protein (xi) SEQUENCE DESCRIPTION: SEQ ID NO:27:

Met Asn Asp Val Gln Leu Asp Gln Ala Arg Thr Glu Glu His Pro Pro
 1               5                  10                  15

Gly Val Tyr Asp Ala Thr Thr Arg Leu Ala Ala Ser Trp Tyr Val Ala
                20                  25                  30

Met Arg Ser Asp Asp Leu Lys Asp Lys Pro Thr Glu Leu Met Leu Phe
            35                  40                  45
```

```
Gly Arg Pro Cys Val Ala Trp Arg Gly Ala Thr Gly Arg Ala Val Val
     50                  55                  60

Met Asp Arg His Cys Ser His Leu Gly Ala Asn Leu Ala Asp Gly Arg
 65                  70                  75                  80

Val Glu Asp Gly Cys Ile Gln Cys Pro Phe His His Trp Arg Tyr Asp
                 85                  90                  95

Glu Gln Gly Gln Cys Val His Ile Pro Gly His Ser Ser Ala Val Ser
                100                 105                 110

Arg Leu Glu Pro Val Pro Arg Gly Ala Arg Gln Pro Thr Leu Val Thr
            115                 120                 125

Ala Glu Arg Tyr Gly Tyr Val Trp Val Trp Tyr Gly Ser Pro Gln Pro
130                 135                 140

Leu His Pro Leu Pro Glu Ile Ala Ala Ala Asp Val Asp Asn Gly Asp
145                 150                 155                 160

Phe Met His Leu His Phe Ala Phe Glu Thr Thr Thr Ala Val Leu Arg
                165                 170                 175

Ile Val Glu Asn Phe Tyr Asp Ala Gln His Ala Asn Pro Val His Ala
                180                 185                 190

Leu Pro Ile Ser Ala Phe Glu Leu Lys Leu Phe Asp Asp Trp Arg Gln
            195                 200                 205

Trp Pro Glu Val Glu Ser Leu Ala Arg Ala Gly Ala Trp Phe Gly Ala
210                 215                 220

Gly Ile Asp Phe Thr Val Asp Arg Tyr Phe Gly Pro Leu Gly Met Leu
225                 230                 235                 240

Ser Arg Ala Leu Gly Leu Ser Met Ser Gln Met Asn Leu His Phe Asp
                245                 250                 255

Gly Tyr Pro Gly Gly Cys Val Met Thr Val Ala Leu Asp Gly Asp Phe
            260                 265                 270

Lys Tyr Lys Leu Leu Gln Cys Val Thr Pro Val Ser Asp Gly Lys Asn
            275                 280                 285

Val Met His Met Leu Ile Ser Ile Lys Lys Val Gly Gly Ala Leu Arg
290                 295                 300

Arg Ala Thr Asp Tyr Val Leu Phe Gly Leu Gln Thr Arg Gln Ala Ala
305                 310                 315                 320

Gly Tyr Asp Val Lys Ile Trp Asn Gly Met Lys Pro Asp Gly Gly Gly
                325                 330                 335

Ala Tyr Ser Lys Tyr Asp Lys Leu Val Leu Lys Tyr Arg Ala Phe Tyr
            340                 345                 350

Arg Asp Trp Val Asp Arg Val Ala Glu Ala Thr Ala Arg Pro Arg Arg
            355                 360                 365

Arg Glu
370

(2) INFORMATION FOR SEQ ID NO:28:

(i) SEQUENCE CHARACTERISTICS:
        (A) LENGTH: 8931 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

-continued (iv) ANTI-SENSE: NO (vi) ORIGINAL SOURCE:
    (A) ORGANISM: Burkholdaria cepacia (ix) FEATURE:
    (A) NAME/KEY: CDS
    (B) LOCATION: 657..2267
    (D) OTHER INFORMATION: /product= "PrnA"

(ix) FEATURE:
    (A) NAME/KEY: CDS
    (B) LOCATION: 2270..3355
    (D) OTHER INFORMATION: /product= "PrnB"

(ix) FEATURE:
    (A) NAME/KEY: CDS
    (B) LOCATION: 3421..5121
    (D) OTHER INFORMATION: /product= "PrnC"

(ix) FEATURE:
    (A) NAME/KEY: CDS
    (B) LOCATION: 5145..6266
    (D) OTHER INFORMATION: /product= "PrnD"

(xi) SEQUENCE DESCRIPTION: SEQ ID NO:28:

```
GGTACCAGCA GCACGATTGC GGCGTAGAAC GACATTTTCA GCATGGGGCT CAATGTCAAC    60

ATGGGTGAAC CTCGTTTTTC CAACGATTGG TTTGGTGCGG ATCATCATAA GTCGCGGAAA   120

GTGCCACTGA CAACTCTTGT TCTTCGCATT TGAGATAGTG AAACGCGCGC GAGCGATTGC   180

TTCATCCGCT TATCACGATA TTCGAGTCTT TGGTATGAAT TATCCGGTTC CAAATTAAAA   240

TCCGAGAATC TGAAATTGTC ATTACAATTG ATCCGGAAAT TTCAAGGTTC CAGGTCGAAG   300

TTGCCGAAAT GAATTTATTG GTATTTTAAC GGAGTAATTT TTGCGGGGTC GTATTCGGTA   360

ATGTGACGTC GGCCACAGGT GCGTCTGGCG GGGAGCCGAA AAACAGGGAT AATTCAATGG   420

TCATGCATTA ACCATCAAAT TGCTGACAAA TATTGTTTTC AATATGAAAT GATTTCTTGT   480

CGACGCACAT CGTATTCAGT ATCTGAACCG AAGATGAAA  TCTCGGGTAA ACAAATAAA    540

AATCCTGTCA ACATGCCAG  TTTGATTTAA TTAATCGACA GCATATTCTA AACGCGGATC   600

AATTGAGCAC CCTCGCAGAA GTCCATTCGG GTTTCAAATC CTATGGGAAG CGCGTC       656
```

| ATG AGC CAT CCG ATC AAG AAT ATC GTC ATC GTG GGC GGC GGC ACC GCG | 704 |
| Met Ser His Pro Ile Lys Asn Ile Val Ile Val Gly Gly Gly Thr Ala | |
| 1               5                   10                  15      | |

| GGC TGG ATG TCC GCC TCG TAC CTC GTC CGG GCA CTC CAG CAG CAG GCA | 752 |
| Gly Trp Met Ser Ala Ser Tyr Leu Val Arg Ala Leu Gln Gln Gln Ala | |
|             20                  25                  30          | |

| AAC ATC ACG CTC ATC GAG TCC GAG GCG ATC CCG CGG ATC GGC GTG GGC | 800 |
| Asn Ile Thr Leu Ile Glu Ser Glu Ala Ile Pro Arg Ile Gly Val Gly | |
|     35                  40                  45                  | |

| GAG GCG ACC ATC CCG AAT TTG CAG AAG GTG TTC TTC GAC TTC CTC GGG | 848 |
| Glu Ala Thr Ile Pro Asn Leu Gln Lys Val Phe Phe Asp Phe Leu Gly | |
| 50                  55                  60                      | |

| ATA CCG GAG CGG GAG TGG ATG CCC CAG GTG AAC GGC GCG TTC AAG TCC | 896 |
| Ile Pro Glu Arg Glu Trp Met Pro Gln Val Asn Gly Ala Phe Lys Ser | |
| 65                  70                  75                  80  | |

| GCC ATC AAG TTC GTG AAC TGG AGG AAG TCG CCC GAC CGC TCG CGC GAC | 944 |
| Ala Ile Lys Phe Val Asn Trp Arg Lys Ser Pro Asp Arg Ser Arg Asp | |
|             85                  90                  95          | |

| GAC CAC TTC TAC CAT CTG TTC GGC AGC GTG CCG AAC TGC GAC GGC GTG | 992 |
| Asp His Phe Tyr His Leu Phe Gly Ser Val Pro Asn Cys Asp Gly Val | |
|         100                 105                 110             | |

```
CCG CTG ACC CAT TAC TGG CTG CGC AAG CGC GAG CAG GGC TTC CAG CAG      1040
Pro Leu Thr His Tyr Trp Leu Arg Lys Arg Glu Gln Gly Phe Gln Gln
        115                 120                 125

CCG ATG GAG TAC GCG TGC TAC CCG CAG CCC GAG GCG CTC GAC GCC AGG      1088
Pro Met Glu Tyr Ala Cys Tyr Pro Gln Pro Glu Ala Leu Asp Ala Arg
    130                 135                 140

CTG GCA CCG TGC CTG CTC GAC GGC ACC CGC CAG ATG CCC CAC GCA TGG      1136
Leu Ala Pro Cys Leu Leu Asp Gly Thr Arg Gln Met Pro His Ala Trp
145                 150                 155                 160

CAC TTC GAC GCG CAC CTG GTG GCC GAT TTC CTG AAG CGC TGG GCC GTC      1184
His Phe Asp Ala His Leu Val Ala Asp Phe Leu Lys Arg Trp Ala Val
                165                 170                 175

GGG CGC GGG GTG ACA CGC GTG GTC GAC GAG GTC GTG GAG GTT CAC CTG      1232
Gly Arg Gly Val Thr Arg Val Val Asp Glu Val Val Glu Val His Leu
            180                 185                 190

AAC GAG CGC GGC GAC ATC GCC AGC CTG TCC ACC AAG GAA GGG CGG ACG      1280
Asn Glu Arg Gly Asp Ile Ala Ser Leu Ser Thr Lys Glu Gly Arg Thr
        195                 200                 205

CTC GAG GCG GAC CTG TTC ATC GAC TGC TCC GGC ATG CGG GGG CTC TTG      1328
Leu Glu Ala Asp Leu Phe Ile Asp Cys Ser Gly Met Arg Gly Leu Leu
    210                 215                 220

ATC AAC CAG GCC CTG AAA GAG CCC TTC ATC GAC ATG TCC GAC TAC CTG      1376
Ile Asn Gln Ala Leu Lys Glu Pro Phe Ile Asp Met Ser Asp Tyr Leu
225                 230                 235                 240

CTG TGC GAC AGC GCG GTC GCC AGC GCG GTG CCC AAC GAC GAC GCG CGC      1424
Leu Cys Asp Ser Ala Val Ala Ser Ala Val Pro Asn Asp Asp Ala Arg
                245                 250                 255

GTG GGG ATC GAG CCG TAC ACC TCC GCG ATC GCG ATG AAC TCG GGG TGG      1472
Val Gly Ile Glu Pro Tyr Thr Ser Ala Ile Ala Met Asn Ser Gly Trp
            260                 265                 270

ACC TGG AAG ATT CCG ATG CTG GGC CGG TTC GGC AGC GGC TAC GTG TTC      1520
Thr Trp Lys Ile Pro Met Leu Gly Arg Phe Gly Ser Gly Tyr Val Phe
        275                 280                 285

TCG AGC AAG TTC ACG TCG CGC GAC CAG GCC ACC GCC GAC TTC CTC AAC      1568
Ser Ser Lys Phe Thr Ser Arg Asp Gln Ala Thr Ala Asp Phe Leu Asn
    290                 295                 300

CTC TGG GGC CTG TCG GAC AAG CAG CCG CTC AAC CAG ATC AAG TTC CGG      1616
Leu Trp Gly Leu Ser Asp Lys Gln Pro Leu Asn Gln Ile Lys Phe Arg
305                 310                 315                 320

GTC GGG CGC AAC GGC CGG GCG TGG GTC AAC AAC TGC GTC GCG ATC GGG      1664
Val Gly Arg Asn Gly Arg Ala Trp Val Asn Asn Cys Val Ala Ile Gly
                325                 330                 335

TTG TCG TCG TGC TTT CTG GAG CCG CTG GAA TCG ACG GGG ATC TAC TTC      1712
Leu Ser Ser Cys Phe Leu Glu Pro Leu Glu Ser Thr Gly Ile Tyr Phe
            340                 345                 350

ATC TAC GCG GCG CTT TAC CAG CTC GTG AAG CAC TTC CCC GAC ACC GGG      1760
Ile Tyr Ala Ala Leu Tyr Gln Leu Val Lys His Phe Pro Asp Thr Gly
        355                 360                 365

TTC GAT CCG CGG TTG AGA GAC GCG TTC AAC GCC GAG ATC GTC TAC ATG      1808
Phe Asp Pro Arg Leu Arg Asp Ala Phe Asn Ala Glu Ile Val Tyr Met
    370                 375                 380

TTC GAC GAC TGC CGG GAT TTC GTC CAG GCG CAC TAT TTC ACC GCG TCG      1856
Phe Asp Asp Cys Arg Asp Phe Val Gln Ala His Tyr Phe Thr Ala Ser
385                 390                 395                 400

CGC GAC GAC ACA CCG TTC TGG CTC GCG AAC CGG CAC GAC CTG CGG CTC      1904
Arg Asp Asp Thr Pro Phe Trp Leu Ala Asn Arg His Asp Leu Arg Leu
                405                 410                 415

TCT GAC GCC ATC AAG GAC AAG GTC GAA CGC TAC AAG GCG GGG CTG CCG      1952
Ser Asp Ala Ile Lys Asp Lys Val Glu Arg Tyr Lys Ala Gly Leu Pro
            420                 425                 430
```

```
CTG ACC ACC ACG TCG TTC GAC GAC GCC ACG TAC TAC GAA ACG TTC GAC         2000
Leu Thr Thr Thr Ser Phe Asp Asp Ala Thr Tyr Tyr Glu Thr Phe Asp
            435                 440                 445

TAC GAA TTC AAG AAC TTC TGG TTG AAC GGC AAC TAC TAC TGC ATC TTT         2048
Tyr Glu Phe Lys Asn Phe Trp Leu Asn Gly Asn Tyr Tyr Cys Ile Phe
    450                 455                 460

GCC GGC CTG GGG CTG CTG CCC GAC CGG TCG CTG CCG CTC CTG CGG CAC         2096
Ala Gly Leu Gly Leu Leu Pro Asp Arg Ser Leu Pro Leu Leu Arg His
465                 470                 475                 480

CGG CCG GCG TCG GTC GAC AAG GCC GAG GCG ATG TTC GCC CGC ATC CGG         2144
Arg Pro Ala Ser Val Asp Lys Ala Glu Ala Met Phe Ala Arg Ile Arg
                485                 490                 495

CGC GAG GCC GAG CGT CTG CGC GCG AGC CTG CCG ACG AAC TAT GAC TAC         2192
Arg Glu Ala Glu Arg Leu Arg Ala Ser Leu Pro Thr Asn Tyr Asp Tyr
            500                 505                 510

CTG CGG TCG CTG CGT GAC GGC GAG GCT GGG CGG GCT CGC AGC CGG CCC         2240
Leu Arg Ser Leu Arg Asp Gly Glu Ala Gly Arg Ala Arg Ser Arg Pro
        515                 520                 525

GGG CCG GTC GCG GCG CCG GAG ACG CTG TA GTG GAG CGC GCC CTG GGC          2287
Gly Pro Val Ala Ala Pro Glu Thr Leu     Met Glu Arg Ala Leu Gly
530                 535             1                   5

CGG GCA CGC GCA TTC GCG GCC ACG CAC GCC GCG GTG GCG GCG TGC GAT         2335
Arg Ala Arg Ala Phe Ala Ala Thr His Ala Ala Val Ala Ala Cys Asp
                10                  15                  20

CCG CTG CGC GCG CGG GCG CTC GTG CTG CAG CTG CCG GCC CTG AAT CGC         2383
Pro Leu Arg Ala Arg Ala Leu Val Leu Gln Leu Pro Ala Leu Asn Arg
            25                  30                  35

AAG GAC GAC GTG CCC GGC ATC GTC GGC CTG CTG CGC GAG TTT CTC CCG         2431
Lys Asp Asp Val Pro Gly Ile Val Gly Leu Leu Arg Glu Phe Leu Pro
        40                  45                  50

ACG CGC GGC GTG CCG TCC GGC TGG GGC TTC GTC GAA GCC GCC GCC GCG         2479
Thr Arg Gly Val Pro Ser Gly Trp Gly Phe Val Glu Ala Ala Ala Ala
55                  60                  65                  70

ATG CGG GAC ATC GGG TTC TTC CTG GGG TCG CTG AAG CGG CAC GGA CAC         2527
Met Arg Asp Ile Gly Phe Phe Leu Gly Ser Leu Lys Arg His Gly His
                75                  80                  85

GAG CCC GTG GAC GCA GTG CCC GGG CTC GAG CCG GTG CTG CTC GAC CTC         2575
Glu Pro Val Asp Ala Val Pro Gly Leu Glu Pro Val Leu Leu Asp Leu
            90                  95                  100

GCG CGT GTG ACC GAC CTG CCG CCG CGC GAG ACG CTC CTG CAT GTG ACG         2623
Ala Arg Val Thr Asp Leu Pro Pro Arg Glu Thr Leu Leu His Val Thr
        105                 110                 115

GTC TGG AAC CCC GCG ACG GCC GAC GCG CAG CGG AGC TAC ACC GGG CTC         2671
Val Trp Asn Pro Ala Thr Ala Asp Ala Gln Arg Ser Tyr Thr Gly Leu
120                 125                 130

GGC GAC GAA GCG CAC CTG CTC GAG AGC GTG CGC ATC TCG ATG GCG TCC         2719
Gly Asp Glu Ala His Leu Leu Glu Ser Val Arg Ile Ser Met Ala Ser
135                 140                 145                 150

CTC GAG GCG GCC ATC GCG CTG ACC GTC GAG CTA TAC GAC GTG CCG CTG         2767
Leu Glu Ala Ala Ile Ala Leu Thr Val Glu Leu Tyr Asp Val Pro Leu
                155                 160                 165

CGC TCG CCC GCG TTC GAG GAA GGG TGC GTC GAG CTG GCG GCC CAT CTG         2815
Arg Ser Pro Ala Phe Glu Glu Gly Cys Val Glu Leu Ala Ala His Leu
            170                 175                 180

CAG AAA ATG GTC GAA TCG ATC GTC TAC GCG TAC CGC TTC ATC TCG CCG         2863
Gln Lys Met Val Glu Ser Ile Val Tyr Ala Tyr Arg Phe Ile Ser Pro
        185                 190                 195

CAA GTC TTC TAC GAC GAG CTT CGC CCG TTC TAC GAA CCG ATT CGG GTC         2911
Gln Val Phe Tyr Asp Glu Leu Arg Pro Phe Tyr Glu Pro Ile Arg Val
200                 205                 210
```

```
GGC GGC CGG AGC TAC CTT GGC CCC GGC GCC GTG GAA ATG CCC CTC TTC      2959
Gly Gly Arg Ser Tyr Leu Gly Pro Gly Ala Val Glu Met Pro Leu Phe
215                 220                 225                 230

GTG CTG GAG CAC GTG TTG TGG GGT TCG CAA TCG GAC CAC CCG GCT TAT      3007
Val Leu Glu His Val Leu Trp Gly Ser Gln Ser Asp His Pro Ala Tyr
                235                 240                 245

CTG GAA TTC AAG GAG ACG TAC CTG CCC TAT GTG CTT CCC GCG TTC AGG      3055
Leu Glu Phe Lys Glu Thr Tyr Leu Pro Tyr Val Leu Pro Ala Phe Arg
            250                 255                 260

GCG ATC TAC GCC CGG TTC GCC GGA AGG CAG GCG CTC GTC GAC CGC GTG      3103
Ala Ile Tyr Ala Arg Phe Ala Gly Arg Gln Ala Leu Val Asp Arg Val
        265                 270                 275

CTC GGC GAG GCG CAA GCG GCC CGC GAG CGG GGC GAG CCC GTC GGG GCA      3151
Leu Gly Glu Ala Gln Ala Ala Arg Glu Arg Gly Glu Pro Val Gly Ala
    280                 285                 290

GGG CTG GCG GCC CTC GAG CGG ATC TTC GAG ATC CTG CTG CAC TTC CGG      3199
Gly Leu Ala Ala Leu Glu Arg Ile Phe Glu Ile Leu Leu His Phe Arg
295                 300                 305                 310

GCG CCT CAC CTC AAA TTG GCG GAG CGC ACG TAC GCG GCC GGG CAA ACC      3247
Ala Pro His Leu Lys Leu Ala Glu Arg Thr Tyr Ala Ala Gly Gln Thr
                315                 320                 325

GGC CCC ACG ATC GGC AGC GGC GGG TAC GCA CCC AGC ATG CTC GGC GAT      3295
Gly Pro Thr Ile Gly Ser Gly Gly Tyr Ala Pro Ser Met Leu Gly Asp
            330                 335                 340

CTG CTG ACG CTC ACG CGC GAC GCA CGG TCC CGC CTC CAC GCC GTG CTC      3343
Leu Leu Thr Leu Thr Arg Asp Ala Arg Ser Arg Leu His Ala Val Leu
        345                 350                 355

GCC GAG ACC TGA TACCTGACGC TTGACGCCTG ACGCGCTTGG CCATGTGTTC          3395
Ala Glu Thr *
    360

CATCTCACCA GGAGAGCTTG CCCCC ATG ACT CAG AAG AGC ATT GCA AAC GAG     3447
                            Met Thr Gln Lys Ser Ile Ala Asn Glu
                              1                 5

CGC GAT AAC CAC CAC TTC GAC GTG ATC ATC CTC GGC TCG GGC ATG TCC      3495
Arg Asp Asn His His Phe Asp Val Ile Ile Leu Gly Ser Gly Met Ser
 10              15                  20                  25

GGC ACC CAG ATG GGG GCC ATC CTG GCC AAA CAA AAG TTT CGT GTC CTG      3543
Gly Thr Gln Met Gly Ala Ile Leu Ala Lys Gln Lys Phe Arg Val Leu
                 30                  35                  40

ATC ATC GAG GAG TCG TCG CAC CCT CGG TTC ACG ATC GGC GAA TCG TCG      3591
Ile Ile Glu Glu Ser Ser His Pro Arg Phe Thr Ile Gly Glu Ser Ser
             45                  50                  55

ATC CCC GAG ACG TCC CTG ATG AAC CGC ATC ATC GCC GAT CGC TAC GGC      3639
Ile Pro Glu Thr Ser Leu Met Asn Arg Ile Ile Ala Asp Arg Tyr Gly
         60                  65                  70

ATT CCG GAG CTG GAC CAC ATC ACG TCG TTC TAT GCG ACT CAG CGT TAC      3687
Ile Pro Glu Leu Asp His Ile Thr Ser Phe Tyr Ala Thr Gln Arg Tyr
     75                  80                  85

GTC GCG TCG AGC ACG GGC ATC AAG CGC AAC TTC GGC TTC GTG TTC CAC      3735
Val Ala Ser Ser Thr Gly Ile Lys Arg Asn Phe Gly Phe Val Phe His
 90                  95                 100                 105

AAG CCG GGC GAG GAG CAC GAC CCG AAG GAG TTC ACG CAG TGC GTC ATT      3783
Lys Pro Gly Glu Glu His Asp Pro Lys Glu Phe Thr Gln Cys Val Ile
                110                 115                 120

CCG GAG CTG CCG TGG GGG CCC GAG AGC CAT TAT TAC CGG CAG GAC GTC      3831
Pro Glu Leu Pro Trp Gly Pro Glu Ser His Tyr Tyr Arg Gln Asp Val
            125                 130                 135

GAC GCC TAC CTG CTG CAA GCG GCC ATC AAA TAC GGC TGT ACG GTG CGC      3879
Asp Ala Tyr Leu Leu Gln Ala Ala Ile Lys Tyr Gly Cys Thr Val Arg
        140                 145                 150
```

```
CAG AGG ACG AGC GTG ACC GAC TAT CAC GCC GAC AAG GAC GGT GTC GCG      3927
Gln Arg Thr Ser Val Thr Asp Tyr His Ala Asp Lys Asp Gly Val Ala
    155                 160                 165

GTG GCC ACC GCC CAG GGC GAA CGG TTC ACG GGC CGG TAC ATG ATC GAC      3975
Val Ala Thr Ala Gln Gly Glu Arg Phe Thr Gly Arg Tyr Met Ile Asp
170             175                 180                 185

TGC GGG GGG CCC CGC GCG CCG CTC GCG ACC AAG TTC AAC CTC CGC GAA      4023
Cys Gly Gly Pro Arg Ala Pro Leu Ala Thr Lys Phe Asn Leu Arg Glu
                190                 195                 200

GAA CCG TGC CGC TTC AAG ACG CAC TCG CGC AGC CTC TAC ACG CAC ATG      4071
Glu Pro Cys Arg Phe Lys Thr His Ser Arg Ser Leu Tyr Thr His Met
            205                 210                 215

CTC GGG GTC AAG CCG TTC GAC GAC ATC TTC AAG GTC AAG GGG CAG CGC      4119
Leu Gly Val Lys Pro Phe Asp Asp Ile Phe Lys Val Lys Gly Gln Arg
        220                 225                 230

TGG CGC TGG CAC GAA GGG ACC TTG CAC CAC ATG TTC GAG GGC GGC TGG      4167
Trp Arg Trp His Glu Gly Thr Leu His His Met Phe Glu Gly Gly Trp
    235                 240                 245

CTC TGG GTG ATT CCG TTC AAC AAC CAC GCG CGG TCG ACC AAC AAC CTG      4215
Leu Trp Val Ile Pro Phe Asn Asn His Ala Arg Ser Thr Asn Asn Leu
250                 255                 260                 265

GTG AGC GTC GGC CTG CAG CTC GAC CCG CGT GTC TAC CCG AAG ACG GAT      4263
Val Ser Val Gly Leu Gln Leu Asp Pro Arg Val Tyr Pro Lys Thr Asp
                270                 275                 280

ATC CCC GCG CAG CAG GAG TTC GAC GAA TTC CTC GCG CGG TTC CCG AGC      4311
Ile Pro Ala Gln Gln Glu Phe Asp Glu Phe Leu Ala Arg Phe Pro Ser
            285                 290                 295

ATC GGC GCG CAG TTT CGC GAT GCC GTG CCA GTG CGC GAC TGG GTC AAG      4359
Ile Gly Ala Gln Phe Arg Asp Ala Val Pro Val Arg Asp Trp Val Lys
        300                 305                 310

ACC GAT CGC CTG CAG TTC TCG TCG CGC GCG TGC GTC GGC GAC CGT TAC      4407
Thr Asp Arg Leu Gln Phe Ser Ser Arg Ala Cys Val Gly Asp Arg Tyr
    315                 320                 325

TGC CTG ATG CTG CAC GCG AAC GGG TTC ATC GAC CCG CTC TTC TCC CGC      4455
Cys Leu Met Leu His Ala Asn Gly Phe Ile Asp Pro Leu Phe Ser Arg
330                 335                 340                 345

GGG CTC GAG AAC ACC GCG GTG ACC ATT CAC GCG CTC GCG GCG CGT CTC      4503
Gly Leu Glu Asn Thr Ala Val Thr Ile His Ala Leu Ala Ala Arg Leu
                350                 355                 360

ATC AAG GCG CTG CGC GAC GAC GAT TTT TCT CCC GAG CGC TTC GAG TAC      4551
Ile Lys Ala Leu Arg Asp Asp Asp Phe Ser Pro Glu Arg Phe Glu Tyr
            365                 370                 375

ATC GAG CGT CTG CAG CAG AAG CTG CTG GAT CAC AAC GAC GAC TTC GTC      4599
Ile Glu Arg Leu Gln Gln Lys Leu Leu Asp His Asn Asp Asp Phe Val
        380                 385                 390

AGC TGC TGT TAC ACG GCG TTC TCG GAC TTC CGG CTG TGG GAC GCG TTC      4647
Ser Cys Cys Tyr Thr Ala Phe Ser Asp Phe Arg Leu Trp Asp Ala Phe
    395                 400                 405

CAC CGG TTG TGG GCG GTC GGC ACG ATC CTC GGG CAG TTC CGG CTC GTG      4695
His Arg Leu Trp Ala Val Gly Thr Ile Leu Gly Gln Phe Arg Leu Val
410                 415                 420                 425

CAG GCC CAC GCG AGG TTC CGC GCC TCG CGC AAC GAG CGT GAC CTC GAT      4743
Gln Ala His Ala Arg Phe Arg Ala Ser Arg Asn Glu Arg Asp Leu Asp
                430                 435                 440

CAC CTC GAC GAC AAC GCG CCG TAT CTC GGC TTC CTG TGC GCT GAC ATG      4791
His Leu Asp Asp Asn Ala Pro Tyr Leu Gly Phe Leu Cys Ala Asp Met
            445                 450                 455

GAG GGG TAC TAC CAG TTG TTC AAC GAC GCC AAG GCC GAG GTC GAA GCC      4839
Glu Gly Tyr Tyr Gln Leu Phe Asn Asp Ala Lys Ala Glu Val Glu Ala
        460                 465                 470
```

```
GTG AGC GCC GGG CGA AAG ACG GCC GGC GAG GCC GCC GCG CGG ATT CAT    4887
Val Ser Ala Gly Arg Lys Thr Ala Gly Glu Ala Ala Ala Arg Ile His
    475                 480                 485

GTC CTC ATC AAC GAG CGG GAG TTC GCG AAG CCG ATG TTC GGC TTC GGG    4935
Val Leu Ile Asn Glu Arg Glu Phe Ala Lys Pro Met Phe Gly Phe Gly
490                 495                 500                 505

TAC TGC ATC ACC GGG GCC AAA CCG CAG CTC AAC AAC TCG AAG TAC AGC    4983
Tyr Cys Ile Thr Gly Ala Lys Pro Gln Leu Asn Asn Ser Lys Tyr Ser
                510                 515                 520

CTG CTG CCG GCG ATG AAG CTG CTG CAC TGG ACG CAG ACC AGC GCG CCG    5031
Leu Leu Pro Ala Met Lys Leu Leu His Trp Thr Gln Thr Ser Ala Pro
                525                 530                 535

GCA GAG GTG AAG AAG TAC TTC GAC TAC AAC CCG ATG TTC GCG CTG CTC    5079
Ala Glu Val Lys Lys Tyr Phe Asp Tyr Asn Pro Met Phe Ala Leu Leu
                540                 545                 550

AGG GCG TAC GTC ACC ACC CGC ATC GGC CTG GCG CTG AAG TAG            5121
Arg Ala Tyr Val Thr Thr Arg Ile Gly Leu Ala Leu Lys *
                555                 560                 565

TCGGCCGACA CTGCCACGAG AAC ATG GAC GAC GTT CAA TTT CAA TTG CAA      5171
                       Met Asp Asp Val Gln Phe Gln Leu Gln
                         1               5

CAA GCG GAT GCC CGG GAG CAA CCG TCG GGG GCG TAC GAC GCG ACC ACG    5219
Gln Ala Asp Ala Arg Glu Gln Pro Ser Gly Ala Tyr Asp Ala Thr Thr
 10                  15                  20                  25

CGC GTG GCC GCG AGC TGG TAC GTC GCG ATG CGC TCG GAC GAC CTC AAG    5267
Arg Val Ala Ala Ser Trp Tyr Val Ala Met Arg Ser Asp Asp Leu Lys
                 30                  35                  40

GAC AAG CCG CTG GAA CTG ACG CTC TTC GGG CGG CCG TGC GTG GCG TGG    5315
Asp Lys Pro Leu Glu Leu Thr Leu Phe Gly Arg Pro Cys Val Ala Trp
                 45                  50                  55

CGC GGC GCG ATG GGG CGG GCC GTG GTG ATG GAC CGC CAC TGC TCG CAC    5363
Arg Gly Ala Met Gly Arg Ala Val Val Met Asp Arg His Cys Ser His
                 60                  65                  70

CTC GGC GCG AAC CTG GCC GAC GGG CAG GTC AAG GAC GGG TGC ATC CAG    5411
Leu Gly Ala Asn Leu Ala Asp Gly Gln Val Lys Asp Gly Cys Ile Gln
 75                  80                  85

TGC CCG TTT CAC CAC TGG CGG TAC GAC GAG CAG GGC CAG TGC GTA CAC    5459
Cys Pro Phe His His Trp Arg Tyr Asp Glu Gln Gly Gln Cys Val His
 90                  95                 100                 105

ATT CCC GGC CAC AGC GAG GCG GTG CAC CGG CTG GAG CCC GTG CCG CGC    5507
Ile Pro Gly His Ser Glu Ala Val His Arg Leu Glu Pro Val Pro Arg
                110                 115                 120

GGC GCG CGC CAG CCG ACG CTG GTC ACC ACC GAG CGG TAC GGC TAC GTG    5555
Gly Ala Arg Gln Pro Thr Leu Val Thr Thr Glu Arg Tyr Gly Tyr Val
                125                 130                 135

TGG GTC TGG TAC GGC TCG CCG CAG CCG CTG CAC CCG TTG CCC GAC ATC    5603
Trp Val Trp Tyr Gly Ser Pro Gln Pro Leu His Pro Leu Pro Asp Ile
                140                 145                 150

GCC GCG GCC GAC GTC GAC AAC GGC GAC TTC ATG CAC CTG CAC TTC GCG    5651
Ala Ala Ala Asp Val Asp Asn Gly Asp Phe Met His Leu His Phe Ala
155                 160                 165

TTC GAG ACG ACG ACG GCG GTC TTG CGG ATC GTC GAG AAC TTC TAC GAC    5699
Phe Glu Thr Thr Thr Ala Val Leu Arg Ile Val Glu Asn Phe Tyr Asp
170                 175                 180                 185

GCG CAG CAT GCG CAC CCG GTC CAC GCG CTG CCG ATC TCG GCG TTC GAG    5747
Ala Gln His Ala His Pro Val His Ala Leu Pro Ile Ser Ala Phe Glu
                190                 195                 200

CTC AAG CTC TGC GAC GAC TGG CGC CCG TGG CCG GAG GTC GAG CCG CTG    5795
Leu Lys Leu Cys Asp Asp Trp Arg Pro Trp Pro Glu Val Glu Pro Leu
                205                 210                 215
```

```
GCT CGG GCG GGC GCG TGG TTC GGC GCC GGG ATC GAC TTC ACC GTG AAC        5843
Ala Arg Ala Gly Ala Trp Phe Gly Ala Gly Ile Asp Phe Thr Val Asn
        220                 225                 230

CGG TAC TTC GGG CCA CTC GGC ATG CTG TCG CGC GCG CTC GGC CTG AGC        5891
Arg Tyr Phe Gly Pro Leu Gly Met Leu Ser Arg Ala Leu Gly Leu Ser
        235                 240                 245

ATG TCG CAG ATG AAC CTG CAC TTC GAC GGC TAC CCC GGC GGG TGC GTG        5939
Met Ser Gln Met Asn Leu His Phe Asp Gly Tyr Pro Gly Gly Cys Val
250                 255                 260                 265

ATG ACC GTC GCG CTG GAC GGA GAC GCC AAA TAC AAG CTG CTC CAG TGT        5987
Met Thr Val Ala Leu Asp Gly Asp Ala Lys Tyr Lys Leu Leu Gln Cys
                270                 275                 280

GTG ACG CCG GTG AGC GAC GGC AGG AAC GTC ATG CAC ATG CTC ATC TCG        6035
Val Thr Pro Val Ser Asp Gly Arg Asn Val Met His Met Leu Ile Ser
        285                 290                 295

ATC AGG AAG GCC GGC GGC CCC GTG CGC CGC GCG ATC GAC TAC GTG CTG        6083
Ile Arg Lys Ala Gly Gly Pro Val Arg Arg Ala Ile Asp Tyr Val Leu
        300                 305                 310

TTC GGA CTG CAG ACC AGG CAG GCG GCG GGA TAC GAC GTC AAG ATC TGG        6131
Phe Gly Leu Gln Thr Arg Gln Ala Ala Gly Tyr Asp Val Lys Ile Trp
        315                 320                 325

AAC GGG ATG AAG CCG GAC GGC GGC GGC GCG TAC AGC AAG TAC GAC AAG        6179
Asn Gly Met Lys Pro Asp Gly Gly Gly Ala Tyr Ser Lys Tyr Asp Lys
330                 335                 340                 345

CTC GTG CTC AAG TAC CGC GCG TTC TAC CGG GGC TGG GTC GAC CGC GTC        6227
Leu Val Leu Lys Tyr Arg Ala Phe Tyr Arg Gly Trp Val Asp Arg Val
                350                 355                 360

GCG TCG AGC GAG CGG CAA GGC GTG AGC CGG AGG TCC TAG CCGACGCCGG         6276
Ala Ser Ser Glu Arg Gln Gly Val Ser Arg Arg Ser  *
                365                 370

CCCCGGTCAG CGGGCCGGCA TCGGCAACGC ATCAATACGA GAGACCGAAT CCGAACGGAT      6336

ACAACGGATG CGCGGTATCG TGCGGCACGT CTTCCCGCTG CGCCGCGACC TCCGCCATCG      6396

ACGACGGCAG CTCGAACGGC AGCTTCCCTT GCGGTTGGCC TTTCCCGGTC AGCACGTCGA      6456

ACAGCGCGGC ATCGGTCACG CCGAAATTCG CGAGGATCGC GGTGGCCTTG TCCTGCACGT      6516

TGGTCAGGAT CGCGGGACGA TCCATGTACA CCGAGACGAT CGACTTCGGC GCAAGCGCGG      6576

CCTGCTTGAT GGCCTCGTAG TCCGCACTGC CGTCGACGAA CGCGAGACTG CCCTCGTGCT      6636

GCATCGAGCC GAACATGTAG TTCGGGTGCA ACGTCTGATA GGGCGTGCTC ACGCGGAGAA      6696

TCGCCACGTC CGCGGCTTGC GGCGTATCGA CGACCTGATA ACCGTATTGC CGCGCGACGG      6756

CGGGATCGAT GCCGTACAGC CAGACCTTCT TGCCCGACGC CGTCATCGGC AGCAGCTTGC      6816

CGTCGTTCTG CAGCAGCACC ATCGAGCGGC GCTGCGCATC GAGTGCCTGG GCCTGGAAGT      6876

CGGCGTTTCC GACGATCTTG CCGGCCGCGT CCGCATCGAC ATACGGATGG TCGAACAGGC      6936

CTTGCTGGAA TTTCTGCAGC AGCACGCGAT AGGCCGACTC CGACAGGCGC GCTTCCGACA      6996

ACTGCCCGCG ATTGACGGCG TCGATGAGGT CGCTCGGATC GTCGTCTCCG CCGAACTGGT      7056

CGATGCCGGC GTTGACCGCG CGCGTGAAGC GCTGCACGCG GGTCGCGCCC TCCATCCCCC      7116

AGGGCATGCC CAGTCCGACG AACGACGGCG CGCCCGACGA CACACCGTTG ATGCAGTTCG      7176

CGTCGCAGTC GTCGGCGATC AGCCAGTCGG ACACGATCAC GCCCTTGAAG CCGTATTTCC      7236

CGCGCAGCAG GTCGGTCAGC AACGCCTTGT CGTAGGCGCC GCCGACCGGC TCCAGCGTGA      7296

TGCCGTCGAC CGTCACCGTC ATGTCCGGTT CGGAATAGGT CGGCATGACC GAGCCGACGT      7356

TGGCGGCGAA GGCGCCTTCG AACGGCTTCA GGTGATAGGC GAAATTGTTG CCCGGATAGG      7416

TCGCATAGCG GCCGTAGTAA TTGTGGCTGT CGAACCCGAG TTTCTGCGCG CCATATCCGG      7476
```

-continued

```
CCCAGTGCTT GACGACCGCG ATGACGCTAT TGGCCTGGAT GACGTTGCTG CCGCCCTGGA    7536

AGCCTTCGAT ATAGGCCTGG ACTTGCGTGC GGGCGAGATC GGAGTCTTCG CCGAAGGTGC    7596

CGTTGATGCG TGCCCAGCGC GGCTCGGTCG CCAGATCGGT TGCGGTGAA AGCGCTACGG    7656

TGATGCCGAC GGCGCGATAC TCCTGGCGCG CGATGTCGCC GAATTTTCGC GTGAGTGCCG    7716

TATCGCCGAT CGCGGCGAAG CCGAGCGTTT CCGGCCACTG CGAGAAACCG CTCCTGCCTG    7776

CGCTTGCGCC AAGCGTGTAC TGGAAATGAT TGCGCGGGTC GGAGCTGATC GACACCGGGA    7836

TGCCGAGCCG CGACTGCTCC GCCAGCGTCT GAATCTGGTT GGCCTGGTCG CCATGGTGC    7896

GCGCATCGGC ACTCATGCGC GTGATATAGG TGTTGACGCC CCGCTGATTG ATGAGCGTCT    7956

TGAGCGCCGC CAGGTCGTAC GCGGAGCCGG TGCCCGCACC GGTCGTGTCG TTCAGCACGG    8016

GTGCGGTGCC GTGCATCATC AGGCCGGCTT TTTCGGCCAG CGTGAGGCGG CCGACCAGGT    8076

CCCGCGCACG CACGTCGGCA CTCAGCCGCC AGTCTTCGTA CGGTTCGAGC TGACCGCTCT    8136

TGTCCATGTC CTTGAACTTC AGGCCGTCCC GGGTGATCAG GTTCAACGTG GTGTAGCCGA    8196

AGTCCTGCTG CGCGACGGGC GGGGCAGAGG AGTCGACGCC GCCGCAGGCA AACAGTCCCA    8256

GCGTGAGCGC GGTGCCGGAT GCGGCCCGTG CCGATCGGCG AATGGCTGAT CTCGTGATGC    8316

GTTGCATTGC TTGTCTCCTG AATCGGATTT TTTGGCGCGG CCGTGATGCA TGACGCAGGG    8376

CCGCCGGCCA CTTTACCGAG CTGTTTCAGG GGACGTTTTG CCGCCGGGTG CAGTTTTTGC    8436

CCCGATGGGG CGCGATGTGC CGGGCAATGC GACCGGGCGG ATTTTCAACG CGGCCTATCG    8496

GCTTCGCGAG CCGGCTTGCC GCTCGTCCGC CCGCGCATGC TATGCATGAA CGGCCACCCG    8556

ATACCGGGTG GTCTGTCGAT AGACGGCGTC CGGATGAAGG ATCACGTCGC CGCTCAGGCC    8616

GGGCATGTTC ACCTGGTCAG GAAAACCGCC CGCCTCCAGG CACAGCGCCG CATGTTGCGT    8676

GCAACGTGTG CCGCCGCTCA CGCGCAGGCC ATCGAGATAG TTGCCCGTAT AGAGTTGCAG    8736

GCCCCGCTGA TCGGTCGACA CGATCAGCTC GCGGCCGCTT TCCGGATCGT AGACGCGTGC    8796

GACGGGCCGG GCCTCGTGCG TGCCGTCGCC CAGGACGAAG CAATGATCGA AGCCGCGCGC    8856

GCGGGCCAGT TGCGCGTGCG GCCAGTCGAG GCGCGCGCCG ATCGGCGCGC TGTGCCGGAA    8916

ATCGAACGCG GTACC                                                     8931
```

(2) INFORMATION FOR SEQ ID NO:29:

(i) SEQUENCE CHARACTERISTICS:
        (A) LENGTH: 537 amino acids
        (B) TYPE: amino acid
        (D) TOPOLOGY: linear (ii) MOLECULE TYPE: protein (xi) SEQUENCE DESCRIPTION: SEQ ID NO:29:

```
Met Ser His Pro Ile Lys Asn Ile Val Ile Gly Gly Gly Thr Ala
 1               5                  10                  15

Gly Trp Met Ser Ala Ser Tyr Leu Val Arg Ala Leu Gln Gln Gln Ala
                20                  25                  30

Asn Ile Thr Leu Ile Glu Ser Glu Ala Ile Pro Arg Ile Gly Val Gly
            35                  40                  45

Glu Ala Thr Ile Pro Asn Leu Gln Lys Val Phe Phe Asp Phe Leu Gly
        50                  55                  60

Ile Pro Glu Arg Glu Trp Met Pro Gln Val Asn Gly Ala Phe Lys Ser
65                  70                  75                  80

Ala Ile Lys Phe Val Asn Trp Arg Lys Ser Pro Asp Arg Ser Arg Asp
                85                  90                  95
```

-continued

```
Asp His Phe Tyr His Leu Phe Gly Ser Val Pro Asn Cys Asp Gly Val
             100                 105                 110

Pro Leu Thr His Tyr Trp Leu Arg Lys Arg Glu Gln Gly Phe Gln Gln
             115                 120                 125

Pro Met Glu Tyr Ala Cys Tyr Pro Gln Pro Glu Ala Leu Asp Ala Arg
             130                 135                 140

Leu Ala Pro Cys Leu Leu Asp Gly Thr Arg Gln Met Pro His Ala Trp
145                  150                 155                 160

His Phe Asp Ala His Leu Val Ala Asp Phe Leu Lys Arg Trp Ala Val
                 165                 170                 175

Gly Arg Gly Val Thr Arg Val Val Asp Glu Val Val Glu Val His Leu
                 180                 185                 190

Asn Glu Arg Gly Asp Ile Ala Ser Leu Ser Thr Lys Glu Gly Arg Thr
             195                 200                 205

Leu Glu Ala Asp Leu Phe Ile Asp Cys Ser Gly Met Arg Gly Leu Leu
             210                 215                 220

Ile Asn Gln Ala Leu Lys Glu Pro Phe Ile Asp Met Ser Asp Tyr Leu
225                 230                 235                 240

Leu Cys Asp Ser Ala Val Ala Ser Ala Val Pro Asn Asp Asp Ala Arg
                 245                 250                 255

Val Gly Ile Glu Pro Tyr Thr Ser Ala Ile Ala Met Asn Ser Gly Trp
             260                 265                 270

Thr Trp Lys Ile Pro Met Leu Gly Arg Phe Gly Ser Gly Tyr Val Phe
             275                 280                 285

Ser Ser Lys Phe Thr Ser Arg Asp Gln Ala Thr Ala Asp Phe Leu Asn
             290                 295                 300

Leu Trp Gly Leu Ser Asp Lys Gln Pro Leu Asn Gln Ile Lys Phe Arg
305                 310                 315                 320

Val Gly Arg Asn Gly Arg Ala Trp Val Asn Asn Cys Val Ala Ile Gly
                 325                 330                 335

Leu Ser Ser Cys Phe Leu Glu Pro Leu Glu Ser Thr Gly Ile Tyr Phe
                 340                 345                 350

Ile Tyr Ala Ala Leu Tyr Gln Leu Val Lys His Phe Pro Asp Thr Gly
             355                 360                 365

Phe Asp Pro Arg Leu Arg Asp Ala Phe Asn Ala Glu Ile Val Tyr Met
             370                 375                 380

Phe Asp Asp Cys Arg Asp Phe Val Gln Ala His Tyr Phe Thr Ala Ser
385                 390                 395                 400

Arg Asp Asp Thr Pro Phe Trp Leu Ala Asn Arg His Asp Leu Arg Leu
                 405                 410                 415

Ser Asp Ala Ile Lys Asp Lys Val Glu Arg Tyr Lys Ala Gly Leu Pro
             420                 425                 430

Leu Thr Thr Thr Ser Phe Asp Asp Ala Thr Tyr Tyr Glu Thr Phe Asp
             435                 440                 445

Tyr Glu Phe Lys Asn Phe Trp Leu Asn Gly Asn Tyr Tyr Cys Ile Phe
             450                 455                 460

Ala Gly Leu Gly Leu Leu Pro Asp Arg Ser Leu Pro Leu Leu Arg His
465                 470                 475                 480

Arg Pro Ala Ser Val Asp Lys Ala Glu Ala Met Phe Ala Arg Ile Arg
                 485                 490                 495

Arg Glu Ala Glu Arg Leu Arg Ala Ser Leu Pro Thr Asn Tyr Asp Tyr
             500                 505                 510
```

```
Leu Arg Ser Leu Arg Asp Gly Glu Ala Gly Arg Ala Arg Ser Arg Pro
            515                 520                 525

Gly Pro Val Ala Ala Pro Glu Thr Leu
    530                 535
```

(2) INFORMATION FOR SEQ ID NO:30:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:30:

```
Met Glu Arg Ala Leu Gly Arg Ala Arg Ala Phe Ala Ala Thr His Ala
  1               5                  10                  15

Ala Val Ala Ala Cys Asp Pro Leu Arg Ala Arg Ala Leu Val Leu Gln
                 20                  25                  30

Leu Pro Ala Leu Asn Arg Lys Asp Asp Val Pro Gly Ile Val Gly Leu
             35                  40                  45

Leu Arg Glu Phe Leu Pro Thr Arg Gly Val Pro Ser Gly Trp Gly Phe
 50                  55                  60

Val Glu Ala Ala Ala Ala Met Arg Asp Ile Gly Phe Phe Leu Gly Ser
 65                  70                  75                  80

Leu Lys Arg His Gly His Glu Pro Val Asp Ala Val Pro Gly Leu Glu
                 85                  90                  95

Pro Val Leu Leu Asp Leu Ala Arg Val Thr Asp Leu Pro Pro Arg Glu
                100                 105                 110

Thr Leu Leu His Val Thr Val Trp Asn Pro Ala Thr Ala Asp Ala Gln
            115                 120                 125

Arg Ser Tyr Thr Gly Leu Gly Asp Glu Ala His Leu Leu Glu Ser Val
        130                 135                 140

Arg Ile Ser Met Ala Ser Leu Glu Ala Ala Ile Ala Leu Thr Val Glu
145                 150                 155                 160

Leu Tyr Asp Val Pro Leu Arg Ser Pro Ala Phe Glu Glu Gly Cys Val
                165                 170                 175

Glu Leu Ala Ala His Leu Gln Lys Met Val Glu Ser Ile Val Tyr Ala
            180                 185                 190

Tyr Arg Phe Ile Ser Pro Gln Val Phe Tyr Asp Glu Leu Arg Pro Phe
        195                 200                 205

Tyr Glu Pro Ile Arg Val Gly Gly Arg Ser Tyr Leu Gly Pro Gly Ala
210                 215                 220

Val Glu Met Pro Leu Phe Val Leu Glu His Val Leu Trp Gly Ser Gln
225                 230                 235                 240

Ser Asp His Pro Ala Tyr Leu Glu Phe Lys Glu Thr Tyr Leu Pro Tyr
                245                 250                 255

Val Leu Pro Ala Phe Arg Ala Ile Tyr Ala Arg Phe Ala Gly Arg Gln
            260                 265                 270

Ala Leu Val Asp Arg Val Leu Gly Glu Ala Gln Ala Ala Arg Glu Arg
        275                 280                 285

Gly Glu Pro Val Gly Ala Gly Leu Ala Ala Leu Glu Arg Ile Phe Glu
290                 295                 300

Ile Leu Leu His Phe Arg Ala Pro His Leu Lys Leu Ala Glu Arg Thr
305                 310                 315                 320
```

Tyr Ala Ala Gly Gln Thr Gly Pro Thr Ile Gly Ser Gly Gly Tyr Ala
                325                 330                 335

Pro Ser Met Leu Gly Asp Leu Leu Thr Leu Thr Arg Asp Ala Arg Ser
            340                 345                 350

Arg Leu His Ala Val Leu Ala Glu Thr
        355                 360

(2) INFORMATION FOR SEQ ID NO:31:

(i) SEQUENCE CHARACTERISTICS:
        (A) LENGTH: 566 amino acids
        (B) TYPE: amino acid
        (D) TOPOLOGY: linear (ii) MOLECULE TYPE: protein (xi) SEQUENCE DESCRIPTION: SEQ ID NO:31:

Met Thr Gln Lys Ser Ile Ala Asn Glu Arg Asp Asn His His Phe Asp
 1               5                  10                  15

Val Ile Ile Leu Gly Ser Gly Met Ser Gly Thr Gln Met Gly Ala Ile
                20                  25                  30

Leu Ala Lys Gln Lys Phe Arg Val Leu Ile Ile Glu Glu Ser Ser His
            35                  40                  45

Pro Arg Phe Thr Ile Gly Glu Ser Ser Ile Pro Glu Thr Ser Leu Met
 50                  55                  60

Asn Arg Ile Ile Ala Asp Arg Tyr Gly Ile Pro Glu Leu Asp His Ile
65                  70                  75                  80

Thr Ser Phe Tyr Ala Thr Gln Arg Tyr Val Ala Ser Ser Thr Gly Ile
                85                  90                  95

Lys Arg Asn Phe Gly Phe Val Phe His Lys Pro Gly Glu Glu His Asp
            100                 105                 110

Pro Lys Glu Phe Thr Gln Cys Val Ile Pro Glu Leu Pro Trp Gly Pro
        115                 120                 125

Glu Ser His Tyr Tyr Arg Gln Asp Val Asp Ala Tyr Leu Leu Gln Ala
    130                 135                 140

Ala Ile Lys Tyr Gly Cys Thr Val Arg Gln Arg Thr Ser Val Thr Asp
145                 150                 155                 160

Tyr His Ala Asp Lys Asp Gly Val Ala Val Ala Thr Ala Gln Gly Glu
                165                 170                 175

Arg Phe Thr Gly Arg Tyr Met Ile Asp Cys Gly Gly Pro Arg Ala Pro
            180                 185                 190

Leu Ala Thr Lys Phe Asn Leu Arg Glu Glu Pro Cys Arg Phe Lys Thr
        195                 200                 205

His Ser Arg Ser Leu Tyr Thr His Met Leu Gly Val Lys Pro Phe Asp
    210                 215                 220

Asp Ile Phe Lys Val Lys Gly Gln Arg Trp Arg Trp His Glu Gly Thr
225                 230                 235                 240

Leu His His Met Phe Glu Gly Gly Trp Leu Trp Val Ile Pro Phe Asn
                245                 250                 255

Asn His Ala Arg Ser Thr Asn Asn Leu Val Ser Val Gly Leu Gln Leu
            260                 265                 270

Asp Pro Arg Val Tyr Pro Lys Thr Asp Ile Pro Ala Gln Gln Glu Phe
        275                 280                 285

Asp Glu Phe Leu Ala Arg Phe Pro Ser Ile Gly Ala Gln Phe Arg Asp
    290                 295                 300

```
Ala Val Pro Val Arg Asp Trp Val Lys Thr Asp Arg Leu Gln Phe Ser
305                 310                 315                 320

Ser Arg Ala Cys Val Gly Asp Arg Tyr Cys Leu Met Leu His Ala Asn
            325                 330                 335

Gly Phe Ile Asp Pro Leu Phe Ser Arg Gly Leu Glu Asn Thr Ala Val
                340                 345                 350

Thr Ile His Ala Leu Ala Ala Arg Leu Ile Lys Ala Leu Arg Asp Asp
            355                 360                 365

Asp Phe Ser Pro Glu Arg Phe Glu Tyr Ile Glu Arg Leu Gln Gln Lys
        370                 375                 380

Leu Leu Asp His Asn Asp Asp Phe Val Ser Cys Cys Tyr Thr Ala Phe
385                 390                 395                 400

Ser Asp Phe Arg Leu Trp Asp Ala Phe His Arg Leu Trp Ala Val Gly
                405                 410                 415

Thr Ile Leu Gly Gln Phe Arg Leu Val Gln Ala His Ala Arg Phe Arg
            420                 425                 430

Ala Ser Arg Asn Glu Arg Asp Leu Asp His Leu Asp Asp Asn Ala Pro
            435                 440                 445

Tyr Leu Gly Phe Leu Cys Ala Asp Met Glu Gly Tyr Tyr Gln Leu Phe
        450                 455                 460

Asn Asp Ala Lys Ala Glu Val Glu Ala Val Ser Ala Gly Arg Lys Thr
465                 470                 475                 480

Ala Gly Glu Ala Ala Arg Ile His Val Leu Ile Asn Glu Arg Glu
                485                 490                 495

Phe Ala Lys Pro Met Phe Gly Phe Gly Tyr Cys Ile Thr Gly Ala Lys
                500                 505                 510

Pro Gln Leu Asn Asn Ser Lys Tyr Ser Leu Leu Pro Ala Met Lys Leu
            515                 520                 525

Leu His Trp Thr Gln Thr Ser Ala Pro Ala Glu Val Lys Lys Tyr Phe
        530                 535                 540

Asp Tyr Asn Pro Met Phe Ala Leu Leu Arg Ala Tyr Val Thr Thr Arg
545                 550                 555                 560

Ile Gly Leu Ala Leu Lys
                565

(2) INFORMATION FOR SEQ ID NO:32:

(i) SEQUENCE CHARACTERISTICS:
        (A) LENGTH:   373 amino acids
        (B) TYPE: amino acid
        (D) TOPOLOGY: linear (ii) MOLECULE TYPE: protein (xi) SEQUENCE DESCRIPTION: SEQ ID NO:32:

Met Asp Asp Val Gln Phe Gln Leu Gln Gln Ala Asp Ala Arg Glu Gln
1               5                   10                  15

Pro Ser Gly Ala Tyr Asp Ala Thr Thr Arg Val Ala Ala Ser Trp Tyr
            20                  25                  30

Val Ala Met Arg Ser Asp Asp Leu Lys Asp Lys Pro Leu Glu Leu Thr
            35                  40                  45

Leu Phe Gly Arg Pro Cys Val Ala Trp Arg Gly Ala Met Gly Arg Ala
        50                  55                  60

Val Val Met Asp Arg His Cys Ser His Leu Gly Ala Asn Leu Ala Asp
65                  70                  75                  80
```

```
Gly Gln Val Lys Asp Gly Cys Ile Gln Cys Pro Phe His His Trp Arg
                85                  90                  95
Tyr Asp Glu Gln Gly Gln Cys Val His Ile Pro Gly His Ser Glu Ala
            100                 105                 110
Val His Arg Leu Glu Pro Val Pro Arg Gly Ala Arg Gln Pro Thr Leu
        115                 120                 125
Val Thr Thr Glu Arg Tyr Gly Tyr Val Trp Val Trp Tyr Gly Ser Pro
    130                 135                 140
Gln Pro Leu His Pro Leu Pro Asp Ile Ala Ala Ala Asp Val Asp Asn
145                 150                 155                 160
Gly Asp Phe Met His Leu His Phe Ala Phe Glu Thr Thr Ala Val
                165                 170                 175
Leu Arg Ile Val Glu Asn Phe Tyr Asp Ala Gln His Ala His Pro Val
                180                 185                 190
His Ala Leu Pro Ile Ser Ala Phe Glu Leu Lys Leu Cys Asp Asp Trp
            195                 200                 205
Arg Pro Trp Pro Glu Val Glu Pro Leu Ala Arg Ala Gly Ala Trp Phe
        210                 215                 220
Gly Ala Gly Ile Asp Phe Thr Val Asn Arg Tyr Phe Gly Pro Leu Gly
225                 230                 235                 240
Met Leu Ser Arg Ala Leu Gly Leu Ser Met Ser Gln Met Asn Leu His
                245                 250                 255
Phe Asp Gly Tyr Pro Gly Gly Cys Val Met Thr Val Ala Leu Asp Gly
            260                 265                 270
Asp Ala Lys Tyr Lys Leu Leu Gln Cys Val Thr Pro Val Ser Asp Gly
        275                 280                 285
Arg Asn Val Met His Met Leu Ile Ser Ile Arg Lys Ala Gly Gly Pro
    290                 295                 300
Val Arg Arg Ala Ile Asp Tyr Val Leu Phe Gly Leu Gln Thr Arg Gln
305                 310                 315                 320
Ala Ala Gly Tyr Asp Val Lys Ile Trp Asn Gly Met Lys Pro Asp Gly
                325                 330                 335
Gly Gly Ala Tyr Ser Lys Tyr Asp Lys Leu Val Leu Lys Tyr Arg Ala
            340                 345                 350
Phe Tyr Arg Gly Trp Val Asp Arg Val Ala Ser Ser Glu Arg Gln Gly
        355                 360                 365
Val Ser Arg Arg Ser
370
```

(2) INFORMATION FOR SEQ ID NO:33:

(i) SEQUENCE CHARACTERISTICS:
        (A) LENGTH: 5996 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Myxococcus fulvus (ix) FEATURE:
        (A) NAME/KEY: CDS
        (B) LOCATION: 172..1284
        (D) OTHER INFORMATION: /product= "PrnB"

```
     (ix) FEATURE:
           (A) NAME/KEY: CDS
           (B) LOCATION: 1341..3038
           (D) OTHER INFORMATION: /product= "PrnC"

(ix) FEATURE:
           (A) NAME/KEY: CDS
           (B) LOCATION: 3100..4239
           (D) OTHER INFORMATION: /product= "PrnD"

(ix) FEATURE:
           (A) NAME/KEY: CDS
           (B) LOCATION: complement (4258..5880)
           (D) OTHER INFORMATION: /product= "PrnA"

(xi) SEQUENCE DESCRIPTION: SEQ ID NO:33:

TGCCGCCACG GGAGGCCCGC AGCCCCGCCC CGCACAGCGA TTACCTGCCA GGAATTGCGG      60

TGGGCGCGGC CTTGACGCGC TCGTGACGCA TTGACTGGAT TTTATATAGA CACAAGCACA     120

TGTTAGAGTC TGGACAAGGG GCTCGGTGGC GCTTTCACGA GGGTGTCTTT G ATG AAT     177
                                                       Met Asn
                                                         1

CCG GGG CAG AAC TTT TCA TCC ACA CAT GAA GTC ATC GCC ACG CTC GAT     225
Pro Gly Gln Asn Phe Ser Ser Thr His Glu Val Ile Ala Thr Leu Asp
      5                  10                  15

CCG TTG GAT GCA TTG GCG ACC ATG CGG CGC CTG CCT GAG CTG AAT CAG     273
Pro Leu Asp Ala Leu Ala Thr Met Arg Arg Leu Pro Glu Leu Asn Gln
 20                  25                  30

CGG AGC GAC GTG CGA GGG GTT CTG GAG TTG CTC CAG GGC ATT CTC CCC     321
Arg Ser Asp Val Arg Gly Val Leu Glu Leu Leu Gln Gly Ile Leu Pro
 35                  40                  45                  50

AGG TTG GAG ATT GTC GAG CGG TGG GAC TTT CCG GTG GCA GCA GCC GCC     369
Arg Leu Glu Ile Val Glu Arg Trp Asp Phe Pro Val Ala Ala Ala Ala
              55                  60                  65

ATG CGT GAC ATT GGA TTC TTC CTG GGC TCC CTC AAG AGG CAT GGA CAT     417
Met Arg Asp Ile Gly Phe Phe Leu Gly Ser Leu Lys Arg His Gly His
                  70                  75                  80

GAG CCC GTC GAG GTG GTT CCG GGA CTG GAG CCC ATC CTG CTG GCG CTC     465
Glu Pro Val Glu Val Val Pro Gly Leu Glu Pro Ile Leu Leu Ala Leu
              85                  90                  95

GCC CGG GCG ACA CAG CTG CCT CCC CGG GAG ACC CTG CTC CAC GTG ACA     513
Ala Arg Ala Thr Gln Leu Pro Pro Arg Glu Thr Leu Leu His Val Thr
100                 105                 110

GTC TGG AAC CCG GCC GCG GAC GAG CTG GAG CGC CGG TAC ACC TGC TGC     561
Val Trp Asn Pro Ala Ala Asp Glu Leu Glu Arg Arg Tyr Thr Cys Cys
115                 120                 125                 130

CGC GAC GAG GTT CAC CTG TTG GAG AGC GTC AGG CTT TCC ATG GCG GCG     609
Arg Asp Glu Val His Leu Leu Glu Ser Val Arg Leu Ser Met Ala Ala
                135                 140                 145

CTG GAG TCG GCG CTT CAC CTC ACG GTG GAA CTG TAC GAC GTG CCA CTC     657
Leu Glu Ser Ala Leu His Leu Thr Val Glu Leu Tyr Asp Val Pro Leu
            150                 155                 160

GAC TCC GCC TCG TTC GCG CCA ATG TGC GAC GAA ATC ACA AGC CAC CTC     705
Asp Ser Ala Ser Phe Ala Pro Met Cys Asp Glu Ile Thr Ser His Leu
            165                 170                 175

AAG AAG ATG GTG GAC TCC ATC GTC TAC GCC TAT CGC AAC ATC TCA CCC     753
Lys Lys Met Val Asp Ser Ile Val Tyr Ala Tyr Arg Asn Ile Ser Pro
            180                 185                 190

CGC ACC TTC ATG CAA GAG CTC AGG CCC TAC TAC GAG CCC ATC CGG GTG     801
Arg Thr Phe Met Gln Glu Leu Arg Pro Tyr Tyr Glu Pro Ile Arg Val
195                 200                 205                 210
```

-continued

| | |
|---|---|
| GGA GGC CAA TCC TAC CTG GGG CCC GGC GCC GTG GAG ATG CCA CTC TTC<br>Gly Gly Gln Ser Tyr Leu Gly Pro Gly Ala Val Glu Met Pro Leu Phe<br>             215                   220                   225 | 849 |
| GTG TTG GAG CAT GTC CTG TGG GGC TCA CGC GTG GAG CAC CCG GGC TAC<br>Val Leu Glu His Val Leu Trp Gly Ser Arg Val Glu His Pro Gly Tyr<br>             230                   235                   240 | 897 |
| AAG GAC TTC AAG GAG ACG TAT GTG CCC TAC GTC CTC CCC CGG TTC CGG<br>Lys Asp Phe Lys Glu Thr Tyr Val Pro Tyr Val Leu Pro Arg Phe Arg<br>             245                   250                   255 | 945 |
| GCC GTC TAC CAC CAG TTC TCG GAC CAA CCC TCC GTG CTT GAT CGC GTG<br>Ala Val Tyr His Gln Phe Ser Asp Gln Pro Ser Val Leu Asp Arg Val<br>260                   265                   270 | 993 |
| CTG GAG GGA GCG GGA GGC CCC GAG TCC CAG ACG GAG CAC CAT CGG CTC<br>Leu Glu Gly Ala Gly Gly Pro Glu Ser Gln Thr Glu His His Arg Leu<br>275                   280                   285                   290 | 1041 |
| GGA CTG AAG GCC CTG GAC AAG GTT TTC GAT GTG CTG CTG CGC TTT CGG<br>Gly Leu Lys Ala Leu Asp Lys Val Phe Asp Val Leu Leu Arg Phe Arg<br>             295                   300                   305 | 1089 |
| GCG CCC CAC GTG AAG CTG GCG GAG CAG GCC TAT CTG TCC CAG CAG GAG<br>Ala Pro His Val Lys Leu Ala Glu Gln Ala Tyr Leu Ser Gln Gln Glu<br>                 310                   315                   320 | 1137 |
| AAC CAC TCC GTG GGC AGC GGA GGC TAT GCG CCT GGC ATG CTC GAG GAG<br>Asn His Ser Val Gly Ser Gly Gly Tyr Ala Pro Gly Met Leu Glu Glu<br>             325                   330                   335 | 1185 |
| CTG CTC GCG CTC ACC CGC GAG GCA CGG CTG CGT CTG ACC CTG GCT TCG<br>Leu Leu Ala Leu Thr Arg Glu Ala Arg Leu Arg Leu Thr Leu Ala Ser<br>340                   345                   350 | 1233 |
| CGC GCC CCC TCC GCG AGC GGA GAG CCG GCC TTG AAG CAC ACC GCG CGG<br>Arg Ala Pro Ser Ala Ser Gly Glu Pro Ala Leu Lys His Thr Ala Arg<br>355                   360                   365                   370 | 1281 |
| TGA GCCCACCGTT GACACCCTTC ATTCAGCTCG AGTCCCCCTC TGGGAGAACT GCGTCC<br>* | 1340 |
| ATG AAA CCG ACG GTC AAT GCG CAT CAC GAC AGC AAT CAC TTC GAT GTC<br>Met Lys Pro Thr Val Asn Ala His His Asp Ser Asn His Phe Asp Val<br> 1                5                    10                      15 | 1388 |
| ATC ATC CTG GGC TCG GGA ATG TCA GGC AGC CAG ATG GGC GCC ATC CTC<br>Ile Ile Leu Gly Ser Gly Met Ser Gly Ser Gln Met Gly Ala Ile Leu<br>              20                    25                    30 | 1436 |
| GGC CGG CAG GGC TTC CGG GTT CTC ATC GTC GAG GAG TCG ACC CAT CCC<br>Gly Arg Gln Gly Phe Arg Val Leu Ile Val Glu Glu Ser Thr His Pro<br>         35                    40                    45 | 1484 |
| CGC TTC ACG ATT GGC GAG TCC TCC ATC CCC GAG ACC TCG TTG ATG AAC<br>Arg Phe Thr Ile Gly Glu Ser Ser Ile Pro Glu Thr Ser Leu Met Asn<br>     50                    55                    60 | 1532 |
| CGC ATC ATC GCG GAC CGC TAC GGC GTC CCC GAG ATT GAG GAC ATC ACG<br>Arg Ile Ile Ala Asp Arg Tyr Gly Val Pro Glu Ile Glu Asp Ile Thr<br>65                   70                   75                   80 | 1580 |
| TCC TTC TAC TCA ACC TTC AAG AAG GTG TCG TCG AGC ACC GGC ATC AAG<br>Ser Phe Tyr Ser Thr Phe Lys Lys Val Ser Ser Ser Thr Gly Ile Lys<br>             85                   90                   95 | 1628 |
| CGC AAC TTC GGC TTC GTC TTC CAC AAG CCC GGC GAG GAG CAC AAC CCC<br>Arg Asn Phe Gly Phe Val Phe His Lys Pro Gly Glu Glu His Asn Pro<br>              100                  105                  110 | 1676 |
| ACG CAG TTC ACC CAG TGC GTC ATT CCC GAG CTG CCC TGG GGC CCC GAG<br>Thr Gln Phe Thr Gln Cys Val Ile Pro Glu Leu Pro Trp Gly Pro Glu<br>         115                   120                  125 | 1724 |
| AGC CAC TAC TAC CGG CAG GAC GTC GAT GCG TAC CTG ATG CAC GCG GCG<br>Ser His Tyr Tyr Arg Gln Asp Val Asp Ala Tyr Leu Met His Ala Ala<br>             130                   135                   140 | 1772 |

```
ATC CGC TAC GGA TGC GTG GTC AAG CAG AAG ACC GTC ATC AAG GAC TAC      1820
Ile Arg Tyr Gly Cys Val Val Lys Gln Lys Thr Val Ile Lys Asp Tyr
145                 150                 155                 160

GAT CTG AGC AAG ACG GGC GTG GCC GTC ACC ACC ACC CAG GGA GAA CAC      1868
Asp Leu Ser Lys Thr Gly Val Ala Val Thr Thr Thr Gln Gly Glu His
            165                 170                 175

TTC ACG GCG CGC TAC ATG ATT GAC TGT GGT GGC CCC CGC GCG CCG CTG      1916
Phe Thr Ala Arg Tyr Met Ile Asp Cys Gly Gly Pro Arg Ala Pro Leu
                180                 185                 190

GCG CTG AAG TTC GGC CTG CGC GAG GAG CCC TGC CGT TAC AAG ACT CAC      1964
Ala Leu Lys Phe Gly Leu Arg Glu Glu Pro Cys Arg Tyr Lys Thr His
            195                 200                 205

TCG CGC ACC CTC TAC ACG CAC ATG GTG GGG GTC AAG CCC TTC GAC GAC      2012
Ser Arg Thr Leu Tyr Thr His Met Val Gly Val Lys Pro Phe Asp Asp
        210                 215                 220

ATC TTC AAG CCC AAG GGT CAG CGG TGG CGG TGG CAC GAG GGC ACG CTC      2060
Ile Phe Lys Pro Lys Gly Gln Arg Trp Arg Trp His Glu Gly Thr Leu
225                 230                 235                 240

CAC CAC ATG TTC CAC GGC GGC TGG CTG TGG GTG ATT CCC TTC AAC AAC      2108
His His Met Phe His Gly Gly Trp Leu Trp Val Ile Pro Phe Asn Asn
                245                 250                 255

CAC TCA CGC GCG ACG AAC GGG CTC GTC AGC GTG GGC CTG CAG TTG GAT      2156
His Ser Arg Ala Thr Asn Gly Leu Val Ser Val Gly Leu Gln Leu Asp
            260                 265                 270

CCC CGC ATC CAC CCG AAG ACA GAG ATT CCA GCG CAG CAG GAG TTC GAC      2204
Pro Arg Ile His Pro Lys Thr Glu Ile Pro Ala Gln Gln Glu Phe Asp
        275                 280                 285

GAG TTC CTC GCG CGC TTC CCG ACC ATC GCC GCG CAG TTC AAG GAC GCC      2252
Glu Phe Leu Ala Arg Phe Pro Thr Ile Ala Ala Gln Phe Lys Asp Ala
290                 295                 300

AGG CCC GTG CGC GAC TGG GTG AAG TCG GAC CGG CTG CAG TAC TCA TCC      2300
Arg Pro Val Arg Asp Trp Val Lys Ser Asp Arg Leu Gln Tyr Ser Ser
305                 310                 315                 320

AAG AGC ACC GTG GGG GAC CGC TAC TGC CTG ATG CTC CAT GCG GCG GGC      2348
Lys Ser Thr Val Gly Asp Arg Tyr Cys Leu Met Leu His Ala Ala Gly
                325                 330                 335

TTC ATT GAT CCG CTC TTC TCT CGG GGG TTG GAG AAT ACG TCG GTG ACC      2396
Phe Ile Asp Pro Leu Phe Ser Arg Gly Leu Glu Asn Thr Ser Val Thr
            340                 345                 350

ATC CAT GCG CTC GCG GCG CGC CTC ATC AAG GCG CTG CGC GAC GAC GAC      2444
Ile His Ala Leu Ala Ala Arg Leu Ile Lys Ala Leu Arg Asp Asp Asp
        355                 360                 365

TTC TCC CCG GAG CGC TTC GAG TAC ATC GAC CGG TTG CAA CAG AAG CTG      2492
Phe Ser Pro Glu Arg Phe Glu Tyr Ile Asp Arg Leu Gln Gln Lys Leu
370                 375                 380

CTG GAG CAC AAC GAC GAC TTC GTG AGC TGC TGC TAC ACG GCC TTC TCC      2540
Leu Glu His Asn Asp Asp Phe Val Ser Cys Cys Tyr Thr Ala Phe Ser
385                 390                 395                 400

GAC TTC GAG CTC TGG GAC GCC TTC CAT CGT CTA TGG GCC GTG GGC ACG      2588
Asp Phe Glu Leu Trp Asp Ala Phe His Arg Leu Trp Ala Val Gly Thr
                405                 410                 415

ATG CTC GGA CAG TTC CGG CTG GTG CAG GCC CAT GCC AGG TTC AGG GAG      2636
Met Leu Gly Gln Phe Arg Leu Val Gln Ala His Ala Arg Phe Arg Glu
            420                 425                 430

GAC CGG AAC GAG GCC CAC CTG GAC CAC CTG GAC GAC AAC CCT CCC CAC      2684
Asp Arg Asn Glu Ala His Leu Asp His Leu Asp Asp Asn Pro Pro His
        435                 440                 445

CTC GGC TAC CTG TGT GCG GAC ATG GAT GCA TAC TGC GAC CTG TTC GAC      2732
Leu Gly Tyr Leu Cys Ala Asp Met Asp Ala Tyr Cys Asp Leu Phe Asp
450                 455                 460
```

```
GCG GCG AAG GCG GAG GTG GAG TCC GTC TCG GAG AAG CGA GCG TCC CCG      2780
Ala Ala Lys Ala Glu Val Glu Ser Val Ser Glu Lys Arg Ala Ser Pro
465                 470                 475                 480

AAG GAA GCC GCG GCG CGC ATC CAT GCG CTG ATT GAG GCA CAG GAG TTC      2828
Lys Glu Ala Ala Ala Arg Ile His Ala Leu Ile Glu Ala Gln Glu Phe
                485                 490                 495

GCG CGG CCG CTC TTC AGC TTT GGC TAC TGC ATC ACC GGC GCC AAC CGG      2876
Ala Arg Pro Leu Phe Ser Phe Gly Tyr Cys Ile Thr Gly Ala Asn Arg
            500                 505                 510

AAC CTC AAC AAC TCC AAG TAC AGC CTC GTG CCC GCG CTG CGG CTG CTG      2924
Asn Leu Asn Asn Ser Lys Tyr Ser Leu Val Pro Ala Leu Arg Leu Leu
        515                 520                 525

CAC TGG ACC CAG AAG GGC GCC CCT CCC GAA GTC AAG AAG TAC TTC GAT      2972
His Trp Thr Gln Lys Gly Ala Pro Pro Glu Val Lys Lys Tyr Phe Asp
    530                 535                 540

TAC AAC CCC ATG TTC TCG TTG CTG AAG TCA TAC GTC GGG AAC CGG CTG      3020
Tyr Asn Pro Met Phe Ser Leu Leu Lys Ser Tyr Val Gly Asn Arg Leu
545                 550                 555                 560

GCG CTC GCG CTG AAG TAG CCGGGAGGCA GACGGCGCAT GGGGCGGGCA             3068
Ala Leu Ala Leu Lys *
                565

GTTCCATCAC GAACTCGAGG GAGTGGAACG A ATG AGC GGC AAC ATC CAC CAG      3120
                                   Met Ser Gly Asn Ile His Gln
                                    1                   5

GAG CCG GAG CGA ATC AGA CAG GCC TCT GGC GTG AAC GAC CTC ACC ACC      3168
Glu Pro Glu Arg Ile Arg Gln Ala Ser Gly Val Asn Asp Leu Thr Thr
        10                  15                  20

CAG ACG GCG GCG AGC TGG TAC GTG GCC ATG AGG TCG GAC GCG CTG CGC      3216
Gln Thr Ala Ala Ser Trp Tyr Val Ala Met Arg Ser Asp Ala Leu Arg
    25                  30                  35

GGC AAG CCC GTC GCC ATC AAG CTC TTC GGG CAG CCG CTC GTG GCC TGG      3264
Gly Lys Pro Val Ala Ile Lys Leu Phe Gly Gln Pro Leu Val Ala Trp
40                  45                  50                  55

CGA GAT GGG GGC GGC CGG CCG GTC GTC ATG GAG CGC TAC TGC TCT CAC      3312
Arg Asp Gly Gly Gly Arg Pro Val Val Met Glu Arg Tyr Cys Ser His
                60                  65                  70

CTG GGC GCG AGT CTG GCC AAG GGC AAG GTG GTG GAA GGA TGC ATT CAA      3360
Leu Gly Ala Ser Leu Ala Lys Gly Lys Val Val Glu Gly Cys Ile Gln
            75                  80                  85

TGC CCC TTC CAC AAC TGG CGC TAC GAC AGC ACG GGG GCA TGC AGC CAT      3408
Cys Pro Phe His Asn Trp Arg Tyr Asp Ser Thr Gly Ala Cys Ser His
        90                  95                  100

GTG CCG GGA CAC AGC ACC GAG GTC CCC CGG CTG GAG CCC ATC CCC CCC      3456
Val Pro Gly His Ser Thr Glu Val Pro Arg Leu Glu Pro Ile Pro Pro
    105                 110                 115

ACG GCC CGC CAG TCT GTC TAC CCC GTG ATG GAG CGG TAC GGC TTT GTC      3504
Thr Ala Arg Gln Ser Val Tyr Pro Val Met Glu Arg Tyr Gly Phe Val
120                 125                 130                 135

TGG GTC TGG TAC GGC ACC AAG GCC CCC CTG TTT CCC CTT CCG GAG ATG      3552
Trp Val Trp Tyr Gly Thr Lys Ala Pro Leu Phe Pro Leu Pro Glu Met
                140                 145                 150

CCG GAG GCG GAG AGT TCC GAG AGT CAT CAG TCC CTG CGC TTC GCC TAT      3600
Pro Glu Ala Glu Ser Ser Glu Ser His Gln Ser Leu Arg Phe Ala Tyr
            155                 160                 165

GAG ACG ACG ACG TCG GTG TTG CGC ATC ATC GAG AAC TTC TAT GAC GCC      3648
Glu Thr Thr Thr Ser Val Leu Arg Ile Ile Glu Asn Phe Tyr Asp Ala
        170                 175                 180

CAG CAC GCG GCT CCG GTG CAT CAA CTG CCC ATC TCC GCC TTC GAG CTG      3696
Gln His Ala Ala Pro Val His Gln Leu Pro Ile Ser Ala Phe Glu Leu
    185                 190                 195
```

```
AAG CTC TTC GAC GAG TCG AGT CCT CCT CCC GGG CAG GAG GCG CTG GCC      3744
Lys Leu Phe Asp Glu Ser Ser Pro Pro Pro Gly Gln Glu Ala Leu Ala
200                 205                 210                 215

CGG GAT GGG GCC TGG TTT GGC GCG GGA ATC GAC TTC CAC GTC GAC CGC      3792
Arg Asp Gly Ala Trp Phe Gly Ala Gly Ile Asp Phe His Val Asp Arg
                220                 225                 230

TAC TTC GGT CCC CTG GGC GTC ATC TCC AGG ACG TTG GGC CTG AGC ATG      3840
Tyr Phe Gly Pro Leu Gly Val Ile Ser Arg Thr Leu Gly Leu Ser Met
            235                 240                 245

AGC CGG ATG CAA TTG CAC TTC GAC GGC TAT CCC GGT GGC TGC ATC ATG      3888
Ser Arg Met Gln Leu His Phe Asp Gly Tyr Pro Gly Gly Cys Ile Met
        250                 255                 260

ACA GTC AGC CTG GAT GGC GAT GTG AAG TAC CGC CTC CTC CAG TGC GTC      3936
Thr Val Ser Leu Asp Gly Asp Val Lys Tyr Arg Leu Leu Gln Cys Val
    265                 270                 275

ACG CCC GTG GAC AAG GAG GAG ACC GTC ATG CAC ATG CTC CTC GCC ATC      3984
Thr Pro Val Asp Lys Glu Glu Thr Val Met His Met Leu Leu Ala Ile
280                 285                 290                 295

AAG AAG GGC GAT GGC GTG GTG CGC AGC GCG GCC AAC TTC ATT CTC TAC      4032
Lys Lys Gly Asp Gly Val Val Arg Ser Ala Ala Asn Phe Ile Leu Tyr
                300                 305                 310

GGC CTC CAG ACC TGG GCA GCC GCC GGC TAT GAC GTG GCC ATC TGG AAC      4080
Gly Leu Gln Thr Trp Ala Ala Ala Gly Tyr Asp Val Ala Ile Trp Asn
            315                 320                 325

AGC ATG AAG GCG GAT GGG GGT GGG GCC TTC AGC AAG TAC GAC CAG CTC      4128
Ser Met Lys Ala Asp Gly Gly Gly Ala Phe Ser Lys Tyr Asp Gln Leu
        330                 335                 340

ATC TTG AAG TAC CGC GCC TTC TAC CGG CGC TGG GTG AAC AAG GTC GCC      4176
Ile Leu Lys Tyr Arg Ala Phe Tyr Arg Arg Trp Val Asn Lys Val Ala
    345                 350                 355

CTG GAG AAC TCG GGC CGA GAG AAG GAC AGC CGT GCG GAC CCG AGG AAG      4224
Leu Glu Asn Ser Gly Arg Glu Lys Asp Ser Arg Ala Asp Pro Arg Lys
360                 365                 370                 375

GGC GCG CAC GGC TAG CTTCGAGGCG CGGGCCTTTC AGCCGGCCCG CTGCCGCTCC      4279
Gly Ala His Gly *
                380

TCTTCCCTGG CGCGAGAACC CCTCGCGTAC AGCGAGGTCA AGTAGTCGTA CTGAGAGGGG   4339

AGCCGCGACA TCATCTGGGC GGTCTTCTGC CGGAGGTCAT CGAACGTCCG CTCCGCTTCC   4399

GCCAGGATAT CGGGGCGGCT GTGGAGCAGC GGCATCGGCT GTCGTGGCAG GTATCCGACC   4459

CCGGCGAAGA TGGACTGGAA GTTGCTGTTG GTCCAGAACC TGTCGAAGCC CGCCTCGAAG   4519

GAGGAGTAGA GCGCATCGTT CGTGTGGTAG CTCCTGCGGA TGGGAATGCC CGCTCGCTGC   4579

AGTTCGAGCA CCTCCTTGAG GGTGTCCGGC AGCTTGAGTT CGTTCTGGTT GGCCTTCCAG   4639

TAGGGCGTGT CGGTGCGCGG TGACGTGCAG AAGTGCAGCA CGATGAAGTC GCGCACGTCA   4699

TCCACCATGT ATGACACACG CTCGTTGAAC TTATCTCGCA GGACTGGCTC GATGTGCTTG   4759

CTCGGGAAGC ACGCCACGAG CTGGTAGAGC GCTGCGTAGA CGAAGTAGAG CCCCGTGGAC   4819

TCCAGCGGTT CGAGGAAGCT GCTCGCCAGA CCGATGCTCA CGCAGTTCTT CACCCAGGAG   4879

CGGCGGCGCC TGCCGGAGAC GAACTTGATG TGGCGCACGT CGAGCGCGTC CGCCTTCTTC   4939

CCGAACCAGG CGCGCACCTC GCGCTCGGCG TCCTCGGGGG TCTGGAAGGC GCTTGAGTAG   4999

ACATACCCGT TGCCCGCACG GCCGTAGAGG GGAATCTCCC AGGTCCACCC GGAGCTGAAG   5059

GCGCTCGCGG TTGTATAGGG GCGGATGCCT TCGGTCGCGG GGTCCGAGGG GATGTTGATG   5119

GCAACGGCGC GGTCCGTGAG CAGGCTGTCA TGGAAGGTGA CTTTCGGTTC GCCCAGCGCC   5179

TGCTCGATGA GCAGACCCGC GAAGCCGGTG CAGTCAATGT AGAGATCCGC CGCGTAGCTC   5239
```

```
CGCCCGCTGG CACCCCGCAG GTGCTTGATG CTTCCTCCGT CGTCGAGCTG GGTATCGACG    5299

ATGTCGTCGC TGATGAAGGT GAGCCCTCGC TCGATGGACC ACTTCTTCAG GAAGTTGGCC    5359

ACCAACAGCG CGTCGAAGTG GTAGGCGTAA TGAACCGCCT TGGTCCCATC CATGTACCGG    5419

GGCGACTTCT GGGCGTCACA GATAGGAGAC GTGGGGTAGC AGGAATACGC CATGGGCTCG    5479

GCGAAGCCCT GGAGTTGATG TTTGTACATC CAGAGGTGAG AGAGCGGCAC TCCCTTCACC    5539

TGGGGCATCT CACCGAAGTT ATGGTAGTAG TGGTCTCCCC CCTGCGATGC GGGCTTCTTC    5599

CAGTTCTGGA ATCGGATGCC CAGCTTGTAG GTGGCCTTGC ACTCAGACAT CCATTCCTCT    5659

TCAGGAATCT CAAGGAAGTC GAACAATTCC TCCTTGATGG TGGGAATGGT GGCCTCGCCA    5719

ACGCCAATCC TGGAATGGT GGGGGACTCA ATGAGTGTGA TGTCGGCGTT GAAATTCAAG    5779

GCCTTGCTCA GATAGGCGGC CGCCATCCAG CCCGAACTCC CTCCCCCGAC AATGATGATC    5839

TTTCTGACCC TGTTGTCATT CTCGACTGAG CTCTGGTCCA TGGTGCTCCC GTAGGGTGTG    5899

TCACGTGAGA AGTAGAATGG AATCGAACGC GCCTAAAGGG CTGCACGCGG AGAGGGTTCG    5959

CGCGTCCAGG GGTATGCAGG AGTCAATCAT GCCTACC                              5996
```

(2) INFORMATION FOR SEQ ID NO:34:

(i) SEQUENCE CHARACTERISTICS:
        (A) LENGTH: 370 amino acids
        (B) TYPE: amino acid
        (D) TOPOLOGY: linear (ii) MOLECULE TYPE: protein (xi) SEQUENCE DESCRIPTION: SEQ ID NO:34:

```
Met Asn Pro Gly Gln Asn Phe Ser Ser Thr His Glu Val Ile Ala Thr
 1               5                  10                  15

Leu Asp Pro Leu Asp Ala Leu Ala Thr Met Arg Arg Leu Pro Glu Leu
            20                  25                  30

Asn Gln Arg Ser Asp Val Arg Gly Val Leu Glu Leu Leu Gln Gly Ile
        35                  40                  45

Leu Pro Arg Leu Glu Ile Val Glu Arg Trp Asp Phe Pro Val Ala Ala
50                  55                  60

Ala Ala Met Arg Asp Ile Gly Phe Phe Leu Gly Ser Leu Lys Arg His
65                  70                  75                  80

Gly His Glu Pro Val Glu Val Pro Gly Leu Glu Pro Ile Leu Leu
                85                  90                  95

Ala Leu Ala Arg Ala Thr Gln Leu Pro Pro Arg Glu Thr Leu Leu His
            100                 105                 110

Val Thr Val Trp Asn Pro Ala Ala Asp Glu Leu Glu Arg Arg Tyr Thr
        115                 120                 125

Cys Cys Arg Asp Glu Val His Leu Leu Glu Ser Val Arg Leu Ser Met
130                 135                 140

Ala Ala Leu Glu Ser Ala Leu His Leu Thr Val Glu Leu Tyr Asp Val
145                 150                 155                 160

Pro Leu Asp Ser Ala Ser Phe Ala Pro Met Cys Asp Glu Ile Thr Ser
                165                 170                 175

His Leu Lys Lys Met Val Asp Ser Ile Val Tyr Ala Tyr Arg Asn Ile
            180                 185                 190

Ser Pro Arg Thr Phe Met Gln Glu Leu Arg Pro Tyr Tyr Glu Pro Ile
        195                 200                 205

Arg Val Gly Gly Gln Ser Tyr Leu Gly Pro Gly Ala Val Glu Met Pro
    210                 215                 220
```

```
Leu Phe Val Leu Glu His Val Leu Trp Gly Ser Arg Val Glu His Pro
225                 230                 235                 240

Gly Tyr Lys Asp Phe Lys Glu Thr Tyr Val Pro Tyr Val Leu Pro Arg
            245                 250                 255

Phe Arg Ala Val Tyr His Gln Phe Ser Asp Gln Pro Ser Val Leu Asp
                260                 265                 270

Arg Val Leu Glu Gly Ala Gly Gly Pro Glu Ser Gln Thr Glu His His
            275                 280                 285

Arg Leu Gly Leu Lys Ala Leu Asp Lys Val Phe Asp Val Leu Leu Arg
290                 295                 300

Phe Arg Ala Pro His Val Lys Leu Ala Glu Gln Ala Tyr Leu Ser Gln
305                 310                 315                 320

Gln Glu Asn His Ser Val Gly Ser Gly Tyr Ala Pro Gly Met Leu
                325                 330                 335

Glu Glu Leu Leu Ala Leu Thr Arg Glu Ala Arg Leu Arg Leu Thr Leu
            340                 345                 350

Ala Ser Arg Ala Pro Ser Ala Ser Gly Glu Pro Ala Leu Lys His Thr
            355                 360                 365

Ala Arg
    370

(2) INFORMATION FOR SEQ ID NO:35:

(i) SEQUENCE CHARACTERISTICS:
        (A) LENGTH: 565 amino acids
        (B) TYPE: amino acid
        (D) TOPOLOGY: linear (ii) MOLECULE TYPE: protein (xi) SEQUENCE DESCRIPTION: SEQ ID NO:35:

Met Lys Pro Thr Val Asn Ala His His Asp Ser Asn His Phe Asp Val
1               5                   10                  15

Ile Ile Leu Gly Ser Gly Met Ser Gly Ser Gln Met Gly Ala Ile Leu
            20                  25                  30

Gly Arg Gln Gly Phe Arg Val Leu Ile Val Glu Glu Ser Thr His Pro
        35                  40                  45

Arg Phe Thr Ile Gly Glu Ser Ser Ile Pro Glu Thr Ser Leu Met Asn
    50                  55                  60

Arg Ile Ile Ala Asp Arg Tyr Gly Val Pro Glu Ile Glu Asp Ile Thr
65                  70                  75                  80

Ser Phe Tyr Ser Thr Phe Lys Val Ser Ser Thr Gly Ile Lys
                85                  90                  95

Arg Asn Phe Gly Phe Val Phe His Lys Pro Gly Glu Glu His Asn Pro
            100                 105                 110

Thr Gln Phe Thr Gln Cys Val Ile Pro Glu Leu Pro Trp Gly Pro Glu
        115                 120                 125

Ser His Tyr Tyr Arg Gln Asp Val Asp Ala Tyr Leu Met His Ala Ala
    130                 135                 140

Ile Arg Tyr Gly Cys Val Val Lys Gln Lys Thr Val Ile Lys Asp Tyr
145                 150                 155                 160

Asp Leu Ser Lys Thr Gly Val Ala Val Thr Thr Thr Gln Gly Glu His
                165                 170                 175

Phe Thr Ala Arg Tyr Met Ile Asp Cys Gly Gly Pro Arg Ala Pro Leu
            180                 185                 190
```

Ala Leu Lys Phe Gly Leu Arg Glu Glu Pro Cys Arg Tyr Lys Thr His
            195                 200                 205

Ser Arg Thr Leu Tyr Thr His Met Val Gly Val Lys Pro Phe Asp Asp
    210                 215                 220

Ile Phe Lys Pro Lys Gly Gln Arg Trp Arg Trp His Glu Gly Thr Leu
225                 230                 235                 240

His His Met Phe His Gly Gly Trp Leu Trp Val Ile Pro Phe Asn Asn
                245                 250                 255

His Ser Arg Ala Thr Asn Gly Leu Val Ser Val Gly Leu Gln Leu Asp
            260                 265                 270

Pro Arg Ile His Pro Lys Thr Glu Ile Pro Ala Gln Gln Glu Phe Asp
        275                 280                 285

Glu Phe Leu Ala Arg Phe Pro Thr Ile Ala Ala Gln Phe Lys Asp Ala
    290                 295                 300

Arg Pro Val Arg Asp Trp Val Lys Ser Asp Arg Leu Gln Tyr Ser Ser
305                 310                 315                 320

Lys Ser Thr Val Gly Asp Arg Tyr Cys Leu Met Leu His Ala Ala Gly
                325                 330                 335

Phe Ile Asp Pro Leu Phe Ser Arg Gly Leu Glu Asn Thr Ser Val Thr
            340                 345                 350

Ile His Ala Leu Ala Ala Arg Leu Ile Lys Ala Leu Arg Asp Asp Asp
        355                 360                 365

Phe Ser Pro Glu Arg Phe Glu Tyr Ile Asp Arg Leu Gln Gln Lys Leu
    370                 375                 380

Leu Glu His Asn Asp Asp Phe Val Ser Cys Cys Tyr Thr Ala Phe Ser
385                 390                 395                 400

Asp Phe Glu Leu Trp Asp Ala Phe His Arg Leu Trp Ala Val Gly Thr
                405                 410                 415

Met Leu Gly Gln Phe Arg Leu Val Gln Ala His Ala Arg Phe Arg Glu
            420                 425                 430

Asp Arg Asn Glu Ala His Leu Asp His Leu Asp Asp Asn Pro Pro His
        435                 440                 445

Leu Gly Tyr Leu Cys Ala Asp Met Asp Ala Tyr Cys Asp Leu Phe Asp
    450                 455                 460

Ala Ala Lys Ala Glu Val Glu Ser Val Ser Lys Arg Ala Ser Pro
465                 470                 475                 480

Lys Glu Ala Ala Ala Arg Ile His Ala Leu Ile Glu Ala Gln Glu Phe
                485                 490                 495

Ala Arg Pro Leu Phe Ser Phe Gly Tyr Cys Ile Thr Gly Ala Asn Arg
            500                 505                 510

Asn Leu Asn Asn Ser Lys Tyr Ser Leu Val Pro Ala Leu Arg Leu Leu
        515                 520                 525

His Trp Thr Gln Lys Gly Ala Pro Pro Glu Val Lys Lys Tyr Phe Asp
    530                 535                 540

Tyr Asn Pro Met Phe Ser Leu Leu Lys Ser Tyr Val Gly Asn Arg Leu
545                 550                 555                 560

Ala Leu Ala Leu Lys
                565

(2) INFORMATION FOR SEQ ID NO:36:

(i) SEQUENCE CHARACTERISTICS:
        (A) LENGTH: 379 amino acids
        (B) TYPE: amino acid
        (D) TOPOLOGY: linear (ii) MOLECULE TYPE: protein (xi) SEQUENCE DESCRIPTION: SEQ ID NO:36:

```
Met Ser Gly Asn Ile His Gln Glu Pro Glu Arg Ile Arg Gln Ala Ser
 1               5                  10                  15

Gly Val Asn Asp Leu Thr Thr Gln Thr Ala Ala Ser Trp Tyr Val Ala
             20                  25                  30

Met Arg Ser Asp Ala Leu Arg Gly Lys Pro Val Ala Ile Lys Leu Phe
         35                  40                  45

Gly Gln Pro Leu Val Ala Trp Arg Asp Gly Gly Arg Pro Val Val
     50                  55                  60

Met Glu Arg Tyr Cys Ser His Leu Gly Ala Ser Leu Ala Lys Gly Lys
 65                  70                  75                  80

Val Val Glu Gly Cys Ile Gln Cys Pro Phe His Asn Trp Arg Tyr Asp
                 85                  90                  95

Ser Thr Gly Ala Cys Ser His Val Pro Gly His Ser Thr Glu Val Pro
            100                 105                 110

Arg Leu Glu Pro Ile Pro Pro Thr Ala Arg Gln Ser Val Tyr Pro Val
        115                 120                 125

Met Glu Arg Tyr Gly Phe Val Trp Val Trp Tyr Gly Thr Lys Ala Pro
130                 135                 140

Leu Phe Pro Leu Pro Glu Met Pro Glu Ala Glu Ser Ser Glu Ser His
145                 150                 155                 160

Gln Ser Leu Arg Phe Ala Tyr Glu Thr Thr Thr Ser Val Leu Arg Ile
                165                 170                 175

Ile Glu Asn Phe Tyr Asp Ala Gln His Ala Ala Pro Val His Gln Leu
            180                 185                 190

Pro Ile Ser Ala Phe Glu Leu Lys Leu Phe Asp Glu Ser Ser Pro Pro
        195                 200                 205

Pro Gly Gln Glu Ala Leu Ala Arg Asp Gly Ala Trp Phe Gly Ala Gly
    210                 215                 220

Ile Asp Phe His Val Asp Arg Tyr Phe Gly Pro Leu Gly Val Ile Ser
225                 230                 235                 240

Arg Thr Leu Gly Leu Ser Met Ser Arg Met Gln Leu His Phe Asp Gly
                245                 250                 255

Tyr Pro Gly Gly Cys Ile Met Thr Val Ser Leu Asp Gly Asp Val Lys
            260                 265                 270

Tyr Arg Leu Leu Gln Cys Val Thr Pro Val Asp Lys Glu Glu Thr Val
        275                 280                 285

Met His Met Leu Leu Ala Ile Lys Lys Gly Asp Gly Val Val Arg Ser
    290                 295                 300

Ala Ala Asn Phe Ile Leu Tyr Gly Leu Gln Thr Trp Ala Ala Ala Gly
305                 310                 315                 320

Tyr Asp Val Ala Ile Trp Asn Ser Met Lys Ala Asp Gly Gly Gly Ala
                325                 330                 335

Phe Ser Lys Tyr Asp Gln Leu Ile Leu Lys Tyr Arg Ala Phe Tyr Arg
            340                 345                 350

Arg Trp Val Asn Lys Val Ala Leu Glu Asn Ser Gly Arg Glu Lys Asp
        355                 360                 365

Ser Arg Ala Asp Pro Arg Lys Gly Ala His Gly
    370                 375                 380
```

-continued (2) INFORMATION FOR SEQ ID NO:37:

(i) SEQUENCE CHARACTERISTICS:
        (A) LENGTH: 540 amino acids
        (B) TYPE: amino acid
        (D) TOPOLOGY: linear (ii) MOLECULE TYPE: protein (xi) SEQUENCE DESCRIPTION: SEQ ID NO:37:

```
Met Asp Gln Ser Ser Val Glu Asn Asp Asn Arg Val Arg Lys Ile Ile
 1               5                  10                  15

Ile Val Gly Gly Ser Ser Gly Trp Met Ala Ala Tyr Leu Ser
            20                  25                  30

Lys Ala Leu Asn Phe Asn Ala Asp Ile Thr Leu Ile Glu Ser Pro Thr
            35                  40                  45

Ile Pro Arg Ile Gly Val Gly Glu Ala Thr Ile Pro Thr Ile Lys Glu
    50                  55                  60

Glu Leu Phe Asp Phe Leu Glu Ile Pro Glu Glu Trp Met Ser Glu
 65                  70                  75                  80

Cys Lys Ala Thr Tyr Lys Leu Gly Ile Arg Phe Gln Asn Trp Lys Lys
                85                  90                  95

Pro Ala Ser Gln Gly Gly Asp His Tyr Tyr His Asn Phe Gly Glu Met
                100                 105                 110

Pro Gln Val Lys Gly Val Pro Leu Ser His Leu Trp Met Tyr Lys His
            115                 120                 125

Gln Leu Gln Gly Phe Ala Glu Pro Met Ala Tyr Ser Cys Tyr Pro Thr
130                 135                 140

Ser Pro Ile Cys Asp Ala Gln Lys Ser Pro Arg Tyr Met Asp Gly Thr
145                 150                 155                 160

Lys Ala Val His Tyr Ala Tyr His Phe Asp Ala Leu Leu Val Ala Asn
                165                 170                 175

Phe Leu Lys Lys Trp Ser Ile Glu Arg Gly Leu Thr Phe Ile Ser Asp
            180                 185                 190

Asp Ile Val Asp Thr Gln Leu Asp Asp Gly Gly Ser Ile Lys His Leu
        195                 200                 205

Arg Gly Ala Ser Gly Arg Ser Tyr Ala Ala Asp Leu Tyr Ile Asp Cys
210                 215                 220

Thr Gly Phe Ala Gly Leu Leu Ile Glu Gln Ala Leu Gly Glu Pro Lys
225                 230                 235                 240

Val Thr Phe His Asp Ser Leu Leu Thr Asp Arg Ala Val Ala Ile Asn
                245                 250                 255

Ile Pro Ser Asp Pro Ala Thr Glu Gly Ile Arg Pro Tyr Thr Thr Ala
            260                 265                 270

Ser Ala Phe Ser Ser Gly Trp Thr Trp Glu Ile Pro Leu Tyr Gly Arg
            275                 280                 285

Ala Gly Asn Gly Tyr Val Tyr Ser Ser Ala Phe Gln Thr Pro Glu Asp
    290                 295                 300

Ala Glu Arg Glu Val Arg Ala Trp Phe Gly Lys Lys Ala Asp Ala Leu
305                 310                 315                 320

Asp Val Arg His Ile Lys Phe Val Ser Gly Arg Arg Arg Ser Trp
                325                 330                 335

Val Lys Asn Cys Val Ser Ile Gly Leu Ala Ser Ser Phe Leu Glu Pro
                340                 345                 350

Leu Glu Ser Thr Gly Leu Tyr Phe Val Tyr Ala Ala Leu Tyr Gln Leu
            355                 360                 365
```

```
Val Ala Cys Phe Pro Ser Lys His Ile Glu Pro Val Leu Arg Asp Lys
    370             375             380

Phe Asn Glu Arg Val Ser Tyr Met Val Asp Asp Val Arg Asp Phe Ile
385             390             395             400

Val Leu His Phe Cys Thr Ser Pro Arg Thr Asp Thr Pro Tyr Trp Lys
            405             410             415

Ala Asn Gln Asn Glu Leu Lys Leu Pro Asp Thr Leu Lys Glu Val Leu
            420             425             430

Glu Leu Gln Arg Ala Gly Ile Pro Ile Arg Arg Ser Tyr His Thr Asn
            435             440             445

Asp Ala Leu Tyr Ser Ser Phe Glu Ala Gly Phe Asp Arg Phe Trp Thr
    450             455             460

Asn Ser Asn Phe Gln Ser Ile Phe Ala Gly Val Gly Tyr Leu Pro Arg
465             470             475             480

Gln Pro Met Pro Leu Leu His Ser Arg Pro Asp Ile Leu Ala Glu Ala
            485             490             495

Glu Arg Thr Phe Asp Asp Leu Arg Gln Lys Thr Ala Gln Met Met Ser
            500             505             510

Arg Leu Pro Ser Gln Tyr Asp Tyr Leu Thr Ser Leu Tyr Ala Arg Gly
        515             520             525

Ser Arg Ala Arg Glu Glu Glu Arg Gln Arg Ala Gly
530             535             540
```

PYRROLNITRIN BIOSYNTHESIS GENES AND USES THEREOF

This application is a Continuation-in-Part of U.S. Ser. No. 08/729,214, filed Oct. 9, 1996, now U.S. Pat. No. 5,817,502 which is itself a Continuation-in-Part of U.S. Ser. No. 08/258,261, filed Jun. 8, 1994, now U.S. Pat. No. 5,639,949, issued Jun. 17, 1997. Said Ser. No. 08/729,214 is also a Continuation-in-Part of International PCT application no. PCT/IB95/00414 filed on May 30, 1995 (WO 95/33818), which is itself a Continuation-in-Part of U.S. Ser. No. 08/258,261, filed Jun. 8, 1994, now U.S. Pat. No. 5,639,949, issued Jun. 17, 1997. The disclosures of each of these parent applications are hereby expressly incorporated in their entireties by reference into the instant disclosure.

FIELD OF THE INVENTION

The present invention relates generally to the protection of host organisms against pathogens, and more particularly to the protection of plants against phytopathogens. In one aspect it provides transgenic plants that have enhanced resistance to phytopathogens and biocontrol organisms with enhanced biocontrol properties. It further provides methods for protecting plants against phytopathogens and methods for the production of antipathogenic substances, including pyrrolnitrin. It particularly provides DNA molecules isolated from pyrrolnitrin-producing organisms that encode enzymes required in the biosynthetic pathway of pyrrolnitrin.

BACKGROUND OF THE INVENTION

Plants routinely become infected by fungi and bacteria, and many microbial species have evolved to utilize the different niches provided by the growing plant. Some phytopathogens have evolved to infect foliar surfaces and are spread through the air, from plant-to-plant contact or by various vectors, whereas other phytopathogens are soil-borne and preferentially infect roots and newly germinated seedlings. In addition to infection by fungi and bacteria, many plant diseases are caused by nematodes which are soil-borne and infect roots, typically causing serious damage when the same crop species is cultivated for successive years on the same area of ground.

Plant diseases cause considerable crop loss from year to year resulting both in economic hardship to farmers and nutritional deprivation for local populations in many parts of the world. The widespread use of fungicides has provided considerable security against phytopathogen attack, but despite $1 billion worth of expenditure on fungicides, worldwide crop losses amounted to approximately 10% of crop value in 1981 (James, Seed Sci. & Technol. 9: 679–685 (1981). The severity of the destructive process of disease depends on the aggressiveness of the phytopathogen and the response of the host, and one aim of most plant breeding programs is to increase the resistance of host plants to disease. Novel gene sources and combinations developed for resistance to disease have typically only had a limited period of successful use in many crop-pathogen systems due to the rapid evolution of phytopathogens to overcome resistance genes. In addition, there are several documented cases of the evolution of fungal strains which are resistant to particular fungicides. As early as 1981, Fletcher and Wolfe (Proc. 1981 Brit. Crop Prot. Conf. (1981)) contended that 24% of the powdery mildew populations from spring barley, and 53% from winter barley showed considerable variation in response to the fungicide triadimenol and that the distribution of these populations varied between barley varieties with the most susceptible variety also giving the highest incidence of less susceptible fungal types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983). Diseases caused by nematodes have also been controlled successfully by pesticide application. Whereas most fungicides are relatively harmless to mammals and the problems with their use lie in the development of resistance in target fungi, the major problem associated with the use of nematicides is their relatively high toxicity to mammals. Most nematicides used to control soil nematodes are of the carbamate, organochlorine or organophosphorous groups and must be applied to the soil with particular care.

In some crop species, the use of biocontrol organisms has been developed as a further alternative to protect crops. Biocontrol organisms have the advantage of being able to colonize and protect parts of the plant inaccessible to conventional fungicides. This practice developed from the recognition that crops grown in some soils are naturally resistant to certain fungal phytopathogens and that the suppressive nature of these soils is lost by autoclaving.

Furthermore, it was recognized that soils which are conducive to the development of certain diseases could be rendered suppressive by the addition of small quantities of soil from a suppressive field (Scher et al. Phytopathology 70: 412–417 (1980). Subsequent research demonstrated that root colonizing bacteria were responsible for this phenomenon, now known as biological disease control (Baker et al. Biological Control of Plant Pathogens, Freeman Press, San Francisco, 1974). In many cases, the most efficient strains of biological disease controlling bacteria are of the species *Pseudomonas fluorescens* (Weller et al. Phytopathology 73: 463–469 (1983); Kloepper et al. Phytopathology 71: 1020–1024 (1981)). Important plant pathogens that have been effectively controlled by seed inoculation with these bacteria include *Gaemannomyces graminis*, the causative agent of take-all in wheat (Cook et al. Soil Biol. Biochem 8: 269–273 (1976)) and the Pythium and Rhizoctonia phytopathogens involved in damping off of cotton (Howell et al. Phytopathology 69: 480–482 (1979)). Several biological disease controlling Pseudomonas strains produce antibiotics which inhibit the growth of fungal phytopathogens (Howell et al. Phytopathology 69: 480–482 (1979); Howell et al. Phytopathology 70: 712–715 (1980)) and these have been implicated in the control of fungal phytopathogens in the rhizosphere. Although biocontrol was initially believed to have considerable promise as a method of widespread application for disease control, it has found application mainly in the environment of glasshouse crops where its utility in controlling soil-borne phytopathogens is best suited for success. Large scale field application of naturally occurring microorganisms has not proven possible due to constraints of microorganism production (they are often slow growing), distribution (they are often short lived) and cost (the result of both these problems). In addition, the success of biocontrol approaches is also largely limited by the identification of naturally occurring strains which may have a limited spectrum of efficacy. Some initial approaches have also been taken to control nematode phytopathogens using biocontrol organisms. Although these approaches are still exploratory, some Streptomyces species have been reported to control the root knot nematode (Meliodogyne spp.) (WO 93/18135 to Research Corporation Technology), and toxins from some *Bacillus thuringiensis* strains (such as *israeliensis*) have been shown to have broad anti-nematode activity and spore or bacillus preparations may thus provide suitable biocontrol opportunities (EP 0 352 052 to Mycogen, WO 93/19604 to Research Corporation Technologies).

The traditional methods of protecting crops against disease, including plant breeding for disease resistance, the continued development of fungicides, and more recently, the identification of biocontrol organisms, have all met with success. It is apparent, however, that scientists must constantly be in search of new methods with which to protect crops against disease. This invention provides novel methods for the protection of plants against phytopathogens.

SUMMARY OF THE INVENTION

The present invention reveals the genetic and biochemical basis for substances produced by particular microorganisms via a multi-gene biosynthetic pathway which have a deleterious effect on the multiplication or growth of plant pathogens. These substances include carbohydrate containing antibiotics such as aminoglycosides, peptide antibiotics, nucleoside derivatives and other heterocyclic antibiotics containing nitrogen and/or oxygen, polyketides, macrocyclic lactones, and quinones.

The invention provides the entire set of genes required for recombinant production of particular antipathogenic substances in a host organism. It further provides methods for the manipulation of APS gene sequences for their expression in transgenic plants. The transgenic plants thus modified have enhanced resistance to attack by phytopathogens. The invention provides methods for the cellular targeting of APS gene products so as to ensure that the gene products have appropriate spatial localization for the availability of the required substrate/s. Further provided are methods for the enhancement of throughput through the APS metabolic pathway by overexpression and overproduction of genes encoding substrate precursors.

The invention further provides a novel method for the identification and isolation of the genes involved in the biosynthesis of any particular APS in a host organism.

The invention also describes improved biocontrol strains which produce heterologous APSs and which are efficacious in controlling soil-borne and seedling phytopathogens outside the usual range of the host.

Thus, the invention provides methods for disease control. These methods involve the use of transgenic plants expressing APS biosynthetic genes and the use of biocontrol agents expressing APS genes.

The invention further provides methods for the production of APSs in quantities large enough to enable their isolation and use in agricultural formulations. A specific advantage of these production methods is the chirality of the molecules produced; production in transgenic organisms avoids the generation of populations of racemic mixtures, within which some enantiomers may have reduced activity.

In a preferred embodiment, the present invention provides a nucleic acid molecule isolated from a microbe capable of producing pyrrolnitrin, wherein the nucleic acid molecule encodes at least one enzyme required in the biosynthetic pathway of pyrrolnitrin. The nucleic acid molecule is preferably DNA, but in an alternate embodiment may be RNA. The source of the nucleic acid of the invention is any microbe capable of producing pyrrolnitrin, and is preferably one of the following bacteria: a Pseudomonas species such as *Pseudomonas fluorescens* or *Pseudomonas pyrrocinia*, a Burkholdaria species such as *Burkholdaria cepacia*, or a Myxococcus species such as *Myxococcus fulvus*.

An especially preferred embodiment of the nucleic acid molecule of the invention encompasses a DNA molecule or its complement that hybridizes to SEQ ID NO:1, 23, 28, or 33 under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C.

In one embodiment, the nucleic acid molecule of the invention encodes a PrnA enzyme that catalyzes the conversion of D- and L-tryptophan to 7-chlorotryptophan. Such a PrnA enzyme preferably has an amino acid sequence that is substantially similar to an amino sequence selected from the group consisting of SEQ ID NOs:2, 24, 29, and 37, and more preferably has an amino acid sequence selected from the group consisting of SEQ ID NOs:2, 24, 29, and 37. In this embodiment, the nucleic acid molecule of the invention or its complement preferably hybridizes to either ORF1 of SEQ ID NO:1, ORF1 of SEQ ID NO:23, ORF1 of SEQ ID NO:28, or ORF4 of SEQ ID NO:33 under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C., and more preferably has a sequence selected from the group consisting of: ORF1 of SEQ ID NO:1, ORF1 of SEQ ID NO:23, ORF1 of SEQ ID NO:28, and ORF4 of SEQ ID NO:33.

In another embodiment, the nucleic acid molecule of the invention encodes a PrnB enzyme that catalyzes the conversion of 7-chlorotryptophan to monodechloroaminopyrrolnitrin. Such a PrnB enzyme preferably has an amino acid sequence that is substantially similar to an amino sequence selected from the group consisting of SEQ ID NOs:3, 25, 30, and 34, and more preferably has an amino acid sequence selected from the group consisting of SEQ ID NOs:3, 25, 30, and 34. In this embodiment, the nucleic acid molecule of the invention or its complement preferably hybridizes to either ORF2 of SEQ ID NO:1, ORF2 of SEQ ID NO:23, ORF2 of SEQ ID NO:28, or ORF1 of SEQ ID NO:33 under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C., and more preferably has a nucleotide sequence selected from the group consisting of: ORF2 of SEQ ID NO:1, ORF2 of SEQ ID NO:23, ORF2 of SEQ ID NO:28, and ORF1 of SEQ ID NO:33.

In yet another embodiment, the nucleic acid molecule of the invention encodes a PrnC enzyme that catalyzes the conversion of monodechloroaminopyrrolnitrin to aminopyrrolnitrin. Such a PrnC enzyme preferably has an amino acid sequence that is substantially similar to an amino sequence selected from the group consisting of SEQ ID NOs:4, 26, 31, and 35, and more preferably has an amino acid sequence selected from the group consisting of SEQ ID NOs:4, 26, 31, and 35. In this embodiment, the nucleic acid molecule of the invention or its complement preferably hybridizes to either ORF3 of SEQ ID NO:1, ORF3 of SEQ ID NO:23, ORF3 of SEQ ID NO:28, or ORF2 of SEQ ID NO:33 under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C., and more preferably has a nucleotide sequence selected from the group consisting of: ORF3 of SEQ ID NO:1, ORF3 of SEQ ID NO:23, ORF3 of SEQ ID NO:28, and ORF2 of SEQ ID NO:33.

In still another embodiment, the nucleic acid molecule of the invention encodes a PrnD enzyme that catalyzes the conversion of aminopyrrolnitrin to pyrrolnitrin. Such a PrnD enzyme preferably has an amino acid sequence that has an amino acid sequence that is substantially similar to an amino sequence selected from the group consisting of SEQ ID NOs:5, 27, 32, and 36, and more preferably has an amino acid sequence selected from the group consisting of SEQ ID NOs:5, 27, 32, and 36. In this embodiment, the nucleic acid molecule of the invention or its complement preferably hybridizes to either ORF4 of SEQ ID NO:1, ORF4 of SEQ ID NO:23, ORF4 of SEQ ID NO:28, or ORF3 of SEQ ID NO:33 under the following conditions: hybridization at 7% sodium dodecyl sulfate (SDS), 0.5 M NaPO$_4$ pH 7.0, 1 mM EDTA at 50° C.; wash with 2×SSC, 1% SDS, at 50° C., and more preferably has a nucleotide sequence selected from the group consisting of: ORF4 of SEQ ID NO:1, ORF43 of SEQ ID NO:23, ORF4 of SEQ ID NO:28, and ORF3 of SEQ ID NO:33.

The present invention also encompasses a chimeric construct comprising a promoter operatively linked to a nucleic acid molecule isolated from a microbe capable of producing pyrrolnitrin, wherein the nucleic acid molecule encodes at least one enzyme required in the biosynthetic pathway of pyrrolnitrin. The present invention further encompasses an expression vector comprising a nucleic acid molecule isolated from a microbe capable of producing pyrrolnitrin, wherein the nucleic acid molecule encodes at least one enzyme required in the biosynthetic pathway of pyrrolnitrin. The present invention still further encompasses a microbial host transformed with such an expression vector, whereby the microbial host produces pyrrolnitrin. Such a microbial host according to the invention is preferably a strain of bacteria such as Pseudomonas, Bacillus, or E. coli.

Additional aspects of the present invention include the following: a method for controlling or inhibiting the growth of a phytopathogen by applying an effective amount of a microbial host, which has been transformed to recombinantly produce pyrrolnitrin, to an environment in which the phytopathogen may grow; a method for controlling or inhibiting the growth of a phytopathogen by applying an effective amount of a microbial host, which has been transformed to recombinantly produce pyrrolnitrin, to a plant or plant part in order to protect said plant or plant part from the phytopathogen; and a method for controlling or inhibiting the growth of a phytopathogen by applying an effective amount of a microbial host, which has been transformed to recombinantly produce pyrrolnitrin, to to seed in order to protect a plant that develops from said seed from the phytopathogen. Transgenic microbial hosts may also be applied to plants or plant parts (e.g., fruit) after the plants or plant parts have been harvested.

Still another aspect of the present invention includes a method for producing pyrrolnitrin in a recombinant microbial host by (a) transforming a microbial host with a nucleic acid molecule isolated from a microbe capable of producing pyrrolnitrin, wherein the nucleic acid molecule encodes at least one enzyme required in the biosynthetic pathway of pyrrolnitrin; and (b) growing the transformed microbial host under conditions that allow biosynthesis of pyrrolnitrin in the microbial host.

The present invention further includes an isolated enzyme encoded by the nucleic acid molecule of the invention. According to a preferred embodiment, the isolated enzyme may be either PrnA, PrnB, PrnC, or PrnD.

The present invention is still further directed to a nucleic acid molecule isolated from a microbial host capable of producing pyrrolnitrin, wherein the nucleic acid molecule or its complement hybridizes to SEQ ID NO:1, 23, 28, or 33 under the following conditions: hybridization at 7% sodium dodecyl sulfate (SDS), 0.5 M NaPO$_4$ pH 7.0, 1 mM EDTA at 50° C.; wash with 2×SSC, 1% SDS, at 50° C. Also encompassed are a chimeric construct comprising a promoter operatively linked to such a DNA molecule, an expression vector comprising such a DNA molecule, and a transgenic microbial host into which such a DNA molecule has been introduced.

DEFINITIONS

As used in the present application, the following terms have the meanings set out below.

Antipathogenic Substance:

A substance which requires one or more nonendogenous enzymatic activities foreign to a plant to be produced in a host where it does not naturally occur, which substance has a deleterious effect on the multiplication or growth of a pathogen (i.e. pathogen). By "nonendogenous enzymatic activities" is meant enzymatic activities that do not naturally occur in the host where the antipathogenic substance does not naturally occur. A pathogen may be a fungus, bacteria, nematode, virus, viroid, insect or combination thereof, and may be the direct or indirect causal agent of disease in the host organism. An antipathogenic substance can prevent the multiplication or growth of a phytopathogen or can kill a phytopathogen. An antipathogenic substance may be synthesized from a substrate which naturally occurs in the host. Alternatively, an antipathogenic substance may be synthesized from a substrate that is provided to the host along with the necessary nonendogenous enzymatic activities. An antipathogenic substance may be a carbohydrate containing antibiotic, a peptide antibiotic, a heterocyclic antibiotic containing nitrogen, a heterocyclic antibiotic containing oxygen, a heterocyclic antibiotic containing nitrogen and oxygen, a polyketide, a macrocyclic lactone, and a quinone. Antipathogenic substance is abbreviated as "APS" throughout the text of this application.

Anti-phytopathogenic substance:

An antipathogenic substance as herein defined which has a deleterious effect on the multiplication or growth of a plant pathogen (i.e. phytopathogen).

Biocontrol agent:

An organism which is capable of affecting the growth of a pathogen such that the ability of the pathogen to cause a disease is reduced. Biocontrol agents for plants include microorganisms which are capable of colonizing plants or the rhizosphere. Such biocontrol agents include gram-negative microorganisms such as Pseudomonas, Enterobacter and Serratia, the gram-positive microorganism Bacillus and the fungi Trichoderma and Gliocladium. Organisms may act as biocontrol agents in their native state or when they are genetically engineered according to the invention.

Pathogen:

Any organism which causes a deleterious effect on a selected host under appropriate conditions. Within the scope of this invention the term pathogen is intended to include fungi, bacteria, nematodes, viruses, viroids and insects.

Isolated:

In the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, a transgenic host cell.

Promoter or Regulatory DNA Sequence:

An untranslated DNA sequence which assists in, enhances, or otherwise affects the transcription, translation or expression of an associated structural DNA sequence which codes for a protein or other DNA product. The promoter DNA sequence is usually located at the 5' end of a translated DNA sequence, typically between 20 and 100 nucleotides from the 5' end of the translation start site.

Coding DNA Sequence:

A DNA sequence that is translated in an organism to produce a protein.

Operatively Linked to/Associated With:

Two DNA sequences which are "associated" or "operatively linked" are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Construction/Fusion DNA Sequence:

A recombinant DNA sequence in which a promoter or regulatory DNA sequence is operatively linked to, or associated with, a DNA sequence that codes for an mRNA or which is expressed as a protein, such that the regulator DNA sequence is able to regulate transcription or expression of the associated DNA sequence. The regulator DNA sequence of the chimeric construction is not normally operatively linked to the associated DNA sequence as found in nature. The terms "heterologous" or "non-cognate" are used to indicate a recombinant DNA sequence in which the promoter or regulator DNA sequence and the associated DNA sequence are isolated from organisms of different species or genera.

Substantially Similar:

In the context of the present invention, a nucleic acid molecule such as a DNA molecule that has at least 60 percent sequence identity with the portion(s) of SEQ ID NO:1, 23, 28, or 33 that codes for one or more pyrrolnitrin biosynthesis enzymes. A substantially similar nucleotide sequence hybridizes specifically to SEQ ID NO:1, 23, 28, or 33, or fragments thereof, under the following conditions: hybridization at 7% sodium dodecyl sulfate (SDS), 0.5 M NaPO$_4$ pH 7.0, 1 mM EDTA at 50° C.; wash with 2×SSC, 1% SDS, at 50° C. With respect to enzymes, "substantially similar" as used herein means an amino acid sequence that is at least 90% identical to the amino acid sequence of one of the pyrrolnitrin biosynthesis enzymes described herein (SEQ ID NOs:2–5, 24–27, 29–32, and 34–37).

BRIEF DESCRIPTION OF THE SEQUENCES IN THE SEQUENCE LISTING

SEQ ID NO:1: . . . DNA sequence of the *Pseudomonas fluorescens* pyrrolnitrin gene region.
SEQ ID NO:2: . . . *Ps. fluorescens* PrnA protein sequence.
SEQ ID NO:3: . . . *Ps. fluorescens* PrnB protein sequence.
SEQ ID NO:4: . . . *Ps. fluorescens* PrnC protein sequence.
SEQ ID NO:5: . . . *Ps. fluorescens* PrnD protein sequence.
SEQ ID NO:6: . . . Sequence of the soraphen gene cluster.
SEQ ID NO:7: . . . Sequence of a plant consensus translation initiator (Clontech).
SEQ ID NO:8: . . . Sequence of a plant consensus translation initiator (Joshi).
SEQ ID NO:9: . . . Sequence of an oligonucleotide for use in a molecular adaptor.
SEQ ID NO:10: . . . Sequence of an oligonucleotide for use in a molecular adaptor.
SEQ ID NO:11: . . . Sequence of an oligonucleotide for use in a molecular adaptor.
SEQ ID NO:12: . . . Sequence of an oligonucleotide for use in a molecular adaptor.
SEQ ID NO:13: . . . Sequence of an oligonucleotide for use in a molecular adaptor.
SEQ ID NO:14: . . . Sequence of an oligonucleotide for use in a molecular adaptor.
SEQ ID NO:15: . . . Oligonucleotide used to change restriction site.
SEQ ID NO:16: . . . Oligonucleotide used to change restriction site.
SEQ ID NO:17: . . . Sequence of the phenazine gene cluster.
SEQ ID NO:18: . . . Protein sequence for phz1 from the phenazine gene cluster.
SEQ ID NO:19: . . . Protein sequence for phz2 from the phenazine gene cluster.
SEQ ID NO:20: . . . Protein sequence for phz3 from the phenazine gene cluster.
SEQ ID NO:21: . . . DNA sequence for phz4 of the phenazine gene cluster.
SEQ ID NO:22: . . . Protein sequence for phz4 from the phenazine gene cluster.
SEQ ID NO:23: . . . DNA sequence of the *Pseudomonas pyrrocinia* pyrrolnitrin gene region.
SEQ ID NO:24: . . . *Ps. pyrrocinia* PrnA protein sequence.
SEQ ID NO:25: . . . *Ps. pyrrocinia* PrnB protein sequence.
SEQ ID NO:26: . . . *Ps. pyrrocinia* PrnC protein sequence.
SEQ ID NO:27: . . . *Ps. pyrrocinia* PrnD protein sequence.
SEQ ID NO:28: . . . DNA sequence of the *Burkholdaria cepacia* pyrrolnitrin gene region.
SEQ ID NO:29: . . . *B. cepacia* PrnA protein sequence.
SEQ ID NO:30: . . . *B. cepacia* PrnB protein sequence.
SEQ ID NO:31: . . . *B. cepacia* PrnC protein sequence.
SEQ ID NO:32: . . . *B. cepacia* PrnD protein sequence.
SEQ ID NO:33: . . . DNA sequence of the *Myxococcus fulvus* pyrrolnitrin gene region.
SEQ ID NO:34: . . . *M. fulvus* PrnB protein sequence.
SEQ ID NO:35: . . . *M. fulvus* PrnC protein sequence.
SEQ ID NO:36: . . . *M. fulvus* PrnD protein sequence.
SEQ ID NO:37: . . . *M. fulvus* PrnA protein sequence.

DEPOSITS

| Clone | Accession Number | Date of Deposit |
| --- | --- | --- |
| pJL3 | NRRL B-21254 | May 20, 1994 |
| p98/1 | NRRL B-21255 | May 20, 1994 |
| pCIB169 | NRRL B-21256 | May 20, 1994 |
| pCIB3350 | NRRL B-21257 | May 20, 1994 |
| pCIB3351 | NRRL B-21258 | May 20, 1994 |
| pPEH66 | NRRL B-21598 | July 9, 1996 |
| pPEH76 | NRRL B-21599 | July 9, 1996 |
| pPEH78 | NRRL B-21600 | July 9, 1996 |
| pPEH80 | NRRL B-21601 | July 9, 1996 |

DETAILED DESCRIPTION OF THE INVENTION

Production of Antipathogenic Substances by Microorganisms

Many organisms produce secondary metabolites and some of these inhibit the growth of other organisms. Since the discovery of penicillin, a large number of compounds with antibiotic activity have been identified, and the number continues to increase with ongoing screening efforts. Antibiotically active metabolites comprise a broad range of chemical structures. The most important include: aminoglycosides (e.g. streptomycin) and other carbohydrate containing antibiotics, peptide antibiotics (e.g. β-lact APS, rhizocticin (see Rapp, C. et al., *Liebigs Ann. Chem.*: 655–661 (1988)), nucleoside derivatives (e.g. blasticidin S) and other heterocyclic antibiotics containing nitrogen (e.g. phenazine and pyrrolnitrin) and/or oxygen, polyketides (e.g. soraphen), macrocyclic lactones (e.g. erythromycin) and quinones (e.g. tetracycline).

Aminoglycosides and Other Carbohydrate Containing Antibiotics

The aminoglycosides are oligosaccharides consisting of an aminocyclohexanol moiety glycosidically linked to other amino sugars. Streptomycin, one of the best studied of the group, is produced by *Streptomyces griseus*. The biochemistry and biosynthesis of this compound is complex (for review see Mansouri et al. in: Genetics and Molecular Biology of Industrial Microorganisms (ed.: Hershberger et al.), American Society for Microbiology, Washington, D.C. pp. 61–67 (1989)) and involves 25 to 30 genes, 19 of which have been analyzed so far (Retzlaff et al. in: Industrial Microorganisms: Basic and Applied Molecular Genetics (ed.: Baltz et al.), American Society for Microbiology, Washington, D.C. pp. 183–194 (1993)). Streptomycin, and many other aminoglycosides, inhibits protein synthesis in the target organisms.

Peptide Antibiotics

Peptide antibiotics are classifiable into two groups: (1) those which are synthesized by enzyme systems without the participation of the ribosomal apparatus, and (2) those which require the ribosomally-mediated translation of an mRNA to provide the precursor of the antibiotic.

Non-Ribosomal Peptide Antibiotics

Non-Ribosomal Peptide Antibiotics are assembled by large, multifunctional enzymes which activate, modify, polymerize and in some cases cyclize the subunit amino acids, forming polypeptide chains. Other acids, such as aminoadipic acid, diaminobutyric acid, diaminopropionic acid, dihydroxyamino acid, isoserine, dihydroxybenzoic acid, hydroxyisovaleric acid, (4R)-4-[(E)-2-butenyl]-4,N-dimethyl-L-threonine, and ornithine are also incorporated (Katz & Demain, Bacteriological Review 41: 449–474 (1977); Kleinkauf & von Dohren, Annual Review of Microbiology 41: 259–289 (1987)). The products are not encoded by any mRNA, and ribosomes do not directly participate in their synthesis. Peptide antibiotics synthesized non-ribosomally can in turn be grouped according to their general structures into linear, cyclic, lactone, branched cyclopeptide, and depsipeptide categories (Kleinkauf & von Dohren, European Journal of Biochemistry 192: 1–15 (1990)). These different groups of antibiotics are produced by the action of modifying and cyclizing enzymes; the basic scheme of polymerization is common to them all. Non-ribosomally synthesized peptide antibiotics are produced by both bacteria and fungi, and include edeine, linear gramicidin, tyrocidine and gramicidin S from *Bacillus brevis*, mycobacillin from *Bacillus subtilis*, polymyxin from *Bacillus polymiyxa*, etamycin from *Streptomyces griseus*, echinomycin from *Streptomyces echinatus*, actinomycin from *Streptomyces clavuligerus*, enterochelin from *Escherichia coli*, gamma-(alpha-L-aminoadipyl)-L-cysteinyl-D-valine (ACV) from *Aspergillus nidulans*, alamethicine from *Trichoderma viride*, destruxin from *Metarhizium anisolpliae*, enniatin from *Fusarium oxysporum*, and beauvericin from *Beauveria bassiana*. Extensive functional and structural similarity exists between the prokaryotic and eukaryotic systems, suggesting a common origin for both. The activities of peptide antibiotics are similarly broad, toxic effects of different peptide antibiotics in animals, plants, bacteria, and fungi are known (Hansen, Annual Review of Microbiology 47: 535–564 (1993); Katz & Demain, Bacteriological Reviews 41: 449–474 (1977); Kleinkauf & von Dohren, Annual Review of Microbiology 41: 259–289 (1987); Kleinkauf & von Dohren, European Journal of Biochemistry 192: 1–15 (1990); Kolter & Moreno, Annual Review of Microbiology 46: 141–163 (1992)).

Ribosomally-Synthesized Peptide Antibiotics

Ribosomally-Synthesized Peptide Antibiotics are characterized by the existence of a structural gene for the antibiotic itself, which encodes a precursor that is modified by specific enzymes to create the mature molecule. The use of the general protein synthesis apparatus for peptide antibiotic synthesis opens up the possibility for much longer polymers to be made, although these peptide antibiotics are not necessarily very large. In addition to a structural gene, further genes are required for extracellular secretion and immunity, and these genes are believed to be located close to the structural gene, in most cases probably on the same operon. Two major groups of peptide antibiotics made on ribosomes exist: those which contain the unusual amino acid lanthionine, and those which do not. Lanthionine-containing antibiotics (lantibiotics) are produced by gram-positive bacteria, including species of Lactococcus, Staphylococcus, Streptococcus, Bacillus, and Streptomyces. Linear lantibiotics (for example, nisin, subtilin, epidermin, and gallidermin), and circular lantibiotics (for example, duramycin and cinnamycin), are known (Hansen, Annual Review of Microbiology 47: 535–564 (1993); Kolter & Moreno, Annual Review of Microbiology 46: 141–163 (1992)). Lantibiotics often contain other characteristic modified residues such as dehydroalanine (DHA) and dehydrobutyrine (DHB), which are derived from the dehydration of serine and threonine, respectively. The reaction of a thiol from cysteine with DHA yields lanthionine, and with DHB yields β-methyllanthionine. Peptide antibiotics which do not contain lanthionine may contain other modifications, or they may consist only of the ordinary amino acids used in protein synthesis. Non-lanthionine-containing peptide antibiotics are produced by both gram-positive and gram-negative bacteria, including Lactobacillus, Lactococcus, Pediococcus, Enterococcus, and Escherichia. Antibiotics in this category include lactacins, lactocins, sakacin A, pediocins, diplococcin, lactococcins, and microcins (Hansen, supra; Kolter & Moreno, supra).

Nucleoside Derivatives and Other Heterocyclic Antibiotics Containing Nitrogen and/or Oxygen These compounds all contain heterocyclic rings but are otherwise structurally diverse and, as illustrated in the following examples, have very different biological activities.

Polyoxins and Nikkomycins

Polyoxins and Nikkomycins are nucleoside derivatives and structurally resemble UDP-N-acetylglucosamine, the substrate of chitin synthase. They have been identified as competitive inhibitors of chitin synthase (Gooday, in: Biochemistry of Cell Walls and Membranes in Fungi (ed.: Kuhn et al.), Springer-Verlag, Berlin p. 61 (1990)). The polyoxins are produced by *Streptomyces cacaoi* and the Nikkomycins are produced by *S. tendae*.

Phenazines

Phenazines are nitrogen-containing heterocyclic compounds with a common planar aromatic tricyclic structure. Over 50 naturally occurring phenazines have been identified, each differing in the substituent groups on the basic ring structure. This group of compounds are found produced in nature exclusively by bacteria, in particular Streptomyces, Sorangium, and Pseudomonas (for review see Turner & Messenger, Advances in Microbiol Physiology 27: 211–275 (1986)). Recently, the phenazine biosynthetic genes of a *P. aureofaciens* strain has been isolated (Pierson & Thomashow MPMI 5: 330–339 (1992)). Because of their planar aromatic structure, it has been proposed that phenazines may form intercalative complexes with DNA (Hollstein & van Gemert, Biochemistry 10: 497 (1971)), and thereby interfere with DNA metabolism. The phenazine myxin was shown to intercalate DNA (Hollstein & Butler, Biochemistry 11: 1345 (1972)) and the phenazine lomofungin was shown to inhibit RNA synthesis in yeast (Cannon & Jiminez, Biochemical Journal 142: 457 (1974); Ruet et al., Biochemistry 14: 4651 (1975)).

Pyrrolnitrin

Pyrrolnitrin is a phenylpyrrole derivative with strong antibiotic activity and has been shown to inhibit a broad range of fungi (Homma et al., Soil Biol. Biochem. 21: 723–728 (1989); Nishida et al., J. Antibiot., ser A, 18: 211–219 (1965)). It was originally isolated from *Pseudomonas pyrrocinia* (Arima et al, J. Antibiot., ser. A, 18: 201–204 (1965)), and has since been isolated from several other Pseudomonas species and Myxococcus species (Gerth et al. J. Antibiot. 35: 1101–1103 (1982)). The compound has been reported to inhibit fungal respiratory electron transport (Tripathi & Gottlieb, J. Bacteriol. 100: 310–318 (1969)) and uncouple oxidative phosphorylation (Lambowitz & Slayman, J. Bacteriol. 112: 1020–1022 (1972)). It has also been proposed that pyrrolnitrin causes generalized lipoprotein membrane damage (Nose & Arima, J. Antibiot., ser A, 22: 135–143 (1969); Carlone & Scannerini, Mycopahtologia et Mycologia Applicata 53: 111–123 (1974)). Pyrrolnitrin is biosynthesized from tryptophan (Chang et al. J. Antibiot. 34: 555–566) and the biosynthetic genes from *P. fluorescens* have now been isolated (see Section C of examples).

Polyketide Synthases

Many antibiotics, in spite of the apparent structural diversity, share a common pattern of biosynthesis. The molecules are built up from two carbon building blocks, the β-carbon of which always carries a keto group, thus the name polyketide. The tremendous structural diversity derives from the different lengths of the polyketide chain and the different side-chains introduced, either as part of the two carbon building blocks, or after the polyketide backbone is formed. The keto groups may also be reduced to hydroxyls or removed altogether. Each round of two carbon addition is carried out by a complex of enzymes called the polyketide synthases (PKS) in a manner similar to fatty acid biosynthesis. The biosynthetic genes for an increasing number of polyketide antibiotics have been isolated and sequenced. It is quite apparent that the PKS genes are structurally conserved. The encoded proteins generally fall into two types: type I proteins are polyfunctional, with several catalytic domains carrying out different enzymatic steps covalently linked together (e.g. PKS for erythromycin, soraphen, and avermectin (Joaua et al. Plasmid 28: 157–165 (1992); MacNeil et al. in: Industrial Microorganisms: Basic and Applied Molecular Genetics, (ed.: Baltz et al.), American Society for Microbiology, Washington D.C. pp. 245–256 (1993)); whereas type II proteins are monofunctional (Hutchinson et al. in: Industrial Microorganisms: Basic and Applied Molecular Genetics, (ed.: Baltz et al.), American Society for Microbiology, Washington D.C. pp. 203–216 (1993)). For the simpler polyketide antibiotics such as actinorhodin (produced by *Streptomyces coelicolor*), the several rounds of two carbon additions are carried out iteratively on PKS enzymes encoded by one set of PKS genes. In contrast, synthesis of the more complicated compounds such as erythromycin and soraphen (see Section E of examples) involves sets of PKS genes organized into modules, with each module carrying out one round of two carbon addition (for review see Hopwood et al. in: Industrial Microorganisms: Basic and Applied Molecular Genetics, (ed.: Baltz et al.), American Society for Microbiology, Washington D.C. pp. 267–275 (1993)).

Macrocyclic Lactones

This group of compounds shares the presence of a large lactone ring with various ring substituents. They can be further classified into subgroups, depending on the ring size and other characteristics. The macrolides, for example, contain 12-, 14-, 16-, or 17-membered lactone rings glycosidically linked to one or more aminosugars and/or deoxysugars. They are inhibitors of protein synthesis, and are particularly effective against gram-positive bacteria. Erythromycin A, a well-studied macrolide produced by *Saccharopolyspora erythraea*, consists of a 14-membered lactone ring linked to two deoxy sugars. Many of the biosynthetic genes have been isolated; all have been located within a 60 kb segment of the *S. erythraea* chromosome. At least 22 closely linked open reading frames have been identified to be likely involved in erythromycin biosynthesis (Donadio et al., in: Industrial Microorganisms: Basic and Applied Molecular Genetics, (ed.: Baltz et al.), American Society for Microbiology, Washington D.C. pp. 257–265 (1993)).

Quinones

Quinones are aromatic compounds with two carbonyl groups on a fully unsaturated ring. The compounds can be broadly classified into subgroups according to the number of aromatic rings present, i.e., benzoquinones, napthoquinones, etc. A well studied group is the tetracyclines, which contain a napthacene ring with different substituents. Tetracyclines are protein synthesis inhibitors and are effective against both gram-positive and gram-negative bacteria, as well as rickettsias, mycoplasma, and spirochetes. The aromatic rings in the tetracyclines are derived from polyketide molecules. Genes involved in the biosynthesis of oxytetracycline (produced by *Streptomyces rimosus*) have been isolated and expressed in *Streptomyces lividans* (Binnie et al. J. Bacteriol. 171: 887–895 (1989)). The PKS genes share homology with those for actinorhodin and therefore encode type II (monofunctional) PKS proteins (Hopewood & Sherman, Ann. Rev. Genet. 24: 37–66 (1990)).

Other Types of APS

Several other types of APSs have been identified. One of these is the antibiotic 2-hexyl-5-propyl-resorcinol which is produced by certain strains of Pseudomonas. It was first isolated from the Pseudomonas strain B-9004 (Kanda et al. J. Antibiot. 28: 935–942 (1975)) and is a dialkyl-substituted derivative of 1,3-dihydroxybenzene. It has been shown to have antipathogenic activity against Gram-positive bacteria (in particular Clavibacter sp.), mycobacteria, and fungi. Another type of APS are the methoxyacrylates, such as strobilurin B. Strobilurin B is produced by Basidiomycetes and has a broad spectrum of fungicidal activity (Anke, T. et al., *Journal of Antibiotics* (Tokyo) 30: 806–810 (1977). In particular, strobilurin B is produced by the fungus *Bolinia lutea*. Strobilurin B appears to have antifungal activity as a result of its ability to inhibit cytochrome b dependent electron transport thereby inhibiting respiration (Becker, W. et al., *FEBS Letters* 132: 329–333 (1981).

Most antibiotics have been isolated from bacteria, actinomycetes, and fungi. Their role in the biology of the host organism is often unknown, but many have been used with great success, both in medicine and agriculture, for the control of microbial pathogens. Antibiotics which have been used in agriculture are: blasticidin S and kasugamycin for the control of rice blast (*Pyricularia oryzae*), validamycin for the control of *Rhizoctonia solani,* prumycin for the control of Botrytis and Sclerotinia species, and mildiomycin for the control of mildew.

To date, the use of antibiotics in plant protection has involved the production of the compounds through chemical synthesis or fermentation and application to seeds, plant parts, or soil. This invention describes the identification and isolation of the biosynthetic genes of a number of antiphytopathogenic substances and further describes the use of these genes to create transgenic plants with enhanced disease resistance characteristics and also the creation of improved biocontrol strains by expression of the isolated genes in organisms which colonize host plants or the rhizosphere. Furthermore, the availability of such genes provides methods for the production of APSs for isolation and application in antipathogenic formulations.

Methods for Isolating Genes for Antipathogenic Substances

Genes encoding antibiotic biosynthetic genes can be isolated using a variety of techniques according to the invention. The simplest procedure for the isolation of APS genes requires the isolation of genomic DNA from an organism identified as producing an APS, and the transfer of the isolated DNA on a suitable plasmid or vector to a host organism which does not produce the APS, followed by the identification of transformed host colonies to which the APS-producing ability has been conferred. Using a technique such as $\lambda$::Tn5 transposon mutagenesis (de Bruijn & Lupski, Gene 27: 131–149 (1984)), the exact region of the transforming APS-conferring DNA can be more precisely defined. Alternatively or additionally, the transforming APS-conferring DNA can be cleaved into smaller fragments and the smallest which maintains the APS-conferring ability further characterized. Whereas the host organism lacking the ability to produce the APS may be a different species to the organism from which the APS derives, a variation of this technique involves the transformation of host DNA into the same host which has had its APS-producing ability disrupted by mutagenesis. In this method, an APS-producing organism is mutated and non-APS producing mutants isolated, and these are complemented by isolated genomic DNA from the APS producing parent strain. A further example of a standard technique used to isolate genes required for APS biosynthesis is the use of transposon mutagenesis to generate mutants of an APS-producing organism which, after mutagenesis, fail to produce the APS. Thus, the region of the host genome responsible for APS production is tagged by the transposon and can be easily recovered and used as a probe to isolate the native genes from the parent strain. APS biosynthetic genes which are required for the synthesis of APSs and which are similar to known APS compounds may be isolatable by virtue of their sequence homology to the biosynthetic genes of the known compounds. Techniques suitable for isolation by homology include standard library screening by DNA hybridization. In addition to DNA molecules that encode enzymes required for APS biosynthesis, corresponding RNA transcripts can be synthesized by standard procedures well known in the art, such as with T7 RNA polymerase (New England Biolabs). Such RNA molecules can be used as probes to isolate APS biosynthetic genes by standard procedures well known in the art.

This invention also describes a novel technique for the isolation of APS biosynthetic genes which may be used to isolate the genes for any APS, and is particularly useful for the isolation of APS biosynthetic genes which may be recalcitrant to isolation using any of the above techniques. One reason why such recalcitrance to isolation may exist is that the standard techniques described above (except for isolation by homology) may preferentially lead to the isolation of regulators of APS biosynthesis. Once such a regulator has been identified, however, it can be used using this novel method to isolate the biosynthetic genes under the control of the isolated regulator. In this method, a library of transposon insertion mutants is created in a strain of microorganism which lacks the regulator or has had the regulator gene disabled by conventional gene disruption techniques. The insertion transposon used carries a promoter-less reporter gene (e.g. lacZ). Once the insertion library has been made, a functional copy of the regulator gene is transferred to the library of cells (e.g. by conjugation or electroporation) and the plated cells are selected for expression of the reporter gene. Cells are assayed before and after transfer of the regulator gene. Colonies which express the reporter gene only in the presence of the regulator gene are insertions adjacent to the promoter of genes regulated by the regulator. Assuming the regulator is specific in its regulation for APS-biosynthetic genes, then the genes tagged by this procedure will be APS-biosynthetic genes. In a preferred embodiment, the isolated regulator gene is the gafA gene described in PCT application WO 94/01561, which regulates the expression of the biosynthetic genes for pyrrolnitrin. Thus, this method is a preferred method for the isolation of the biosynthetic genes for pyrrolnitrin. WO 94/01561 (Intl. Appl. No. PCT/US93/06300) is hereby expressly incorporated by reference in its entirety.

In order for the isolated APS genes to be of use in transgenic expression, it is important that all the genes required for synthesis from a particular metabolite be identified and isolated. Using combinations of, or all the techniques described above, this is possible for any known APS. As most APS biosynthetic genes are clustered together in microorganisms, usually encoded by a single operon, the identification of all the genes will be possible from the identification of a single locus in an APS-producing microorganism. In addition, as regulators of APS biosynthetic genes are believed to regulate the whole pathway, then the isolation of the biosynthetic genes via their regulators is a particularly attractive method of isolating these genes. In many cases the regulator will control transcription of the single entire operon, thus facilitating the isolation of genes using this strategy.

Using the methods described in this application, biosynthetic genes for any APS can be isolated from a microorganism, and using the methods of gene manipulation and transgenic plant production described in this specification, the isolated APS biosynthetic genes can be modified and expressed in transgenic plants. Suitable APS biosynthetic genes include those described at the beginning of this section, viz. aminoglycosides and other carbohydrate containing antibiotics (e.g. streptomycin), peptide antibiotics (both non-ribosomally and ribosomally synthesized types), nucleoside derivatives and other heterocyclic antibiotics containing nitrogen and/or oxygen (e.g. polyoxins, nikkomycins, phenazines, and pyrrolnitrin), polyketides, macrocyclic lactones and quinones (e.g. soraphen, erythromycin and tetracycline). Expression in transgenic plants will be under the control of an appropriate promoter and involves appropriate cellular targeting considering the likely precursors required for the particular APS under consideration. Whereas the invention is intended to include the expression in transgenic plants of any APS gene isolatable by the procedures described in this specification, those which are particularly preferred include pyrrolnitrin, soraphen, phenazine, and the peptide antibiotics gramicidin and epidermin. The isolated biosynthetic genes can also be expressed in soil-borne or plant colonizing organisms for the purpose of conferring and enhancing biocontrol efficacy in these organisms. Particularly preferred APS genes for this purpose are those that encode pyrrolnitrin, soraphen, phenazine, and the peptide antibiotics.

Production of Antipathogenic Substances in Heterologous Microbial Hosts

Isolated APS genes can be expressed in heterologous bacterial or fungal hosts to enable the production of the APS with greater efficiency than might be possible from native hosts. Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely on yeast vectors and include the use of Pichia, Saccharomyces and Kluyveromyces (Sreekrishna, In: Industrial microorganisms: basic and applied molecular genetics, Baltz, Hegeman, and Skatrud eds., American Society for Microbiology, Washington (1993); Dequin & Barre, Biotechnology 12:173–177 (1994); van den Berg et al., Biotechnology 8:135–139 (1990)).

Isolated APS genes can also be expressed in heterologous bacterial and fungal hosts with the aim of increasing the efficacy of biocontrol strains of such bacterial and fungal hosts. Microorganisms which are suitable for the heterologous overexpression of APS genes are all microorganisms which are capable of colonizing plants or the rhizosphere. As such they will be brought into contact with phytopathogenic fungi, bacteria and nematodes causing an inhibition of their growth. These include gram-negative microorganisms such as Pseudomonas, Enterobacter and Serratia, the gram-positive microorganism Bacillus and the fungi Trichoderma and Gliocladium. Particularly preferred heterologous hosts are *Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum* and *Gliocladium virens*. In preferred embodiments of the invention the biosynthetic genes for pyrrolnitrin, soraphen, phenazine, and peptide antibiotics are transferred to the particularly preferred heterologous hosts listed above. In a particularly preferred embodiment, the biosynthetic genes for phenazine and/or soraphen are transferred to and expressed in *Pseudomonas fluorescens* strain CGA267356 (described in the published application EU 0 472 494 and in WO 94/01561) which has biocontrol utility due to its production of pyrrolnitrin (but not phenazine). In another preferred embodiment, the biosynthetic genes for pyrrolnitrin and/or soraphen are transferred to *Pseudomonas aureofaciens* strain 30-84 which has biocontrol characteristics due to its production of phenazine. Expression in heterologous biocontrol strains requires the selection of vectors appropriate for replication in the chosen host and a suitable choice of promoter. Alternately, RNA transcripts of the APS genes can be introduced into host cells, whereby enzymes required for APS biosynthesis are expressed from the RNA. Techniques are well known in the art for expression in gram-negative and gram-positive bacteria and fungi and are described elsewhere in this specification.

A further embodiment of the invention provides a method for controlling or inhibiting the growth of a plant pathogenic fungus by applying the genetically engineered biocontrol strains of the invention to an environment in which the plant pathogenic fungus may grow. This can be to the plant/s or parts of the plant/s (before or after harvest) or to the seeds (prior to planting) of the plant/s to be protected, or alternatively to soil in which the plant/s to be protected are growing or will grow. The biocontrol strains are applied in an effective amount; that is, in an amount sufficient to control or inhibit the pathogen. The rate of application may vary according to the crop to be protected, the efficacy of the biocontrol strain, the pathogen to be controlled, and the severity of the disease pressure. Generally, the rate of application is about $1.3 \times 10^5$ cfu/cm to about $1.3 \times 10^{10}$ cfu/cm, specifically about $1.3 \times 10^6$ cfu/cm to about $1.3 \times 10^9$ cfu/cm, more specifically about $1.3 \times 10^7$ cfu/cm to about $1.3 \times 10^8$ cfu/cm Expression of Genes for Anti-phytopathogenic Substances in Plants The APS biosynthetic genes of this invention are expressed in transgenic plants thus causing the biosynthesis of the selected APS in the transgenic plants. In this way transgenic plants with enhanced resistance to phytopathogenic fungi, bacteria and nematodes are generated. For their expression in transgenic plants, the APS genes and adjacent sequences may require modification and optimization.

Although in many cases genes from microbial organisms can be expressed in plants at high levels without modification, low expression in transgenic plants may result from APS genes having codons which are not preferred in plants. It is known in the art that all organisms have specific preferences for codon usage, and the APS gene codons can be changed to conform with plant preferences, while maintaining the amino acids encoded. Furthermore, high expression in plants is best achieved from coding sequences which have at least 35% GC content, and preferably more than 45%. Microbial genes which have low GC contents may express poorly in plants due to the existence of ATTTA motifs which may destabilize messages, and AATAAA motifs which may cause inappropriate polyadenylation. In addition, potential APS biosynthetic genes can be screened for the existence of illegitimate splice sites which may cause message truncation. All changes required to be made within the APS coding sequence such as those described above can be made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy). The preferred APS biosynthetic genes may be unmodified genes, should these be expressed at high levels in target transgenic plant species, or alternatively may be genes modified by the removal of destabilization and inappropriate polyadenylation motifs and illegitimate splice sites, and further modified by the incorporation of plant preferred codons, and further with a GC content preferred for expression in plants. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)).

For efficient initiation of translation, sequences adjacent to the initiating methionine may require modification. The sequences cognate to the selected APS genes may initiate translation efficiently in plants, or alternatively may do so inefficiently. In the case that they do so inefficiently, they can be modified by the inclusion of sequences known to be effective in plants. Joshi has suggested an appropriate consensus for plants (NAR 15: 6643–6653 (1987); SEQ ID NO:8)) and Clontech suggests a further consensus translation initiator (1993/1994 catalog, page 210; SEQ ID NO:7). These consensuses are suitable for use with the APS biosynthetic genes of this invention. The sequences are incorporated into the APS gene construction, up to and including the ATG (whilst leaving the second amino acid of the APS gene unmodified), or alternatively up to and including the GTC subsequent to the ATG (with the possibility of modifying the second amino acid of the transgene).

Expression of APS genes in transgenic plants is behind a promoter shown to be functional in plants. The choice of promoter will vary depending on the temporal and spatial requirements for expression, and also depending on the target species. For the protection of plants against foliar pathogens, expression in leaves is preferred; for the protection of plants against ear pathogens, expression in inflorescences (e.g. spikes, panicles, cobs etc.) is preferred; for protection of plants against root pathogens, expression in roots is preferred; for protection of seedlings against soil-borne pathogens, expression in roots and/or seedlings is preferred. In many cases, however, protection against more than one type of phytopathogen will be sought, and thus expression in multiple tissues will be desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the APS biosynthetic genes. In some cases, expression of APSs in plants may provide protection against insect pests. Transgenic expression of the biosynthetic genes for the APS beauvericin (isolated from *Beauveria bassiana*) may, for example provide protection against insect pests of crop plants.

Preferred promoters which are expressed constitutively include the CaMV 35S and 19S promoters, and promoters from genes encoding actin or ubiquitin. Further preferred constitutive promoters are those from the 12(4-28), CP21, CP24, CP38, and CP29 genes whose cDNAs are provided by this invention.

The APS genes of this invention can also be expressed under the regulation of promoters which are chemically regulated. This enables the APS to be synthesized only when the crop plants are treated with the inducing chemicals, and APS biosynthesis subsequently declines. Preferred technology for chemical induction of gene expression is detailed in the published application EP 0 332 104 (to Ciba-Geigy) and U.S. Pat. No. 5,614,395 (incorporated herein by reference). A preferred promoter for chemical induction is the tobacco PR-1a promoter.

A preferred category of promoters is that which is wound inducible. Numerous promoters have been described which are expressed at wound sites and also at the sites of phytopathogen infection. These are suitable for the expression of APS genes because APS biosynthesis is turned on by phytopathogen infection and thus the APS only accumulates when infection occurs. Ideally, such a promoter should only be active locally at the sites of infection, and in this way APS only accumulates in cells which need to synthesize the APS to kill the invading phytopathogen. Preferred promoters of this kind include those described by Stanford et al. Mol. Gen. Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis and many of these have been isolated from both monocotyledons and dicotyledons. A preferred promoter is the maize PEPC promoter from the phosphoenol carboxylase gene (Hudspeth & Grula, Plant Molec. Biol. 12: 579–589 (1989)). A preferred promoter for root specific expression is that described by de Framond (FEBS 290: 103–106 (1991); EP 0 452 269 to Ciba-Geigy) and a further preferred root-specific promoter is that from the T-1 gene provided by this invention. A preferred stem specific promoter is that described in patent application WO 93/07278 (to Ciba-Geigy) and which drives expression of the maize trpA gene.

Preferred embodiments of the invention are transgenic plants expressing APS biosynthetic genes in a root-specific fashion. In an especially preferred embodiment of the invention the biosynthetic genes for pyrrolnitrin are expressed behind a root specific promoter to protect transgenic plants against the phytopathogen Rhizoctonia. In another especially preferred embodiment of the invention the biosynthetic genes for phenazine are expressed behind a root specific promoter to protect transgenic plants against the phytopathogen *Gaeumannomyces graminis*. Further preferred embodiments are transgenic plants expressing APS biosynthetic genes in a wound-inducible or pathogen infection-inducible manner. For example, a further especially preferred embodiment involves the expression of the biosynthetic genes for soraphen behind a wound-inducible or pathogen-inducible promoter for the control of foliar pathogens.

In addition to the selection of a suitable promoter, constructions for APS expression in plants require an appropriate transcription terminator to be attached downstream of the heterologous APS gene. Several such terminators are available and known in the art (e.g. tm1 from CaMV, E9 from rbcS). Any available terminator known to function in plants can be used in the context of this invention.

Numerous other sequences can be incorporated into expression cassettes for APS genes. These include sequences which have been shown to enhance expression such as intron sequences (e.g. from Adh1 and bronze1) and viral leader sequences (e.g. from TMV, MCMV and AMV).

The overproduction of APSs in plants requires that the APS biosynthetic gene encoding the first step in the pathway will have access to the pathway substrate. For each individual APS and pathway involved, this substrate will likely differ, and so too may its cellular localization in the plant. In many cases the substrate may be localized in the cytosol, whereas in other cases it may be localized in some subcellular organelle. As much biosynthetic activity in the plant occurs in the chloroplast, often the substrate may be localized to the chloroplast and consequently the APS biosynthetic gene products for such a pathway are best targeted to the appropriate organelle (e.g. the chloroplast). Subcellular localization of transgene encoded enzymes can be undertaken using techniques well known in the art. Typically, the DNA encoding the target peptide from a known organelle-targeted gene product is manipulated and fused upstream of the required APS gene/s. Many such target sequence are known for the chloroplast and their functioning in heterologous constructions has been shown. In a preferred embodiment of this invention the genes for pyrrolnitrin biosynthesis are targeted to the chloroplast because the pathway substrate tryptophan is synthesized in the chloroplast.

In some situations, the overexpression of APS gene may deplete the cellular availability of the substrate for a particular pathway and this may have detrimental effects on the cell. In situations such as this it is desirable to increase the amount of substrate available by the overexpression of genes which encode the enzymes for the biosynthesis of the substrate. In the case of tryptophan (the substrate for pyrrolnitrin biosynthesis) this can be achieved by overexpressing the trpA and trpB genes as well as anthranilate synthase subunits. Similarly, overexpression of the enzymes for chorismate biosynthesis such as DAHP synthase will be effective in producing the precursor required for phenazine production. A further way of making more substrate available is by the turning off of known pathways which utilize specific substrates (provided this can be done without detrimental side effects). In this manner, the substrate synthesized is channeled towards the biosynthesis of the APS and not towards other compounds.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093–1096 (1986)). For both direct gene transfer and Agrobacterium-mediated transfer, transformation is usually (but not necessarily) undertaken with a selectable marker which may provide resistance to an antibiotic (kanamycin, hygromycin or methatrexate) or a herbicide (basta). The choice of selectable marker is not, however, critical to the invention.

Synthesis of an APS in a transgenic plant will frequently require the simultaneous overexpression of multiple genes encoding the APS biosynthetic enzymes. This can be achieved by transforming the individual APS biosynthetic genes into different plant lines individually, and then crossing the resultant lines. Selection and maintenance of lines carrying multiple genes is facilitated if each the various transformation constructions utilize different selectable markers. A line in which all the required APS biosynthetic genes have been pyramided will synthesize the APS, whereas other lines will not. This approach may be suitable for hybrid crops such as maize in which the final hybrid is necessarily a cross between two parents. The maintenance of different inbred lines with different APS genes may also be advantageous in situations where a particular APS pathway may lead to multiple APS products, each of which has a utility. By utilizing different lines carrying different alternative genes for later steps in the pathway to make a hybrid cross with lines carrying all the remaining required genes it is possible to generate different hybrids carrying different selected APSs which may have different utilities.

Alternate methods of producing plant lines carrying multiple genes include the retransformation of existing lines already transformed with an APS gene or APS genes (and selection with a different marker), and also the use of single transformation vectors which carry multiple APS genes, each under appropriate regulatory control (i.e. promoter, terminator etc.). Given the ease of DNA construction, the manipulation of cloning vectors to carry multiple APS genes is a preferred method.

Production of Antipathogenic Substances in Heterologous Hosts

The present invention also provides methods for obtaining APSs. These APSs may be effective in the inhibition of growth of microbes, particularly phytopathogenic microbes. The APSs can be produced from organisms in which the APS genes have been overexpressed, and suitable organisms for this include gram-negative and gram-positive bacteria and yeast, as well as plants. For the purposes of APS production, the significant criteria in the choice of host organism are its ease of manipulation, rapidity of growth (i.e. fermentation in the case of microorganisms), and its lack of susceptibility to the APS being overproduced. These methods of APS production have significant advantages over the chemical synthesis technology usually used in the preparation of APSs such as antibiotics. These advantages are the cheaper cost of production, and the ability to synthesize compounds of a preferred biological enantiomer, as opposed to the racemic mixtures inevitably generated by organic synthesis. The ability to produce stereochemically appropriate compounds is particularly important for molecules with many chirally active carbon atoms. APSs produced by heterologous hosts can be used in medical (i.e. control of pathogens and/or infectious disease) as well as agricultural applications.

Formulation of Antipathogenic Compositions

The present invention further embraces the preparation of antifungal compositions in which the active ingredient is the antibiotic substance produced by the recombinant biocontrol agent of the present invention or alternatively a suspension or concentrate of the microorganism. The active ingredient is homogeneously mixed with one or more compounds or groups of compounds described herein. The present invention also relates to methods of treating plants, which comprise application of the active ingredient, or antifungal compositions containing the active ingredient, to plants.

The active ingredients of the present invention are normally applied in the form of compositions and can be applied to the crop area, plant, or plant part to be treated, either before or after harvest, simultaneously or in succession, with further compounds. These compounds can be both fertilizers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying active ingredients of the present invention or an agrochemical composition which contains at least one of the active ingredients is leaf application. The number of applications and the rate of application depend on the intensity of infestation by the corresponding phytopathogen (type of fungus). However, the active ingredients can also penetrate the plant through the roots via the soil (systemic action) by impregnating the locus of the plant with a liquid composition, or by applying the compounds in solid form to the soil, e.g. in granular form (soil application). The active ingredients may also be applied to seeds (coating) by impregnating the seeds either with a liquid formulation containing active ingredients, or coating them with a solid formulation. In special cases, further types of application are also possible, for example, selective treatment of the plant stems or buds.

The active ingredients are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 500 g a.i./ha.

The formulations, compositions or preparations containing the active ingredients and, where appropriate, a solid or liquid adjuvant, are prepared in known manner, for example by homogeneously mixing and/or grinding the active ingredients with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one C8–C22 alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

The agrochemical compositions usually contain from about 0.1 to about 99%, preferably about 0.1 to about 95%, and most preferably from about 3 to about 90% of the active ingredient, from about 1 to about 99.9%, preferably from abut 1 to about 99%, and most preferably from about 5 to about 95% of a solid or liquid adjuvant, and from about 0 to about 25%, preferably about 0.1 to about 25%, and most preferably from about 0.1 to about 20% of a surfactant.

Whereas commercial products are preferably formulated as concentrates, the end user will normally employ dilute formulations.

EXAMPLES

The following examples serve as further description of the invention and methods for practicing the invention. They are not intended as being limiting, rather as providing guidelines on how the invention may be practiced.

A. Identification of Microorganisms that Produce Antipathogenic Substances

Microorganisms can be isolated from many sources and screened for their ability to inhibit fungal or bacterial growth in vitro. Typically the microorganisms are diluted and plated on medium onto or into which fungal spores or mycelial fragments, or bacteria have been or are to be introduced. Thus, zones of clearing around a newly isolated bacterial colony are indicative of antipathogenic activity.

Example 1

Isolation of Microorganisms with Anti-Rhizoctonia Properties from Soil

A gram of soil (containing approximately $10^6$–$10^8$ bacteria) is suspended in 10 ml sterile water. After vigorously mixing, the soil particles are allowed to settle. Appropriate dilutions are made and aliquots are plated on nutrient agar plates (or other growth medium as appropriate) to obtain 50–100 colonies per plate. Freshly cultured Rhizoctonia mycelia are fragmented by blending and suspensions of fungal fragments are sprayed on to the agar plates after the bacterial colonies have grown to be just visible. Bacterial isolates with antifungal activities can be identified by the fungus-free zones surrounding them upon further incubation of the plates.

The production of bioactive metabolites by such isolates is confirmed by the use of culture filtrates in place of live colonies in the plate assay described above. Such bioassays can also be used for monitoring the purification of the metabolites. Purification may start with an organic solvent extraction step and depending on whether the active principle is extracted into the organic phase or left in the aqueous phase, different chromatographic steps follow. These chromatographic steps are well known in the art. Ultimately, purity and chemical identity are determined using spectroscopic methods.

B. Isolating Antipathogenic Biosynthetic Genes from Microorganisms

Example 2

Shotgun Cloning Antipathogenic Biosynthetic Genes from their Native Source

Related biosynthetic genes are typically located in close proximity to each other in microorganisms and more than one open reading frame is often encoded by a single operon. Consequently, one approach to the isolation of genes which encode enzymes in a single biosynthetic pathway is the transfer of genome fragments from a microorganism containing said pathway to one which does not, with subsequent screening for a phenotype conferred by the pathway.

In the case of biosynthetic genes encoding enzymes leading to the production of an antipathogenic substance (APS), genomic DNA of the antipathogenic substance producing microorganism is isolated, digested with a restriction endonuclease such as Sau3A, size fractionated for the isolation of fragments of a selected size (the selected size depends on the vector being used), and fragments of the selected size are cloned into a vector (e.g. the BamHI site of a cosmid vector) for transfer to *E. coli*. The resulting *E. coli* clones are then screened for those which are producing the antipathogenic substance. Such screens may be based on the direct detection of the antipathogenic substance, such as a biochemical assay.

Alternatively, such screens may be based on the adverse effect associated with the antipathogenic substance upon a target pathogen. In these screens, the clones producing the antipathogenic substance are selected for their ability to kill or retard the growth of the target pathogen. Such an inhibitory activity forms the basis for standard screening assays well known in the art, such as screening for the ability to produce zones of clearing on a bacterial plate impregnated with the target pathogen (e.g. spores where the target pathogen is a fungus, cells where the target pathogen is a bacterium). Clones selected for their antipathogenic activity can then be further analyzed to confirm the presence of the antipathogenic substance using the standard chemical and biochemical techniques appropriate for the particular antipathogenic substance.

Further characterization and identification of the genes encoding the biosynthetic enzymes for the antipathogenic substance is achieved as follows. DNA inserts from positively identified *E. coli* clones are isolated and further digested into smaller fragments. The smaller fragments are then recloned into vectors and reinserted into *E. coli* with subsequent reassaying for the antipathogenic phenotype. Alternatively, positively identified clones can be subjected to λ::Tn5 transposon mutagenesis using techniques well known in the art (e.g. de Bruijn & Lupski, Gene 27: 131–149 (1984)). Using this method a number of disruptive transposon insertions are introduced into the DNA shown to confer APS production to enable a delineation of the precise region/s of the DNA which are responsible for APS production. Subsequently, determination of the sequence of the smallest insert found to confer antipathogenic substance production on *E. coli* will reveal the open reading frames required for APS production. These open reading frames can ultimately be disrupted (see below) to confirm their role in the biosynthesis of the antipathogenic substance.

Various host organisms such as Bacillus and yeast may be substituted for *E. coli* in the techniques described using suitable cloning vectors known in the art for such host. The choice of host organism has only one limitation; it should not be sensitive to the antipathogenic substance for which the biosynthetic genes are being cloned.

Example 3

Isolating Biosynthetic Genes for an Antipathogenic Substance using Transposon Mutagenesis In many microorganisms which are known to produce antipathogenic substances, transposon mutagenesis is a routine technique used for the generation of insertion mutants.

This technique has been used successfully in Pseudomonas (e.g. Lam et al., *Plasmid* 13:200–204 (1985)), Bacillus (e.g. Youngman et al., *Proc. Natl. Acad. Sci. USA* 80:2305–2309 (1983)), Staphylococcus (e.g. Pattee, *J. Bacteriol.* 145:479–488 (1981)), and Streptomyces (e.g. Schauer et al., *J. Bacteriol.* 173:5060–5067 (1991)), among others. The main requirement for the technique is the ability to introduce a transposon containing plasmid into the microorganism enabling the transposon to insert itself at a random position in the genome. A large library of insertion mutants is created by introducing a transposon carrying plasmid into a large number of microorganisms. Introduction of the plasmid into the microorganism can be by any appropriate standard technique such as conjugation, direct gene transfer techniques such as electroporation.

Once a transposon library has been created in the manner described above, the transposon insertion mutants are assayed for production of the APS. Mutants which do not produce the APS would be expected to predominantly occur as the result of transposon insertion into gene sequences required for APS biosynthesis. These mutants are therefore selected for further analysis.

DNA from the selected mutants which is adjacent to the transposon insert is then cloned using standard techniques. For instance, the host DNA adjacent to the transposon insert may be cloned as part of a library of DNA made from the genomic DNA of the selected mutant. This adjacent host DNA is then identified from the library using the transposon as a DNA probe. Alternatively, if the transposon used contains a suitable gene for antibiotic resistance, then the insertion mutant DNA can be digested with a restriction endonuclease which will be predicted not to cleave within this gene sequence or between its sequence and the host insertion point, followed by cloning of the fragments thus generated into a microorganism such as *E. coli* which can then be subjected to selection using the chosen antibiotic.

Sequencing of the DNA beyond the inserted transposon reveals the adjacent host sequences. The adjacent sequences can in turn be used as a hybridization probe to redone the undisrupted native host DNA using a non-mutant host library. The DNA thus isolated from the non-mutant is characterized and used to complement the APS deficient phenotype of the mutant. DNA which complements may contain either APS biosynthetic genes or genes which regulate all or part of the APS biosynthetic pathway. To be sure isolated sequences encode biosynthetic genes they can be transferred to a heterologous host which does not produce the APS and which is insensitive to the APS (such as *E. coli*). By transferring smaller and smaller pieces of the isolated DNA and the sequencing of the smallest effective piece, the APS genes can be identified. Alternatively, positively identified clones can be subjected to λ::Tn5 transposon mutagenesis using techniques well known in the art (e.g. de Bruijn & Lupski, Gene 27: 131–149 (1984)). Using this method a number of disruptive transposon insertions are introduced into the DNA shown to confer APS production to enable a delineation of the precise region/s of the DNA which are responsible for APS production. These latter steps are undertaken in a manner analogous to that described in example 1. In order to avoid the possibility of the isolated genes not being expressed in the heterologous host due to the non-functioning of their heterologous promoter, the isolated genes can be transferred to an expression vector where they will be fused to a promoter known to function in the heterologous host. In the case of *E. coli* an example of a suitable expression vector is pKK223 which utilizes the tac promoter. Similar suitable expression vectors also exist for other hosts such as yeast and are well known in the art. In general such fusions will be easy to undertake because of the operon-type organization of related genes in microorganisms and the likelihood that the biosynthetic enzymes required for APS biosynthesis will be encoded on a single transcript requiring only a single promoter fusion.

Example 4

Isolating Antipathogenic Biosynthetic Genes using Mutagenesis and Complementation A similar method to that described above involves the use of non-insertion mutagenesis techniques (such as chemical mutagenesis and radiation mutagenesis) together with complementation. The APS producing microorganism is subjected to non-insertion mutagenesis and mutants which lose the ability to produce the APS are selected for further analysis. A gene library is prepared from the parent APS-producing strain. One suitable approach would be the ligation of fragments of 20–30 kb into a vector such as pVK100 (Knauf et al. Plasmid 8: 45–54 (1982)) and then transformation into *E. coli* harboring the tra+ plasmid pRK2013 which would enable the transfer by triparental conjugation back to the selected APS-minus mutant (Ditta et al. Proc. Natl. Acad. Sci. USA 77: 7247–7351 (1980)). A further suitable approach would be the transfer back to the mutant of the gene library via electroporation. In each case subsequent selection is for APS production. Selected colonies are further characterized by the retransformation of APS-minus mutant with smaller fragments of the complementing DNA to identify the smallest successfully complementing fragment which is then subjected to sequence analysis. As with example 2, genes isolated by this procedure may be biosynthetic genes or genes which regulate the entire or part of the APS biosynthetic pathway. To be sure that the isolated sequences encode biosynthetic gene they can be transferred to a heterologous host which does not produce the APS and is insensitive to the APS (such as *E. coli*). These latter steps are undertaken in a manner analogous to that described in example 2.

Example 5

Isolating Antipathogenic Biosynthetic Genes by Exploiting Regulators which Control the Expression of the Biosynthetic Genes A further approach in the isolation of APS biosynthetic genes relies on the use of regulators which control the expression of these biosynthetic genes. A library of transposon insertion mutants is created in a strain of microorganism which lacks the regulator or has had the regulator gene disabled by conventional gene disruption techniques. The insertion transposon used carries a promoter-less reporter gene (e.g. lacZ). Once the insertion library has been made, a functional copy of the regulator gene is transferred to the library of cells (e.g. by conjugation or electroporation) and the plated cells are selected for expression of the reporter gene. Cells are assayed before and after transfer of the regulator gene. Colonies which express the reporter gene only in the presence of the regulator gene are insertions adjacent to the promoter of genes regulated by the regulator. Assuming the regulator is specific in its regulation for APS-biosynthetic genes, then the genes tagged by this procedure will be APS-biosynthetic genes. These genes can then be isolated and further characterized using the techniques described in example 2.

Example 6

Isolating Antipathogenic Biosynthetic Genes by Homology

Standard DNA techniques can be used for the isolation of novel antipathogenic biosynthetic genes by virtue of their homology to known genes. A DNA library of the microorganism of interest is made and then probed with radiolabelled DNA derived from the gene/s for APS biosynthesis from a different organism. The newly isolated genes are characterized and sequences and introduced into a heterologous microorganism or a mutant APS-minus strain of the native microorganisms to demonstrate their conferral of APS production.

C. Isolation and Characterization of Pyrrolnitrin Biosynthetic Genes

Pyrrolnitrin is a phenylpyrole compound having excellent antifungal activity that is produced by various strains of bacteria, especially those of the genus Pseudomonas such as *Pseudomonas fluorescens* and *Pseudomonas pyrrocinia,* but also for example by strains of Burkholdaria and Myxococcus. *P. fluorescens* strains which produce pyrrolnitrin have been shown to be effective biocontrol strains against Rhizoctonia and Pythium fungal pathogens (WO 94/01561). For example, *P. fluorescens* strain CGA267356 (described in WO 94/01561), which is hereinafter designated "MOCG134", is characterized extensively in the instant application. Thus, CGA267356 and MOCG134 are synonymous and both refer to the same *P. fluorescens* strain. Likewise, *P. fluorescens* strain "MOCG133", as described herein, is the same strain as CGA267355.

It is now well established that pyrrolnitrin is synthesized from the amino acid tryptophan. However, there has been some controversy in the relevant literature regarding the biosynthetic pathway for the synthesis of pyrrolnitrin. The group of H. Floss has proposed that ring rearrangement of the indole ring of tryptophan to form the phenylpyrrole structure of pyrrolnitrin occurs prior to the addition of the two chlorine atoms (Floss et al., Biochem. and Biophys. Res. Comm. 45: 781–787 (1971); Chang et al., J. Antibiot. 34: 555–566 (1981)). On the other hand, reports by the group of Lingens have suggested that the first step in pyrrolnitrin biosynthesis is the addition of one chlorine at the 7 position of tryptophan, followed by the ring reorganization, the addition of the second chlorine at the 3 position of pyrrolnitrin and oxidation of the amino group to a nitro group (Salcher and Lingens, J. Gen. Microbiol. 121: 465–471 (1980), incorporated herein by reference).

Examples in this section set forth the isolation and characterization of genetic loci from pyrrolnitrin-producing strains of Pseudomonas, Burkholdaria, and Myxococcus that contain four open reading frames (ORFs). These four ORFs correspond to four genes necessary for the synthesis of pyrrolnitrin, which have been designated prnA, prnB, prnC, and prnD. Furthermore, the examples below set forth the construction of independent deletion mutants in each of the four prn genes, as well as a mutant in which the entire prn gene region was deleted. In each case, a DNA fragment within the coding sequence of each prn gene was removed and replaced with a kanamycin resistance gene to facilitate replacement of the wild-type gene with the deleted gene in *P. fluorescens* by homologous recombination. As expected, none of these prn deletion mutants were capable of synthesizing pyrrolnitrin. In addition, each of the prn genes, including the native ribosome binding site and the entire coding sequence, was amplified by PCR and isolated separately. The DNA sequence of each gene was determined in order to verify that no PCR induced errors were present, and the genes were juxtaposed with the tac promoter to cause expression of the genes in Pseudomonas. (The tac promoter is derived from *E. coli* and is expressed constitutively and strongly in Pseudomonas.) Each of the tac/prn gene constructs was cloned into a broad host range plasmid for mobilization and maintenance in Pseudomonas.

The above-described prn deletion mutants of *P. fluorescens,* the tac/prn gene constructs, and the wild-type *P. fluorescens* strain were used to elucidate the role of each protein encoded by the prn genes in the biosynthesis of pyrrolnitrin. (See Example 12A.) The evidence demonstrating the function of the proteins encoded by each of the genes is summarized as follows:

prnA

1. The prnB deletion mutant (ΔORF2 aka prnBΔ) was shown to accumulate 7-chlorotryptophan (CT).
2. The prnA deletion mutant (ΔORF1 aka prnAΔ) was able to produce pyrrolnitrin when it was fed 7-chlorotryptophan or aminopyrrolnitrin (AP).
3. When the tac/prnA gene was expressed in the prn deletion mutant lacking all prn genes (prnΔ aka ΔORF1–4), CT was produced.

These results indicate that the prnA protein product is required to catalyze the chlorination of tryptophan to form CT.

prnB

1. The prnC deletion mutant (ΔORF3 aka prnCΔ) was shown to accumulate monodechloroaminopyrrolnitrin (MCA).
2. The prnB deletion mutant (prnBΔ) was able to produce pyrrolnitrin when it was fed MCA or AP, but not when it was fed CT.
3. When the tac/prnB was expressed in the prnΔ deletion mutant, MCA was produced when CT was supplied in the medium.

These results indicate that the prnB protein product is required to catalyze conversion of CT to MCA, including the ring rearrangement and decarboxylation reactions.

prnC

1. The prnD deletion mutant (ΔORF4 aka prnDΔ) was shown to accumulate AP.
2. The prnC deletion mutant was able to produce pyrrolnitrin when it was fed AP, but not when fed other intermediates.
3. When the tac/prnC was expressed in the prnΔ deletion mutant, AP was produced when MCA was supplied in the medium.

These results indicate that the prnC protein product is required to catalyze the conversion of MCA to AP, including the addition of a chlorine atom at the 3 position of MCA.

prnD

1. The prnD deletion mutant (prnDΔ) produced high amounts of AP, but no pyrrolnitrin.
2. The prnD deletion mutant was unable to produce pyrrolnitrin when it was fed AP.
3. When the tac/prnD was expressed in the prnΔ deletion mutant, pyrrolnitrin was produced when AP was supplied in the medium.

These results indicate that the prnD protein product is required to catalyze the final step in pyrrolnitrin biosynthesis, the conversion of AP to pyrrolnitrin by the oxidation of the amino group of AP to a nitro group.

In summary, the protein products of the prnA, prnB, prnC, and prnD genes, are necessary to catalyze steps 1, 2, 3, and 4, respectively, in the biosynthetic pathway of pyrrolnitrin (Salcher and Lingens, 1980). In addition, the functions assigned to the four prn genes account for all of the enzymatic steps expected for the biosynthesis of pyrrolnitrin. This indicates that the four prn genes comprise the entire pyrrolnitrin biosynthetic operon. Additional support for this comes from the fact that introduction of the prn gene cluster containing the four prn genes into other bacterial strains resulted in the production of pyrrolnitrin by these strains, which beforehand were not known to be capable of pyrrolnitrin synthesis.

In addition to isolating and characterizing pyrrolnitrin biosynthetic genes from *Pseudomonas fluorescens,* homologous pyrrolnitrin biosynthetic genes were cloned from other bacteria, including species substantially divergent from *Ps. fluorescens.* Example 12C below sets forth the isolation of prn genes from *Pseudomonas pyrrocinia, Burkholdaria cepacia,* and *Myxococcus fulvus.* Introduction of any these prn biosynthetic operons into a mutant strain of *Ps. fluorescens* in which the native prn genes had been deleted restored the ability to produce pyrrolnitrin to the mutant strain.

Example 7

Use of the gafA Regulator Gene for the Isolation of Pyrrolnitrin Biosynthetic Genes from Pseudomonas The gene cluster encoding pyrrolnitrin biosynthetic enzymes was isolated using the basic principle described in example 5 above. The regulator gene used in this isolation procedure was the gafA gene from *Pseudomonas fluorescens* and is known to be part of a two-component regulatory system controlling certain biocontrol genes in Pseudomonas. The gafA gene is described in detail in co-assigned U.S. Pat. Nos. 5,670,350 and 5,710,031, which are hereby incorporated by reference in their entireties and in the published application WO 94/01561. gafA is further described in Gaffney et al. (Molecular Plant-Microbe Interactions 7(4): 455–463 (1994), hereby incorporated in its entirety by reference) where it is referred to as "ORF5". The gafA gene has been shown to regulate pyrrolnitrin biosynthesis, chitinase, gelatinase and cyanide production. Strains which lack the gafA gene or which express the gene at low levels (and in consequence gafA-regulated genes also at low levels) are suitable for use in this isolation technique.

Example 8

Isolation of Pyrrolnitrin Biosynthesis Genes in Pseudomonas

The transfer of the gafA gene from MOCG 134 (CGA267356) to closely related non-pyrrolnitrin producing wild-type strains of *Pseudomonas fluorescens* results in the ability of these strains to produce pyrrolnitrin. (Hill et al. Applied And Environmental Microbiology 60 78–85 (1994)); see also, Gaffney et al., MPMI (1994)). This indicates that these closely related strains have the structural genes needed for pyrrolnitrin biosynthesis but are unable to produce the compound without activation from the gafA gene. One such closely related strain, MOCG133 (CGA267355), was used for the identification of the pyrrolnitrin biosynthesis genes. The transposon TnCIB116 (Lam, New Directions in Biological Control: Alternatives for Suppressing Agricultural Pests and Diseases, pp. 767–778, Alan R. Liss, Inc. (1990)) was used to mutagenize MOCG133. This transposon, a Tn5 derivative, encodes kanamycin resistance and contains a promoterless lacZ reporter gene near one end. The transposon was introduced into MOCG133 by conjugation, using the plasmid vector pCIB116 (Lam, New Directions in Biological Control: Alternatives for Suppressing Agricultural Pests and Diseases, pp. 767–778, Alan R. Liss, Inc. (1990)) which can be mobilized into MOCG133, but cannot replicate in that organism. Most, if not all, of the kanamycin resistant transconjugants were therefore the result of transposition of TnCIB116 into different sites in the MOCG133 genome. When the transposon integrates into the bacterial chromosome behind an active promoter the lacZ reporter gene is activated. Such gene activation can be monitored visually by using the substrate X-gal, which releases an insoluble blue product upon cleavage by the lacZ gene product. Kanamycin resistant transconjugants were collected and arrayed on master plates which were then replica plated onto lawns of *E. coli* strain S17-1 (Simon et al., Bio/technology 1:784–791 (1983)) transformed with a plasmid carrying the wide host range RK2 origin of replication, a gene for tetracycline selection and the gafA gene. *E. coli* strain S17-1 contains chromosomally integrated tra genes for conjugal transfer of plasmids. Thus, replica plating of insertion transposon mutants onto a lawn of the S17-1/gafA *E. coli* results in the transfer to the insertion transposon mutants of the gafA-carrying plasmid and enables the activity of the lacZ gene to be assayed in the presence of the gafA regulator (expression of the host gafA is insufficient to cause lacZ expression, and introduction of gafA on a multicopy plasmid is more effective). Insertion mutants which had a "blue" phenotype (i.e. lacZ activity) only in the presence of gafA were identified. In these mutants, the transposon had integrated within genes whose expression were regulated by gafA. These mutants (with introduced gafA) were assayed for their ability to produce cyanide, chitinase, and pyrrolnitrin (as described in Gaffney et al., MPMI (1994))—activities known to be regulated by gafA (Gaffney et al., MPMI (1994)). One mutant did not produce pyrrolnitrin but did produce cyanide and chitinase, indicating that the transposon had inserted in a genetic region involved only in pyrrolnitrin biosynthesis. DNA sequences flanking one end of the transposon were cloned by digesting chromosomal DNA isolated from the selected insertion mutant with XhoI, ligating the fragments derived from this digestion into the XhoI site of pSP72 (Promega, cat. #P2191) and selecting the *E. coli* transformed with the products of this ligation on kanamycin. The unique XhoI site within the transposon cleaves beyond the gene for kanamycin resistance and enabled the flanking region derived from the parent MOCG 133 strain to be concurrently isolated on the same XhoI fragment. In fact the XhoI site of the flanking sequence was found to be located approximately 1 kb away from the end on the transposon. A subfragment of the isolated XhoI fragment derived exclusively from the ~1 kb flanking sequence was then used to isolate the native (i.e. non-disrupted) gene region from a cosmid library of strain MOCG 134. The cosmid library was made from partially Sau3A digested MOCG 134 DNA, size selected for fragments of between 30 and 40 kb and cloned into the unique BamHI site of the cosmid vector pCIB119 which is a derivative of c2XB (Bates & Swift, Gene 26: 137–146 (1983)) and pRK290 (Ditta et al. Proc. Natl. Acad. Sci. USA 77: 7247–7351 (1980)). pCIB119 is a double-cos site cosmid vector which has the wide host range RK2 origin of replication and can therefore replicate in Pseudomonas as well as *E. coli.* Several clones were isolated from the MOCG 134 cosmid clone library using the ~1 kb flanking sequence as a hybridization probe. Of these one clone was found to restore pyrrolnitrin production to the transposon insertion mutant which had lost its ability to produce pyrrolnitrin. This clone had an insertion of ~32 kb and was designated pCIB169. A viable culture of *E. coli* DH5α containing cosmid clone pCIB169 was deposited at the Agricultural Research Culture Collection (NRRL), 1815 N. University Street, Peoria, Ill. 61604 on May 20, 1994, and assigned accession number NRRL B-21256.

Example 9

Mapping and Tn5 Mutagenesis of pCIB169

The 32 kb insert of clone pCIB169 was subcloned into pCIB189 in *E. coli* HB101, a derivative of pBR322 which contains a unique NotI cloning site. A convenient NotI site within the 32 kb insert as well as the presence of NotI sites flanking the BamHI cloning site of the parent cosmid vector pCIB119 allowed the subcloning of fragments of 14 and 18 kb into pCIB189. These clones were both mapped by restriction digestion. λ Tn5 transposon mutagenesis was carried out on both the 14 and 18 kb subclones using techniques well known in the art (e.g. de Bruijn & Lupski, Gene 27: 131–149 (1984). λ Tn5 phage conferring kanamycin resistance was used to transfect both the 14 and the 18 kb subclones described above. λ Tn5 transfections were done at a multiplicity of infection of 0.1 with subsequent selection on kanamycin. Following mutagenesis plasmid DNA was prepared and retransformed into E. coli HB101 with kanamycin selection to enable the isolation of plasmid clones carrying Tn5 insertions. A total of 30 independent Tn5 insertions were mapped along the length of the 32 kb insert. Each of these insertions was crossed into MOCG 134 via double homologous recombination and verified by Southern hybridization using the Tn5 sequence and the pCIB189 vector as hybridization probes to demonstrate the occurrence of double homologous recombination i.e. the replacement of the wild-type MOCG 134 gene with the Tn5-insertion gene. Pyrrolnitrin assays were performed on each of the insertions that were crossed into MOCG 134 and a genetic region of approximately 6 kb was identified to be involved in pyrrolnitrin production. This region was found to be centrally located in pCIB169 and was easily subcloned as an XbaI/NotI fragment into pBluescript II KS (Promega). The XbaI/NotI subclone was designated pPRN5.9X/N.

Example 10

Identification of Open Reading Frames in the Isolated Genetic Region

The genetic region involved in pyrrolnitrin production was subcloned into six fragments for sequencing in the vector pBluescript II KS. These fragments spanned the ~6 kb XbaI/NotI fragment described above and extended from the EcoRI site on the left side to the rightmost HindIII site. The sequence of the inserts of clones pPRN1.77E, pPRN1.01E, pPRN1.24E, pPRN2.18E/N, pPRN0.8H/N, and pPRN2.7H was determined using the Taq DyeDeoxy Terminator Cycle Sequencing Kit supplied by Applied Biosystems, Inc., Foster City, Calif. following the protocol supplied by the manufacturer. Sequencing reactions were run on a Applied Biosystems 373A Automated DNA Sequencer and the raw DNA sequence was assembled and edited using the "INHERIT" software package also from Applied Biosystems, Inc. A contiguous DNA sequence of 7 kb was obtained corresponding to the EcoRI/HindIII fragment.

DNA sequence analysis was performed on the contiguous 7 kb sequence using the GCG software package from Genetics Computer Group, Inc. Madison, Wis. The pattern recognition program "FRAMES" was used to search for open reading frames (ORFs) in all six translation frames of the DNA sequence. Four open reading frames were identified using this program and the codon frequency table from ORF2 of the gafA gene region which was previously published (WO 94/05793). These ORFs lie entirely within the ~6 kb XbaI/NotI fragment referred to in Example 9 and are contained within the sequence disclosed as SEQ ID NO:1. By comparing the codon frequency usage table from MOCG134 DNA sequence of the gafA region to these four open reading frames, very few rare codons were used indicating that codon usage was similar in both of these gene regions. This strongly suggested that the four open reading frames were biologically significant to the production of pyrrolnitrin. At a 3' position to the fourth reading frame numerous ρ-independent stem loop structures were found suggesting a region where transcription could be stopped. It was thus apparent that all four ORFs were translated from a single transcript. Sequence data obtained for the regions beyond the four identified ORFs revealed a fifth open reading frame which was subsequently determined to not be involved in pyrrolnitrin synthesis based on E. coli expression studies.

Example 11

Expression of Pyrrolnitrin Biosynthetic Genes in E. coli

To determine if the four prn genes comprised the entire pyrrolnitrin biosynthetic operon, these genes were transferred into E. coli which was then assayed for pyrrolnitrin production. The expression vector pKK223-3 was used to over-express the isolated operon in E. coli. (Brosius & Holy, Proc. Natl. Acad. Sci. USA 81: 6929 (1984)). pKK223-3 contains a strong tac promoter which, in the appropriate host, is regulated by the lac repressor and induced by the addition of isopropyl-β-D-thiogalactoside (IPTG) to the bacterial growth medium. This vector was modified by the addition of further useful restriction sites to the existing multiple cloning site to facilitate the cloning of the ~6 kb XbaI/NotI fragment (see example 7) and a 10 kb XbaI/KpnI fragment for expression studies. In each case the isolated fragment was under the control of the E. coli tac promoter (with IPTG induction), but was cloned in a transcriptional fusion so that the ribosome binding site used would be that derived from Pseudomonas. Each of these clones was transformed into E. coli XL1-blue host cells and induced with 2.5 mM IPTG before being assayed for pyrrolnitrin by thin layer chromatography. Cultures were grown for 24 h after IPTG induction in 10 ml L broth at 37° C. with rapid shaking, then extracted with an equal volume of ethyl acetate. The organic phase was recovered, allowed to evaporated under vacuum and the residue dissolved in 20 µl of methanol. Silica gel thin layer chromatography (TLC) plates were spotted with 10 µl of extract and run with toluene as the mobile phase. The plates were allowed to dry and sprayed with van Urk's reagent to visualize. Urk's reagent comprises 1 g p-Dimethylaminobenzaldehyde in 50 ml 36% HCl and 50 ml 95% ethanol. Under these conditions pyrrolnitrin appears as a purple spot on the TLC plate. This assay confirmed the presence of pyrrolnitrin in both of the expression constructs. HPLC and mass spectrometry analysis further confirmed the presence of pyrrolnitrin in both of the extracts. HPLC analysis can be undertaken directly after redissolving in methanol (in this case the sample is redissolved in 55% methanol) using a Hewlett Packard Hypersil ODS column (5 µM) of dimensions 100×2.1 mm. Pyrrolnitrin elutes after about 14 min.

Example 12

Construction of Pyrrolnitrin Gene Deletion Mutants

To further demonstrate the involvement of the 4 ORFs in pyrrolnitrin biosynthesis, independent deletions were created in each ORF and transferred back into Pseudomonas fluorescens strain MOCG134 by homologous recombination to create deletion mutants designated MOCG134ΔORF1, MOCG134ΔORF2, MOCG134ΔORF3, and MOCG134ΔORF4. In addition, a deletion mutant designated MOCG134ΔORF1–4 was created, whereupon all of the ORFs were deleted. Each ORF is identified within the sequence disclosed as SEQ ID NO:1.

ORFs 1–4 (SEQ ID NO:1)

A 16 kb KpnI fragment that includes the four ORFs from plasmid pCIB169 was cloned into a derivative of the plasmid vector pKK223-3 obtained from Pharmacia Biochemicals. The EcoRI, NotI, and BamHI sites in pKK223-3 were removed to create a modified pKK223-3 plasmid. The modified pKK223-3 containing the 16 kb KpnI fragment was digested with EcoRI and NotI to remove ORFs 1–4, including the 1.8, 1.0, and 1.2 kb EcoRI fragments and the 2.2 kb EcoRI/NotI fragment, and BamHI linkers were added to the EcoRI and NotI ends prior to religation, thus leaving a BamHI restriction site at the location of the deleted fragments. The NPTII gene was cloned on a BamHI fragment into the unique BamHI site in the position of the deleted fragments. The new plasmid, designated pKK (ΔORF1–4), was verified by restriction enzyme digestion and agarose gel electrophoresis.

ORF1 (prnA)

The plasmid pPRN1.77E was digested with MluI to liberate a 78 bp fragment internally from ORF1. The remaining 4.66 kb vector-containing fragment was recovered, religated with T4 DNA ligase, and transformed into the E. coli host strain DH5α. This new plasmid was linearized with MluI and the Klenow large fragment of DNA polymerase I was used to create blunt ends (Maniatis et al. Molecular Cloning, Cold Spring Harbor Laboroatory (1982)). The neomycin phosphotransferase II (NPTII) gene cassette from pUC4K (Pharmacia) was ligated into the plasmid by blunt end ligation and the new construct, designated pBS (ΔORF1), was transformed into DH5α. The construct contained a 78 bp deletion of ORF1 at which position the NPTII gene conferring kanamycin resistance had been inserted. The insert of this plasmid (i.e. ORF1 with NPTII insertion) was then excised from the pBluescript II KS vector with EcoRI, ligated into the EcoRI site of the vector pBR322 and transformed into the E. coli host strain HB101. The new plasmid was verified by restriction enzyme digestion and designated pBR322(ΔORF1).

ORF2 (prnB)

The plasmids pPRN1.24E and pPRN1.01E containing contiguous EcoRI fragments spanning ORF2 were double digested with EcoRI and XhoI. The 1.09 kb fragment from pPRN1.24E and the 0.69 Kb fragment from pPRN1.01E were recovered and ligated together into the EcoRI site of pBR322. The resulting plasmid was transformed into the host strain DH5α and the construct was verified by restriction enzyme digestion and electrophoresis. The plasmid was then linearized with XhoI, the NPTII gene cassette from pUC4K was inserted, and the new construct, designated pBR(ΔORF2), was transformed into HB101. The construct was verified by restriction digestions and agarose gel electrophoresis and contains NPTII within a 472 bp deletion of the ORF2 gene.

ORF3 (prnC)

The plasmid pPRN2.56Sph was digested with PstI to liberate a 350 bp fragment. The remaining 2.22 kb vector-containing fragment was recovered and the NPTII gene cassette from pUC4K was ligated into the PstI site. This intermediate plasmid, designated pUC(ΔORF3), was transformed into DH5α and verified by restriction digestion and agarose gel electrophoresis. The gene deletion construct was excised from pUC with SphI and ligated into the SphI site of pBR322. The new plasmid, designated pBR(ΔORF3), was verified by restriction enzyme digestion and agarose gel electrophoresis. This plasmid contains the NPTII gene within a 350 bp deletion of the ORF3 gene.

ORF4 (prnD)

The plasmid pPRN2.18E/N was digested with AatII to liberate 156 bp fragment. The remaining 2.0 kb vector-containing fragment was recovered, religated, transformed into DH5α, and verified by restriction enzyme digestion and electrophoresis. The new plasmid was linearized with AatII and T4 DNA polymerase was used to create blunt ends. The NPTII gene cassette was ligated into the plasmid by blunt-end ligation and the new construct, designated pBS (ΔORF4), was transformed into DH5α. The insert was excised from the pBluescript II KS vector with EcoRI, ligated into the EcoRI site of the vector pBR322 and transformed into the E. coli host strain HB101. The identity of the new plasmid, designated pBR (ΔORF4), was verified by restriction enzyme digestion and agarose gel electrophoresis. This plasmid contains the NPTII gene within a 264 bp deletion of the ORF4 gene.

Km$^R$ Control

To control for possible effects of the kanamycin resistance marker, the NPTII gene cassette from pUC4K was inserted upstream of the pyrrolnitrin gene region. The plasmid pPRN2.5S (a subclone of pPRN7.2E) was linearized with PstI and the NPTII cassette was ligated into the PstI site. This intermediate plasmid was transformed into DH5α and verified by restriction digestions and agarose gel electrophoresis. The gene insertion construct was excised from pUC with SphI and ligated into the SphI site of pBR322. The new plasmid, designated pBR(2.5SphIKm$^R$), was verified by restriction enzyme digestion and agarose gel electrophoresis. It contains the NPTII region inserted upstream of the pyrrolnitrin gene region.

Each of the gene deletion constructs was mobilized into MOCG134 by triparental mating using the helper plasmid pRK2013 in E. coli HB101. Gene replacement mutants were selected by plating on Pseudomonas Minimal Medium (PMM) supplemented with 50 mg/ml kanamycin and counterselected on PMM supplemented with 30 mg/ml tetracycline. Putative perfect replacement mutants were verified by Southern hybridization by probing EcoRI digested DNA with pPRN18Not, pBR322 and an NPTII cassette obtained from pUC4K (Pharmacia 1994 catalog no. 27-4958-01). Verification of perfect replacement was apparent by lack of hybridization to pBR322, hybridization of pPRN18Not to an appropriately size-shifted EcoRI fragment (reflecting deletion and insertion of NPTII), hybridization of the NPTII probe to the shifted band, and the disappearance of a band corresponding a deleted fragment.

After verification, deletion mutants were tested for production of pyrrolnitrin, 2-hexyl-5-propyl-resorcinol, cyanide, and chitinase production. A deletion in any one of the ORFs (MOCG134ΔORF1, MOCG134ΔORF2, MOCG134ΔORF3, or MOCG134ΔORF4) or of all ORFs (MOCG134ΔORF1–4), abolished pyrrolnitrin production, but did not affect production of the other substances. The presence of the NPTII gene cassette in the Km$^R$ control had no effect on the production of pyrolnitrin, 2-hexyl-5-propyl-resorcinol, cyanide or chitinase. These experiments demonstrated the requirement of each of the four ORFs for pyrrolnitrin production.

Example 12A

Identification of Translation Initiation Sites of ORFs 1–4

Initially, the four ORFs identified in the analysis of the nucleotide sequence of the prn gene region (SEQ ID NO:1)

represented the largest possible coding regions starting with ATG translation initiation codons. However, examination of the deduced amino acid sequence of these ORFs revealed the presence of alternative, in-frame ATG methionine translation initiation sites in all of the ORFs. In order to identify the minimum functional coding region for each ORF, the potential coding regions beginning with each of the possible ATG initiation codons for each of the ORFs, including the region immediately upstream of the ATG start codon that would contain the associated ribosome binding site, were amplified by PCR and isolated. The isolated coding regions were subsequently fused to a tac promoter lacking an indigenous ribosome binding site in order to provide constitutive expression in Pseudomonas and were cloned into the mobilizible, broad host plasmid vector pRK290. The resulting plasmids containing the tac promoter/ORF fusions were transferred by triparental mating into the corresponding prn⁻ MOCG134ΔORF deletion mutant. Functional complementation of the deletion mutations was determined by assessing each complemented mutant for its ability to produce pyrrolnitrin (see table below).

Examination of the ORF1 coding region revealed the presence of two additional in-frame ATG methionine codons located in the N-terminal portion of the deduced amino acid sequence of ORF1. Each of the three potential ORF1 coding sequences was amplified, isolated and fused to the tac promoter as described. After introduction of the plasmids containing the three different versions of ORF1 (ORF1-A, ORF1-B, and ORF1-C) into the MOCG134ΔORF1 mutant, it was determined that ORF1-A and ORF1-B complemented the prn⁻ phenotype of the MOCG134ΔORF1 mutant, while ORF1-C did not. Therefore, ORF1-B is the shortest functional ORF1 coding region and it is the only potential ORF1 coding region of the three that is preceded by a typical ribosome binding site. Based on these results, it can be determined that ORF1-B represents the true coding sequence of this gene.

In the case of ORF2, there are two potential in-frame ATG translation initiation codons and DNA fragments beginning with each were constructed (ORF2-C and -D), but neither was capable of complementing the prn⁻ phenotype of mutant MOCG134ΔORF2. Further examination of the region upstream of the ORF2 coding sequence revealed the presence of two in-frame GTG codons that could serve as translation initiation codons. The first GTG codon is preceded by a typical ribosome binding site whereas the second such codon, as well as the shorter coding sequences that have ATG initiation codons, lack good ribosome binding sites. ORF2 fragments incorporating the GTG translation start codons were constructed in the manner described above and each was introduced into mutant MOCG134ΔORF2. The longer version of ORF2, ORF2-A, with a GTG start codon was shown to complement the prn⁻ phenotype of mutant MOCG134ΔORF2 while the shorter fragment, ORF2-B, did not. These results indicate that the functional ORF2 coding region begins with the first GTG translation start codon. The GTG translation initiation codon of ORF2 overlaps one base with the TAG translation stop codon of ORF1, indicating translational coupling of the two genes.

Three different potential ORF3 genes were tested in the same manner and only the longest, ORF3-A, which contains a good ribosome binding site upstream of the ATG start codon, was able to complement mutant MOCG134ΔORF3. A similar result was demonstrated for ORF4 as only the largest of three possible ORFs, ORF4-A, complemented the prn⁻ phenotype of mutant MOCG134ΔORF4.

These results indicate that ORF1 includes 1617 nucleotides that encode a protein having 538 amino acids (SEQ ID NO:2) with a size of 61,075 daltons. ORF2 includes 1086 nucleotides that encode a protein consisting of 361 amino acids (SEQ ID NO:3) with a size of 39,920 daltons. ORF3 includes 1704 nucleotides that encode a protein with 567 amino acids (SEQ ID NO:4) and a size of 65,037 daltons. Finally, ORF4 includes 1092 nucleotides that encode a protein with 363 amino acids (SEQ ID NO:5) and a size of 40,650 daltons.

Characteristics of DNA fragments representing potential coding sequences of the four ORFs that were used to identify translation initiation sites of pyrrolnitrin genes.

| Fragment | Start of amplified fragment[a] | Putative start codon[b] | Stop codon[c] | End of amplified segment | Amino acids in the encoded protein | Pyrrolnitrin production[d] |
|---|---|---|---|---|---|---|
| ORF1-A | 294 | 357 | 2039 | 2056 | 560 | + |
| OFR1-B | 396 | 423 | 2039 | 2056 | 538 | + |
| OFR1-C | 438 | 477 | 2039 | 2056 | 520 | − |
| ORF2-A | 2026 | 2039 | 3124 | 3167 | 361 | + |
| OFR2-B | 2145 | 2162 | 3124 | 3167 | 320 | − |
| ORF2-C | 2215 | 2249 | 3124 | 3167 | 291 | − |
| ORF2-D | 2440 | 2480 | 3124 | 3167 | 214 | − |
| ORF3-A | 3131 | 3167 | 4870 | 4905 | 567 | + |
| ORF3-B | 3208 | 3236 | 4870 | 4905 | 544 | − |
| ORF3-C | 3330 | 3356 | 4870 | 4905 | 504 | − |
| ORF4-A | 4852 | 4895 | 5986 | 6123 | 363 | + |
| ORF4-B | 4868 | 4991 | 5986 | 6123 | 331 | − |
| ORF4-C | 5015 | 5087 | 5986 | 6123 | 299 | − |

[a]All position numbers refer to the sequence of the pyrrolnitrin gene cluster shown in SEQ ID NO: 1
[b]The first base of the putative start codon
[c]The last base of the stop codon
[d]Determined by TLC after introduction into the corresponding MOCG134 deletion mutant Example 12B Function of the Pyrrolnitrin Biosynthesis Enzymes In order to study the biological function of the proteins encoded by ORFs 1–4, especially in relation to the enzymatic steps hypothesized to be involved in pyrrolnitrin synthesis (Salcher and Lingens, 1980), experiments were conducted using the ORF deletion mutants of *P. fluorescens* strain MOCG134 described in Example 12 and the individual ORF coding sequences expressed from the *E. coli* tac promoter in the broad host range plasmid pRK290. The latter were constructed by amplifying each coding sequence for the individual ORFs by polymerase chain reaction (PCR) using specific primers for each ORF. A DNA fragment containing the tac promoter sequence and a ribosome binding site was cloned with the fragments containing the ORF coding sequences such that the promoter was properly juxtaposed with the coding sequence to cause expression of the ORF. The DNA sequence of each tac/ORF gene construction was determined to insure that no sequence errors caused by PCR were incorporated into the amplified ORF fragments. Each tac/ORF gene construction was cloned into the plasmid pRK290 and the plasmids containing ORF1, ORF2, ORF3, and ORF4 were designated pRK-ORF1, pRK-ORF2, pRK-ORF3, and pRK-ORF4, respectively.

Function of Protein Encoded by ORF1 (prnA)

The *P. fluorescens* MOCG134 mutant containing a chromosomal deletion internal to ORF2 (MOCG134ΔORF2) was demonstrated to produce 7-chlorotryptophan but none of the other intermediates in the biosynthetic pathway of pyrrolnitrin. The corresponding ORF1 deletion mutant, MOCG134ΔORF1, was able to produce pyrrolnitrin if it was fed 7-chlorotryptophan or aminopyrrolnitrin. Furthermore, when the pRK-ORF1 plasmid containing the tac/ORF1 fragment was introduced into mutant MOCG134ΔORF1–4, it was demonstrated to produce 7-chlorotryptophan. These data demonstrate that the protein encoded by ORF1 (prnA) is required to catalyze the chlorination of D- and L-tryptophan to form 7-chlorotryptophan. It has been determined that NADH is required as a co-substrate for activity of the ORF1 protein and, unlike all previously described halogenases, it does not require hydrogen peroxide for activity. Furthermore, the coding sequence of ORF1 has no similarity to the coding sequences of known chloroperoxidase genes or any other genes.

Function of Protein Encoded by ORF2 (prnB)

The mutant MOCG134ΔORF3, lacking a functional ORF3, was demonstrated to produce monodechloroaminopyrrolnitrin, but not aminopyrrolnitrin or pyrrolnitrin. Mutant MOCG134ΔORF2 was capable of pyrrolnitrin synthesis if fed monodechloroaminopyrrolnitrin or aminopyrrolnitrin, but was unable to produce pyrrolnitrin if fed 7-chlorotryptophan. MOCG134ΔORF1–4 containing pRK-ORF2 was able to convert 7-chlorotryptophan to monodechloroaminopyrrolnitrin, while the mutant without a plasmid was not. Furthermore, MOCG134ΔORF1–4 containing ORF1 and ORF2 operatively linked to the tac promoter on plasmid pRK290 produced monodechloroaminopyrrolnitrin but did not produce aminopyrrolnitrin. These data demonstrate that the protein product of ORF2 (prnB) is required to catalyze the rearrangement of the indole ring of 7-chlorotryptophan to a phenylpyrrole and the decarboxylation involved in the transformation of 7-chlorotryptophan to monodechloroaminopyrrolnitrin.

Function of Protein Encoded by ORF3 (prnC)

Mutant MOCG134ΔORF4 was demonstrated to produce aminopyrrolnitrin and mutant MOCG134ΔORF3 produced monodechloroaminopyrrolnitrin, but not aminopyrrolnitrin. Mutant MOCG134ΔORF3 was able to produce pyrrolnitrin if it was fed aminopyrrolnitrin, but not when fed monodechloroaminopyrrolnitrin. MOCG134ΔORF1–4 containing pRK-ORF3 was able to convert monodechloroaminopyrrolnitrin to aminopyrrolnitrin, but MOCG134ΔORF1–4 lacking this plasmid was unable to catalyze this reaction. These data demonstrate that the protein encoded by ORF3 (prnC) is required to catalyze the chlorination of monodechloroaminopyrrolnitrin at carbon 3 to form aminopyrroinitrin. Like the protein encoded by ORF1, the ORF3 protein is a halogenase and it was demonstrated to require NADH as a co-substrate. Also, like the ORF1 protein and unlike other previously described halogenases, the ORF3 protein does not require hydrogen peroxide for activity. A recent report demonstrates that the haloperoxidases described previously have no biological role in the synthesis of pyrrolnitrin (Kirner et al., (1996) Microbiol. 142: 2129–2135).

Function of Protein Encoded by ORF4 (prnD)

Mutant MOCG134ΔORF4 was shown to produce aminopyrrolnitrin, but not pyrrolnitrin. This mutant was unable to produce pyrrolnitrin when fed aminopyrrolnitrin. The mutant MOCG134ΔORF1–4 containing plasmid pRK-ORF4 was able to produce pyrrolnitrin if fed aminopyrrolnitrin, while the mutant lacking this plasmid was not. These data indicate that the protein encoded by ORF4 (prnD) is required to catalyze the oxidation of the amino group of aminopyrrolnitrin to a nitro group to form pyrrolnitrin.

Example 12C

Isolation of Pyrrolnitrin Biosynthetic Genes in Other Microorganisms

As set forth below in this example, the prn biosynthetic operon from *Pseudomonas fluorescens* strain MOCG134 was used to isolate homologous pyrrolnitrin biosynthetic genes from other pyrrolnitrin-producing bacteria. Probes were produced by isolating DNA fragments containing the four prn genes from MOCG134 and labeling the fragments with radioactive [$^{32}$P]-dCTP using an Oligolabeling kit from Pharmacia. Two different fragments were used: the 5.9 kb XbaI to NotI fragment from pPRN5.8X/N (bases 320 to 6190 in SEQ ID NO:1) and the 5.7 kb ApaI fragment from pPRN5.8X/N (bases 499 to 6078 in SEQ ID NO:1).

Hybridizations of the radioactive probes and subsequent washings were carried out as described by Church and Gilbert (Proc. Natl. Acad. Sci. USA, 81:1991–1995 (1984)). All hybridizations and washings were carried out under high stringency conditions (65° C.) except where noted otherwise. If desired, hybridization may also be carried out under the following conditions: hybridization at 7% sodium dodecyl sulfate (SDS), 0.5 M NaPO$_4$ pH 7.0, 1 mM EDTA at 50° C.; wash with 2×SSC, 1% SDS, at 50° C.

(1) Isolation of Pyrrolnitrin Biosynthetic Genes from *Pseudomonas pyrrocinia*

In 1964 Arima et al. first reported the isolation and characterization of pyrrolnitrin from Pseudomonas (Arima et al., Agr. Biol. Chem., 28:575–576 (1964)). The strain was named *Pseudomonas pyrrocinia* in relation to its production of pyrrolnitrin (Imanaka et al., J. Antibiotics ser. A, 28:205–206 (1965)). We obtained an isolate of *Pseudomonas pyrrocinia* from K. -H. van Pée (Microbiology Institute, University of Hohenheim, Germany) and prepared total DNA for use in the instant example. A second isolate of *Pseudomonas pyrrocinia* was obtained from the American Type Culture Collection (catalog number 15958, American Type Culture Collection, Rockville, Md.) and total DNA was prepared. The ATCC isolate was compared to the isolate obtained from K. -H. van Pée by Southern analysis and the two isolates were shown to be identical. A sample of the DNA prepared from the isolate of *Pseudomonas pyrrocinia* from K. -H. van Pée was digested with the restriction enzyme BamHI. The resulting fragments were separated by agarose gel electrophoresis and transferred to a nylon membrane. The membrane was hybridized with a prn gene probe and a single BamHI fragment from the *Ps. pyrrocinia* DNA that hybridized strongly was identified.

A second sample of *Ps. pyrrocinia* DNA was digested with BamHI and separated by agarose gel electrophoresis as described above. The portion of the gel corresponding to the hybridizing band was excised and the DNA was extracted. The extracted DNA was ligated with pBluescript II vector DNA (Stratagene Cloning Systems, La Jolla, Calif.) using T4 DNA ligase. The vector DNA had previously been digested with BamHI and treated with calf intestinal phosphatase. *E. coli* strain DH5α cells were transformed with the ligated DNA and plated on LB agar supplemented with 100 mg/ml ampicillin. Individual colonies were selected and inoculated onto fresh plates to produce a library of approximately 400 clones.

The colonies were grown overnight at 37° C. then transferred to Colony/Plaque Screen membranes (NEN Research Products, Boston, Mass.), lysed, and fixed according to the manufacturer's protocol. The membranes were hybridized with a prn gene probe and three colonies were identified which contained DNA that hybridized strongly. These colonies were used to inoculate broth cultures from which plasmid DNA was purified using a Wizard Miniprep DNA purification Kit (Promega Corp., Madison, Wis.). Samples of plasmid DNA from the clones and genomic DNA from *Ps. pyrrocinia* were digested with BamHI or EcoRI, separated by agarose gel electrophoresis and transferred to a nylon membrane. The membrane was hybridized with a prn gene probe. One clone, pPEH80, was selected which contained a BamHI DNA fragment that hybridized strongly to the probe and was identical in size to the hybridizing BamHI fragment from *Ps. pyrrocinia* genomic DNA. Restriction analysis indicated that this clone contains insert DNA of approximately 20 kb in length comprised of six internal EcoRI fragments and two BamHI - EcoRI fragments. Four of the EcoRI fragments hybridized strongly to the prn gene probe and were identical in size to hybridizing EcoRI fragments from *Ps. pyrrocinia* genomic DNA. These data demonstrate that pPEH80 contains a DNA region isolated from *Ps. pyrrocinia* that is highly homologous to the pyrrolnitrin gene region from MOCG134.

Each fragment from pPEH80 which hybridized to the prn gene probe was subcloned into pBluescript vector and the DNA sequence was determined using Taq DyeDeoxy Terminator Cycle Sequencing Kits and Dye Primer Cycle Sequencing Kits (Applied Biosystems, Inc., Foster City, Calif.). Sequencing reactions were run on an Applied Biosystems 373A Automated DNA Sequencer and the raw DNA sequence data were assembled and edited using Sequencher software (Gene Codes Corporation, Inc., Ann Arbor, Mich.). Orientations of the fragments within pPEH80 were verified by sequencing pPEH80 DNA across the EcoRI restriction sites. The consensus sequence for the prn gene region from *Ps. pyrrocinia* is shown in SEQ ID NO:23.

The consensus sequence of the pyrrolnitrin gene region from *Ps. pyrrocinia* (SEQ ID NO:23) was compared to the sequence of the pyrrolnitrin gene region from MOCG134 (SEQ ID NO:1). Four open reading frames (ORFs) were identified in the prn gene region from *Ps. pyrrocinia* (SEQ ID NO:23) which have very strong homology to ORFs 1–4 (prnA–D) in the pyrrolnitrin gene region of MOCG134 (SEQ ID NO:1). ORFs 1–4 from *Ps. pyrrocinia* also are arranged in the same order as ORFs 1–4 in MOCG134. The DNA sequences and predicted amino acid sequences of the four prn genes were compared between the two species using the Clustal alignment method in the MegAlign software package (DNA Star, Inc. Madison, Wis.). Results are shown in the table below. Overall, between the two species the nucleotide identity was >91% and the predicted amino acid identity was >86%.

Comparisons of the pyrrolnitrin gene sequences from *Ps fluorescens* strain MOCG134 and *Ps. pyrrocinia*. For each gene the coding regions were compared using the Clustal alignment method.

| Gene | Percent Identity | |
| --- | --- | --- |
| | Nucleotide | Amino Acid |
| prnA | 94.2 | 94.4 |
| prnB | 91.3 | 86.5 |
| prnC | 95.6 | 95.2 |
| prnD | 92.2 | 90.7 |

The 20 kb BamHI DNA fragment was excised from pPEH80 and was subcloned into the broad host range vector pRK290. The resulting plasmid was transferred to the *Pseudomonas fluorescens* strain MOCG134ΔORF1–4 (Example 12) by tri-parental mating as described in Example 12. The presence of the plasmid was confirmed by antibiotic resistance and by plasmid DNA extraction, restriction digest, and agarose gel electrophoresis. Pyrrolnitrin production was measure by extraction and TLC as described in Example 12. The presence of the plasmid restored the ability to produce pyrrolnitrin to the mutant strain. These results confirmed that the insert DNA in pPEH80 contains functional genes from *Ps. pyrrocinia* that comprise the entire pyrrolnitrin biosynthetic operon.

(2) Isolation of Pyrrolnitrin Biosynthetic Genes from *Burkholdaria cepacia*

An isolate of *Burkholdaria cepacia* strain LT-4-12W was obtained from W. J. Janisiewicz of the USDA-ARS Appalachian Fruit Research Station. This bacterium has been shown to produce pyrrolnitrin and the related phenylpyrrole antibiotic 2-chloro pyrrolnitrin (J. N. Roitman, N. E. Mahoney and W. J. Janisiewicz, Applied Microbiology and Biotechnology 34:381–386 (1990)). Strain LT-4-12W was previously known as *Pseudomonas cepacia*. At that time, the genus Pseudomonas consisted of phylogenetically unrelated groups of proteobacteria (Palleroni, N. J., "Present situation in the taxonomy of aerobic pseudomonads", pages 105–115 in Pseudomonads: Molecular Biology and Biotechnology, E. Galli et al. (eds.), American Society for Microbiology, Washington, D.C. (1992)). Recently, *Ps. cepacia* and eight related species were reclassified into the new genus Burkholdaria (G. J. Olsen et al., Journal of Bacteriology 176:1–6 (1994), T. Urakami et al., International Journal of Systematic Bacteriology 44:235–245 (1994)).

Genomic DNA was extracted from strain LT-4-12W and a sample of the DNA was digested with KpnI. The resulting fragments were separated by agarose gel electrophoresis and transferred to a nylon membrane. The membrane was hybridized with a prn gene probe as described above. A single KpnI fragment from the *B. cepacia* DNA which hybridized strongly was identified.

A second sample of *B. cepacia* DNA was digested with KpnI and separated by agarose gel electrophoresis as described above. The portion of the gel corresponding to the hybridizing band was excised and the DNA was extracted. The extracted DNA was ligated with pBluescript II vector DNA (Stratagene) using T4 DNA ligase. The vector DNA had previously been digested with KpnI and treated with calf intestinal phosphatase. *E. coli* strain DH5α cells were transformed with the ligated DNA and plated on LB agar supplemented with 100 mg/ml ampicillin. Individual colonies were selected and inoculated onto fresh plates to produce a library of 580 clones.

The colonies were grown overnight at 37° C. then transferred to Colony/Plaque Screen membranes, lysed and fixed according to the manufacturer's protocol. The membranes were hybridized with a prn gene probe as described above. Five colonies were selected which contained DNA that hybridized strongly to the probe. These colonies were used to inoculate broth cultures from which plasmid DNA was purified using a Wizard Miniprep DNA purification kit. Plasmid DNA from the clones and genomic DNA from *B. cepacia* was digested with KpnI, separated by agarose gel electrophoresis, transferred to a nylon membrane and hybridized with a prn gene probe. One clone, pPEH66, was selected which contains a KpnI DNA fragment of approximately 9.4 kb in length that hybridized strongly to the probe and was identical in size to the hybridizing KpnI fragment from *B. cepacia* genomic DNA.

Samples of pPEH66 plasmid DNA and *B. cepacia* genomic DNA were digested with KpnI, PstI, SacI, and SalI. The fragments were separated by agarose gel electrophoresis and transferred to a nylon membrane. The membrane was hybridized with a probe made from the pyrrolnitrin gene region from MOCG134 as described above. For each enzyme used, multiple internal DNA fragments were identified that hybridized strongly to the probe and that were identical in size to the corresponding hybridizing fragments from *B. cepacia* genomic DNA. These data demonstrate that pPEH66 contains a DNA region isolated from *B. cepacia* strain LT-4-12W that is highly homologous to the pyrrolnitrin genes from *Ps. fluorescens* strain MOCG134.

The 9.4 kb KpnI DNA fragment was excised from pPEH66 and was subcloned into the broad host range vector pRK290. The resulting plasmid was transferred to the Pseudomonas strain MOCG134ΔORF1–4 (Example 12) by tri-parental mating as described in Example 12. The presence of the plasmid was confirmed by antibiotic resistance and by plasmid DNA extraction, restriction digest, and agarose gel electrophoresis. Pyrrolnitrin production was measured by extraction and TLC as described in Example 12. The presence of the plasmid restored the ability to produce pyrrolnitrin to the mutant *Pseudomonas fluorescens* strain. These results confirmed that the insert DNA in pPEH66 contains functional genes from *B. cepacia* strain LT-4-12W that comprise the entire pyrrolnitrin biosynthetic operon.

The sequence of the DNA insert of pPEH66 was determined by using commonly known techniques. Raw sequence data were assembled and edited using Sequencher software (Gene Codes Corporation, Inc., Ann Arbor, Mich.). The prn genes from *B. cepacia* were identified by homology to the sequence of prnABCD from MOCG134. The consensus sequence for the DNA insert is shown in SEQ ID NO:28.

Four open reading frames (ORFs) were identified in the prn gene region from *B. cepacia* (SEQ ID NO:28) that have very strong homology to ORFs 1–4 (prnA–D) in the pyrrolnitrin gene region of MOCG134 (SEQ ID NO:1). ORFs 1–4 from *B. cepacia* also are arranged in the same order as ORFs 1–4 in MOCG134.

(3) Isolation of Pyrrolnitrin Biosynthetic Genes from *Myxococcus fulvus*

An isolate of *Myxococcus fulvus* strain Mx f147 was obtained from K. -H. van Pée. This bacterium was shown to produce pyrrolnitrin by Gerth and co-workers (K. Gerth et al., Journal of Antibiotics 35:1101–1103 (1982)).

Genomic DNA was extracted and a sample of the DNA was digested with BamHI. The resulting fragments were separated by agarose gel electrophoresis and transferred to a nylon membrane which was hybridized with a prn gene probe as described above. Hybridization and washing were carried out under moderate stringency conditions (55° C.). Two fragments of approximately 8 and 5 kb in length from the *Mx. fulvus* DNA, which hybridized to the probe, were identified.

A second sample of *Mx. fulvus* DNA was digested with BamHI and separated by agarose gel electrophoresis as described above. The portions of the gel corresponding to the hybridizing bands were excised and the DNA was extracted. For each gel portion, the extracted DNA was ligated with pBluescript II vector DNA (Stratagene) using T4 DNA ligase. The vector DNA had previously been digested with BamHI and treated with calf intestinal phosphatase. *E. coli* strain DH5α cells were transformed with the ligated DNA and plated on LB agar supplemented with 100 mg/ml ampicillin. Individual colonies were selected and inoculated onto fresh plates to produce two libraries, one for the 8 kb fragment and one for the 5 kb fragment.

The plates were incubated overnight and the bacterial colonies were scraped from the surfaces for DNA extraction. For initial screening, individual colonies were combined into pools, each containing 16 to 20 clones. Plasmid DNA was extracted as follows: The bacterial cells were dispersed in 500 ml of a solution containing 0.8% sucrose, 0.05% Triton X-100, 50 mM EDTA and 50 mM Tris, pH 8.0. Thirty ml of a solution of lysozyme (10 mg/ml) was added and the tubes were incubated at room temperature for 5 to 15 minutes, then placed into a boiling water bath for 60 sec. The tubes were centrifuged for 10 min at 16,000×g and the pellets were removed. The DNA was precipitated by adding 500 ml isopropanol and centrifuging 5 min at 16,000×g. The pellets were rinsed with 500 ml of ice-cold 75% ethanol, dried and dissolved in 50 ml TE solution (10 mM Tris, pH 8.0, 1 mM EDTA).

Samples of each plasmid DNA extract and a sample of *Mx. fulvus* genomic DNA were digested with BamHI, separated by agarose gel electrophoresis, transferred to nylon, and hybridized with a prn gene probe. Hybridization and washing were carried out at 55° C. Pools that contained the desired clones were identified by the presence of a hybridizing band that was the same size as one of the hybridizing bands in *Mx. fulvus* genomic DNA.

The individual clones from the selected pools were used to inoculate broth cultures from which plasmid DNA was extracted as described above. Samples of plasmid DNA from each individual clone and a sample of *Mx. fulvus* genomic DNA were digested with BamHI, separated by agarose gel electrophoresis, transferred to nylon, and hybridized with a prn gene probe. Hybridization and washing were carried out at 55° C. Two clones that contained hybridizing bands were identified. The clone pPEH76 contains an inserted BamHI fragment of approximately 8 kb, which is identical in size to the 8 kb hybridizing fragment from *Mx. fulvus* genomic DNA. pPEH78 contains an inserted BamHI fragment of approximately 5 kb, which is identical in size to the 5 kb hybridizing fragment from *Mx. fulvus* genomic DNA. These data demonstrate that pPEH76 and pPEH78 contain DNA regions isolated from *Mx. fulvus* strain Mx f147 that are homologous to the pyrrolnitrin biosynthetic genes from *Pseudomonas fluorescens* strain MOCG134.

To test the function of the genes isolated from *Mx. fulvus*, it was necessary to determine the native orientation of the 5 and 8 kb BamHI DNA fragments in the *Mx. fulvus* genome. The ends of the DNA inserts in each clone were sequenced, and oligonucleotide primers were designed to anneal within the inserts (100 to 300 bp from end) and initiate PCR extension toward the proximal BamHI cloning site. Four PCR reactions were performed using *Mx. fulvus* genomic DNA as template and four different primer combinations (A+C, A+D, B+C, or B+D). For each possible orientation of the two BamHI fragments, only one primer combination would amplify a PCR product. For each primer, the distance to the proximal BamHI site was known, so the length of the PCR products could be calculated. Only one primer combination (B+D) produced a PCR product of the expected size. This experiment verified that the 5 kb and 8 kb fragments are adjacent to each other in the *Mx. fulvus* genome and revealed the native orientation of the two fragments relative to each other.

Both fragments were subcloned into the broad host range vector pRK290. A clone was selected which contained both fragments in the native orientation by using restriction analysis and the PCR method described above. This plasmid was introduced into MOCG134Δprn by triparental mating as described in Example 12. Pyrrolnitrin production was assessed by extraction and TLC as described in Example 12. The presence of the plasmid in the mutant strain resulted in pyrrolnitrin production, demonstrating that the DNA fragments isolated from Mx. fulvus and contained in pPEH76 and pPEH78 contain functional genes that comprise the entire pyrrolnitrin biosynthetic operon.

The sequence of the DNA inserts of pPEH76 and pPEH78 were determined by using commonly known techniques. Raw sequence data were assembled and edited using Sequencher software (Gene Codes Corporation, Inc., Ann Arbor, Mich.). The prn genes from M. fulvus were identified by homology to the sequence of prnABCD from MOCG134. The consensus sequence for prn gene coding region from M. fulvus is shown in SEQ ID NO:33.

Four open reading frames (ORFs) were identified in the prn gene region from M. fulvus (SEQ ID NO:33) that have very strong homology to ORFs 1–4 in the pyrrolnitrin gene region of MOCG134 (SEQ ID NO:1). However, ORFs 1–4 from M. fulvus are not arranged in the same order as ORFs 1–4 in MOCG134. In M. fulvus, ORF1 is the prnB gene, ORF2 is the prnC gene, ORF3 is the prnD gene, ORF4 is on the complementary strand and is the prnA gene.

(4) Comparing prn Gene Clusters From P. fluorescens, P. pyrrocinia, B. cepacia, and M. fulvus (SEQ ID NOs:1, 23, 28, and 33, respectively)

For P. fluorescens, P. pyrrocinia and B. cepacia, the organization of the prn genes within the clusters is identical. Furthermore, in each of these three gene clusters, the start codon for the prnB gene is GTG and that codon overlaps the prnA stop codon by 1 base. Thus, in these organisms, the prnA and prnB genes are apparently translationally coupled.

In M. fulvus, however, the prnB gene begins with ATG and is the first gene in the cluster. The prnC and prnD genes are arranged in the same manner as in the other three bacteria; however, the prnA gene is located downstream of prnD and is transcribed in the opposite direction.

The DNA sequences and predicted amino acid sequences of the four prn genes were compared among the four species (P. fluorescens MOCG134, Pseudomonas pyrrocinia, Burkholdaria cepacia strain LT-4-12W and Myxococcus fulvus) using the Clustal alignment method in the MegAlign software package (DNA Star, Inc., Madison, Wis.). The results are shown in the tables below.

Similarity Percentage Among DNA Sequences of prn Genes:

|  | P. fluorescens | P. pyrrocinia | B. cepacia |
|---|---|---|---|
| prnA | | | |
| M. fulvus | 50.2 | 49.4 | 50.7 |
| B. cepacia | 90.6 | 93.3 | |
| P. pyrrocinia | 94.2 | | |
| prnB | | | |
| M. fulvus | 57.3 | 59.2 | 57.9 |
| B. cepacia | 85.7 | 89.9 | |
| P. pyrrocinia | 91.1 | | |
| prnC | | | |
| M. fulvus | 74.2 | 74.5 | 74.1 |
| B. cepacia | 91.4 | 92.7 | |
| P. pyrrocinia | 95.6 | | |
| prnD | | | |
| M. fulvus | 61.2 | 60.7 | 60.1 |
| B. cepacia | 88.5 | 90.8 | |
| P. pyrrocinia | 92.1 | | |

Similarity Percentage Among Predicted Amino Acid Sequences of prn Gene Products:

|  | P. fluorescens | P. pyrrocinia | B. cepacia |
|---|---|---|---|
| PrnA | | | |
| M. fulvus | 44.7 | 44.5 | 45.2 |
| B. cepacia | 89.4 | 92.2 | |
| P. pyrrocinia | 94.4 | | |
| PrnB | | | |
| M. fulvus | 61.6 | 61.9 | 59.4 |
| B. cepacia | 80.9 | 85.6 | |
| P. pyrrocinia | 86.2 | | |
| PrnC | | | |
| M. fulvus | 79.3 | 79.5 | 79.2 |
| B. cepacia | 93.7 | 94.2 | |
| P. pyrrocinia | 95.2 | | |
| PrnD | | | |
| M. fulvus | 62.1 | 62.0 | 61.5 |
| B. cepacia | 87.6 | 88.1 | |
| P. pyrrocinia | 91.2 | | |

D. Isolation of Resorcinol Biosynthetic Genes 2-hexyl-5-propyl-resorcinol is a further APS produced by certain strains of Pseudomonas. It has been shown to have antipathogenic activity against Gram-positive bacteria (in particular Clavibacter spp.), mycobacteria, and fungi.

Example 13

Isolation of Genes Encoding Resorcinol from Pseudomonas

Two transposon-insertion mutants have been isolated which lack the ability to produce the antipathogenic substance 2-hexyl-5-propyl-resorcinol which is a further substance known to be under the global regulation of the gafA gene in Pseudomonas fluorescens (WO 94/01561). The insertion transposon TnCIB116 was used to generate libraries of mutants in MOCG134 and a gafA⁻ derivative of MOCG134 (BL1826). The former was screened for changes in fungal inhibition in vitro; the latter was screened for genes regulated by gafA after introduction of gafA on a plasmid (see Section C). Selected mutants were characterized by HPLC to assay for production of known compounds such as pyrrolnitrin and 2-hexyl-5-propyl-resorcinol. The HPLC assay enabled a comparison of the novel mutants to the wild-type parental strain. In each case, the HPLC peak corresponding to 2-hexyl-5-propyl-resorcinol was missing in the mutant. The mutant derived from MOCG134 is designated BL1846. The mutant derived from BL1826 is designated BL1911. HPLC for resorcinol follows the same procedure as for pyrrolnitrin (see example 11) except that 100% methanol is applied to the column at 20 min to elute resorcinol.

The resorcinol biosynthetic genes can be isolated from the above-identified mutants in the following manner. Genomic DNA is prepared from the mutants, and clones containing the transposon insertion and adjacent Pseudomonas sequence are obtained by selecting for kanamycin resistant clones (kanamycin resistance is encoded by the transposon). The isolated Pseudomonas sequence is then used as a probe to identify the native sequences from a genomic library of P. fluorescens MOCG134. The isolated native genes are likely to represent resorcinol biosynthetic genes.

E. Isolating Soraphen Biosynthetic Genes

Soraphen is a polyketide antibiotic produced by the myxobacterium *Sorangium cellulosum*. This compound has broad antifungal activities which make it useful for agricultural applications. In particular, soraphen has activity against a broad range of foliar pathogens.

Example 14

Isolation of the Soraphen Gene Cluster from Sorangium

Genomic DNA was isolated from *Sorangium cellulosum* and partially digested with Sau3A. Fragments of between 30 and 40 kb were size selected and cloned into the cosmid vector pHC79 (Hohn & Collins, Gene 11: 291–298 (1980)) which had been previously digested with BamHI and treated with alkaline phosphatase to prevent self ligation. The cosmid library thus prepared was probed with a 4.6 kb fragment which contains the graI region of *Streptomyces violaceoruber* strain Tü22 encoding ORFs 1–4 responsible for the biosynthesis of granaticin in *S. violaceoraber*. Cosmid clones which hybridized to the graI probe were identified and DNA was prepared for analysis by restriction digestion and further hybridization. Cosmid p98/1 was identified to contain a 1.8 kb SalI fragment which hybridized strongly to the graI region; this SalI fragment was located within a larger 6.5 kb PvuI fragment within the ~40 kb insert of p98/1. Determination of the sequence of part of the 1.8 kb SalI insert revealed homology to the acetyltransferase proteins required for the synthesis of erythromycin. Restriction mapping of the cosmid p98/1 was undertaken. The DNA sequence of the soraphen gene cluster is disclosed in SEQ ID NO:6. *E. coli* HB101 containing p98/1 was deposited at the Agricultural Research Culture Collection (NRRL), 1815 N. University Street, Peoria, Ill. 61604 on May 20, 1994, and assigned accession number NRRL B-21255.

Example 15

Functional Analysis of the Soraphen Gene Cluster

The regions within p98/1 that encode proteins with a role in the biosynthesis of soraphen were identified through gene disruption experiments. Initially, DNA fragments were derived from cosmid p98/1 by restriction with PvuI and cloned into the unique PvuI cloning site (which is within the gene for ampicillin resistance) of the wide host-range plasmid pSUP2021 (Simon et al. in: Molecular Genetics of the Bacteria-Plant Interaction (ed.: A Puhler), Springer Verlag, Berlin pp. 98–106 (1983)). Transformed *E. coli* HB101 was selected for resistance to chloramphenicol, but sensitivity to ampicillin. Selected colonies carrying appropriate inserts were transferred to *Sorangium cellulosum* SJ3 by conjugation using the method described in the published application EP 0 501 921 and EP the later app. (both to Ciba-Geigy). Plasmids were transferred to *E. coli* ED8767 carrying the helper plasmid pUZ8 (Hedges & Mathew, Plasmid 2: 269–278 (1979)) and the donor cells were incubated with *Sorangium cellulosum* SJ3 cells from a stationary phase culture for conjugative transfer essentially as described in EP 0 501 921 (example 5) and EP the later app. (example 2). Selection was on kanamycin, phleomycin and streptomycin. It has been determined that no plasmids tested thus far are capable of autonomous replication in *Sorangium cellulosum*, but rather, integration of the entire plasmid into the chromosome by homologous recombination occurs at a site within the cloned fragment at low frequency. These events can be selected for by the presence of antibiotic resistance markers on the plasmid. Integration of the plasmid at a given site results in the insertion of the plasmid into the chromosome and the concomitant disruption of this region from this event. Therefore, a given phenotype of interest, i.e. soraphen production, can be assessed, and disruption of the phenotype will indicate that the DNA region cloned into the plasmid must have a role in the determination of this phenotype.

Recombinant pSUP2021 clones with PvuI inserts of approximate size 6.5 kb (pSN105/7), 10 kb (pSN120/10), 3.8 kb (pSN120/43-39) and 4.0 kb (pSN120/46) were selected. pSN105/7 was shown by digestion with PvuI and SalI to contain the 1.8 kb fragment referred to above in example 14. Gene disruptions with the 3.8, 4.0, 6.5, and 10 kb PvuI fragments all resulted in the elimination of soraphen production. These results indicate that all of these fragments contain genes or fragments of genes with a role in the production of this compound.

Subsequently gene disruption experiments were performed with two BglII fragments derived from cosmid p98/1. These were of size 3.2 kb and 2.9 kb. These fragments were cloned into the BamHI site of plasmid pCIB132 that was derived from pSUP2021. The ~5 kb NotI fragment of pSUP2021 was excised and inverted, followed by the removal of the ~3 kb BamHI fragment. Neither of these BglII fragments was able to disrupt soraphen biosynthesis when reintroduced into Sorangium using the method described above. This indicates that the DNA of these fragments has no role in soraphen biosynthesis. Examination of the DNA sequence indicates the presence of a thioesterase domain 5' to, but near the BglII site at location 32.4. In addition, there are transcription stop codons immediately after the thioesterase domain which are likely to demarcate the end of the ORF1 coding region. As the 2.9 and 3.2 kb BglII fragments are immediately to the right of these sequences it is likely that there are no other genes downstream from ORF1 that are involved in soraphen biosynthesis.

Delineation of the left end of the biosynthetic region required the isolation of two other cosmid clones, pJL1 and pJL3, that overlap p98/1 on the left end, but include more DNA leftwards of p98/1. These were isolated by hybridization with the 1.3 kb BamHI fragment on the extreme left end of p98/1 (map location 0.0–1.3) to the *Sorangium cellulosum* gene library. It should be noted that the BamHI site at 0.0 does not exist in the *S. cellulosum* chromosome but was formed as an artifact from the ligation of a Sau3A restriction fragment derived from the *Sorangium cellulosum* genome into the BamHI cloning site of pHC79. Southern hybridization with the 1.3 kb BamHI fragment demonstrated that pJL1 and pJL3 each contain an approximately 12.5 kb BamHI fragment that contains sequences common to the 1.3 kb fragment as this fragment is in fact delineated by the BamHI site at position 1.3. Gene disruption experiments using the 12.5 kb BamHI fragment indicated that this fragment contains sequences that are involved in the synthesis of soraphen. Gene disruption using smaller EcoRV fragments derived from this region and also indicated the requirement of this region for soraphen biosynthesis. For example, two EcoRV fragments of 3.4 and 1.1 kb located adjacent to the distal BamHI site at the left end of the 12.5 kb fragment resulted in a reduction in soraphen biosynthesis when used in gene disruption experiments. *E. coli* HB101 containing pJL3 was deposited at the Agricultural Research Culture Collection (NRRL), 1815 N. University Street, Peoria, Ill. 61604 on May 20, 1994, and assigned accession number NRRL B-21254.

Example 16

Sequence Analysis of the Soraphen Gene Cluster

The DNA sequence of the soraphen gene cluster was determined from the PvuI site at position 2.5 to the BglII site at position 32.4 using the Taq DyeDeoxy Terminator Cycle Sequencing Kit supplied by Applied Biosystems, Inc., Foster City, Calif. following the protocol supplied by the manufacturer. Sequencing reactions were run on a Applied Biosystems 373A Automated DNA Sequencer and the raw DNA sequence was assembled and edited using the "INHERIT" software package also from Applied Biosystems, Inc. The pattern recognition program "FRAMES" was used to search for open reading frames (ORFs) in all six translation frames of the DNA sequence. In total approximately 30 kb of contiguous DNA was assembled and this corresponds to the region determined to be critical to soraphen biosynthesis in the disruption experiments described in Example 15. This sequence encodes two ORFs which have the structure described below.

ORF1

ORF1 is approximately 25.5 kb in size and encodes five biosynthetic modules with homology to the modules found in the erythromycin biosynthetic genes of *Saccharopolyspora erythraea* (Donadio et al. Science 252: 675–679 (1991)). Each module contains a β-ketoacylsynthase (KS), an acyltransferase (AT), a ketoreductase (KR) and an acyl carrier protein (ACP) domain as well as β-ketone processing domains which may include a dehydratase (DH) and/or enoyl reductase (ER) domain. In the biosynthesis of the polyketide structure each module directs the incorporation of a new two carbon extender unit and the correct processing of the β-ketone carbon.

ORF2

In addition to ORF1, DNA sequence data from the p98/1 fragment spanning the PvuI site at 2.5 kb and the SmaI site at 6.2 kb, indicated the presence of a further ORF (ORF2) immediately adjacent to ORF1. The DNA sequence demonstrates the presence of a typical biosynthetic module that appears to be encoded on an ORF whose 5' end is not yet sequenced and is some distance to the left. By comparison to other polyketide biosynthetic gene units and the number of carbon atoms in the soraphen ring structure it is likely that there should be a total of eight modules in order to direct the synthesis of 17 carbon molecule soraphen. Since there are five modules in ORF1 described above, it was predicted that ORF2 contains a further three and that these would extend beyond the left end of cosmid p98/1. This is entirely consistent with the gene description of Example 15. The cosmid clones pJL1 and pJL3 extending beyond the left end of p98/1 presumable carry the sequence encoding the remaining modules required for soraphen biosynthesis.

Example 17

Soraphen: Requirement for Methylation

Synthesis of polyketides typically requires, as a first step, the condensation of a starter unit (commonly acetate) and an extender unit (malonate) with the loss of one carbon atom in the form of $CO_2$ to yield a three-carbon chain. All subsequent additions result in the addition of two carbon units to the polyketide ring (Donadio et al. Science 252: 675–679 (1991)). Since soraphen has a 17-carbons ring, it is likely that there are 8 biosynthetic modules required for its synthesis. Five modules are encoded in ORF1 and a sixth is present at the 3' end of ORF2. As explained above, it is likely that the remaining two modules are also encoded by ORF2 in the regions that are in the 15 kb BamHI fragment from pJL1 and pJL3 for which the sequence has not yet been determined.

The polyketide modular biosynthetic apparatus present in *Sorangium cellulosum* is required for the production of the compound, soraphen C, which has no antipathogenic activity. The structure of this compound is the same as that of the antipathogenic soraphen A with the exception that the O-methyl groups of soraphen A at positions 6, 7, and 14 of the ring are hydroxyl groups. These are methylated by a specific methyltransferase to form the active compound soraphen A. A similar situation exists in the biosynthesis of erythromycin in *Saccharopolyspora erythraea*. The final step in the biosynthesis of this molecule is the methylation of three hydroxl groups by a methyltransferase (Haydock et al., Mol. Gen. Genet. 230: 120–128 (1991)). It is highly likely, therefore, that a similar methyltransferase (or possibly more than one) operates in the biosynthesis of soraphen A (soraphen C is unmethylated and soraphen B is partially methylated). In all polyketide biosynthesis systems examined thus far, all of the biosynthetic genes and associated methylases are clustered together (Summers et al. J Bacteriol 174: 1810–1820 (1992)). It is also probable, therefore, that a similar situation exists in the soraphen operon and that the gene encoding the methyltransferase/s required for the conversion of soraphen B and C to soraphen A is located near the ORF1 and ORF2 that encode the polyketide synthase. The results of the gene disruption experiments described above indicate that this gene is not located immediately downstream from the 3' end of ORF1 and that it is likely located upstream of ORF2 in the DNA contained in pJL1 and pJL3. Thus, using standard techniques in the art, the methyltransferase gene can be isolated and sequenced.

Soraphen Determination

*Sorangium cellulosum* cells were cultured in a liquid growth medium containing an exchange resin, XAD-5 (Rohm and Haas) (5% w/v). The soraphen A produced by the cells bound to the resin which was collected by filtration through a polyester filter (Sartorius B 420-47-N) and the soraphen was released from the resin by extraction with 50 ml isopropanol for 1 hr at 30° C. The isopropanol containing soraphen A was collected and concentrated by drying to a volume of approximately 1 ml. Aliquots of this sample were analyzed by HPLC at 210 nm to detect and quantify the soraphen A. This assay procedure is specific for soraphen A (fully methylated); partially and non-methylated soraphen forms have a different $R_T$ and are not measured by this procedure. This procedure was used to assay soraphen A production after gene disruption.

F. Isolation and Characterization of Phenazine Biosynthetic Genes

The phenazine antibiotics are produced by a variety of Pseudomonas and Streptomyces species as secondary metabolites branching off the shikimic acid pathway. It has been postulated that two chorismic acid molecules are condensed along with two nitrogens derived from glutamine to form the three-ringed phenazine pathway precursor phenazine-1,6-dicarboxylate. However, there is also genetic evidence that anthranilate is an intermediate between chorismate and phenazine-1,6-dicarboxylate (Essar et al., J. Bacteriol. 172: 853–866 (1990)). In *Pseudomonas aureofaciens* 30–84, production of three phenazine antibiotics, phenazine-1-carboxylic acid, 2-hydroxyphenazine-1-carboxylic acid, and 2-hydroxyphenazine, is the major mode of action by which the strain protects wheat from the fungal phytopathogen *Gaeumannomyces graminis* var. *tritici* (Pierson & Thomashow, MPMI 5: 330–339 (1992)). Likewise, in *Pseudomonas fluorescens* 2–79, phenazine production is a major factor in the control of *G. graminis* var. *tritici* (Thomashow & Weller, J. Bacteriol. 170: 3499–3508 (1988)).

Example 18

Isolation of Phenazine Biosynthetic Genes from *Pseudomonas aureofaciens*

Pierson & Thomashow (supra) have previously described the cloning of a cosmid which confers a phenazine biosynthesis phenotype on transposon insertion mutants of *Pseudomonas aureofaciens* strain 30–84 which were disrupted in their ability to synthesize phenazine antibiotics. A mutant library of strain 30–84 was made by conjugation with *E. coli* S17-1(pSUP1021) and mutants unable to produce phenazine antibiotics were selected. Selected mutants were unable to produce phenazine carboxylic acid, 2-hydroxyphenaxine or 2-hydroxyphenazine carboxylic acid. These mutants were transformed by a cosmid genomic library of strain 30–84 leading to the isolation of cosmid pLSP259 which had the ability to complement phenazine mutants by the synthesis of phenazine carboxylic acid, 2-hydroxy-phenazine and 2-hydroxyphenazinecarboxylic acid. pLSP259 was further characterized by transposon mutagenesis using the λ::Tn5 phage described by de Bruijn & Lupski (Gene 27: 131–149 (1984)). Thus a segment of approximately 2.8 kb of DNA was identified as being responsible for the phenazine complementing phenotype; this 2.8 kb segment is located within a larger 9.2 kb EcoRI fragment of pLSP259. Transfer of the 9.2 kb EcoRI fragment and various deletion derivatives thereof to *E. coli* under the control of the lacZ promoter was undertaken to assay for the production in *E. coli* of phenazine. The shortest deletion derivative which was found to confer biosynthesis of all three phenazine compounds to *E. coli* contained an insert of approximately 6 kb and was designated pLSP18-6H3del3. This plasmid contained the 2.8 kb segment previously identified as being critical to phenazine biosynthesis in the host 30–84 strain and was provided by Dr. L S Pierson (Department of Plant Pathology, U Arizona, Tucson, Ariz.) for sequence characterization. Other deletion derivatives were able to confer production of phenazinecarboxylic acid on *E. coli*, without the accompanying production of 2-hydroxyphenazine and 2-hydroxyphenazinecarboxylic acid suggesting that at least two genes might be involved in the synthesis of phenazine and its hydroxy derivatives.

The DNA sequence comprising the genes for the biosynthesis of phenazine is disclosed in SEQ ID NO:17. Determination of the DNA sequence of the insert of pLSP18-6H3del3 revealed the presence of four ORFs within and adjacent to the critical 2.8 kb segment. ORF1 (SEQ ID NO:18) was designated phz1, ORF2 (SEQ ID NO:19) was designated phz2, and ORF3 (SEQ ID NO:20) was designated phz3, and ORF4 (SEQ ID NO:22) was designated phz4. phlB is approximately 1.35 kb in size and has homology at the 5' end to the entB gene of *E. coli*, which encodes isochorismatase. phz2 is approximately 1.15 kb in size and has some homology at the 3' end to the trpG gene which encodes the beta subunit of anthranilate synthase. phz3 is approximately 0.85 kb in size. phz4 is approximately 0.65 kb in size and is homologous to the pdxH gene of *E. coli* which encodes pyridoxamine 5'-phosphate oxidase.

Phenazine Determination

Thomashow et al. (Appl Environ Microbiol 56: 908–912 (1990)) describe a method for the isolation of phenazine. This involves acidifying cultures to pH 2.0 with HCl and extraction with benzene. Benzene fractions are dehydrated with $Na_2SO_4$ and evaporated to dryness. The residue is redissolved in aqueous 5% $NaHCO_3$, reextracted with an equal volume of benzene, acidified, partitioned into benzene and redried. Phenazine concentrations are determined after fractionation by reverse-phase HPLC as described by Thomashow et al. (supra).

G. Isolating Peptide Antipathogenic Genes

This group of substances is diverse and is classifiable into two groups: (1) those which are synthesized by enzyme systems without the participation of the ribosomal apparatus, and (2) those which require the ribosomally-mediated translation of an mRNA to provide the precursor of the antibiotic.

Non-Ribosomal Peptide Antibiotics

Non-Ribosomal Peptide Antibiotics are assembled by large, multifunctional enzymes which activate, modify, polymerize and in some cases cyclize the subunit amino acids, forming polypeptide chains. Other acids, such as aminoadipic acid, diaminobutyric acid, diaminopropionic acid, dihydroxyamino acid, isoserine, dihydroxybenzoic acid, hydroxyisovaleric acid, (4R)-4-[(E)-2-butenyl]-4,N-dimethyl-L-threonine, and ornithine are also incorporated (Katz & Demain, Bacteriological Review 41: 449–474 (1977); Kleinkauf & von Dohren, Annual Review of Microbiology 41: 259–289 (1987)). The products are not encoded by any mRNA, and ribosomes do not directly participate in their synthesis. Peptide antibiotics synthesized non-ribosomally can in turn be grouped according to their general structures into linear, cyclic, lactone, branched cyclopeptide, and depsipeptide categories (Kleinkauf & von Dohren, European Journal of Biochemistry 192: 1–15 (1990)). These different groups of antibiotics are produced by the action of modifying and cyclizing enzymes; the basic scheme of polymerization is common to them all. Non-ribosomally synthesized peptide antibiotics are produced by both bacteria and fungi, and include edeine, linear gramicidin, tyrocidine and gramicidin S from *Bacillus brevis*, mycobacillin from *Bacillus subtilis*, polymyxin from *Bacillus polymixa*, etamycin from *Streptomyces griseus*, echinomycin from *Streptomyces echinatus*, actinomycin from *Streptomyces clavuligerus*, enterochelin from *Escherichia coli*, gamma-(alpha-L-aminoadipyl)-L-cysteinyl-D-valine (ACV) from *Aspergillus nidulans*, alamethicine from *Trichoderma viride*, destruxin from *Metarhizium anisolpliae*, enniatin from *Fusarium oxysporum*, and beauvericin from *Beauveria bassiana*. Extensive functional and structural similarity exists between the prokaryotic and eukaryotic systems, suggesting a common origin for both. The activities of peptide antibiotics are similarly broad, toxic effects of different peptide antibiotics in animals, plants, bacteria, and fungi are known (Hansen, Annual Review of Microbiology 47: 535–564 (1993); Katz & Demain, Bacteriological Reviews 41: 449–474 (1977); Kleinkauf & von Dohren, Annual Review of Microbiology 41: 259–289 (1987); Kleinkauf & von Dohren, European Journal of Biochemistry 192: 1–15 (1990); Kolter & Moreno, Annual Review of Microbiology 46: 141–163 (1992)).

Amino acids are activated by the hydrolysis of ATP to form an adenylated amino or hydroxy acid, analogous to the charging reactions carried out by aminoacyl-tRNA synthetases, and then covalent thioester intermediates are formed between the amino acids and the enzyme(s), either at specific cysteine residues or to a thiol donated by pantetheine. The amino acid-dependent hydrolysis of ATP is often used as an assay for peptide antibiotic enzyme complexes (Ishihara, et al., Journal of Bacteriology 171: 1705–1711 (1989)). Once bound to the enzyme, activated amino acids may be modified before they are incorporated into the polypeptide. The most common modifications are epimerization of L-amino (hydroxy) acids to the D- form, N-acylations, cyclizations and N-methylations. Polymerization occurs through the participation of a pantetheine cofactor, which allows the activated subunits to be sequentially added to the polypeptide chain. The mechanism by which the peptide is released from the enzyme complex is important in the determination of the structural class in which the product belongs. Hydrolysis or aminolysis by a free amine of the thiolester will yield a linear (unmodified or terminally aminated) peptide such as edeine; aminolysis of the thiolester by amine groups on the peptide itself will give either cyclic (attack by terminal amine), such as gramicidin S, or branched (attack by side chain amine), such as bacitracin, peptides; lactonization with a terminal or side chain hydroxy will give a lactone, such as destruxin, branched lactone, or cyclodepsipeptide, such as beauvericin.

The enzymes which carry out these reactions are large multifunctional proteins, having molecular weights in accord with the variety of functions they perform. For example, gramicidin synthetases 1 and 2 are 120 and 280 kDa, respectively; ACV synthetase is 230 kDa; enniatin synthetase is 250 kDa; bacitracin synthetases 1, 2, 3 are 335, 240, and 380 kDa, respectively (Katz & Demain, Bacteriological Reviews 41: 449–474 (1977); Kleinkauf & von Dohren, Annual Review of Microbiology 41: 259–289 (1987); Kleinkauf & von Dohren, European Journal of Biochemistry 192: 1–15 (1990). The size and complexity of these proteins means that relatively few genes must be isolated in order for the capability for the complete nonribosomal synthesis of peptide antibiotics to be transferred. Further, the functional and structural homology between bacterial and eukaryotic synthetic systems indicates that such genes from any source of a peptide antibiotic can be isolated using the available sequence information, current functional information, and conventional microbiological techniques. The production of a fungicidal, insecticidal, or batericidal peptide antibiotic in a plant is expected to produce an advantage with respect to the resistance to agricultural pests.

Example 19

Isolation of Gramicidin S Biosynthesis Genes

Gramicidin S is a cyclic antibiotic peptide and has been shown to inhibit the germination of fungal spores (Murray, et al., Letters in Applied Microbiology 3: 5–7 (1986)), and may therefore be useful in the protection of plants against fungal diseases. The gramicidin S biosynthesis operon (grs) from *Bacillus brevis* ATCC 9999 has been isolated and sequenced, including the entire coding sequences for gramicidin synthetase 1 (GS1, grsA), another gene in the operon of unknown function (grsT), and GS2 (grsB) (Kratzschmar, et al., Journal of Bacteriology 171:

5422–5429 (1989); Krause, et al., Journal of Bacteriology 162: 1120–1125 (1985)). By methods well known in the art, pairs of PCR primers are designed from the published DNA sequence which are suitable for amplifying segments of approximately 500 base pairs from the grs operon using isolated *Bacillus brevis* ATCC 9999 DNA as a template. The fragments to be amplified are (1) at the 3' end of the coding region of grsB, spanning the termination codon, (2) at the 5' end of the grsB coding sequence, including the initiation codon, (3) at the 3' end of the coding sequence of grsA, including the termination codon, (4) at the 5' end of the coding sequence of grsA, including the initiation codon, (5) at the 3' end of the coding sequence of grsT, including the termination codon, and (6) at the 5' end of the coding sequence of grsT, including the initiation codon. The amplified fragments are radioactively or nonradioactively labeled by methods known in the art and used to screen a genomic library of *Bacillus brevis* ATCC 9999 DNA constructed in a vector such as λEMBL3. The 6 amplified fragments are used in pairs to isolate cloned fragments of genomic DNA which contain intact coding sequences for the three biosynthetic genes. Clones which hybridize to probes 1 and 2 will contain an intact grsB sequence, those which hybridize to probes 3 and 4 will contain an intact grsA gene, those which hybridize to probes 5 and 6 will contain an intact grsT gene. The isolated grsA is introduced into *E. coli* and extracts prepared by lysing transformed bacteria through methods known in the art are tested for activity by the determination of phenylalanine-dependent ATP-PP$_i$ exchange (Krause, et al., Journal of Bacteriology 162: 1120–1125 (1985)) after removal of proteins smaller than 120 kDa by gel filtration chromatography. GrsB is tested similarly by assaying gel-filtered extracts from transformed bacteria for proline, valine, ornithine and leucine-dependent ATP-PP$_i$ exchange.

Example 20

Isolation of Penicillin Biosynthesis Genes

A 38 kb fragment of genomic DNA from *Penicillium chrysogenum* transfers the ability to synthesize penicillin to fungi, *Aspergillus niger*, and *Neurospora crassa*, which do not normally produce it (Smith, et al., Bio/Technology 8: 39–41 (1990)). The genes which are responsible for biosynthesis, delta-(L-alpha-aminoadipyl)-L-cysteinyl-D-valine synthetase, isopenicillin N synthetase, and isopenicillin N acyltranferase have been individually isolated from *P. chrysogenum* and *Aspergillus nidulans*, and their sequences determined (Ramon, et al., Gene 57: 171–181 (1987); Smith, et al., EMBO Journal 9: 2743–2750 (1990); Tobin, et al., Journal of Bacteriology 172: 5908–5914 (1990)). The isolation of these genes is accomplished by following the PCR-based approach described above to obtain probes of approximately 500 base pairs from genomic DNA from either *Penicillium chrysogenum* (for example, strain AS-P-78, from Antibioticos, S. A., Leon, Spain), or from *Aspergillus nidulans* for example, strain G69. Their integrity and function may be checked by transforming the non-producing fungi listed above and assaying for antibiotic production and individual enzyme activities as described (Smith, et al., Bio/Technology 8: 39–41 (1990)).

Example 21

Isolation of Bacitracin A Biosynthesis Genes

Bacitracin A is a branched cyclopeptide antibiotic which has potential for the enhancement of disease resistance to bacterial plant pathogens. It is produced by *Bacillus licheniformis* ATCC 10716, and three multifunctional enzymes, bacitracin synthetases (BA) 1, 2, and 3, are required for its synthesis. The molecular weights of BA1, BA2, and BA3 are 335 kDa, 240 kDa, and 380 kDa, respectively. A 32 kb fragment of *Bacillus licheniformis* DNA which encodes the BA2 protein and part of the BA3 protein shows that at least these two genes are linked (Ishihara, et al., Journal of Bacteriology 171: 1705–1711 (1989)). Evidence from gramicidin S, penicillin, and surfactin biosynthetic operons suggest that the first protein in the pathway, BA1, will be encoded by a gene which is relatively close to BA2 and BA3. BA3 is purified by published methods, and it is used to raise an antibody in rabbits (Ishihara, et al. supra). A genomic library of *Bacillus licheniformis* DNA is transformed into *E. coli* and clones which express antigenic determinants related to BA3 are detected by methods known in the art. Because BA1, BA2, and BA3 are antigenically related, the detection method will provide clones encoding each of the three enzymes. The identity of each clone is confirmed by testing extracts of transformed *E. coli* for the appropriate amino acid-dependent ATP-PP$_i$ exchange. Clones encoding BA1 will exhibit leucine-, glutamic acid-, and isoleucine-dependent ATP-PP$_i$ exchange, those encoding BA2 will exhibit lysine- and ornithine-dependent exchange, and those encoding BA3 will exhibit isoleucine, phenylalanine-, histidine-, aspartic acid-, and asparagine-dependent exchange. If one or two genes are obtained by this method, the others are isolated by "walking" techniques known in the art.

Example 22

Isolation of Beauvericin and Destruxin Biosynthesis Genes

Beauvericin is an insecticidal hexadepsipeptide produced by the fungus *Beauveria bassiana* (Kleinkauf & von Dohren, European Journal of Biochemistry 192: 1–15 (1990)) which will provide protection to plants from insect pests. It is an analog of enniatin, a phytotoxic hexadepsipeptide produced by some phytopathogenic species of Fusarium (Burmeister & Plattner, Phytopathology 77: 1483–1487 (1987)). Destruxin is an insecticidal lactone peptide produced by the fungus *Metarhizium anisopliae* (James, et al., Journal of Insect Physiology 39: 797–804 (1993)). Monoclonal antibodies directed to the region of the enniatin synthetase complex responsible for N-methylation of activated amino acids cross react with the synthetases for beauvericin and destruxin, demonstrating their structural relatedness (Kleinkauf & von Dohren, European Journal of Biochemistry 192: 1–15 (1990)). The gene for enniatin synthetase gene (esyn1) from *Fusarium scirpi* has been isolated and sequenced (Haese, et al., Molecular Microbiology 7: 905–914 (1993)), and the sequence information is used to carry out a cloning strategy for the beauvericin synthetase and destruxin synthetase genes as described above. Probes for the beauvericin synthetase (BE) gene and the destruxin synthetase (DXS) gene are produced by amplifying specific regions of *Beauveria bassiana* genomic DNA or *Metarhizium anisopliae* genomic DNA using oligomers whose sequences are taken from the enniatin synthetase sequence as PCR primers. Two pairs of PCR primers are chosen, with one pair capable of causing the amplification of the segment of the BE gene spanning the initiation codon, and the other pair capable of causing the amplification of the segment of the BE gene which spans the termination codon. Each pair will cause the production of a DNA fragment which is approximately 500 base pairs in size. Library of genomic DNA from *Beauveria bassiana* and *Metarhizium anisopliae* are probed with the labeled fragments, and clones which hybridize to both of them are chosen. Complete coding sequences of beauvericin synthetase will cause the appearance of phenylalanine-dependent ATP-PP$_i$ exchange in an appropriate host, and that of destruxin will cause the appearance of valine-, isoleucine-, and alanine-dependent ATP-PP$_i$ exchange. Extracts from these transformed organisms will also carry out the cell-free biosynthesis of beauvericin and destruxin, respectively.

Example 23

Isolating genes for the Biosynthesis of an Unknown Peptide Antibiotic

The genes for any peptide antibiotic are isolated by the use of conserved regions within the coding sequence. The functions common to all peptide antibiotic synthetases, that is, amino acid activation, ATP-, and pantotheine binding, are reflected in a repeated domain structure in which each domain spans approximately 600 amino acids. Within the domains, highly conserved sequences are known, and it is expected that related sequences will exist in any peptide antibiotic synthetase, regardless of its source. The published DNA sequences of peptide synthetase genes, including gramicidin synthetases 1 and 2 (Hori, et al., Journal of Biochemistry 106: 639–645 (1989); Krause, et al., Journal of Bacteriology 162: 1120–1125 (1985); Turgay, et al., Molecular Microbiology 6: 529–546 (1992)), tyrocidine sythethase 1 and 2 (Weckermann, et al., Nucleic Acids Research 16: 11841 (1988)), ACV synthetase (MacCabe, et al., Journal of Biological Chemistry 266: 12646–12654 (1991)), enniatin synthetase (Haese, et al., Molecular Microbiology 7: 905–914 (1993)), and surfactin synthetase (Fuma, et al., Nucleic Acids Research 21: 93–97 (1993); Grandi, et al., Eleventh International Spores Conference (1992)) are compared and the individual repeated domains are identified. The domains from all the synthetases are compared as a group, and the most highly conserved sequences are identified. From these conserved sequences, DNA oligomers are designed which are suitable for hybridizing to all of the observed variants of the sequence, and another DNA sequence which lies, for example, from 0.1 to 2 kilobases away from the first DNA sequence, is used to design another DNA oligomer. Such pairs of DNA oligomers are used to amplify by PCR the intervening segment of the unknown gene by combining them with genomic DNA prepared from the organism which produces the antibiotic, and following a PCR amplification procedure. The fragment of DNA which is produced is sequenced to confirm its identity, and used as a probe to identify clones containing larger segments of the peptide synthetase gene in a genomic library. A variation of this approach, in which the oligomers designed to hybridize to the conserved sequences in the genes were used as hybridization probes themselves, rather than as primers of PCR reactions, resulted in the identification of part of the surfactin synthetase gene from *Bacillus subtilis* ATCC 21332 (Borchert, et al., FEMS Microbiological Letters 92: 175–180 (1992)). The isolated genomic DNA which hybridizes to the PCR-generated probe is sequenced, and the complete coding sequence is obtained by "walking" procedures. Such "walking" procedures will also yield other genes required for the peptide antibiotic synthesis, because they are known to be clustered.

Another method of obtaining the genes which code for the synthetase(s) of a novel peptide antibiotic is by the detection of antigenic determinants expressed in a heterologous host after transformation with an appropriate genomic library made from DNA from the antibiotic-producing organism. It is expected that the common structural features of the synthetases will be evidenced by cross-reactions with antibodies raised against different synthetase proteins. Such antibodies are raised against peptide synthetases purified from known antibiotic-producing organisms by known methods (Ishihara, et al., Journal of Bacteriology 171: 1705–1711 (1989)). Transformed organisms bearing fragments of genomic DNA from the producer of the unknown peptide antibiotic are tested for the presence of antigenic determinants which are recognized by the anti-peptide synthetase antisera by methods known in the art. The isolated genomic DNA carried by cells which are identified by the antisera are recovered and sequenced. "Walking" techniques, as described earlier, are used to obtain both the entire coding sequence and other biosynthetic genes.

Another method of obtaining the genes which code for the synthetase of an unknown peptide antibiotic is by the purification of a protein which has the characteristics of the appropriate peptide synthetase, and determining all or part of its amino acid sequence. The amino acids present in the antibiotic are determined by first purifying it from a chloroform extract of a culture of the antibiotic-producing organism, for example by reverse phase chromatography on a $C_{18}$ column in an ethanol-water mixture. The composition of the purified compound is determined by mass spectrometry, NMR, and analysis of the products of acid hydrolysis. The amino or hydroxy acids present in the peptide antibiotic will produce ATP-$PP_i$ exchange when added to a peptide-synthetase-containing extract from the antibiotic-producing organism. This reaction is used as an assay to detect the presence of the peptide synthetase during the course of a protein purification scheme, such as are known in the art. A substantially pure preparation of the peptide synthetase is used to determine its amino acid sequence, either by the direct sequencing of the intact protein to obtain the N-terminal amino acid sequence, or by the production, purification, and sequencing of peptides derived from the intact peptide synthetase by the action of specific proteolytic enzymes, as are known in the art. A DNA sequence is inferred from the amino acid sequence of the synthetase, and DNA oligomers are designed which are capable of hybridizing to such a coding sequence. The oligomers are used to probe a genomic library made from the DNA of the antibiotic-producing organism. Selected clones are sequenced to identify them, and complete coding sequences and associated genes required for peptide biosynthesis are obtained by using "walking" techniques. Extracts from organisms which have been transformed with the entire complement of peptide biosynthetic genes, for example bacteria or fungi, will produce the peptide antibiotic when provided with the required amino or hydroxy acids, ATP, and pantetheine.

Further methods appropriate for the isolation of genes required for the synthesis of non-ribosomal peptide antibiotics are described in Section B of the examples.

Ribosomally-Synthesized Peptide Antibiotics

Ribosomally-Synthesized Peptide Antibiotics are characterized by the existence of a structural gene for the antibiotic itself, which encodes a precursor that is modified by specific enzymes to create the mature molecule. The use of the general protein synthesis apparatus for peptide antibiotic synthesis opens up the possibility for much longer polymers to be made, although these peptide antibiotics are not necessarily very large. In addition to a structural gene, further genes are required for extracellular secretion and immunity, and these genes are believed to be located close to the structural gene, in most cases probably on the same operon. Two major groups of peptide antibiotics made on ribosomes exist: those which contain the unusual amino acid lanthionine, and those which do not. Lanthionine-containing antibiotics (lantibiotics) are produced by gram-positive bacteria, including species of Lactococcus, Staphylococcus, Streptococcus, Bacillus, and Streptomyces. Linear lantibiotics (for example, nisin, subtilin, epidermin, and gallidermin), and circular lantibiotics (for example, duramycin and cinnamycin), are known (Hansen, Annual Review of Microbiology 47: 535–564 (1993); Kolter & Moreno, Annual Review of Microbiology 46: 141–163 (1992)). Lantibiotics often contain other characteristic modified residues such as dehydroalanine (DHA) and dehydrobutyrine (DHB), which are derived from the dehydration of serine and threonine, respectively. The reaction of a thiol from cysteine with DHA yields lanthionine, and with DHB yields β-methyllanthionine. Peptide antibiotics which do not contain lanthionine may contain other modifications, or they may consist only of the ordinary amino acids used in protein synthesis. Non-lanthionine-containing peptide antibiotics are produced by both gram-positive and gram-negative bacteria, including Lactobacillus, Lactococcus, Pediococcus, Enterococcus, and Escherichia. Antibiotics in this category include lactacins, lactocins, sakacin A, pediocins, diplococcin, lactococcins, and microcins (Hansen, supra; Kolter & Moreno, supra). In general, peptide antibiotics whose synthesis is begun on ribosomes are subject to several types of post-translational processing, including proteolytic cleavage and modification of amino acid side chains, and require the presence of a specific transport and/or immunity mechanism. The necessity for protection from the effects of these antibiotics appears to contrast strongly with the lack of such systems for nonribosomal peptide antibiotics. This may be rationalized by considering that the antibiotic activity of many ribosomally-synthesized peptide antibiotics is directed at a narrow range of bacteria which are fairly closely related to the producing organism. In this situation, a particular method of distinguishing the producer from the competitor is required, or else the advantage is lost. As antibiotics, this property has limited the usefulness of this class of molecules for situations in which a broad range of activity if desirable, but enhances their attractiveness in cases when a very limited range of activities is advantageous. In eukaryotic systems, which are not known to be sensitive to any of this type of peptide antibiotic, it is not clear if production of a ribosomally-synthesized peptide antibiotic necessitates one of these transport systems, or if transport out of the cell is merely a matter of placing the antibiotic in a better location to encounter potential pathogens. This question can be addressed experimentally, as shown in the examples which follow.

Example 24

Isolating Genes for the Biosynthesis of a Lantibiotic

Examination of genes linked to the structural genes for the lantibiotics nisin, subtilin, and epidermin show several open reading frames which share sequence homology, and the predicted amino acid sequences suggest functions which are necessary for the maturation and transport of the antibiotic. The spa genes of *Bacillus subtilis* ATCC 6633, including spaS, the structural gene encoding the precursor to subtilin, have been sequenced (Chung & Hansen, Journal of Bacteriology 174: 6699–6702 (1992); Chung, et al., Journal of Bacteriology 174: 1417–1422 (1992); Klein, et al., Applied and Environmental Microbiology 58: 132–142 (1992)). Open reading frames were found only upstream of spaS, at least within a distance of 1–2 kilobases. Several of the open reading frames appear to part of the same transcriptional unit, spaE, spaD, spaB, and spaC, with a putative promoter upstream of spaE. Both spaB, which encodes a protein of 599 amino acids, and spaD, which encodes a protein of 177 amino acids, share homology to genes required for the transport of hemolysin, coding for the HylB and HlyD proteins, respectively. SpaE, which encodes a protein of 851 amino acids, is homologous to nisB, a gene linked to the structural gene for nisin, for which no function is known. SpaC codes for a protein of 442 amino acids of unknown function, but disruption of it eliminates production of subtilin. These genes are contained on a segment of genomic DNA which is approximately 7 kilobases in size (Chung & Hansen, Journal of Bacteriology 174: 6699–6702 (1992); Chung, et al., Journal of Bacteriology 174: 1417–1422 (1992); Klein, et al., Applied and Environmental Microbiology 58: 132–142 (1992)). It has not been clearly demonstrated if these genes are completely sufficient to confer the ability to produce subtilin. A 13.5 kilobasepair (kb) fragment from plasmid Tü32 of *Staphylococcus epidermis* Tü3298 containing the structural gene for epidermin (epiA), also contains five open reading frames denoted epiA, epiB, epiC, epiD, epiQ, and epiP. The genes epiBC are homologous to the genes spaBC, while epiQ appears to be involved in the regulation of the expression of the operon, and epiP may encode a protease which acts during the maturation of pre-epidermin to epidermin. EpiD encodes a protein of 181 amino acids which binds the coenzyme flavin mononucleotide, and is suggested to perform post-translational modification of pre-epidermin (Kupke, et al., Journal of Bacteriology 174: (1992); Peschel, et al., Molecular Microbiology 9: 31–39 (1993); Schnell, et al., European Journal of Biochemistry 204: 57–68 (1992)). It is expected that many, if not all, of the genes required for the biosynthesis of a lantibiotic will be clustered, and physically close together on either genomic DNA or on a plasmid, and an approach which allows one of the necessary genes to be located will be useful in finding and isolating the others. The structural gene for a lantibiotic is isolated by designing oligonucleotide probes based on the amino acid sequence determined from a substantially purified preparation of the lantibiotic itself, as has been done with the lantibiotics lacticin 481 from *Lactococcus lactis* subsp. *lactis* CNRZ 481 (Piard, et al., Journal of Biological Chemistry 268: 16361–16368 (1993)), streptococcin A-FF22 from *Streptococcus pyogenes* FF22 (Hynes, et al., Applied and Environmental Microbiology 59: 1969–1971 (1993)), and salivaricin A from *Streptococcus salivarius* 203P (Ross, et al., Applied and Environmental Microbiology 59: 2014–2021 (1993)). Fragments of bacterial DNA approximately 10–20 kilobases in size containing the structural gene are isolated and sequenced to determine regions of homology to the characterized genes in the spa, epi, and nis operons. Open reading frames which have homology to any of these genes or which lie in the same transcriptional unit as open reading frames having homology to any of these genes are isolated individually using techniques known in the art. A fragment of DNA containing all of the associated reading frames and no others is transformed into a non-producing strain of bacteria, such as *Esherichia coli*, and the production of the lantibiotic analyzed, in order to demonstrate that all the required genes are present.

Example 25

Isolating Genes for the Biosynthesis of a Non-Lanthionine Containing, Ribosomally Synthesized Peptide Antibiotic The lack of the extensive modifications present in lantibiotics is expected to reduce the number of genes required to account for the complete synthesis of peptide antibiotics exemplified by lactacin F, sakacin A, lactococcin A, and helveticin J. Clustered genes involved in the biosynthesis of antibiotics were found in *Lactobacillus johnsonii* VPI11088, for lactacin F (Fremaux, et al., Applied and Environmental Microbiology 59: 3906–3915 (1993)), in *Lactobacillus sake* Lb706 for sakacin A (Axelsson, et al., Applied and Environmental Microbiology 59: 2868–2875 (1993)), in *Lactococcus lactis* for lactococcin A (Stoddard, et al., Applied and Environmental Microbiology 58: 1952–1961 (1992)), and in *Pediococcus acidilactici* for pediocin PA-1 (Marugg, et al., Applied and Environmental Microbiology, 58: 2360–2367 (1992)). The genes required for the biosynthesis of a novel non-lanthionine-containing peptide antibiotic are isolated by first determining the amino acid sequence of a substantially purified preparation of the antibiotic, designing DNA oligomers based on the amino acid sequence, and probing a DNA library constructed from either genomic or plasmid DNA from the producing bacterium. Fragments of DNA of 5–10 kilobases which contain the structural gene for the antibiotic are isolated and sequenced. Open reading frames which have homology to sakB from *Lactobacillus sake*, or to lafX, ORFY, or ORFZ from *Lactobacillus johnsonii*, or which are part of the same transcriptional unit as the antibiotic structural gene or genes having homology to those genes previously mentioned are individually isolated by methods known in the art. A fragment of DNA containing all of the associated reading frames and no others is transformed into a non-producing strain of bacteria, such as *Esherichia coli*, and the production of the antibiotic analyzed, in order to demonstrate that all the required genes are present.

H. Expression of Antibiotic Biosynthetic Genes in Microbial Hosts

Example 26

Overexpression of APS Biosynthetic Genes for Overproduction of APS using Fermentation-Type Technology The APS biosynthetic genes of this invention can be expressed in heterologous organisms for the purposes of their production at greater quantities than might be possible from their native hosts. A suitable host for heterologous expression is *E. coli* and techniques for gene expression in *E. coli* are well known. For example, the isolated APS genes can be expressed in *E. coli* using the expression vector pKK223 as described in example 11 The isolated genes can be fused in transcriptional fusion, so as to use the available ribosome binding site cognate to the heterologous gene. This approach facilitates the expression of operons which encode more than one open reading frame as translation of the individual ORFs will thus be dependent on their cognate ribosome binding site signals. Alternatively APS genes can be fused to the vector's ATG (e.g. as an NcoI fusion) so as to use the *E. coli* ribosome binding site. For multiple ORF expression in *E. coli* (e.g. in the case of operons with multiple ORFs) this type of construct would require a separate promoter to be fused to each ORF. It is possible, however, to fuse the first ATG of the APS operon to the *E. coli* ribosome binding site while requiring the other ORFs to utilize their cognate ribosome binding sites. These types of construction for the overexpression of genes in *E. coli* are well known in the art. Suitable bacterial promoters include the lac promoter, the tac (trp/lac) promoter, and the Pλ promoter from bacteriophage λ. Suitable commercially available vectors include, for example, pKK223-3, pKK233-

2, pDR540, pDR720, pYEJ001 and pPL-Lambda (from Pharmacia, Piscataway, N.J.).

Similarly, gram positive bacteria, notably Bacillus species and particularly *Bacillus licheniformis,* are used in commercial scale production of heterologous proteins and can be adapted to the expression of APS biosynthetic genes (e.g. Quax et al., In: Industrial Microorganisms: Basic and Applied Molecular Genetics, Eds.: Baltz et al., American Society for Microbiology, Washington (1993)). Regulatory signals from a highly expressed Bacillus genes (e.g. amylase promoter, Quax et al., supra) are used to generate transcriptional fusions with the APS biosynthetic genes.

In some instances, high level expression of bacterial genes has been achieved using yeast systems, such as the methylotrophic yeast *Pichia pastoris* (Sreekrishna, In: Industrial microorganisms: basic and applied molecular genetics, Baltz, Hegeman, and Skatrud eds., American Society for Microbiology, Washington (1993)). The APS gene(s) of interest are positioned behind 5' regulatory sequences of the Pichia alcohol oxidase gene in vectors such as pHIL-D1 and pHIL-D2 (Sreekrishna, supra). Such vectors are used to transform Pichia and introduce the heterologous DNA into the yeast genome. Likewise, the yeast *Saccharomyces cerevisiae* has been used to express heterologous bacterial genes (e.g. Dequin & Barre, Biotechnology 12:173–177 (1994)). The yeast *Kluyveromyces lactis* is also a suitable host for heterologous gene expression (e.g. van den Berg et al., Biotechnology 8:135–139 (1990)).

Overexpression of APS genes in organisms such as *E. coli,* Bacillus and yeast, which are known for their rapid growth and multiplication, will enable fermentation-production of larger quantities of APSs. The choice of organism may be restricted by the possible susceptibility of the organism to the APS being overproduced; however, the likely susceptibility can be determined by the procedures outlined in Section J. The APSs can be isolated and purified from such cultures (see "G") for use in the control of microorganisms such as fungi and bacteria.

I. Expression of Antibiotic Biosynthetic Genes in Microbial Hosts for Biocontrol Purposes The isolated APS biosynthetic genes of this invention can be utilized to increase the efficacy of biocontrol strains of various microorganisms. One possibility is the transfer of the genes for a particular APS back into its native host under stronger transcriptional regulation to cause the production of larger quantities of the APS. Another possibility is the transfer of genes to a heterologous host, causing production in the heterologous host of an APS not normally produced by that host.

Microorganisms which are suitable for the heterologous overexpression of APS genes are all microorganisms which are capable of colonizing plants or the rhizosphere. As such they will be brought into contact with phytopathogenic fungi causing an inhibition of their growth. These include gram-negative microorganisms such as Pseudomonas, Enterobacter and Serratia, the gram-positive microorganism Bacillus and the fungi Trichoderma and Gliocladium. Particularly preferred heterologous hosts are *Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum* and *Gliocladium virens.*

Example 27

Expression of APS Biosynthetic Genes in *E. coli* and Other Gram-Negative Bacteria Many genes have been expressed in gram-negative bacteria in a heterologous manner. Example 11 describes the expression of genes for pyrrolnitrin biosynthesis in *E. coli* using the expression vector pKK223-3 (Pharmacia catalogue #27-4935-01). This vector has a strong tac promoter (Brosius, J. et al., Proc. Natl. Acad. Sci. USA 81) regulated by the lac repressor and induced by IPTG. A number of other expression systems have been developed for use in *E. coli* and some are detailed in E (above). The thermoinducible expression vector $pP_L$ (Pharmacia #27-4946-01) uses a tightly regulated bacteriophage λ promoter which allows for high level expression of proteins. The lac promoter provides another means of expression but the promoter is not expressed at such high levels as the tac promoter. With the addition of broad host range replicons to some of these expression system vectors, production of antifungal compounds in closely related gram negative-bacteria such as Pseudomonas, Enterobacter, Serratia and Erwinia is possible. For example, pLRKD211 (Kaiser & Kroos, Proc. Natl. Acad. Sci. USA 81: 5816–5820 (1984)) contains the broad host range replicon ori T which allows replication in many gram-negative bacteria.

In *E. coli,* induction by IPTG is required for expression of the tac (i.e. trp-lac) promoter. When this same promoter (e.g. on wide-host range plasmid pLRKD211) is introduced into Pseudomonas it is constitutively active without induction by IPTG. This trp-lac promoter can be placed in front of any gene or operon of interest for expression in Pseudomonas or any other closely related bacterium for the purposes of the constitutive expression of such a gene. If the operon of interest contains the information for the biosynthesis of an APS, then an otherwise biocontrol-minus strain of a gram-negative bacterium may be able to protect plants against a variety of fungal diseases. Thus, genes for antifungal compounds can therefore be placed behind a strong constitutive promoter, transferred to a bacterium that normally does not produce antifungal products and which has plant or rhizosphere colonizing properties turning these organisms into effective biocontrol strains. Other possible promoters can be used for the constitutive expression of APS genes in gram-negative bacteria. These include, for example, the promoter from the Pseudomonas regulatory genes gafA and lemA (WO 94/01561) and the *Pseudomonas savastanoi* IAA operon promoter (Gaffney et al., J. Bacteriol. 172: 5593–5601 (1990).

U.S. patent application Ser. No. 08/977,306, incorporated herein by reference, describes the following genetically engineered biocontrol strains of Pseudomonas that are able to effectively control pathogenic attack on crop plants: CGA376146, CGA364473, CGA375258, CGA376148, CGA364476, CGA375260, CGA375259, CGA378584, CGA267pPhz, CGA364474, CGA364475, CGA366259, CGA376150, NOA402208, NOA402212, NOA402214, NOA402216, CGA267356/Phl, NOA409068, NOA413174, NOA413175, NOA413176, NOA413177, and NOA413178. These biocontrol strains produce at least one antifungal substance that is capable of inhibiting a broad spectrum of plant pathogens such as Rhizoctonia and Pythium. In particular, the biocontrol strains of the invention produce enhanced quantities of pyrrolnitrin, giving the strains increased biocontrol properties.

Another genetically engineered biocontrol strain of Pseudomonas with enhanced biocontrol properties is strain CGA313167. CGA313167 consists of parent strain CGA267356 (U.S. Pat. No. 5,348,742) containing a plasmid that consists of the broad-host range plasmid pRK290 with the 11 kb EcoRI fragment derived from the chromosome of strain CGA267356 that contains the native gafA gene (U.S. Pat. No. 5,710,031). Strain CGA313167 produces about 2.5-fold more pyrrolnitrin than the parent strain and is more active in biocontrol assays.

Example 28

Expression of APS Biosynthetic Genes in Gram-Positive Bacteria

Heterologous expression of genes encoding APS genes in gram-positive bacteria is another means of producing new biocontrol strains. Expression systems for Bacillus and Streptomyces are the best characterized. The promoter for the erythromycin resistance gene (ermR) from *Streptococcus pneumoniae* has been shown to be active in gram-positive aerobes and anaerobes and also in *E. coli* (Trieu-Cuot et al., Nucl Acids Res 18: 3660 (1990)). A further antibiotic resistance promoter from the thiostreptone gene has been used in Streptomyces cloning vectors (Bibb, Mol Gen Genet 199: 26–36 (1985)). The shuttle vector pHT3101 is also appropriate for expression in Bacillus (Lereclus, FEMS Microbiol Lett 60: 211–218 (1989)). By expressing an operon (such as the pyrrolnitrin operon) or individual APS encoding egens under control of the ermR or other promoters it will be possible to convert soil bacilli into strains able to protect plants against microbial diseases. A significant advantage of this approach is that many gram-positive bacteria produce spores which can be used in formulations that produce biocontrol products with a longer shelf life. Bacillus and Streptomyces species are aggressive colonizers of soils. In fact both produce secondary metabolites including antibiotics active against a broad range of organisms and the addition of heterologous antifungal genes including (including those encoding pyrrolnitrin, soraphen, phenazine or cyclic peptides) to gram-positive bacteria may make these organisms even better biocontrol strains.

Example 29

Expression of APS Biosynthetic Genes in Fungi

*Trichoderma harzianum* and *Gliocladium virens* have been shown to provide varying levels of biocontrol in the field (U.S. Pat. No. 5,165,928 and U.S. Pat. No. 4,996,157, both to Cornell Research Foundation). The successful use of these biocontrol agents will be greatly enhanced by the development of improved strains by the introduction of genes for APSs. This could be accomplished by a number of ways which are well known in the art. One is protoplast mediated transformation of the fungus by PEG or electroporation-mediated techniques. Alternatively, particle bombardment can be used to transform protoplasts or other fungal cells with the ability to develop into regenerated mature structures. The vector pAN7-1, originally developed for Aspergillus transformation and now used widely for fungal transformation (Curragh et al., *Mycol. Res.* 97(3): 313–317 (1992); Tooley et al., *Curr. Genet.* 21: 55–60 (1992); Punt et al., Gene 56: 117–124 (1987)) is engineered to contain the pyrrolnitrin operon, or any other genes for APS biosynthesis. This plasmid contains the *E. coli* the hygromycin B resistance gene flanked by the *Aspergillus nidulans* gpd promoter and the trpC terminator (Punt et al., Gene 56: 117–124 (1987)).

J. In Vitro Activity of Anti-phytopathogenic Substances Against Plant Pathogens

Example 30

Bioassay Procedures for the Detection of Antifungal Activity

Inhibition of fungal growth by a potential antifungal agent can be determined in a number of assay formats. Macroscopic methods which are commonly used include the agar diffusion assay (Dhingra & Sinclair, Basic Plant Pathology Methods, CRC Press, Boca Raton, Fla. (1985)) and assays in liquid media (Broekaert et al., FEMS Microbiol. Lett. 69: 55–60.(1990)). Both types of assay are performed with either fungal spores or mycelia as inocula. The maintenance of fungal stocks is in accordance with standard mycological procedures. Spores for bioassay are harvested from a mature plate of a fungus by flushing the surface of the culture with sterile water or buffer. A suspension of mycelia is prepared by placing fungus from a plate in a blender and homogenizing until the colony is dispersed. The homogenate is filtered through several layers of cheesecloth so that larger particles are excluded. The suspension which passes through the cheesecloth is washed by centrifugation and replacing the supernatant with fresh buffer. The concentration of the mycelial suspension is adjusted empirically, by testing the suspension in the bioassay to be used.

Agar diffusion assays may be performed by suspending spores or mycelial fragments in a solid test medium, and applying the antifungal agent at a point source, from which it diffuses. This may be done by adding spores or mycelia to melted fungal growth medium, then pouring the mixture into a sterile dish and allowing it to gel. Sterile filters are placed on the surface of the medium, and solutions of antifungal agents are spotted onto the filters. After the liquid has been absorbed by the filter, the plates are incubated at the appropriate temperature, usually for 1–2 days. Growth inhibition is indicated by the presence of zones around filters in which spores have not germinated, or in which mycelia have not grown. The antifungal potency of the agent, denoted as the minimal effective dose, may be quantified by spotting serial dilutions of the agent onto filters, and determining the lowest dose which gives an observable inhibition zone. Another agar diffusion assay can be performed by cutting wells into solidified fungal growth medium and placing solutions of antifungal agents into them. The plate is inoculated at a point equidistant from all the wells, usually at the center of the plate, with either a small aliquot of spore or mycelial suspension or a mycelial plug cut directly from a stock culture plate of the fungus. The plate is incubated for several days until the growing mycelia approach the wells, then it is observed for signs of growth inhibition. Inhibition is indicated by the deformation of the roughly circular form which the fungal colony normally assumes as it grows. Specifically, if the mycelial front appears flattened or even concave relative to the uninhibited sections of the plate, growth inhibition has occurred. A minimal effective concentration may be determined by testing diluted solutions of the agent to find the lowest at which an effect can be detected.

Bioassays in liquid media are conducted using suspensions of spores or mycelia which are incubated in liquid fungal growth media instead of solid media. The fungal inocula, medium, and antifungal agent are mixed in wells of a 96-well microtiter plate, and the growth of the fungus is followed by measuring the turbidity of the culture spectrophotometrically. Increases in turbidity correlate with increases in biomass, and are a measure of fungal growth. Growth inhibition is determined by comparing the growth of the fungus in the presence of the antifungal agent with growth in its absence. By testing diluted solutions of antifungal inhibitor, a minimal inhibitory concentration or an $EC_{50}$ may be determined.

Example 31

Bioassay Procedures for the Detection of Antibacterial Activity

A number of bioassays may be employed to determine the antibacterial activity of an unknown compound. The inhibition of bacterial growth in solid media may be assessed by dispersing an inoculum of the bacterial culture in melted medium and spreading the suspension evenly in the bottom of a sterile Petri dish. After the medium has gelled, sterile filter disks are placed on the surface, and aliquots of the test material are spotted onto them. The plate is incubated overnight at an appropriate temperature, and growth inhibition is observed as an area around a filter in which the bacteria have not grown, or in which the growth is reduced compared to the surrounding areas. Pure compounds may be characterized by the determination of a minimal effective dose, the smallest amount of material which gives a zone of inhibited growth. In liquid media, two other methods may be employed. The growth of a culture may be monitored by measuring the optical density of the culture, in actuality the scattering of incident light. Equal inocula are seeded into equal culture volumes, with one culture containing a known amount of a potential antibacterial agent. After incubation at an appropriate temperature, and with appropriate aeration as required by the bacterium being tested, the optical densities of the cultures are compared. A suitable wavelength for the comparison is 600 nm. The antibacterial agent may be characterized by the determination of a minimal effective dose, the smallest amount of material which produces a reduction in the density of the culture, or by determining an $EC_{50}$, the concentration at which the growth of the test culture is half that of the control. The bioassays described above do not differentiate between bacteriostatic and bacteriocidal effects. Another assay can be performed which will determine the bacteriocidal activity of the agent. This assay is carried out by incubating the bacteria and the active agent together in liquid medium for an amount of time and under conditions which are sufficient for the agent to exert its effect. After this incubation is completed, the bacteria may be either washed by centrifugation and resuspension, or diluted by the addition of fresh medium. In either case, the concentration of the antibacterial agent is reduced to a point at which it is no longer expected to have significant activity. The bacteria are plated and spread on solid medium and the plates are incubated overnight at an appropriate temperature for growth. The number of colonies which arise on the plates are counted, and the number which appeared from the mixture which contained the antibacterial agent is compared with the number which arose from the mixture which contained no antibacterial agent. The reduction in colony-forming units is a measure of the bacteriocidal activity of the agent. The bacteriocidal activity may be quantified as a minimal effective dose, or as an $EC_{50}$, as described above. Bacteria which are used in assays such as these include species of Agrobacterium, Erwinia, Clavibacter, Xanthomonas, and Pseudomonas.

Example 32

Antipathogenic Activity Determination of APSs

APSs are assayed using the procedures of examples 30 and 31 above to identify the range of fungi and bacteria against which they are active. The APS can be isolated from the cells and culture medium of the host organism normally producing it, or can alternatively be isolated from a heterologous host which has been engineered to produce the APS. A further possibility is the chemical synthesis of APS compounds of known chemical structure, or derivatives thereof.

Example 33

Antimicriobial Activity Determination of Pyrrolnitrin

The anti-phytopathogenic activity of a fluorinated 3-cyano-derivative of pyrrolnitrin (designated CGA173506) was observed against the maize fungal phytopathgens *Diplodia maydis, Colletotrichum graminicola,* and *Gibberella zeae-maydis.* Spores of the fungi were harvested and suspended in water. Approximately 1000 spores were inoculated into potato dextrose broth and either CGA173506 or water in a total volume of 100 microliters in the wells of 96-well microtiter plates suitable for a plate reader. The compound CGA173506 was obtained as a 50% wettable powder, and a stock suspension was made up at a concentration of 10 mg/ml in sterile water. This stock suspension was diluted with sterile water to provide the 173506 used in the tests. After the spores, medium, and 173506 were mixed, the turbidity in the wells was measured by reading the absorbance at 600 nm in a plate reader. This reading was taken as the background turbidity, and was subtracted from readings taken at later times. After 46 hours of incubation, the presence of 1 microgram/ml of 173506 was determined to reduce the growth of *Diplodia maydis* by 64%, and after 120 hours, the same concentration of 173506 inhibited the growth of *Colletotrichum graminicola* by 50%. After 40 hours of incubation, the presence of 0.5 microgram/ml of 173506 gave 100% inhibition of *Gibberella zeae-maydis.*

K. Expression of Antibiotic Biosynthetic Genes in Transgenic Plants

Example 34

Modification of Coding Sequences and Adjacent Sequences

The isolated APS biosynthetic genes described in this application can be modified for expression in transgenic plant hosts. This is done with the aim of producing extractable quantities of APS from transgenic plants (i.e. for similar reasons to those described in Section E above), or alternatively the aim of such expression can be the accumulation of APS in plant tissue for the provision of pathogen protection on host plants. A host plant expressing genes for the biosynthesis of an APS and which produces the APS in its cells will have enhanced resistance to phytopathogen attack and will be thus better equipped to withstand crop losses associated with such attack.

The transgenic expression in plants of genes derived from microbial sources may require the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence will not be required. It is sufficient to isolate a fragment containing the ORF of interest and to insert it downstream of a plant promoter. For example, Gaffney et al. (Science 261: 754–756 (1993)) have expressed the Pseudomonas nahG gene in transgenic plants under the control of the CaMV 35S promoter and the CaMV tml terminator successfully without modification of the coding sequence and with x bp of the Pseudomonas gene upstream of the ATG still attached, and y bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as Bacillus. These problems may apply to the APS biosynthetic genes of this invention and the modification of these genes can be undertaken using techniques now well known in the art. The following problems may be encountered:

(1) Codon Usage.

The preferred codon usage in plants differs from the preferred codon usage in certain microorganisms. Comparison of the usage of codons within a isolated microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

(2) GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

(3) Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210) have suggested the sequence GTCGACCATGGTC (SEQ ID NO:7) as a consensus translation initiator for the expression of the *E. coli* uidA gene in plants. Further, Joshi (NAR 15: 6643–6653 (1987)) has compared many plant sequences adjacent to the ATG and suggests the consensus TAAACA ATGGCT (SEQ ID NO:8). In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | | |
|---|---|---|---|---|---|---|---|---|---|---|
| | −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which APS genes are being incorporated, and the sequence adjacent to the ATG modified to incorporate the preferred nucleotides.

(4) Removal of Illegitimate Splice Sites.

Genes isolated from non-plant sources and not optimized for expression in plants may also contain motifs which may be recognized in plants as 5' or 3' splice sites, and be cleaved, thus generating truncated or deleted messages. These sites can be removed using the techniques described in pending application Ser. No. 07/961,944, hereby incorporated by reference.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy). In most cases it is preferable to assay the expression of gene constructions using transient assay protocols (which are well known in the art) prior to their transfer to transgenic plants.

Example 35

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, Gene 19: 259–268 (1982); Bevan et al., Nature 304:184–187 (1983)), the bar gene which confers resistance to the herbicide phosphinothricin (White et al., Nucl Acids Res 18: 1062 (1990), Spencer et al. Theor Appl Genet 79: 625–631(1990)), the hph gene which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)).

(1) Construction of Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below the construction of two typical vectors is described.

Construction of pCIB200 and pCIB2001

The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, J Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et al., Plant Molecular Biology 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., Gene 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between E. coli and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof

The binary vector pCIB10 contains a gene encoding kanamycin resistance for selection in plants, T-DNA right and left border sequences and incorporates sequences from the wide host-range plasmid pRK252 allowing it to replicate in both E. coli and Agrobacterium. Its construction is described by Rothstein et al. (Gene 53: 153–161 (1987)). Various derivatives of pCIB10 have been constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

(2) Construction of Vectors Suitable for non-Agrobacterium Transformation

Transformation without the use of Agrobacterium tumefaciens circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the E. coli GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from Streptomyces viridochromogenes was excised and inserted into the HpaI site of pCIB3060 (Thompson et al. EMBO J 6: 2519–2523 (1987)). This generated pCIB3064 which comprises the bar gene under the control of the CaMV 35S promoter and terminator for herbicide selection, a gene fro ampicillin resistance (for selection in E. coli) and a polylinker with the unique sites SphI, PstI, HindIII, and BamHI. This vector is suitable for the cloning of plant expression cassettes containing their own regulatory signals.

Construction of pSOG19 and pSOG35 pSOG35 is a transformation vector which utilizes the E. coli gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the E. coli dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Example 36

Requirements for Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above in example B.

Promoter Selection

The selection of promoter used in expression cassettes will determine the spatial and temporal expression pattern of the transgene in the transgenic plant. Selected promoters will express transgenes in specific cell types (such as leaf epidermal cells, meosphyll cells, root cortex cells) or in specific tissues or organs (roots, leaves or flowers, for example) and this selection will reflect the desired location of biosynthesis of the APS. Alternatively, the selected promoter may drive expression of the gene under a light-induced or other temporally regulated promoter. A further alternative is that the selected promoter be chemically regulated. This would provide the possibility of inducing the induction of the APS only when desired and caused by treatment with a chemical inducer.

Transcriptional Terminators

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase terminator, the pea rbcS E9 terminator. These can be used in both monocoylyedons and dicotyledons.

Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adhl gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develep 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15; 65–79 (1990))

Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the aminoterminal end of various proteins and which is cleaved during chloroplast import yielding the mature protein (e.g. Comai et al. J. Biol. Chem. 263: 15104–15109 (1988)). These signal sequences can be fused to heterologous gene products to effect the import of heterologous products into the chloroplast (van den Broeck et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al. (Proc. Natl. Acad. Sci. USA 82: 6512–6516 (1985)).

In addition sequences have been characterized which cause the targeting of gene products to other cell compartments. Aminoterminal sequences are responsible for targeting to the ER, the apoplast, and extracellular secretion from aleurone cells (Koehler & Ho, Plant Cell 2: 769–783 (1990)). Additionally, aminoterminal sequences in conjunction with carboxyterminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the aminoterminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gen. Genet. 205: 446–453 (1986)). These construction techniques are well known in the art and are equally applicable to mitochondria and peroxisomes. The choice of targeting which may be required for APS biosynthetic genes will depend on the cellular localization of the precursor required as the starting point for a given pathway. This will usually be cytosolic or chloroplastic, although it may is some cases be mitochondrial or peroxisomal. The gene products of APS biosynthetic genes will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

Example 37

Examples of Expression Cassette Construction

The present invention encompasses the expression of genes encoding APSs under the regulation of any promoter which is expressible in plants, regardless of the origin of the promoter.

Furthermore, the invention encompasses the use of any plant-expressible promoter in conjunction with any further sequences required or selected for the expression of the APS gene. Such sequences include, but are not restricted to, transcriptional terminators, extraneous sequences to enhance expression (such as introns [e.g. Adh intron 1], viral sequences [e. g. TMV-Ω]), and sequences intended for the targeting of the gene product to specific organelles and cell compartments.

Constitutive Expression: the CaMV 35S Promoter

Construction of the plasmid pCGN1761 is described in the published patent application EP 0 392 225 (example 23). pCGN1761 contains the "double" 35S promoter and the tml transcriptional terminator with a unique EcoRI site between the promoter and the terminator and has a pUC-type backbone. A derivative of pCGN1761 was constructed which has a modified polylinker which includes NotI and XhoI sites in addition to the existing EcoRI site. This derivative was designated pCGN1761ENX. pCGN1761ENX is useful for the cloning of cDNA sequences or gene sequences (including microbial ORF sequences) within its polylinker for the purposes of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglI sites 3' to the terminator for transfer to transformation vectors such as those described above in example 35. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter.

Modification of pCGN1761ENX by Optimization of the Translational Initiation Site For any of the constructions described in this section, modifications around the cloning sites can be made by the introduction of sequences which may enhance translation. This is particularly useful when genes derived from microorganisms are to be introduced into plant expression cassettes as these genes may not contain sequences adjacent to their initiating methionine which may be suitable for the initiation of translation in plants. In cases where genes derived from microorganisms are to be cloned into plant expression cassettes at their ATG it may be useful to modify the site of their insertion to optimize their expression. Modification of pCGN1761ENX is described by way of example to incorporate one of several optimized sequences for plant expression (e.g. Joshi, supra).

pCGN1761ENX is cleaved with SphI, treated with T4 DNA polymerase and religated, thus destroying the SphI site located 5' to the double 35S promoter. This generates vector pCGN1761ENX/Sph-. pCGN1761ENX/Sph- is cleaved with EcoRI, and ligated to an annealed molecular adaptor of the sequence 5'-AATTCTAAAGCATGCCGATCGG-3' (SEQ ID NO:9)/5'-AATTCCGATCGGCATGCTTTA-3' (SEQ ID NO:10). This generates the vector pCGNSENX which incorporates the quasi-optimized plant translational initiation sequence TAAA-C adjacent to the ATG which is itself part of an SphI site which is suitable for cloning heterologous genes at their initiating methionine. Downstream of the SphI site, the EcoRI, NotI, and XhoI sites are retained.

An alternative vector is constructed which utilizes an NcoI site at the initiating ATG. This vector, designated pCGN1761NENX is made by inserting an annealed molecular adaptor of the sequence 5'-AATTCTAAACCATGGCGATCGG-3' (SEQ ID NO:11)/5'AATTCCGATCGCCATGGTTTA-3' (SEQ ID NO:12) at the pCGN1761ENX EcoRI site (Sequence ID's 14 & 15). Thus, the vector includes the quasi-optimized sequence TAAACC adjacent to the initiating ATG which is within the NcoI site. Downstream sites are EcoRI, NotI, and XhoI. Prior to this manipulation, however, the two NcoI sites in the pCGN1761ENX vector (at upstream positions of the 5' 35S promoter unit) are destroyed using similar techniques to those described above for SphI or alternatively using "inside-outside" PCR (Innes et al. PCR Protocols: A guide to methods and applications. Academic Press, New York (1990); see Example 41). This manipulation can be assayed for any possible detrimental effect on expression by insertion of any plant cDNA or reporter gene sequence into the cloning site followed by routine expression analysis in plants.

Expression under a Chemically Regulatable Promoter

This section describes the replacement of the double 35S promoter in pCGN1761ENX with any promoter of choice; by way of example the chemically regulated PR-1a promoter is described. The promoter of choice is preferably excised from its source by restriction enzymes, but can alternatively be PCR-amplified using primers which carry appropriate terminal restriction sites. Should PCR-amplification be undertaken, then the promoter should be resequenced to check for amplification errors after the cloning of the amplified promoter in the target vector. The chemically regulatable tobacco PR-1a promoter is cleaved from plasmid pCIB1004 (see EP 0 332 104, example 21 for construction) and transferred to plasmid pCGN1761ENX. pCIB1004 is cleaved with NcoI and the resultant 3' overhang of the linearized fragment is rendered blunt by treatment with T4 DNA polymerase. The fragment is then cleaved with HindIII and the resultant PR-1a promoter containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. Selected APS genes can be inserted into this vector, and the fusion products (i.e. promoter-gene-terminator) can subsequently be transferred to any selected transformation vector, including those described in this application.

Constitutive Expression: the Actin Promoter

Several isoforms of actin are known to be expressed in most cell types and consequently the actin promoter is a good choice for a constitutive promoter. In particular, the promoter from the rice Act1 gene has been isolated and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the Act1 promoter have been constructed specifically for use in monocotyledons (McElroy et al. Mol. Gen. Genet. 231: 150–160 (1991)). These incorporate the Act1-intron 1, Adh1 5' flanking sequence and Adh1-intron 1 (from the maize alcohol dehydrogenase gene) and sequence from the CaMV 35S promoter. Vectors showing highest expression were fusions of 35S and the Act1 intron or the Act1 5' flanking sequence and the Act1 intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for the expression of APS biosynthetic genes and are particularly suitable for use in monocotyledonous hosts. For example, promoter containing fragments can be removed from the McElroy constructions and used to replace the double 35S promoter in pCGN1761ENX, which is then available for the insertion or specific gene sequences. The fusion genes thus constructed can then be transferred to appropriate transformation vectors. In a separate report the rice Act1 promoter with its first intron has also been found to direct high expression in cultured barley cells (Chibbar et al. Plant Cell Rep. 12: 506–509 (1993)).

Constitutive Expression: the Ubiquitin Promoter

Ubiquitin is another gene product known to accumulate in many call types and its promoter has been isolated from several species for use in transgenic plants (e.g. sunflower—Binet et al. Plant Science 79: 87–94 (1991), maize—Christensen et al. Plant Molec. Biol. 12: 619–632 (1989)). The maize ubiquitin promoter has been developed in transgenic monocot systems and its sequence and vectors constructed for monocot transformation are disclosed in the patent publication EP 0 342 926 (to Lubrizol). Further, Taylor et al. (Plant Cell Rep. 12: 491–495 (1993)) describe a vector (pAHC25) which comprises the maize ubiquitin promoter and first intron and its high activity in cell suspensions of numerous monocotyledons when introduced via microprojectile bombardment. The ubiquitin promoter is clearly suitable for the expression of APS biosynthetic genes in transgenic plants, especially monocotyledons. Suitable vectors are derivatives of pAHC25 or any of the transformation vectors described in this application, modified by the introduction of the appropriate ubiquitin promoter and/or intron sequences.

Root Specific Expression

A preferred pattern of expression for the APSs of the instant invention is root expression. Root expression is particularly useful for the control of soil-borne phytopathogens such as Rhizoctonia and Pythium. Expression of APSs only in root tissue would have the advantage of controlling root invading phytopathogens, without a concomitant accumulation of APS in leaf and flower tissue and seeds. A suitable root promoter is that described by de Framond (FEBS 290: 103–106 (1991)) and also in the published patent application EP 0 452 269 (to Ciba-Geigy). This promoter is transferred to a suitable vector such as pCGN1761ENX for the insertion of an APS gene of interest and subsequent transfer of the entire promoter-gene-terminator cassette to a transformation vector of interest.

Wound Inducible Promoters

Wound-inducible promoters are particularly suitable for the expression of APS biosynthetic genes because they are typically active not just on wound induction, but also at the sites of phytopathogen infection. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. (supra) describe the 5' upstream sequences of the dicotyledonous potato wun1 gene. Xu et al. (supra) show that a wound inducible promoter from the dicotyledon potato (pin2) is active in the monocotyledon rice. Further, Rohrmeier & Lehle (supra) describe the cloning of the maize Wip1 cDNA which is wound induced and which can be used to isolated the cognate promoter using standard techniques. Similarly, Firek et al. (supra) and Warner et al. (supra) have described a wound induced gene from the monocotyledon *Asparagus officinalis* which is expressed at local wound and pathogen invasion sites. Using cloning techniques well known in the art, these promoters can be transferred to suitable vectors, fused to the APS biosynthetic genes of this invention, and used to express these genes at the sites of phytopathogen infection.

Pith Preferred Expression

Patent Application WO 93/07278 (to Ciba-Geigy) describes the isolation of the maize trpA gene which is preferentially expressed in pith cells. The gene sequence and promoter extend up to –1726 from the start of transcription are presented. Using standard molecular biological techniques, this promoter or parts thereof, can be transferred to a vector such as pCGN1761 where it can replace the 35S promoter and be used to drive the expression of a foreign gene in a pith-preferred manner. In fact fragments containing the pith-preferred promoter or parts thereof can be transferred to any vector and modified for utility in transgenic plants.

Pollen-Specific Expression

Patent Application WO 93/07278 (to Ciba-Geigy) further describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a foreign gene in a pollen-specific manner. In fact fragments containing the pollen-specific promoter or parts thereof can be transferred to any vector and modified for utility in transgenic plants.

Leaf-Specific Expression

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

Expression with Chloroplast Targeting

Chen & Jagendorf (J. Biol. Chem. 268: 2363–2367 (1993) have described the successful use of a chloroplast transit peptide for import of a heterologous transgene. This peptide used is the transit peptide from the rbcS gene from *Nicotiana plumbaginifolia* (Poulsen et al. Mol. Gen. Genet. 205: 193–200 (1986)). Using the restriction enzymes DraI and SphI, or Tsp509I and SphI the DNA sequence encoding this transit peptide can be excised from plasmid prbcS-8B (Poulsen et al. supra) and manipulated for use with any of the constructions described above. The DraI-SphI fragment extends from –58 relative to the initiating rbcS ATG to, and including, the first amino acid (also a methionine) of the mature peptide immediately after the import cleavage site, whereas the Tsp509I-SphI fragment extends from –8 relative to the initiating rbcS ATG to, and including, the first amino acid of the mature peptide. Thus, these fragment can be appropriately inserted into the polylinker of any chosen expression cassette generating a transcriptional fusion to the untranslated leader of the chosen promoter (e.g. 35S, PR-1a, actin, ubiquitin etc.), whilst enabling the insertion of a required APS gene in correct fusion downstream of the transit peptide. Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected APS gene. Ideally the ATG of the SphI site is maintained and comprises the first ATG of the selected APS gene. Chen & Jagendorf (supra) provide consensus sequences for ideal cleavage for chloroplast import, and in each case a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al. (Eds.) Methods in Chloroplast Molecular Biology, Elsevier. pp 1081–1091 (1982)) and Wasmann et al. (Mol. Gen. Genet. 205: 446–453 (1986)). Typically the best approach may be to generate fusions using the selected APS gene with no modifications at the aminoterminus, and only to incorporate modifications when it is apparent that such fusions are not chloroplast imported at high efficiency, in which case modifications may be made in accordance with the established literature (Chen & Jagendorf, supra; Wasman et al., supra; Ko & Ko, J. Biol. Chem. 267: 13910–13916(1992)).

A preferred vector is constructed by transferring the DraI-SphI transit peptide encoding fragment from prbcS-8B to the cloning vector pCGN1761ENX/Sph-. This plasmid is cleaved with EcoRI and the termini rendered blunt by treatment with T4 DNA polymerase. Plasmid prbcS-8B is cleaved with SphI and ligated to an annealed molecular adaptor of the sequence 5'-CCAGCTGGAATTCCG-3' (SEQ ID NO:13)/5'-CGGAATTCCAGCTGGCATG-3' (SEQ ID NO:14). The resultant product is 5'-terminally phosphorylated by treatment with T4 kinase. Subsequent cleavage with DraI releases the transit peptide encoding fragment which is ligated into the blunt-end ex-EcoRI sites of the modified vector described above. Clones oriented with the 5' end of the insert adjacent to the 3' end of the 35S promoter are identified by sequencing. These clones carry a DNA fusion of the 35S leader sequence to the rbcS-8A promoter-transit peptide sequence extending from –58 relative to the rbcS ATG to the ATG of the mature protein, and including at that position a unique SphI site, and a newly created EcoRI site, as well as the existing NotI and XhoI sites of pCGN1761ENX. This new vector is designated pCGN1761/CT. DNA sequences are transferred to pCGN1761/CT in frame by amplification using PCR techniques and incorporation of an SphI, NsphI, or NlaIII site at the amplified ATG, which following restriction enzyme cleavage with the appropriate enzyme is ligated into SphI-cleaved pCGN1761/CT. To facilitate construction, it may be required to change the second amino acid of an isolated gene, however, in almost all cases the use of PCR together with standard site directed mutagenesis will enable the construction of any desired sequence around the cleavage site and first methionine of the mature protein.

A further preferred vector is constructed by replacing the double 35S promoter of pCGN1761ENX with the BamHI-SphI fragment of prbcS-8A which contains the full-length light regulated rbcS-8A promoter from –1038 (relative to the transcriptional start site) up to the first methionine of the mature protein. The modified pCGN1761 with the destroyed SphI site is cleaved with PstI and EcoRI and treated with T4 DNA polymerase to render termini blunt. prbcS-8A is cleaved SphI and ligated to the annealed molecular adaptor of the sequence described above. The resultant product is 5'-terminally phosphorylated by treatment with T4 kinase. Subsequent cleavage with BamHI releases the promoter-transit peptide containing fragment which is treated with T4 DNA polymerase to render the BamHI terminus blunt. The promoter-transit peptide fragment thus generated is cloned into the prepared pCGN1761ENX vector, generating a construction comprising the rbcS-8A promoter and transit peptide with an SphI site located at the cleavage site for insertion of heterologous genes. Further, downstream of the SphI site there are EcoRI (re-created), NotI, and XhoI cloning sites. This construction is designated pCGN1761rbcS/CT.

Similar manipulations can be undertaken to utilize other GS2 chloroplast transit peptide encoding sequences from other sources (monocotyledonous and dicotyledonous) and from other genes. In addition, similar procedures can be followed to achieve targeting to other subcellular compartments such as mitochondria.

Example 38

Techniques for the Isolation of New Promoters Suitable for the Expression of APS Genes New promoters are isolated using standard molecular biological techniques including any of the techniques described below. Once isolated, they are fused to reporter genes such as GUS or LUC and their expression pattern in transgenic plants analyzed (Jefferson et al. EMBO J. 6: 3901–3907 (1987); Ow et al. Science 234: 856–859 (1986)). Promoters which show the desired expression pattern are fused to APS genes for expression in planta.

Subtractive cDNA Cloning

Subtractive cDNA cloning techniques are useful for the generation of cDNA libraries enriched for a particular population of mRNAs (e.g. Hara et al. Nucl. Acids Res. 19: 1097–7104 (1991)). Recently, techniques have been described which allow the construction of subtractive libraries from small amounts of tissue (Sharma et al. Biotechniques 15: 610–612 (1993)). These techniques are suitable for the enrichment of messages specific for tissues which may be available only in small amounts such as the tissue immediately adjacent to wound or pathogen infection sites.

Differential Screening by Standard Plus/Minus Techniques

λ phage carrying cDNAs derived from different RNA populations (viz. root versus whole plant, stem specific versus whole plant, local pathogen infection points versus whole plant, etc.) are plated at low density and transferred to two sets of hybridization filters (for a review of differential screening techniques see Calvet, Pediatr. Nephrol. 5: 751–757 (1991). cDNAs derived from the "choice" RNA population are hybridized to the first set and cDNAs from whole plant RNA are hybridized to the second set of filters. Plaques which hybridize to the first probe, but not to the second, are selected for further evaluation. They are picked and their cDNA used to screen Northern blots of "choice" RNA versus RNA from various other tissues and sources. Clones showing the required expression pattern are used to isolate gene sequences from a genomic library to enable the isolation of the cognate promoter. Between 500 and 5000 bp of the isolated promoter is then fused to a reporter gene (e.g. GUS, LUC) and reintroduced into transgenic plants for expression analysis.

Differential Screening by Differential Display

RNA is isolated from different sources i.e. the choice source and whole plants as control, and subjected to the differential display technique of Liang and Pardee (Science 257: 967–971 (1992)). Amplified fragments which appear in the choice RNA, but not the control are gel purified and used as probes on Northern blots carrying different RNA samples as described above. Fragments which hybridize selectively to the required RNA are isolated and used as probes to isolate the cDNA and also a genomic DNA fragment from which the promoter can be isolated. The isolated promoter is fused to a the GUS or LUC reporter gene as described above to assess its expression pattern in transgenic plants.

Promoter Isolation Using "Promoter Trap" Technology

The insertion of promoterless reporter genes into transgenic plants can be used to identify sequences in a host plant which drive expression in desired cell types or with a desired strength. Variations of this technique is described by Ott & Chua (Mol. Gen. Genet. 223: 169–179 (1990)) and Kertbundit et al. (Proc. Natl. Acad. Sci. USA 88: 5212–5216 (1991)). In standard transgenic experiments the same principle can be extended to identify enhancer elements in the host genome where a particular transgene may be expressed at particularly high levels.

Example 39

Transformation of Dicotyledons

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton [1313]), EP 0 249 432 (tomato, to Calgene), WO 87/07299 (Brassica, to Calgene), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using $E.$ $coli$ carrying the recombinant binary vector, a helper $E.$ $coli$ strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877(1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 40

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435 ([1280/1281] to Ciba-Geigy), EP 0 392 225 (to Ciba-Geigy) and WO 93/07278 (to Ciba-Geigy) describe techniques for the preparation of callus and protoplasts from an élite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, application WO 93/07278 (to Ciba-Geigy) and Koziel et al. (Biotechnology 11: 194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 2: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497

(1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. Patent application Ser. No. 08/147,161 describes methods for wheat transformation and is hereby incorporated by reference.

Example 41

Expression of Pyrrolnitrin in Transgenic Plants

The GC content of all four pyrrolnitrin ORFs is between 62 and 68% and consequently no AT-content related problems are anticipated with their expression in plants. It may, however, be advantageous to modify the genes to include codons preferred in the appropriate target plant species. Fusions of the kind described below can be made to any desired promoter with or without modification (e.g. for optimized translational initiation in plants or for enhanced expression).

Expression behind the 35S Promoter

Each of the four pyrrolnitrin ORFs is transferred to pBluescript KS II for further manipulation. This is done by PCR amplification using primers homologous to each end of each gene and which additionally include a restriction site to facilitate the transfer of the amplified fragments to the pBluescript vector. For ORF1, the aminoterminal primer includes a SalI site and the carboxyterminal primer a NotI site. Similarly for ORF2, the aminoterminal primer includes a SalI site and the carboxyterminal primer a NotI site. For ORF3, the aminoterminal primer includes a NotI site and the carboxyterminal primer an XhoI site. Similarly for ORF4, the aminoterminal primer includes a NotI site and the carboxyterminal primer an XhoI site. Thus, the amplified fragments are cleaved with the appropriate restriction enzymes (chosen because they do not cleave within the ORF) and are then ligated into pBluescript, also correspondingly cleaved. The cloning of the individual ORFs in pBluescript facilitates their subsequent manipulation.

Destruction of internal restriction sites which are required for further construction is undertaken using the procedure of "inside-outside PCR" (Innes et al. PCR Protocols: A guide to methods and applications. Academic Press, New York (1990)). Unique restriction sites sought at either side of the site to be destroyed (ideally between 100 and 500 bp from the site to be destroyed) and two separate amplifications are set up. One extends from the unique site left of the site to be destroyed and amplifies DNA up to the site to be destroyed with an amplifying oligonucleotide which spans this site and incorporates an appropriate base change. The second amplification extends from the site to be destroyed up to the unique site rightwards of the site to be destroyed. The oligonucleotide spanning the site to be destroyed in this second reaction incorporates the same base change as in the first amplification and ideally shares an overlap of between 10 and 25 nucleotides with the oligonucleotide from the first reaction. Thus the products of both reactions share an overlap which incorporates the same base change in the restriction site corresponding to that made in each amplification. Following the two amplifications, the amplified products are gel purified (to remove the four oligonucleotide primers used), mixed together and reamplified in a PCR reaction using the two primers spanning the unique restriction sites. In this final PCR reaction the overlap between the two amplified fragments provides the priming necessary for the first round of synthesis. The product of this reactions extends from the leftwards unique restriction site to the rightwards unique restriction site and includes the modified restriction site located internally. This product can be cleaved with the unique sites and inserted into the unmodified gene at the appropriate location by replacing the wild-type fragment.

To render ORF1 free of the first of its two internal SphI sites oligonucleotides spanning and homologous to the unique XmaI and EspI are designed. The XmaI oligonucleotide is used in a PCR reaction together with an oligonucleotide spanning the first SphI site and which includes the sequence . . . CCCCC<u>T</u>CATGC . . . (lower strand, SEQ ID NO:15), thus introducing a base change into to SphI site. A second PCR reaction utilizes an oligonucleotide spanning the SphI site (upper strand) incorporating the sequence . . . GCATG<u>A</u>GGGGG . . . (SEQ ID NO:16) and is used in combination with the EspI site-spanning oligonucleotide. The two products are gel purified and themselves amplified with the XmaI and EspI-spanning oligonucleotides and the resultant fragment is cleaved with XmaI and EspI and used to replace the native fragment in the ORF1 clone. According to the above description, the modified SphI site is GCATGA and does not cause a codon change. Other changes in this site are possible (i.e. changing the second nucleotide to a G, T, or A) without corrupting amino acid integrity.

A similar strategy is used to destroy the second SphI site in ORF1. In this case, EspI is a suitable leftwards-located restriction site, and the rightwards-located restriction site is PstI, located close to the 3' end of the gene or alternatively SstI which is not found in the ORF sequence, but immediately adjacent in the pBluescript polylinker. In this case an appropriate oligonucleotide is one which spans this site, or alternatively one of the available and pBluescript sequencing primers. This SphI site is modified to GAATGC or GCATGT or GAATGT. Each of these changes destroys the site without causing a codon change.

To render ORF2 free of its single SphI site a similar procedure is used. Leftward restriction sites are provided by PstI or MluI, and a suitable rightwards restriction site is provided by SstI in the pBluescript polylinker. In this case the site is changed to GCTTGC, GCATGC or GCTTGT; these changes maintain amino acid integrity.

ORF3 has no internal SphI sites.

In the case of ORF4, PstI provides a suitable rightwards unique site, but there is no suitable site located leftwards of the single SphI site to be changed. In this case a restriction site in the pBluescript polylinker can be used to the same effect as already described above. The SphI site is modified to GGATGC, GTATGC, GAATGC, or GCATGT etc.

The removal of SphI sites from the pyrrolnitrin biosynthetic genes as described above facilitates their transfer to the pCGN1761SENX vector by amplification using an aminoterminal oligonucleotide primer which incorporates an SphI site at the ATG and a carboxyterminal primer which incorporates a restriction site not found in the gene being amplified. The resultant amplified fragment is cleaved with SphI and the carboxyterminal enzyme and cloned into pCGN1761SENX. Suitable restriction enzyme sites for incorporation into the carboxyterminal primer are NotI (for all four ORFs), XhoI (for ORF3 and ORF4), and EcoRI (for ORF4). Given the requirement for the nucleotide C at position 6 within the SphI recognition site, in some cases the second codon of the ORF may require changing so as to start with the nucleotide C. This construction fuses each ORF at its ATG to the SphI sites of the translation-optimized vector pCGN1761SENX in operable linkage to the double 35S promoter. After construction is complete the final gene insertions and fusion points are resequenced to ensure that no undesired base changes have occurred.

By utilizing an aminoterminal oligonucleotide primer which incorporates an NcoI site at its ATG instead of an SphI site, ORFs 1–4 can also be easily cloned into to the translation-optimized vector pCGN1761NENX. None of the four pyrrolnitrin biosynthetic gene ORFs carry an NcoI site and consequently there is no requirement in this case to destroy internal restriction sites. Primers for the carboxyterminus of the gene are designed as described above and the cloning is undertaken in a similar fashion. Given the requirement for the nucleotide G at position 6 within the NcoI recognition site, in some cases the second codon of the ORF may require changing so as to start with the nucleotide G. This construction fuses each ORF at its ATG to the NcoI site of pCGN1761NENX in operable linkage to the double 35S promoter.

The expression cassettes of the appropriate pCGN1761-derivative vectors are transferred to transformation vectors. Where possible multiple expression cassettes are transferred to a single transformation vector so as to reduce the number of plant transformations and crosses between transformants which may be required to produce plants expressing all four ORFs and thus producing pyrrolnitrin.

Expression behind 35S with Chloroplast Targeting

The pyrrolnitrin ORFs 1–4 amplified using oligonucleotides carrying an SphI site at their aminoterminus are cloned into the 35S-chloroplast targeted vector pCGN1761/CT. The fusions are made to the SphI site located at the cleavage site of the rbcS transit peptide. The expression cassettes thus created are transferred to appropriate transformation vectors (see above) and used to generate transgenic plants. As tryptophan, the precursor for pyrrolnitrin biosynthesis, is synthesized in the chloroplast, it may be advantageous to express the biosynthetic genes for pyrrolnitrin in the chloroplast to ensure a ready supply of substrate. Transgenic plants expressing all four ORFs will target all four gene products to the chloroplast and will thus synthesize pyrrolnitrin in the chloroplast.

Expression behind rbcS with Chloroplast Targeting

The pyrrolnitrin ORFs 1–4 amplified using oligonucleotides carrying an SphI site at their aminoterminus are cloned into the rbcS-chloroplast targeted vector pCGN1761rbcS/CT. The fusions are made to the SphI site located at the cleavage site of the rbcS transit peptide. The expression cassettes thus created are transferred to appropriate transformation vectors (see above) and used to generate transgenic plants. As tryptophan, the precursor for pyrrolnitrin biosynthesis, is synthesized in the chloroplast, it may be advantageous to express the biosynthetic genes for pyrrolnitrin in the chloroplast to ensure a ready supply of substrate. Transgenic plants expressing all four ORFs will target all four gene products to the chloroplast and will thus synthesize pyrrolnitrin in the chloroplast. The expression of the four ORFs will, however, be light induced.

Example 42

Expression of Soraphen in Transgenic Plants

Clone p98/1 contains the entirety of the soraphen biosynthetic gene ORF1 which encodes five biosynthetic modules for soraphen biosynthesis. The partially sequenced ORF2 contains the remaining three modules, and further required for soraphen biosynthesis is the soraphen methylase located on the same operon.

Soraphen ORF1 is manipulated for expression in transgenic plants in the following manner. A DNA fragment is amplified from the aminoterminus of ORF1 using PCR and p98/1 as template. The 5' oligonucleotide primer includes either an SphI site or an NcoI site at the ATG for cloning into the vectors pCGN1761SENX or pCGNNENX respectively. Further, the 5' oligonucleotide includes either the base C (for SphI cloning) or the base G (for NcoI cloning) immediately after the ATG, and thus the second amino acid of the protein is changed either to a histidine or an aspartate (other amino acids can be selected for position 2 by additionally changing other bases of the second codon). The 3' oligonucleotide for the amplification is located at the first BglII site of the ORF and incorporates a distal EcoRI site enabling the amplified fragment to be cleaved with SphI (or NcoI) and EcoRI, and then cloned into pCGN1761SENX (or pCGN1761NENX). To facilitate cleavage of the amplified fragments, each oligonucleotide includes several additional bases at its 5' end. The oligonucleotides preferably have 12–30 bp homology to the ORF1 template, in addition to the required restriction sites and additional sequences. This manipulation fuses the aminoterminal ~112 amino acids of ORF1 at its ATG to the SphI or NcoI sites of the translation optimized vectors pCGN1761SENX or pCGN1761NENX in linkage to the double 35S promoter. The remainder of ORF1 is carried on three BglII fragments which can be sequentially cloned into the unique BglII site of the above-detailed constructions. The introduction of the first of these fragments is no problem, and requires only the cleavage of the aminoterminal construction with BglII followed by introduction of the first of these fragments. For the introduction of the two remaining fragments, partial digestion of the aminoterminal construction is required (since this construction now has an additional BglII site), followed by introduction of the next BglII fragment. Thus, it is possible to construct a vector containing the entire ~25 kb of soraphen ORF1 in operable fusion to the 35S promoter.

An alternative approach to constructing the soraphen ORF1 by the fusion of sequential restriction fragments is to amplify the entire ORF using PCR. Barnes (Proc. Natl. Acad. Sci USA 91: 2216–2220 (1994)) has recently described techniques for the high-fidelity amplification of fragments by PCR of up to 35 kb, and these techniques can be applied to ORF1. Oligonucleotides specific for each end of ORF1, with appropriate restriction sites added are used to amplify the entire coding region, which is then cloned into appropriate sites in a suitable vector such as pCGN1761 or its derivatives. Typically after PCR amplification, resequencing is advised to ensure that no base changes have arisen in the amplified sequence. Alternatively, a functional assay can be done directly in transgenic plants.

Yet another approach to the expression of the genes for polyketide biosynthesis (such as soraphen) in transgenic plants is the construction, for expression in plants, of transcriptional units which comprise less than the usual complement of modules, and to provide the remaining modules on other transcriptional units. As it is believed that the biosynthesis of polyketide antibiotics such as soraphen is a process which requires the sequential activity of specific modules and that for the synthesis of a specific molecule these activities should be provided in a specific sequence, it is likely that the expression of different transgenes in a plant carrying different modules may lead to the biosynthesis of novel polyketide molecules because the sequential enzymatic nature of the wild-type genes is determined by their configuration on a single molecule. It is assumed that the localization of five specific modules for soraphen biosynthesis on ORF1 is determinatory in the biosynthesis of soraphen, and that the expression of, say three modules on one transgene and the other two on another, together with ORF2, may result in biosynthesis of a polyketide with a different molecular structure and possibly with a different antipathogenic activity. This invention encompasses all such deviations of module expression which may result in the synthesis in transgenic organisms of novel polyketides.

Although specific construction details are only provided for ORF1 above, similar techniques are used to express ORF2 and the soraphen methylase in transgenic plants. For the expression of functional soraphen in plants it is anticipated that all three genes must be expressed and this is done as detailed in this specification.

Fusions of the kind described above can be made to any desired promoter with or without modification (e.g. for optimized translational initiation in plants or for enhanced expression). As the ORFs identified for soraphen biosynthesis are around 70% GC rich it is not anticipated that the coding sequences should require modification to increase GC content for optimal expression in plants. It may, however, be advantageous to modify the genes to include codons preferred in the appropriate target plant species.

Example 43

Expression of Phenazine in Transgenic Plants

The GC content of all the isolated genes encoding biosynthetic enzymes for phenazine synthesis is between 58 and 65% and consequently no AT-content related problems are anticipated with their expression in plants (although it may be advantageous to modify the genes to include codons preferred in the appropriate target plant species.). Fusions of the kind described below can be made to any desired promoter with or without modification (e.g. for optimized translational initiation in plants or for enhanced expression).

Expression behind the 35S Promoter

Each of the three phenazine ORFs is transferred to pBluescript SK II for further manipulation. The phzB ORF is transferred as an EcoRI-BglII fragment isolated from plasmid pLSP18-6H3del3 containing the entire phenazine operon. This fragment is transferred to the EcoRI-BamHI sites of pBluescript SK II. The phzC ORF is transferred from pLSP18-6H3del3 as an XhoI-ScaI fragment cloned into the XhoI-SmaI sites of pBluescript II SK. The phzD ORF is transferred from pLSP18-6H3del3 as a BglII-HindIII fragment into the BamHI-HindIII sites of pBluescript II SK.

Destruction of internal restriction sites which are required for further construction is undertaken using the procedure of "inside-outside PCR" described above (Innes et al. supra). In the case of the phzB ORF two SphI sites are destroyed (one site located upstream of the ORF is left intact). The first of these is destroyed using the unique restriction sites EcoRI (left of the SphI site to be destroyed) and BclI (right of the SphI site). For this manipulation to be successful, the DNA to be BclI cleaved for the final assembly of the inside-outside PCR product must be produced in a dam-minus *E. coli* host such as SCS110 (Stratagene). For the second phzB SphI sites, the selected unique restriction sites are PstI and SpeI, the latter being beyond the phzB ORF in the pBluescript polylinker. The phzC ORF has no internal SphI sites, and so this procedure is not required for phzC. The phzD ORF, however, has a single SphI site which can be removed using the unique restriction sites XmaI and HindIII (the XmaI/SmaI site of the pBluescript polylinker is no longer present due to the insertion of the ORF between the BamHI and HindIII sites).

The removal of SphI sites from the phenazine biosynthetic genes as described above facilitates their transfer to the pCGN1761SENX vector by amplification using an aminoterminal oligonucleotide primer which incorporates an SphI site at the ATG and a carboxyterminal primer which incorporates a restriction site not found in the gene being amplified. The resultant amplified fragment is cleaved with SphI and the carboxyterminal enzyme and cloned into pCGN1761SENX. Suitable restriction enzyme sites for incorporation into the carboxyterminal primer are EcoRI and NotI (for all three ORFs; NotI will need checking when sequence complete), and XhoI (for phzB and phzD). Given the requirement for the nucleotide C at position 6 within the SphI recognition site, in some cases the second codon of the ORF may require changing so as to start with the nucleotide C. This construction fuses each ORF at its ATG to the SphI sites of the translation-optimized vector pCGN1761SENX in operable linkage to the double 35S promoter. After construction is complete the final gene insertions and fusion points are resequenced to ensure that no undesired base changes have occurred.

By utilizing an aminoterminal oligonucleotide primer which incorporates an NcoI site at its ATG instead of an SphI site, the three phz ORFs can also be easily cloned into to the translation-optimized vector pCGN1761NENX. None of the three phenazine biosynthetic gene ORFs carry an NcoI site and consequently there is no requirement in this case to destroy internal restriction sites. Primers for the carboxyterminus of the gene are designed as described above and the cloning is undertaken in a similar fashion. Given the requirement for the nucleotide G at position 6 within the NcoI recognition site, in some cases the second codon of the ORF may require changing so as to start with the nucleotide G. This construction fuses each ORF at its ATG to the NcoI site of pCGN1761NENX in operable linkage to the double 35S promoter.

The expression cassettes of the appropriate pCGN1761-derivative vectors are transferred to transformation vectors. Where possible multiple expression cassettes are transferred to a single transformation vector so as to reduce the number of plant transformations and crosses between transformants which may be required to produce plants expressing all four ORFs and thus producing phenazine.

Expression behind 35S with Chloroplast Targeting

The three phenazine ORFs amplified using oligonucleotides carrying an SphI site at their aminoterminus are cloned into the 35S-chloroplast targeted vector pCGN1761/CT. The fusions are made to the SphI site located at the cleavage site of the rbcS transit peptide. The expression cassettes thus created are transferred to appropriate transformation vectors (see above) and used to generate transgenic plants. As chorismate, the likely precursor for phenazine biosynthesis, is synthesized in the chloroplast, it may be advantageous to express the biosynthetic genes for phenazine in the chloroplast to ensure a ready supply of substrate. Transgenic plants expressing all three ORFs will target all three gene products to the chloroplast and will thus synthesize phenazine in the chloroplast.

Expression Behind rbcS With Chloroplast Targeting

The three phenazine ORFs amplified using oligonucleotides carrying an SphI site at their aminoterminus are cloned into the rbcS-chloroplast targeted vector pCGN1761rbcS/CT. The fusions are made to the SphI site located at the cleavage site of the rbcS transit peptide. The expression cassettes thus created are transferred to appropriate transformation vectors (see above) and used to generate transgenic plants. Aschorismate, the likely precursor for phenazine biosynthesis, is synthesized in the chloroplast, it may be advantageous to express the biosynthetic genes for phenazine in the chloroplast to ensure a ready supply of substrate. Transgenic plants expressing all three ORFs will target all four gene products to the chloroplast and will thus synthesize phenazine in the chloroplast. The expression of the three ORFs will, however, be light induced.

Example 44

Expression of the Non-Ribosomally Synthesized Peptide Antibiotic Gramicidin in Transgenic Plants The three *Bacillus brevis* gramicidin biosynthetic genes grsA, grsB and grsT have been previously isolated and sequenced (Turgay et al. Mol. Microbiol. 6: 529–546 (1992); Kraetzschmar et al. J. Bacteriol. 171: 5422–5429 (1989)). They are 3296, 13358, and 770 bp in length, respectively. These sequences are also published as GenBank accession numbers X61658 and M29703. The manipulations described here can be undertaken using the publicly available clones published by Turgay et al. (supra) and Kraetzschmar et al. (supra), or alternatively from newly isolated clones from *Bacillus brevis* isolated as described herein.

Each of the three ORFs grsA, grsB, and grsT is PCR amplified using oligonucleotides which span the entire coding sequence. The leftward (upstream) oligonucleotide includes an SstI site and the rightward (downstream) oligonucleotide includes an XhoI site. These restriction sites are not found within any of the three coding sequences and enable the amplified products to be cleaved with SstI and XhoI for insertion into the corresponding sites of pBluescript II SK. This generates the clones pBL-GRSa, pBLGRSb and pBLGRSt. The CG content of these genes lies between 35 and 38%. Ideally, the coding sequences encoding the three genes may be remade using the techniques referred to in Section K, however it is possible that the unmodified genes may be expressed at high levels in transgenic plants without encountering problems due to their AT content. In any case it may be advantageous to modify the genes to include codons preferred in the appropriate target plant species.

The ORF grsA contains no SphI site and no NcoI site. This gene can be thus amplified from pBLGSRa using an aminoterminal oligonucleotide which incorporates either an SphI site or an NcoI site at the ATG, and a second carboxyterminal oligonucleotide which incorporates an XhoI site, thus enabling the amplification product to be cloned directly into pCGN1761SENX or pCGN1761NENX behind the double 35S promoter.

The ORF grsB contains no NcoI site and therefore this gene can be amplified using an aminoterminal oligonucleotide containing an NcoI site in the same was as described above for the grsA ORF; the amplified fragment is cleaved with NcoI and XhoI and ligated into pCGN1761NENX. However, the grsB ORF contains three SphI sites and these are destroyed to facilitate the subsequent cloning steps. The sites are destroyed using the "inside-outside" PCR technique described above. Unique cloning sites found within the grsB gene but not within pBluescript II SK are EcoN1, PflM1, and RsrII. Either EcoN1 or PflM1 can be used together with RsrII to remove the first two sites and RsrII can be used together with the ApaI site of the pBluescript polylinker to remove the third site. Once these sites have been destroyed (without causing a change in amino acid), the entirety of the grsB ORF can be amplified using an aminoterminal oligonucleotide including an SphI site at the ATG and a carboxyterminal oligonucleotide incorporating an XhoI site. The resultant fragment is cloned into pCGN1761SENX. In order to successfully PCR-amplify fragments of such size, amplification protocols are modified in view of Barnes (1994, supra) who describes the high fidelity amplification of large DNA fragments. An alternative approach to the transfer of the grsB ORF to pCGN1761SENX without necessitating the destruction of the three SphI restriction sites involves the transfer to the SphI and XhoI cloning sites of pCGN1761SENX of an aminoterminal fragment of grsB by amplification from the ATG of the gene using an aminoterminal oligonucleotide which incorporates a SphI site at the ATG, and a second oligonucleotide which is adjacent and 3' to the PflM1 site in the ORF and which includes an XhoI site. Thus the aminoterminal amplified fragment is cleaved with SphI and XhoI and cloned into pCGN1761SENX. Subsequently the remaining portion of the grsB gene is excised from pBLGRSb using PflMI and XhoI (which cute in the pBluescript polylinker) and cloned into the aminoterminal carrying construction cleaved with PflMI and XhoI to reconstitute the gene.

The ORF grsT contains no SphI site and no NcoI site. This gene can be thus amplified from pBLGSRt using an aminoterminal oligonucleotide which incorporates either an SphI site or an NcoI site at the initiating codon which is changed to ATG (from GTG) for expression in plants, and a second carboxyterminal oligonucleotide which incorporates an XhoI site, thus enabling the amplification product to be cloned directly into pCGN1761SENX or pCGN1761NENX behind the double 35S promoter.

Given the requirement for the nucleotide C at position 6 within the SphI recognition site, and the requirement for the nucleotide G at position 6 within the NcoI recognition site, in some cases the second codon of the ORF may require changing so as to start with the appropriate nucleotide.

Transgenic plants are created which express all three gramicidin biosynthetic genes as described elsewhere in the specification. Transgenic plants expressing all three genes synthesize gramicidin.

Example 45

Expression of the Ribosomally Synthesized Peptide Lantibiotic Epidermin in Transgenic Plants The epiA ORF encodes the structural unit for epidermin biosynthesis and is approximately 420 bp in length (GenBank Accession No. X07840; Schnell et al. Nature 333: 276–278 (1988)). This gene can be subcloned using PCR techniques from the plasmid pTü32 into pBluescript SK II using oligonucleotides carrying the terminal restriction sites BamHI (5') and PstI (3'). The epiA gene sequence has a GC content of 27% and this can be increased using techniques of gene synthesis referred to elsewhere in this specification; this sequence modification may not be essential, however, to ensure high-level expression in plants. Subsequently the epiA ORF is transferred to the cloning vector pCGN1761SENX or pCGN1761NENX by PCR amplification of the gene using an aminoterminal oligonucelotide spanning the initiating methionine and carrying an SphI site (for cloning into pCGN1761SENX) or an NcoI site (for cloning into pCGN1761NENX), together with a carboxy-terminal oligonucleotide carrying an EcoRI, a NotI, or an XhoI site for cloning into either pCGN1761SENX or pCGN1761NENX. Given the requirement for the nucleotide C at position 6 within the SphI recognition site, and the requirement for the nucleotide G at position 6 within the NcoI recognition site, in some cases the second codon of the ORF may require changing so as to start with the appropriate nucleotide.

Using cloning techniques described in this specification or well known in the art, the remaining genes of the epi operon (viz. epiB, epiC, epiD, epiQ, and epiP) are subcloned from plasmid pTü32 into pBluescript SK II. These genes are responsible for the modification and polymerization of the epiA-encoded structural unit and are described in Kupke et al. (J. Bacteriol. 174: 5354–5361 (1992)) and Schnell et al. (Eur. J. Biochem. 204: 57–68 (1992)). The subcloned ORFs are manipulated for transfer to pCGN1761-derivative vectors as described above. The expression cassettes of the appropriate pCGN 1761-derivative vectors are transferred to transformation vectors. Where possible multiple expression cassettes are transferred to a single transformation vector so as to reduce the number of plant transformations and crosses between transformants which may be required to produce plants expressing all required ORFs and thus producing epidermin.

L. Analysis of Transgenic Plants for APS Accumulation

Example 46

Analysis of APS Gene Expression

Expression of APS genes in transgenic plants can be analyzed using standard Northern blot techniques to assess the amount of APS mRNA accumulating in tissues. Alternatively, the quantity of APS gene product can be assessed by Western analysis using antisera raised to APS biosynthetic gene products. Antisera can be raised using conventional techniques and proteins derived from the expression of APS genes in a host such as E. coli. To avoid the raising of antisera to multiple gene products from E. coli expressing multiple APS genes from multiple ORF operons, the APS biosynthetic genes can be expressed individually in E. coli. Alternatively, antisera can be raised to synthetic peptides designed to be homologous or identical to known APS biosynthetic predicted amino acid sequence. These techniques are well known in the art.

Example 47

Analysis of APS Production in Transgenic Plants

For each APS, known protocols are used to detect production of the APS in transgenic plant tissue. These protocols are available in the appropriate APS literature. For pyrrolnitrin, the procedure described in example 11 is used, and for soraphen the procedure described in example 17. For phenazine determination, the procedure described in example 18 can be used. For non-ribosomal peptide antibiotics such as gramicidin S, an appropriate general technique is the assaying of ATP-PP$_i$ exchange. In the case of gramicidin, the grsA gene can be assayed by phenylalanine-dependent ATP-PP$_i$ exchange and the grsB gene can be assayed by proline, valine, ornithine, or leucine-dependent ATP-PP$_i$ exchange. Alternative techniques are described by Gause & Brazhnikova (Lancet 247: 715 (1944)). For ribosomally synthesized peptide antibiotics isolation can be achieved by butanol extraction, dissolving in methanol and diethyl ether, followed by chromatography as described by Allgaier et al. for epidermin (Eur. Ju. Biochem. 160: 9–22 (1986)). For many APSs (e.g. pyrrolnitrin, gramicidin, phenazine) appropriate techniques are provided in the Merck Index (Merck & Co., Rahway, N.J. (1989)).

M. Assay of Disease Resistance in Transgenic Plants

Transgenic plants expressing APS biosynthetic genes are assayed for resistance to phytopathogens using techniques well known in phytopathology. For foliar pathogens, plants are grown in the greenhouse and at an appropriate stage of development inoculum of a phytopathogen of interest is introduced at in an appropriate manner. For soil-borne phytopathogens, the pathogen is normally introduced into the soil before or at the time the seeds are planted. The choice of plant cultivar selected for introduction of the genes will have taken into account relative phytopathogen sensitivity. Thus, it is preferred that the cultivar chosen will be susceptible to most phytopathogens of interest to allow a determination of enhanced resistance.

Assay of Resistance to Foliar Phytopathogens

Example 48

Disease Resistance to Tobacco Foliar Phytopathogens

Transgenic tobacco plants expressing APS genes and shown to poduce APS compound are subjected to the following disease tests.

Phytophthora parasitica/Black Shank

Assays for resistance to Phytophthora parasitica, the causative organism of black shank. are performed on six-week-old plants grown as described in Alexander et al., Pro. Natl. Acad. Sci. USA 90: 7327–7331. Plants are watered, allowed to drain well, and then inoculated by applying 10 mL of a sporangium suspension (300 sporangia/mL) to the soil. Inoculated plants are kept in a greenhouse maintained at 23–25° C. day temperature, and 20–22° C. night temperature. The wilt index used for the assay is as follows: 0=no symptoms; 1=some sign of wilting, with reduced turgidity; 2=clear wilting symptoms, but no rotting or stunting; 3=clear wilting symptoms with stunting, but no apparent stem rot; 4=severe wilting, with visible stem rot and some damage to root system; 5=as for 4, but plants near death or dead, and with severe reduction of root system. All assays are scored blind on plants arrayed in a random design.

Pseudomonas syringae

Pseudomonas syringae pv. tabaci (strain #551) is injected into the two lower leaves of several 6–7 week old plants at a concentration of $10^6$ or $3\times10^6$ per ml in $H_2O$. Six individual plants are evaluated at each time point. Pseudomonas tabaci infected plants are rated on a 5 point disease severity scale, 5=100% dead tissue, 0=no symptoms. A T-test (LSD) is conducted on the evaluations for each day and the groupings are indicated after the Mean disease rating value. Values followed by the same letter on that day of evaluation are not statistically significantly different.

Cercospora nicotianae

A spore suspension of Cercospora nicotianae (ATCC #18366) (100,000–150,000 spores per ml) is sprayed to imminent run-off on to the surface of the leaves. The plants were maintained in 100% humidity for five days. Thereafter the plants are misted with $H_2O$ 5–10 times per day. Six individual plants were evaluated at each time point. Cercospora nicotianae was rated on a % leaf area showing disease symptoms basis. A T-test (LSD) is conducted on the evaluations for each day and the groupings are indicated after the Mean disease rating value. Values followed by the same letter on that day of evaluation are not statistically significantly different.

Statistical Analyses

All tests include non-transgenic tobacco (six plants per assay, or the same cultivar as the transgenic lines) (Alexander et al., Pro. Natl. Acad. Sci. USA 90: 7327–7331). Pairwise T-tests were performed to compare different genotype and treatment groups for each rating date.

Assay of Resistance to Soil-Borne Phytopathogens

Example 49

Resistance to Rhizoctonia solani

Plant assays to determine resistance to Rhizoctonia solani are conducted by planting or transplanting seeds or seedlings into naturally or artificially infested soil. To create artificially infested soil, millet, rice, oat, or other similar seeds are first moistened with water, then autoclaved and inoculated with plugs of the fungal phytopathogen taken from an agar plate. When the seeds are fully overgrown with the phytopathogen, they are air-dried and ground into a powder. The powder is mixed into soil at a rate experimentally determined to cause disease. Disease may be assessed by comparing stand counts, root lesions ratings, and shoot and root weights of transgenic and non-transgenic plants grown in the infested soil. The disease ratings may also be compared to the ratings of plants grown under the same conditions but without phytopathogen added to the soil.

Example 50

Resistance to Pseudomonas solanacearum

Plant assays to determine resistance to Pseudomonas solanacearum are conducted by planting or transplanting seeds or seedlings into naturally or artificially infested soil. To create artificially infested soil, bacteria are grown in shake flask cultures, then mixed into the soil at a rate experimentally determined to cause disease. The roots of the plants may need to be slightly wounded to ensure disease development. Disease may be assessed by comparing stand counts, degree of wilting and shoot and root weights of transgenic and non-transgenic plants grown in the infested soil. The disease ratings may also be compared to the ratings of plants grown under the same conditions but without phytopathogen added to the soil.

Example 51

Resistance to Soil-Borne Fungi which are Vectors for Virus Transmission

Many soil-borne Polymyxa, Olpidium and Spongospora species are vectors for the transmission of viruses. These include (1) Polymyxa betae which transmits Beet Necrotic Yellow Vein Virus (the causative agent of rhizomania disease) to sugar beet, (2) Polymyxa graminis which transmits Wheat Soil-Borne Mosaic Virus to wheat, and Barley Yellow Mosaic Virus and Barley Mild Mosaic Virus to barley, (3) Olpidium brassicae which transmits Tobacco Necrosis Virus to tobacco, and (4) Spongospora subterranea which transmits Potato Mop Top Virus to potato. Seeds or plants expressing APSs in their roots (e.g. constitutively or under root specific expression) are sown or transplanted in sterile soil and fungal inocula carrying the virus of interest are introduced to the soil. After a suitable time period the transgenic plants are assayed for viral symptoms and accumulation of virus by ELISA and Northern blot. Control experiments involve no inoculation, and inoculation with fungus which does not carry the virus under investigation. The transgenic plant lines under analysis should ideally be susceptible to the virus in order to test the efficacy of the APS-based protection. In the case of viruses such as Barley Mild Mosaic Virus which are both Polymyxa-transmitted and mechanically transmissible, a further control is provided by the successful mechanical introduction of the virus into plants which are protected against soil-infection by APS expression in roots.

Resistance to virus-transmitting fungi offered by expression of APSs will thus prevent virus infections of target crops thus improving plant health and yield.

Example 52

Resistance to Nematodes

Transgenic plants expressing APSs are analyzed for resistance to nematodes. Seeds or plants expressing APSs in their roots (e.g. constitutively or under root specific expression) are sown or transplanted in sterile soil and nematode inocula carrying are introduced to the soil. Nematode damage is assessed at an appropriate time point. Root knot nematodes such as Meloidogyne spp. are introduced to transgenic tobacco or tomato expressing APSs. Cyst nematodes such as Heterodera spp. are introduced to transgenic cereals, potato and sugar beet. Lesion nematodes such as Pratylenchus spp. are introduced to transgenic soybean, alfalfa or corn. Reniform nematodes such as Rotylenchulus spp. are introduced to transgenic soybean, cotton, or tomato. Ditylenchus spp. are introduced to transgenic alfalfa. Detailed techniques for screening for resistance to nematodes are provided in Starr (Ed.; Methods for Evaluating Plant Species for resistance to Plant Parasitic Nematodes, Society of Nematologists, Hyattsville, Md. (1990))

Examples of Important Phytopathogens in Agricultural Crop Species

Example 53

Disease Resistance in Maize

Transgenic maize plants expressing APS genes and shown to poduce APS compound are subjected to the following disease tests. Tests for each phytopathogen are conducted according to standard phytopathological procedures.

Leaf Diseases and Stalk Rots (1) Northern Corn Leaf Blight (Helminthosporium turcicum† syn. Exserohilum turcicum).

(2) Anthracnose (Colletotrichum graminicola†—same as for Stalk Rot)

(3) Southern Corn Leaf Blight (Helminthosporium maydis† syn. Bipolaris maydis).

(3) Eye Spot (Kabatiella zeae)
(4) Common Rust (Puccinia sorghi).
(4) Southern Rust (Puccinia polysora).
(5) Gray Leaf Spot (Cercospora zeae-maydis† and C. sorghi)
(6) Stalk Rots (a complex of two or more of the following pathogens—Pythium aphanidermatum†-early, Erwinia chrysanthemi-zeae-early, Colletotrichum graminicola†, Diplodia maydis†, D. macrospora, Gibberella zeae†, Fusarium moniliforme†, Macrophomina phaseolina, Cephalosporium acremonium)
(7) Goss' Disease (Clavibacter nebraskanense)

Important-Ear Molds (1) Gibberella Ear Rot (Gibberella zeae†-same as for Stalk Rot) Aspergillus flavus, A. parasiticus. Aflatoxin
(2) Diplodia Ear Rot (Diplodia maydis† and D. macrospora—same organisms as for Stalk Rot)
(3) Head Smut (Sphacelotheca reiliana—syn. Ustilago reiliana)

Example 54

Disease Resistance in Wheat

Transgenic wheat plants expressing APS genes and shown to poduce APS compound are subjected to the following disease tests. Tests for each pathogen are conducted according to standard phytopathological procedures.

(1) Septoria Diseases (Septoria tritici, S. nodorum)
(2) Powdery Mildew (Erysiphe graminis)
(3) Yellow Rust (Puccinia striiformis)
(4) Brown Rust (Puccinia recondita, P. hordei)
(5) Others-Brown Foot Rot/Seedling Blight (Fusarium culmorum and Fusarium roseum), Eyespot (Pseudocercosporella herpotrichoides), Take-All (Gaeumannomyces graminis)
(6) Viruses (barley yellow mosaic virus, barley yellow dwarf virus, wheat yellow mosaic virus).

N. Assay of Biocontrol Efficacy in Microbial Strains Expressing APS Genes

Example 55

Protection of Cotton against Rhizoctonia solani

Assays to determine protection of cotton from infection caused by Rhizoctonia solani are conducted by planting seeds treated with the biocontrol strain in naturally or artificially infested soil. To create artificially infested soil, millet, rice, oat, or other similar seeds are first moistened with water, then autoclaved and inoculated with plugs of the fungal pathogen taken from an agar plate. When the seeds are fully overgrown with the pathogen, they are air-dried and ground into a powder. The powder is mixed into soil at a rate experimentally determined to cause disease. This infested soil is put into pots, and seeds are placed in furrows 1.5 cm deep. The biocontrol strains are grown in shake flasks in the laboratory. The cells are harvested by centrifugation, resuspended in water, and then drenched over the seeds. Control plants are drenched with water only. Disease may be assessed 14 days later by comparing stand counts and root lesions ratings of treated and nontreated seedlings. The disease ratings may also be compared to the ratings of seedlings grown under the same conditions but without pathogen added to the soil.

Example 56

Protection of Potato against Claviceps michiganese subsp. speedonicum

Claviceps michiganese subsp. speedonicum is the causal agent of potato ring rot disease and is typically spread before planting when "seed" potato tubers are knife cut to generate more planting material. Transmission of the pathogen on the surface of the knife results in the inoculation of entire "seed" batches. Assays to determine protection of potato from the causal agent of ring rot disease are conducted by inoculating potato seed pieces with both the pathogen and the biocontrol strain. The pathogen is introduced by first cutting a naturally infected tuber, then using the knife to cut other tubers into seed pieces. Next, the seed pieces are treated with a suspension of biocontrol bacteria or water as a control. Disease is assessed at the end of the growing season by evaluating plant vigor, yield, and number of tubers infected with Clavibacter.

O. Isolation of APSs from Organisms Expressing the Isolated Genes

Example 57

Extraction Procedures for APS Isolation

Active APSs can be isolated from the cells or growth medium of wild-type of transformed strains that produces the APS. This can be undertaken using known protocols for the isolation of molecules of known characteristics.

For example, for APSs which contain multiple benzene rings (pyrrolnitrin and soraphen) cultures are grown for 24 h in 10 ml L broth at an appropriate temperature and then extracted with an equal volume of ethyl acetate. The organic phase is recovered, allowed to evaporated under vacuum and the residue dissolved in 20 $\mu$l of methanol.

In the case of pyrrolnitrin a further procedure has been used successfully for the extraction of the active antipathogenic compound from the growth medium of the transformed strain producing this antibiotic. This is accomplished by extraction of the medium with 80% acetone followed by removal of the acetone by evaporation and a second extraction with diethyl ether. The diethyl ether is removed by evaporation and the dried extract is resuspended in a small volume of water. Small aliquots of the antibiotic extract applied to small sterile filter paper discs placed on an agar plate will inhibit the growth of Rhizoctonia solani, indicating the presence of the active antibiotic compound.

A preferred method for phenazine isolation is described by Thomashow et al. (Appl Environ Microbiol 56: 908–912 (1990)). This involves acidifying cultures to pH 2.0 with HCl and extraction with benzene. Benzene fractions are dehydrated with $Na_2SO_4$ and evaporated to dryness. The residue is redissolved in aqueous 5% $NaHCO_3$, reextracted with an equal volume of benzene, acidified, partitioned into benzene and redried.

For peptide antibiotics (which are typically hydrophobic) extraction techniques using butanol, methanol, chloroform or hexane are suitable. In the case of gramicidin, isolation can be carried out according to the procedure described by Gause & Brazhnikova (Lancet 247: 715 (1944)). For epidermin, the procedure described by Allgaier et al. for epidermin (Eur. Ju. Biochem. 160: 9–22 (1986)) is suitable and involves butanol extraction, and dissolving in methanol and diethyl ether. For many APSs (e.g. pyrrolnitrin, gramicidin, phenazine) appropriate techniques are provided in the Merck Index (Merck & Co., Rahway, N.J. (1989)).

P. Formulation and Use of Isolated Antibiotics

Antifungal formulations can be made using active ingredients which comprise either the isolated APSs or alternatively suspensions or concentrates of cells which produce them. Formulations can be made in liquid or solid form.

Example 58

Liquid Formulation of Antifungal Compositions

In the following examples, percentages of composition are given by weight:

| 1. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethlene glycol ether (36 moles of ethylene oxide) | 5% | — | — |
| Tributylphenol polyethylene glyco ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160–190°) | — | — | 94% | — |

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgit | — | 90% |

The active ingredient is dissolved in methylene chloride, the solution is sprayed onto the carrier, and the solvent is subsequently evaporated off in vacuo.

| Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 59

Solid Formulation of Antifungal Compositions

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethylene oxide) | 4% |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

Q. Post-Harvest Disease Control

Biocontrol strains, such as those described above in Section I. of the Examples can be used for controlling or inhibiting the growth of plant pathogenic fungi by applying the genetically engineered biocontrol strains to an environment in which the plant pathogenic fungus may grow. For example, this can be to the plant/s or parts of the plant/s after harvest. The biocontrol strains are applied in an effective amount; that is, in an amount sufficient to control or inhibit the pathogen.

Example 60

Evaluation of Biocontrol Agents for Control of Penicillium digitatum (Green Mold) in Citrus Fruit Fruit was harvested from Winter Haven, Fla. and was washed and graded. Fruit were inoculated with Penicillium digitatum by dipping a 2 mm long×1 mm wide needle into a suspension of $10^6$ P. digitatum spores/ml and forcing it into the rind at the equator of each fruit. Within 4–5 hours after inoculation, treatments were applied to the fruit with brushes and the fruit were packed unwaxed into 4/5 bushel fiberboard boxes. Each treatment contained 4 replicated cartons with 60 fruit each. The fruit were stored at 70° F. with 96% relative humidity.

Pseudomonas fluorescens strain CGA267356 is described in U.S. Pat. No. 5,348,742 and genetically modified Pseudomonas fluorescens strain CGA313167 is described above in Example 27. Results are shown in the following tables:

| Control of Green Mold on Valencia Oranges: | | |
|---|---|---|
| | Percent Infected Fruit Storage Time (Days) | |
| Treatment | 5 | 9 |
| Control (water) | 25.0a[1] | 49.2a |
| CGA267356 ($10^9$ viable cells/ml) | 7.9b | 20.4b |
| Imazalil (1000 ppm aqueous suspension) | 1.7b | 3.0c |

[1]Values within each column followed by different letters are significantly different (DMRT, $P = 0.05$)

| Control of Green Mold on Grapefruit: | |
|---|---|
| Treatment | Percent Infected Fruit After 2 Weeks |
| Control (water) | 23.2 |
| CGA313167-Whole Culture; $10^9$ cells/ml | 0 |
| CGA313167-Washed Cells; $10^9$ cells/ml | 5.2 |
| Imazalil (0.5% aqueous suspension) | 0 |

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. A nucleic acid molecule isolated from a microbe capable of producing pyrrolnitrin, wherein said nucleic acid molecule encodes at least one enzyme required in the biosynthetic pathway of pyrrolnitrin.

2. A nucleic acid molecule according to claim 1, which is isolated from a Pseudomonas species.

3. A nucleic acid molecule according to claim 2, which is isolated from Pseudomonas fluorescens.

4. A nucleic acid molecule according to claim 3, wherein said enzyme has an amino acid sequence selected from the group consisting of SEQ ID NOs:2–5.

5. A nucleic acid molecule according to claim 2, which is isolated from Pseudomonas pyrrocinia.

6. A nucleic acid molecule according to claim 5, wherein said enzyme has an amino acid sequence selected from the group consisting of SEQ ID NOs:24–27.

7. A nucleic acid molecule according to claim 1, which is isolated from a Burkholdaria species.

8. A nucleic acid molecule according to claim 7, which is isolated from Burkholdaria cepacia.

9. A nucleic acid molecule according to claim 8, wherein said enzyme has an amino acid sequence selected from the group consisting of SEQ ID NOs:29–32.

10. An expression vector comprising a nucleic acid molecule according to claim 9.

11. A microbial host transformed with an expression vector according to claim 10.

12. A nucleic acid molecule according to claim 1, which is isolated from a Myxococcus species.

13. A nucleic acid molecule according to claim 12, which is isolated from Myxococcus fulvus.

14. A nucleic acid molecule according to claim 13, wherein said enzyme has an amino acid sequence selected from the group consisting of SEQ ID NOs:34–37.

15. An expression vector comprising a nucleic acid molecule according to claim 12.

16. A microbial host transformed with an expression vector according to claim 15.

17. A nucleic acid molecule according to claim 1, wherein said nucleic acid molecule or its complement hybridizes to SEQ ID NO:1, 23, 28, or 33 under the following conditions:
hybridization at 7% sodium dodecyl sulfate (SDS), 0.5 M NaPO$_4$ pH 7.0, 1 mM EDTA at 50° C.; wash with 2× SSC, 1% SDS, at 50° C.

18. A nucleic acid molecule according to claim 1, wherein said enzyme is a PrnA enzyme that catalyzes the conversion of D- and L-tryptophan to 7-chlorotryptophan.

19. A nucleic acid molecule according to claim 18, wherein said enzyme has an amino acid sequence selected from the group consisting of SEQ ID NOs:2, 24, 29, and 37.

20. A nucleic acid molecule according to claim 18, wherein said nucleic acid molecule or its complement hybridizes to either ORF1 of SEQ ID NO:1, ORF1 of SEQ ID NO:23, ORF1 of SEQ ID NO:28, or ORF4 of SEQ ID NO:33 under the following conditions: hybridization at 7% sodium dodecyl sulfate (SDS), 0.5 M NaPO$_4$ pH 7.0, 1 mM EDTA at 50° C.; wash with 2× SSC, 1% SDS, at 50° C.

21. A nucleic acid molecule according to claim 18, wherein said nucleic acid molecule has a sequence selected from the group consisting of: ORF1 of SEQ ID NO:1, ORF1 of SEQ ID NO:23, ORF1 of SEQ ID NO:28, and ORF4 of SEQ ID NO:33.

22. A nucleic acid molecule according to claim 1, wherein said enzyme is a PrnB enzyme that catalyzes the conversion of 7-chlorotryptophan to monodechloroaminopyrrolnitrin.

23. A nucleic acid molecule according to claim 22, wherein said enzyme has an amino acid sequence selected from the group consisting of SEQ ID NOs:3, 25, 30, and 34.

24. A nucleic acid molecule according to claim 19, wherein said nucleic acid molecule or its complement hybridizes to either ORF2 of SEQ ID NO: 1, ORF2 of SEQ ID NO:23, ORF2 of SEQ ID NO:28, or ORF1 of SEQ ID NO:33 under the following conditions: hybridization at 7% sodium dodecyl sulfate (SDS), 0.5 M NaPO$_4$ pH 7.0, 1 mM EDTA at 50° C.; wash with 2× SSC, 1% SDS, at 50° C.

25. A nucleic acid molecule according to claim 19, wherein said nucleic acid molecule has a nucleotide sequence selected from the group consisting of: ORF2 of SEQ ID NO: 1, ORF2 of SEQ ID NO:23, ORF2 of SEQ ID NO:28, and ORF1 of SEQ ID NO:33.

26. A nucleic acid molecule according to claim 1, wherein said enzyme is a PrnC enzyme that catalyzes the conversion of monodechloroaminopyrrolnitrin to aminopyrrolnitrin.

27. A nucleic acid molecule according to claim 26, wherein said enzyme has an amino acid sequence selected from the group consisting of SEQ ID NOs:4, 26, 31, and 35.

28. A nucleic acid molecule according to claim 26, wherein said nucleic acid molecule or its complement hybridizes to either ORF3 of SEQ ID NO: 1, ORF3 of SEQ ID NO:23, ORF3 of SEQ ID NO:28, or ORF2 of SEQ ID NO:33 under the following conditions: hybridization at 7% sodium dodecyl sulfate (SDS), 0.5 M NaPO$_4$ pH 7.0, 1 mM EDTA at 50° C.; wash with 2× SSC, 1% SDS, at 50° C.

29. A nucleic acid molecule according to claim 26, wherein said nucleic acid molecule has a nucleotide sequence selected from the group consisting of: ORF3 of SEQ ID NO: 1, ORF3 of SEQ ID NO:23, ORF3 of SEQ ID NO:28, and ORF2 of SEQ ID NO:33.

30. A nucleic acid molecule according to claim 1, wherein said enzyme is a PrnD enzyme that catalyzes the conversion of aminopyrrolnitrin to pyrrolnitrin.

31. A nucleic acid molecule according to claim 29, wherein said enzyme has an amino acid sequence selected from the group consisting of SEQ ID NOs:5, 27, 32, and 36.

32. A nucleic acid molecule according to claim 29, wherein said nucleic acid molecule or its complement hybridizes to either ORF4 of SEQ ID NO: 1, ORF4 of SEQ ID NO:23, ORF4 of SEQ ID NO:28, or ORF3 of SEQ ID NO:33 under the following conditions: hybridization at 7% sodium dodecyl sulfate (SDS), 0.5 M NaPO$_4$ pH 7.0, 1 mM EDTA at 50° C.; wash with 2× SSC, 1% SDS, at 50° C.

33. A nucleic acid molecule according to claim 29, wherein said nucleic acid molecule has a nucleotide sequence selected from the group consisting of: ORF4 of SEQ ID NO: 1, ORF43 of SEQ ID NO:23, ORF4 of SEQ ID NO:28, and ORF3 of SEQ ID NO:33.

34. A chimeric construct comprising a promoter operatively linked to a nucleic acid molecule according to claim 1.

35. An expression vector comprising a nucleic acid molecule according to claim 1.

36. A DNA molecule isolated from a microbial host capable of producing pyrrolnitrin, wherein said DNA molecule or its complement hybridizes to SEQ ID NO:1, 23, 28, or 33 under the following conditions: hybridization at 7% sodium dodecyl sulfate (SDS), 0.5 M NaPO$_4$ pH 7.0, 1 mM EDTA at 50° C.; wash with 2× SSC, 1% SDS, at 50° C.

37. A chimeric construct comprising a promoter operatively linked to a DNA molecule according to claim 36.

38. An expression vector comprising a DNA molecule according to claim 36.

* * * * *